(12) United States Patent
Sternson et al.

(10) Patent No.: US 12,247,064 B2
(45) Date of Patent: *Mar. 11, 2025

(54) MODIFIED LIGAND-GATED ION CHANNELS AND METHODS OF USE

(71) Applicant: Howard Hughes Medical Institute, Chevy Chase, MD (US)

(72) Inventors: Scott Sternson, Chevy Chase, MD (US); Peter Lee, Chevy Chase, MD (US); Christopher Magnus, Chevy Chase, MD (US)

(73) Assignee: Howard Hughes Medical Institute, Chevy Chase, MD (US)

(*) Notice: Subject to any disclaimer, the term of this patent is extended or adjusted under 35 U.S.C. 154(b) by 1076 days.

This patent is subject to a terminal disclaimer.

(21) Appl. No.: 17/146,906

(22) Filed: Jan. 12, 2021

(65) Prior Publication Data

US 2021/0206831 A1 Jul. 8, 2021

Related U.S. Application Data

(63) Continuation of application No. 16/186,122, filed on Nov. 9, 2018, now Pat. No. 10,961,296.

(60) Provisional application No. 62/584,428, filed on Nov. 10, 2017, provisional application No. 62/729,716, filed on Sep. 11, 2018.

(51) Int. Cl.
  *C07K 14/705* (2006.01)
  *A61K 48/00* (2006.01)

(52) U.S. Cl.
  CPC .... *C07K 14/70571* (2013.01); *A61K 48/0008* (2013.01); *A61K 48/0058* (2013.01); *A61K 48/0066* (2013.01); *A61K 48/0091* (2013.01); *C07K 2319/03* (2013.01)

(58) Field of Classification Search
  CPC .......... C07K 14/70571; C07K 2319/03; A61K 48/0008; A61K 48/0058; A61K 48/0066; A61K 48/0091; A61K 38/00; A61K 45/06
  See application file for complete search history.

(56) References Cited

U.S. PATENT DOCUMENTS

| | | | |
|---|---|---|---|
| 7,186,870 B2 | 3/2007 | Singer et al. | |
| 8,435,762 B2 | 5/2013 | Sternson et al. | |
| 10,961,296 B2* | 3/2021 | Sternson | A61K 45/06 |
| 10,981,962 B2* | 4/2021 | Sternson | A61K 38/012 |
| 11,084,853 B2* | 8/2021 | Sternson | A61P 21/00 |
| 11,124,554 B2 | 9/2021 | Sternson et al. | |
| 2004/0204862 A1 | 10/2004 | Wainer et al. | |
| 2005/0250808 A1 | 11/2005 | Xie et al. | |
| 2009/0048289 A1 | 2/2009 | Tremel et al. | |
| 2009/0123945 A1 | 5/2009 | Gopalakrishnan et al. | |
| 2010/0130420 A1 | 5/2010 | Sternson et al. | |
| 2011/0064750 A1 | 3/2011 | Fahim et al. | |
| 2012/0219967 A1 | 8/2012 | Gopalakrishnan et al. | |
| 2016/0069901 A1 | 3/2016 | Laing et al. | |
| 2018/0009862 A1 | 1/2018 | Sternson et al. | |
| 2018/0193414 A1 | 7/2018 | Greenberg et al. | |
| 2019/0375807 A1 | 12/2019 | Sternson et al. | |
| 2020/0131537 A1 | 4/2020 | Seal et al. | |
| 2020/0316217 A1 | 10/2020 | Cheloha et al. | |
| 2021/0403522 A1 | 12/2021 | Sternson et al. | |
| 2022/0041671 A1 | 2/2022 | Sternson et al. | |
| 2022/0096504 A1 | 3/2022 | Blumstock et al. | |
| 2024/0002463 A1 | 1/2024 | Sternson et al. | |

FOREIGN PATENT DOCUMENTS

| | | |
|---|---|---|
| CN | 101044140 | 9/2007 |
| CN | 106459138 | 2/2017 |
| CN | 107206106 | 9/2017 |
| CN | 110023331 | 7/2019 |
| JP | 2005501510 | 1/2005 |
| JP | 2007516275 | 6/2007 |
| JP | 2011504490 | 2/2011 |
| JP | 2012504966 | 3/2012 |
| WO | WO 2002/059266 | 8/2002 |
| WO | WO2004056867 | 7/2004 |
| WO | WO2010042799 | 4/2010 |
| WO | WO2011014679 | 2/2011 |
| WO | WO2011140279 | 11/2011 |
| WO | WO 2015/069752 | 5/2015 |
| WO | WO 2017/049252 | 3/2017 |
| WO | WO2018009832 | 1/2018 |

(Continued)

OTHER PUBLICATIONS

Whisstock et al. Quaterly Reviews of Biophysics, 2003, "Prediction of protein function from protein sequence and structure", 36(3): 307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10: 8-9. (Year: 2002).*

Chen et al., "Stability of tramadol with three 5-hT3 receptor antagonists in polyolefin bags for patient-controlled delivery systems," Drug Design, Development and Therapy, Jun. 2016, 10:1869-1875.

Search Report in Chinese Appln. No, 20170054322.3, dated Mar. 23, 2022, 7 pages (with English Translation).

(Continued)

*Primary Examiner* — Iqbal H Chowdhury
(74) *Attorney, Agent, or Firm* — Fish & Richardson P.C.

(57) ABSTRACT

This document relates to materials and methods for modulating ligand gated ion channel (LGIC) activity. For example, modified LGICs including at least one LGIC subunit having a modified ligand binding domain (LBD) and/or a modified ion pore domain (IPD) are provided. Also provided are exogenous LGIC ligands that can bind to and activate the modified LGIC, as well as methods of modulating ion transport across the membrane of a cell of a mammal, methods of modulating the excitability of a cell in a mammal, and methods of treating a mammal having a channelopathy.

21 Claims, 43 Drawing Sheets

Specification includes a Sequence Listing.

(56) References Cited

FOREIGN PATENT DOCUMENTS

| WO | WO 2021/035179 | 2/2021 |
|---|---|---|
| WO | WO 2023/147590 | 8/2023 |

OTHER PUBLICATIONS

Extended European Search Report in European Application No. 18876111.8, dated Apr. 8, 2022, 14 pages.
Ferguson et al., "Using DREADDs to investigate addiction behaviors," Curr Opin Behav Sci., Apr. 2015, 2:69-72.
Hansen and Taylor, "Galanthamine and non-competitive inhibitor binding to ACh-binding protein: evidence for a binding site on non-alpha-subunit interfaces of heteromeric neuronal nicotinic receptors," Journal of Molecular Biology, Jun. 15, 2007, 369:895-901.
International Search Report and Written Opinion in International Appln. No. PCT/US2023/20251, mailed on Jul. 25, 2023, 11 pages.
Jones, "The Pharmacology of Cocaine Smoking in Humans," NIDA Research Monograph, 1990, 99:30-41.
Kim, "Channelopathies," Korean Journal of Pediatrics, 2014, 57(1):1-18.
Zimmer et al., "The motivation to self-administer is increased after a history of spiking brain levels of cocaine," Neuropsychopharmacology, Jul. 2012, 37(8):1901-10.
Gradinaru et al., "Molecular and Cellular Approaches for Diversifying and Extending Optogenetics," Cell, Elsevier, Amsterdam, NL, Apr. 2, 2010, 141(1):154-165.
Magnus et al., "Ultrapotent chemogenetics for research and potential clinical applications," Science (American Association for the Advancement of Science), Apr. 12, 2019, 364(6436):eaav5282, 9 pages.
Magnus et al., Research Article Summary: "Ultrapotent chemogenetics for research and potential clinical applications," Science (American Association for the Advancement of Science), Apr. 12, 2019, 364:146.
Partial Supplementary European Search Report in European Application No. 18876111.8, dated Oct. 18, 2021, 15 pages.
Sternson et al., "Chemogenetic Tools to Interrogate Brain Functions," Annual Review of Neuroscience., Jul. 8, 2014, 37(1):387-407.
JP Office Action in Japanese Appln. No. 2019-520933, dated Jan. 6, 2022, 10 pages (with English translation).
Marotta et al., "An Unaltered Orthosteric Site and a Network of Long-Range Allosteric Interactions for PNU-120596 in α7 Nicotinic Acetylcholine Receptors," Chem. Biol., Aug. 20, 2015, 22(8):1063-1073.
Cappelli et al., "The interactions of the 5-HT$_3$ receptor with arylpiperazine, tropane, and quinuclidine ligands," Current Topics in Medicinal Chemistry, 2002, 2(6):599-624, 26 pages.
Celie et al., "Nicotine and Carbamycholine Binding to Nicotinic Acetylcholine Receptors as Studied in AChBP Crystal Structures," Mar. 25, 2004, Neuron, 41: 907-914, 8 pages.
Chenna et al., "Multiple sequence alignment with the Clustal series of programs," Jul. 2003, Nucleis Acids Res., 31(13):3497-3500, 4 pages.
Combrink et al., "Characterization of the naturally occurring Arg344His variant of the human 5-HT 3A receptor," Oct. 2009, Pharmacological Reports, 61(5): 785-797, 13 pages.
Craig et al., "Stable expression and characterisation of a human α7 nicotinic subunit chimera: a tool for functional high-throughput screening," European Journal of Pharmacology, Oct. 11, 2004, 502 (1-2): 31-40.
Extended European Search Report in European Application No. 17824999.1, dated May 28, 2020, 16 pages.
Galzi et al., "Functional significance of aromatic amino acids from three peptide loops of the α7 neuronal nicotinic receptor site investigated by site-directed mutagenesis," FEBS, Elsevier Science Publishers B.V., Dec. 1991, vol. 294, No. 3, pp. 198-202.
Gao et al., "Derivaties of dibenzothiophene for positron emission tomography imaging of α7-nicotinic acetylcholine receptors," Journal of Medicinal Chemistry, 2013, 56(19):7574-7589, 16 pages.
Grutter et al., "Molecular tuning of fast gating in pentameric ligand-gated ion channels," PNAS, Dec. 13, 2005, 102(50): 18207-18212.
International Search Report and Written Opinion in International Application No. PCT/US2017/041147, dated Oct. 18, 2017, 22 pages (with English translation).
Li et al., "Ligand-binding domain of an α7-nicotinic receptor chimera and its complex with agonist," Nat Neurosci., Nov. 5, 2012, 14(10): 1253-1259.
Magnus et al. "Chemical and genetic engineering of selective ligand-ion channel interactions," Science, Sep. 2, 2011 (Sep. 2, 2011), vol. 333, Iss. 6047, pp. 1291-1296. Entire document.
Mazurov et al., "2-(Arylmethyl)-3-substituted quinuclidines as selective α7 nicotinic receptor ligands," Bioorganic & Medicinal Chemistry Letters, Pergamon, Amsterdam, NL, Apr. 15, 2005, vol. 15, No. 8, pp. 2073-2077, XP027801786.
Ngo et al., "Computational complexity, protein structure prediction, and the Levinthal paradox. In Merz and Le Grand (Eds.) The Protein Folding Problem and Tertiary Structure Prediction. Birkhauser:Boston," 1994, pp. 491-495.
PCT International Search Report and Written Opinion in International Appln. No. PCT/US2018/060109, dated Feb. 28, 2019, 22 pages.
PCT Invitation to Pay in International Application No. PCT/US2018/060109, dated Jan. 10, 2019, 4 pages.
Price et al., "Varenicline interactions at the 5-HT3 receptor ligand binding site are revealed by 5-HTBP," ACS Chemical Neuroscience, 2015, 6 (7): 1151-1157, 7 pages.
Rucktooa et al., "Structural Characterization of Binding Mode of Smoking Cessation Drugs to Nicotinic Acetylcholine Receptors through Study of Ligand Complexes with Acetylcholine-binding Protein," Journal of Biological Chemistry, Jul. 6, 2012, vol. 287, No. 28, pp. 23283-23293, XP55073824.
Sadigh-Eteghad et al., "Selective activation of α7 nicotinic acetylcholine receptor by PHA-543613 improves Aβ25-35-mediated cognitive deficits in mice," Neuroscience, Jan. 1, 2015, vol. 298 , pp. 81-93, XP029241092.
Teodoro et al., "A Promising PET Tracer for Imaging of α7 Nicotinic Acetylcholine Receptors in the Brain: Design, Synthesis, and *in Vivo* Evaluation of a Dibenzothiophene-Based Radioligand," Molecules, Oct. 9, 2015, vol. 20, No. 10, pp. 18387-18421, XP55695282.
Walker et al., "Design, synthesis, structure-activity relationship, and in vivo activity of azabicyclic aryl amides as alpha7 nicotinic acetylcholine receptor agonists," Bioorg Med Chem., Dec. 2006, 14(24):8219-48, 30 pages.
Wang et al. "Stability of tramadol with three 5-HT3 receptor antagonists in polyolefin bags for patient-controlled delivery systems," Drug Design, Development and Therapy, Jun. 1, 2016, p. 1869, XP55695596.
Wells, J.A, "Additivity of mutational effects in proteins. Biochemistry," 1990, 29(37):8509-8517.
Wishka et al., "Discovery of N-[(3R)-1-azabicyclo[2.2.2]oct-3-yl]furo[2,3-c]pyridine-5-carboxamide, an agonist of the alpha7 nicotinic acetylcholine receptor, for the potential treatment of cognitive deficits in schizophrenia: synthesis and structure—activity relationship," J Med Chem., Jul. 2006, 49(14):4425-36, 12 pages.
Young et al., "Potentiation of α7 nicotinic acetylcholine receptors via an allosteric transmembrane site," PNAS, Sep. 23, 2008, 105(38): 14686-14691.
Huff et al., "Photoredox-Catalyzed Hydroxymethylation of Heteroaromatic Bases," J. Org. Chem., 2016, 81:6980-6987.
Chiorini et al., "Cloning and Characterization of Adeno-Associated Virus Type 5," Journal of Virology, Feb. 1999, 73(2):1309-1319.
Earley et al., "Adeno-Associated Virus Serotype-Specific Inverted Terminal Repeat Sequence Role in Vector Transgene Expression," Human Gene Therapy, Feb. 2020, 31(3-4):151-162.
Gao et al., "Clades of Adeno-Associated Viruses Are Widely Disseminated in Human Tissues," Journal of Virology, Jun. 2004, 78(12):6381-6388.

(56) References Cited

OTHER PUBLICATIONS

International Preliminary Report on Patentability in International Appln. No. PCT/US2023/061662, mailed on Aug. 15, 2024, 10 pages.
International Search Report and Written Opinion in International Appln. No. PCT/US2023/061662, mailed on Nov. 8, 2023, 14 pages.
Mori et al., "Two novel adeno-associated viruses from cynomolgus monkey: pseudotyping characterization of capsid protein," Virology, Dec. 2004, 330(2):375-383.

* cited by examiner signal peptide 1-22

MRCSPGGVWLALAASLLHVSLQGEFQRKLYKELVKNYNPLERPVANDSQP 50
———————— alpha7 nAChR LBD ————————

LTVYFSLSLLQIMDVDEKNQVLTTNIWLQMSWTDHYLQWNVSEYPGVKTV 100
———————— alpha7 nAChR LBD ————————

RFPDGQIWKPDILLYNSADERFDATFHTNVLVNSSGHCQYLPPGIFKSSC 150
———————— alpha7 nAChR LBD ————————

YIDVRWFPFDVQHCKLKFGSWSYGGWSLDLQMQEADISGYIPNGEWDLVG 200
———————— alpha7 nAChR LBD ————————

IPGKRSERFYECCKEPYPDVTFTVIIRRRPLFYAVSLLLPSIFLMVVDIV 250
——— alpha7 nAChR LBD ——————— 5HT3a IPD ———

GFCLPPDSGERVSFKITLLLGYSVFLIIVSDTLPATIGTPLIGVYFVVCM 300
———————— 5HT3a IPD ————————

ALLVISLAETIFIVRLVHKQDLQRPVPDWLRHLVLDRIAWILCLGEQPMA 350
———————— 5HT3a IPD ————————

HRPPATFQANKTDDCSGSDLLPAMGNHCSHVGGPQDLEKTPRGRGSPLPP 400
———————— 5HT3a IPD ————————

PREASLAVRGLLQELSSIRHFLEKRDEMREVARDWLRVGYVLDRLLFRIY 450
———————— 5HT3a IPD ————————

LLAVLAYSITLVTLWSIWHYS.
——— 5HT3a IPD ———

FIG. 1A signal peptide 1-22

MRCSPGGVWLALAASLLHVSLQGEFQRKLYKELVKNYNPLERPVANDSQP  50
———————————— alpha7 nAChR LBD ————————————

LTVYFSLSLLQIMDVDEKNQVLTTNIWLQMSWTDHYLQWNVSEYPGVKTV  100
———————————— alpha7 nAChR LBD ————————————

RFPDGQIWKPDILLYNSADERFDATFHTNVLVNSSGHCQYLPPGIFKSSC  150
———————————— alpha7 nAChR LBD ————————————

YIDVRWFPFDVQHCKLKFGSWSYGGWSLDLQMQEADISGYIPNGEWDLVG  200
———————————— alpha7 nAChR LBD ————————————

IPGKRSERFYECCKEPYPDVTFTVTMRRMGYYLIQMYIPSLLIVILSWI  250
———— alpha7 nAChR LBD ———————— GlyR IPD ————

SFWINMDAAPARVGLGITTVLTMTTQSSGSRASLPKVSYVKAIDIWMAVC  300
———————————————— GlyR IPD ————————————————

LLFVFSALLEYAAVNFVSRQHKELLRFRRKRRHHKEDEAGEGRFNFSAYG  350
———————————————— GlyR IPD ————————————————

MGPACLQAKDGISVKGANNSNTTNPPPAPSKSPEEMRKLFIQRAKKIDKI  400
———————————————— GlyR IPD ————————————————

SRIGFPMAFLIFNMFYWIIYKIVRREDVHNQ.
———————— GlyR IPD ————————

FIG. 1B signal peptide 1-22

```
MRCSPGGVWLALAASLLHVSLQGEFQRKLYKELVKNYNPLERPVANDSQP                    50
                       ————— alpha7 nAChR LBD —————

LTVYFSLSLLQIMDVDEKNQVLTTNIWLQMSWTDHYLQWNVSEYPGVKTV                   100
————————————————— alpha7 nAChR LBD —————————————————

RFPDGQIWKPDILLYNSADERFDATFHTNVLVNSSGHCQYLPPGIFKSSC                   150
————————————————— alpha7 nAChR LBD —————————————————

YIDVRWFPFDVQHCKLKFGSWSYGGWSLDLQMQEADISGYIPNGEWDLVG                   200
————————————————— alpha7 nAChR LBD —————————————————

IPGKRSERFYECCKEPYPDVTFTVIIRRRPLFYAVSLLLPSIFLMVVDIV                   250
——————— alpha7 nAChR LBD ———————    ——— 5HT3a IPD ———

GFYLPPNSGERVSFKITLLLGYSVFLIIVSDTLPATAIGTPLIGVYFVVC                   300
————————————————————— 5HT3a IPD —————————————————————

MALLVISLAETIFIVRLVHKQDLQQPVPAWLRHLVLERIAWLLCLREQST                   350
————————————————————— 5HT3a IPD —————————————————————

SQRPPATSQATKTDDCSAMGNHCSHMGGPQDFEKSPRDRCSPPPPPREAS                   400
————————————————————— 5HT3a IPD —————————————————————

LAVCGLLQELSSIRQFLEKRDEIREVARDWLRVGSVLDKLLFHIYLLAVL                   450
————————————————————— 5HT3a IPD —————————————————————

AYSITLVMLWSIWQYA.
————— 5HT3a IPD —————
```

FIG. 1C signal peptide 1-22

MRCSPGGVWLALAASLLHVSLQGEFQRKLYKELVKNYNPLERPVANDSQP    50
———————— alpha7 nAChR LBD ————————

LTVYFSLSLLQIMDVDEKNQVLTTNIWLQMSWTDHYLQWNVSEYPGVKTV    100
———————— alpha7 nAChR LBD ————————

RFPDGQIWKPDILLYNSADERFDATFHTNVLVNSSGHCQYLPPGIFKSSC    150
———————— alpha7 nAChR LBD ————————

YIDVRWFPFDVQHCKLKFGSWSYGGWSLDLQMQEADISGYIPNGEWDLVG    200
———————— alpha7 nAChR LBD ————————

IPGKRSERFYECCKEPYPDVTFTVTMRRRTLYYLLQTYFPATLMVMLSWV    250
——— alpha7 nAChR LBD ———          ——— GABA C IPD ———

SFWIDRRAVPARVPLGITTVLTMSTIITGVNASMPRVSYIKAVDIYLWVS    300
——————————— GABA C IPD ———————————

FVFVFLSVLEYAAVNYLTTVQERKEQKLREKLPCTSGLPPPRTAMLDGNY    350
——————————— GABA C IPD ———————————

SDGEVNDLDNYMPENGEKPDRMMVQLTLASERSSPQRKSQRSSYVSMRID    400
——————————— GABA C IPD ———————————

THAIDKYSRITFPAAYILFNLIYWSIFS.
——————— GABA C IPD ———————

FIG. 1D signal peptide 1-22

MGGGRGGIWLALAAALLHVSLQGEFQRRLYKELVKNYNPLERPVANDSQP 50

LTVYFSLSLLQIMDVDEKNQVLTTNIWLQMSWTDHYLQWNMSEYPGVKNV 100

RFPDGQIWKPDILLYNSADERFDATFHTNVGVNASGHCQYLPPGIFKSSC 150

YIDVRWFPFDVQQCKLKFGSWSYGGWSLDLQMQEADISSYIPNGEWDLMG 200

IPGKRNEKFYECCKEPYPDVTYTVTMRRRTLYYGLNLLIPCVLISALALL 250

VFLLPADSGEKISLGITVLLSLTTFMLLVAEIMPATSDSVPLIAQYFAST 300

MIIVGLSVVVTVIVLRYHHHDPDGGKMPKWTRIILLNWCAWFLRMKRPGE 350

DKVRPACQHKPRRCSLASVELSAGAGPPTSNGNLLYIGFRGLEGMHCAPT 400

PDSGVVCGRLACSPTHDEHLMHGAHPSDGDPDLAKILEEVRYIANRNRCQ 450

DESEVICSEWKFAACVVDPLCLMAFSVFTIICTIGILMSAPNFVEAVSKD 500

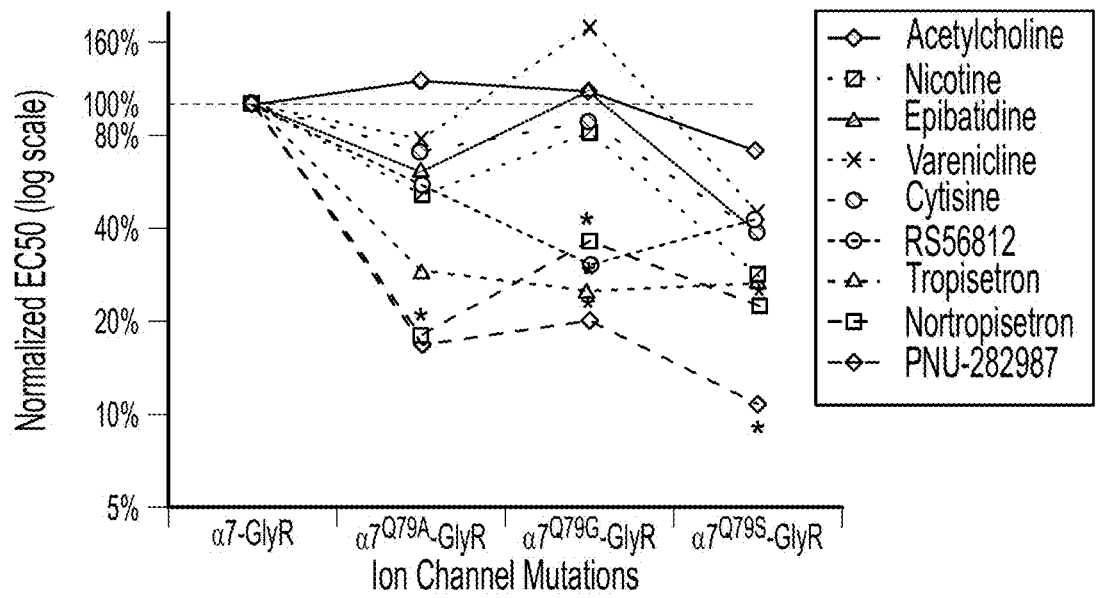
FIG. 4A
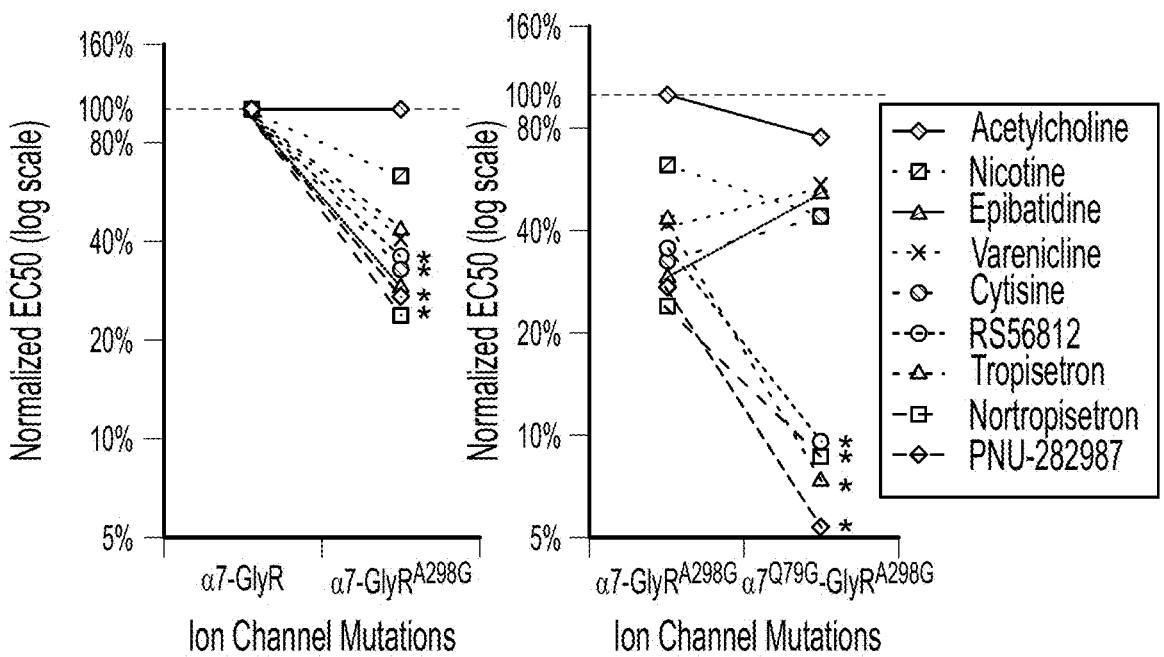
FIG. 4B
FIG. 4C

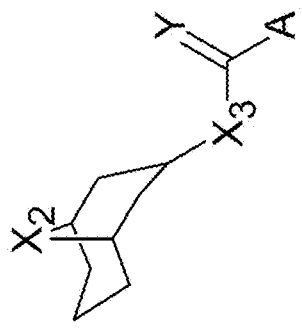

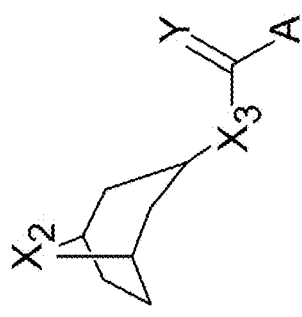

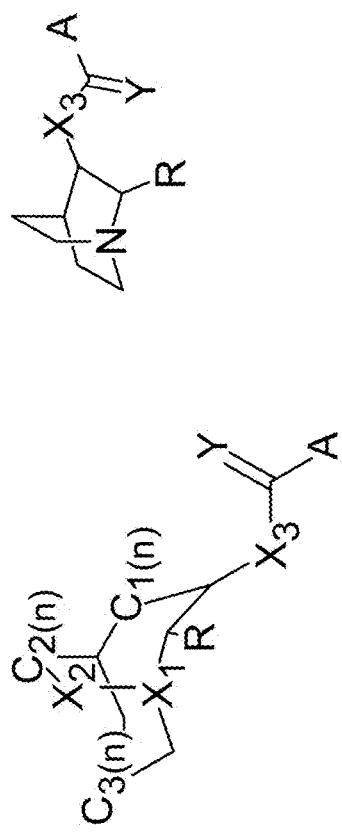

X = CH, CH2, O, NH, NMe
n = 0 or 1
Y = O, S
A = Aromatic
R = Pyridinylmethylene

FIG. 5A

Pharmacophore:
Quinuclidine
$C_{1(n)} = 0$
$C_{2(n)} = 1$
$C_{3(n)} = 0$
$X_1 = N$
$X_2 = CH_2$
$X_3 = O, NH, CH_2$
$Y = O, S$
A = Aromatic
R = Pyridinylmethylene Pharmacophore:
Tropane
$C_{1(n)} = 1$
$C_{2(n)} = 0$
$C_{3(n)} = 0$
$X_1 = CH$
$X_2 = NH, NMe$
$X_3 = O, NH, CH_2$
$Y = O, S$
A = Aromatic Pharmacophore:
9-azabicyclo[3.3.1]nonane
$C_{1(n)} = 1$
$C_{2(n)} = 0$
$C_{3(n)} = 1$
$X_1 = CH$
$X_2 = NH, NMe$
$X_3 = O, NH, CH_2$
$Y = O, S$
A = Aromatic

FIG. 5B

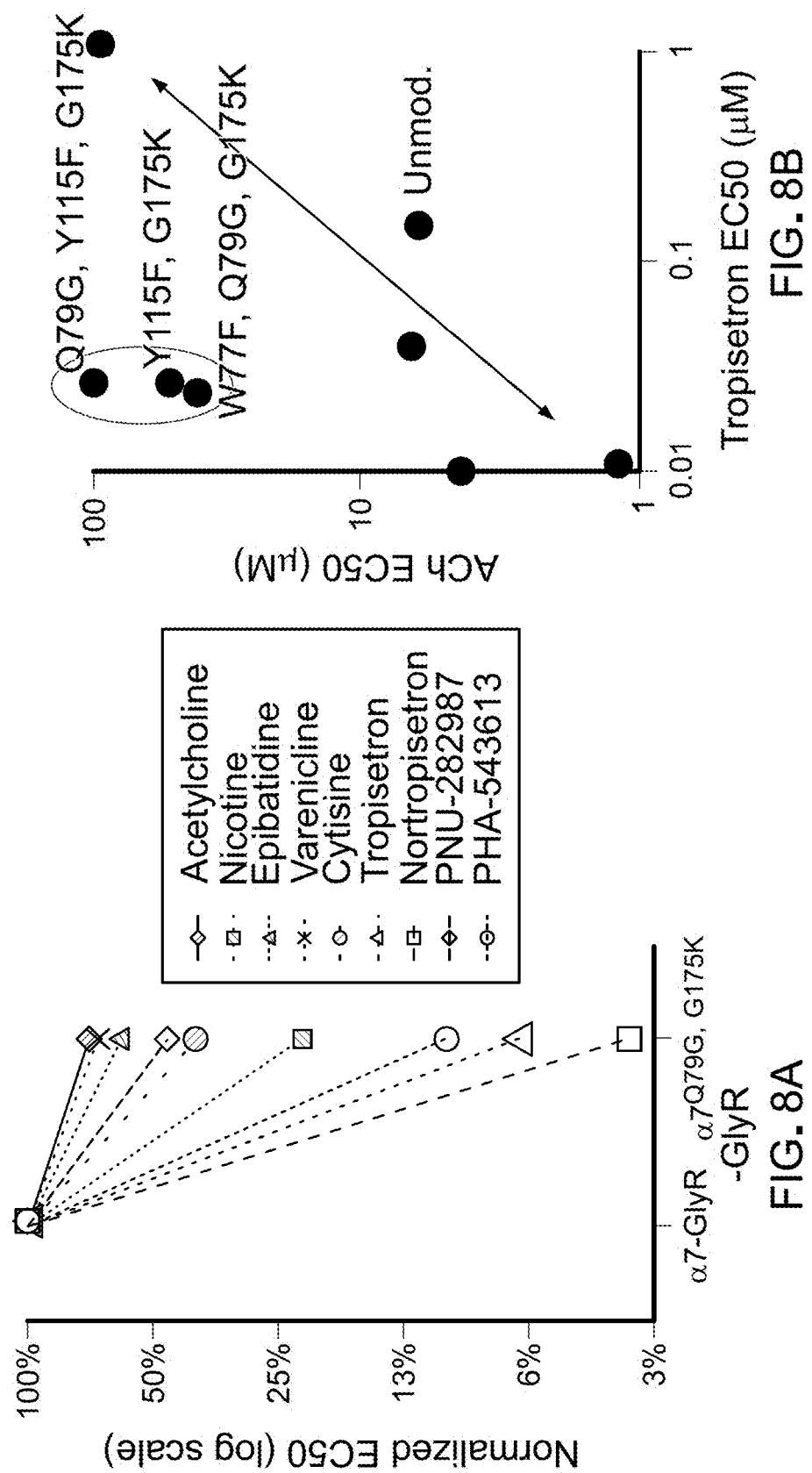

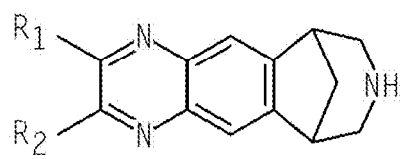
R₁ = H, an aromatic substituent, a methyl containing group, an ethyl containing group, a methoxy containing group, or an amino-containing group
R₂ = H, methyl, or phenyl
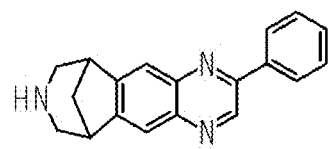
765
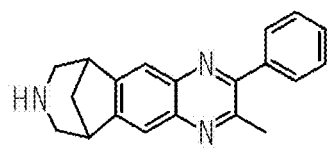
770
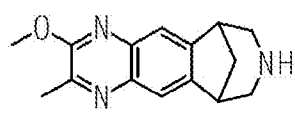
791
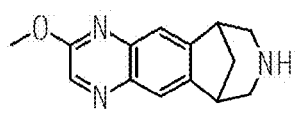
793
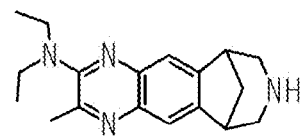
795
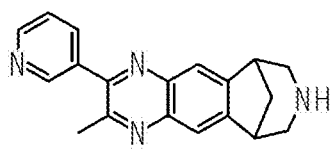
802
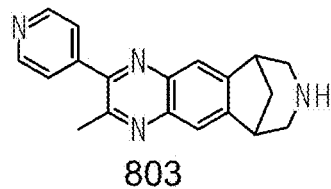
803
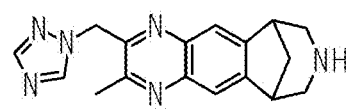
807
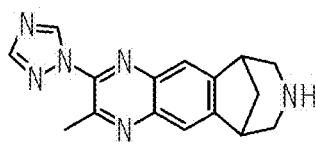
808
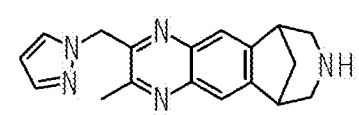
812
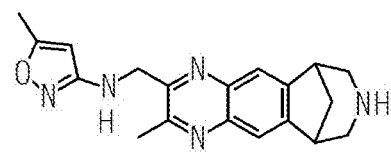
813
FIG. 11A

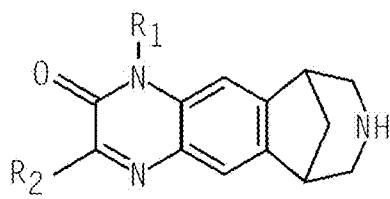
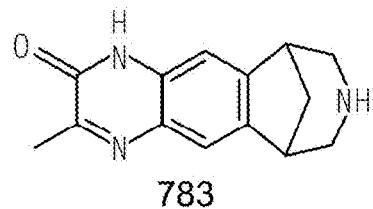
783
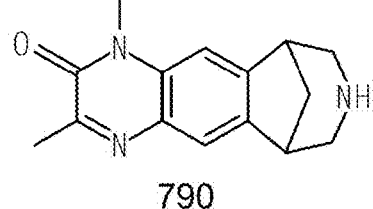
790
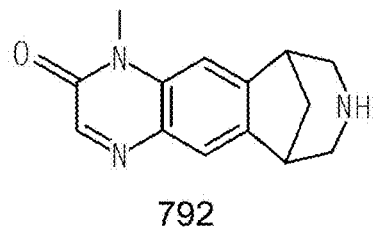
792
R₁ = H or CH3
R₂ = H, CH3, or an aromatic substituent
FIG. 11B
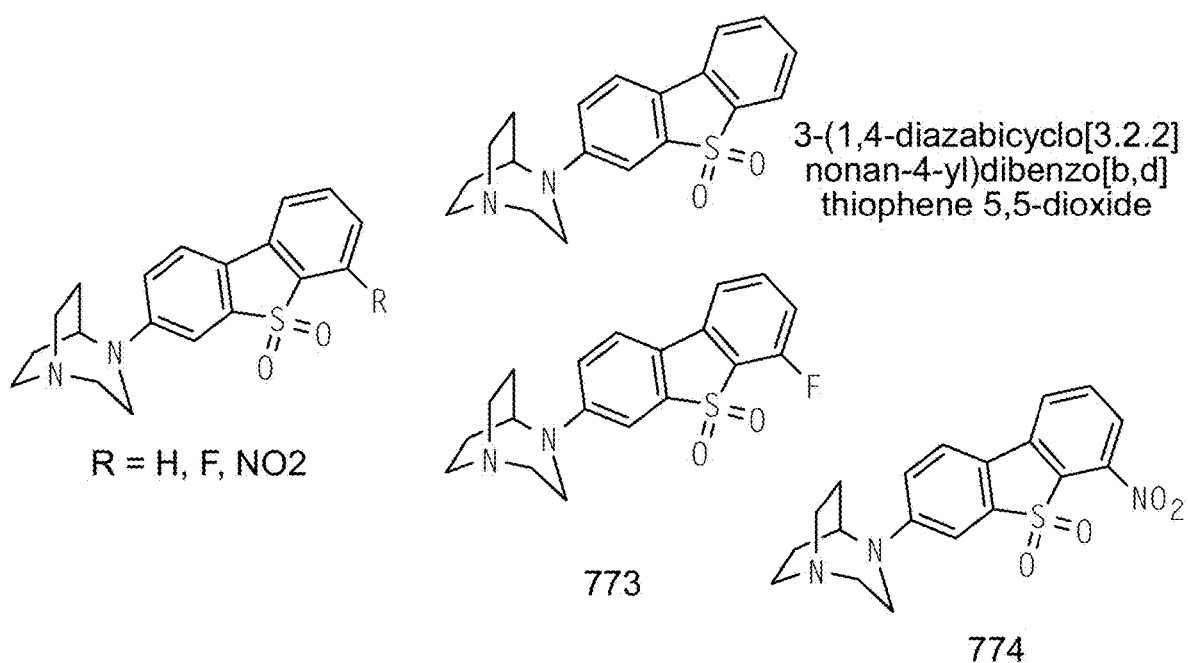
R = H, F, NO2
3-(1,4-diazabicyclo[3.2.2]nonan-4-yl)dibenzo[b,d]thiophene 5,5-dioxide
773
774
FIG. 11C

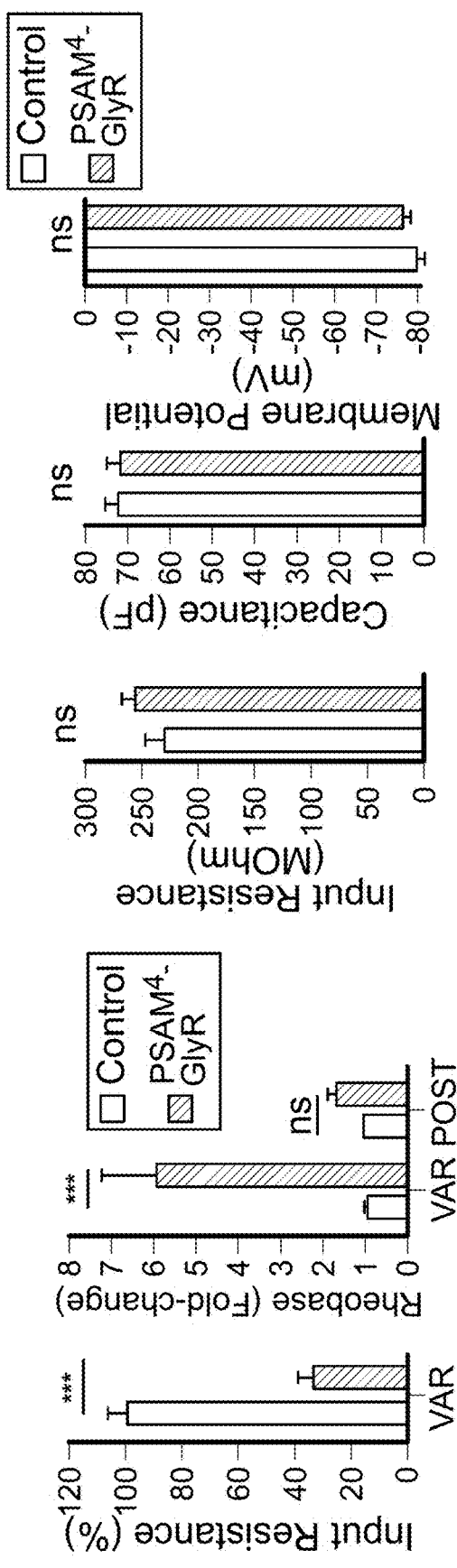
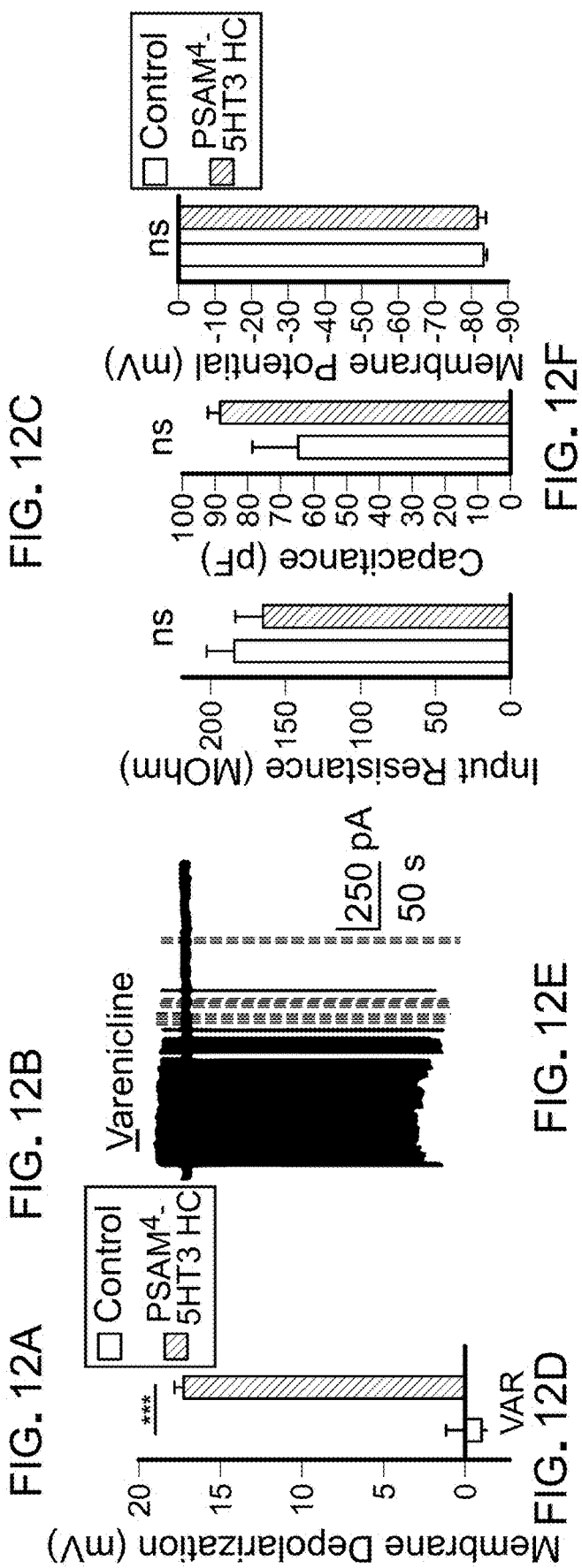
FIG. 12A  FIG. 12B  FIG. 12C
FIG. 12D  FIG. 12E  FIG. 12F

| | α7 nAChR | α7-GlyR | α7-5HT3 | PSAM⁴-GlyR | PSAM⁴-5HT3 | α4β2 agonist | h5HT3 agonist | α4β2 1 mM ACh | LED in vivo |
|---|---|---|---|---|---|---|---|---|---|
| varenicline | not determined | 620 (200) 390-fold | 920 (150) 230-fold | 1.6 (0.1) | 4 (2) | 250 (60) 160-fold | 1,400 (400) 880-fold | 3 2-fold | 0.1 mg/kg |
| 792 | >1,000-fold | >30,000 >10,000-fold | >30,000 >10,000-fold | 2.3 (0.3) | 1.6 (0.2) | | | (agonist) | 1 mg/kg |
| 793 | >1,000-fold | 31,000 (17,000) >10,000-fold | 26,000 (4,200) >10,000-fold | 0.6 (0.4) | 0.9 (0.4) | 520 (100) 230-fold | 40,500 (500) >10,000-fold | 23 (5) 38-fold | 0.03 mg/kg |
| 815 | >1,000-fold | >100,000 >10,000-fold | >100,000 >10,000-fold | 0.5 (1) | 0.8 (0.4) | 610 (250) 1,000-fold | 1,300 (0) 2,200-fold | 21 (4) 42-fold | 0.1 mg/kg |
| 817 | >1,000-fold | >100,000 >10,000-fold | >100,000 >10,000-fold | 0.3 (0.4) | 0.5 (0.2) | >30 >10,000-fold | 1,200 (100) 3,000-fold | 31 (10) 100-fold | 0.1 mg/kg |
| | | | | | | >30 >10,000-fold | 1,500 (100) 5,000-fold | | |

FIG. 14A

MRCSPGGVWLALAASLLHVSLQGEFQRKLYKELVKNYNPLERPVANDSQP 50

LTVYFSLSLLQIMDVDEKNQVLTTNIWLQMSWTDHYLQWNVSEYPGVKTV 100

REPDGQIWKPDILLYNSADERFDATFHTNVGVNSS☐G☐HCLY☐L☐PPGIFKSSC 150

YIDVRWFPFDVQHCKLKFGSWSYGGWSLDLQMQEADISGYIPNGEWDLVG 200

IPGKRSERFYECCKEPFPDVT☐E☐TVTMRRRMGYYLIQMYIPSLLIVILSWI 250

SFWINMDAAPARVGLGITTVLTMTTQSSGSRSSLPKVSYVKAIDIWMAVC 300

LLFVFSALLEYAAVNFVSRQHKELLRFRRKRRHHKEDEAGEGRFNFSAYG 350

MGPACLQAKDGISVKGANNSN<u>FCYENEV</u>TTNPPPAPSKSPEEMRKLFIQR 400

AKKIDKISRIGFPMAFLIFNMFYWIIYKIVRREDVHNQ. 439

FIG. 16

MRRAPSLVLFFLVALCGRGNCGEFQRKLYKELVKNYNPLERPVANDSQPL 50

TVYFSLSLLQIMDVDEKNQVLTTNIWLQMSWTDHYLQWNVSEYPGVKTVR 100

FPDGQIWKPDILLYNSADERFDATFHTNV[G]VNSSGHC[L]YLPPGIFKSSCY 150

IDVRWFPFDVQHCKLK[E]GSWSYGGWSLDLQMQEADISGYIPNGEWDLVGI 200

PGKRSERFYECCKEP[E]PDVTFTVTMRRMGYYLIQMYIPSLLIVILSWIS 250

FWINMDAAPARVGLGITTVLTMTTQSSGSRSSLPKVSYVKAIDIWMAVCL 300

LFVFSALLEYAAVNFVSRQHKELLRFRRKRRHHKEDEAGEGRFNFSAYGM 350

GPACLQAKDGISVKGANNSNFCYENEVTTNPPPAPSKSPEEMRKLFIQRA 400

KKIDKISRIGFPMAFLIFNMFYWIIYKIVRREDVHNQ. 438

FIG. 17

LTVYFSLSLLQIMDVDEKNQVLTTNIWLQMSWTDHYLQWNVSEYPGVKTV    100

REPDGQIWKPDILLYNSADERFDATFHTNV[G]VNSSGHC[L]YLPPGIFKSSC    150

YIDVRWFPFDVQHCKLKFGSWSYGGWSLDLQMQEADISGYIPNGEWDLVG    200

IPGKRSERFYECCKEP[E]PDVTFTVTMRRRMGYYLIQMYIPSLLIVILSWI    250

SFWINMDAAPARVGLGITTVLTMTTQSSGSRSSLPKVSYVKAIDIWMAVC    300

LLFVFSALLEYAAVNFVSRQHKELLRFRRKRRHHKEDEAGEGRFNFSAYG    350

MGPACLQAKDGISVKGANNSNQSQPILNTKEMAPQSKPPEELEMSSMPSP    400

VAPLPARTEGVIDMRSMSSIDSFISCATDFPEATRFTTNPPPAPSKSPEE    450

MRKLFIQRAKKIDKISRIGFPMAFLIFNMFYWIIYKIVRREDVHNQ.    497

FIG. 18

AAV-SYN::PSAM4-GlyR-IRES-EGFP-EPRE

AAV-Syn::PSAM4-GlyR-IRES-EGFP-WPRE

```
AGCGCCCAATACGCAAACCGCCTCTCCCCGCGCGTTGGCCGATTCATTAATGCAGCTGCGCGCTCGCTCGC
TCACTGAGGCCGCCCGGGCAAAGCCCGGGCGTCGGGCGACCTTTGGTCGCCCGGCCTCAGTGAGCGAGCGA
GCGCGCAGAGAGGGAGTGGCCAACTCCATCACTAGGGGTTCCTTGTAGTTAATGATTAACCCGCCATGCTA
CTTATCTACGTAGCCATGCTCTAGGAAGATCCGAGCTCCAGTGTGCTGGAATTCGCCCTTTTCAGTATTTA
AATTGACGACCGACCCCGACCCACTGGACAAGCACCCAACCCCCATTCCCCAAATTGCGCATCCCCTATCA
GAGAGGGGGAGGGGAAACAGGATGCGGCGAGGCGCGTGCGCACTGCCAGCTTCAGCACCGCGGACAGTGCC
TTCGCCCCGCCTGGCGGCGCGCGCCACCGCCGCCTCAGCACTGAAGGCGCGCTGACGTCACTCGCCGGTC
CCCCGCAAACTCCCCTTCCCGGCCACCTTGGTCGCGTCCGCGCCGCCGCCGGCCCAGCCGGACCGCACCAC
GCGAGGCGCGAGATAGGGGGCACGGGCGCGACCATCTGCGCTGCGGCGCCGGCGACTCAGCGCTGCCTCA
GTCTGCGGTGGGCAGCGGAGGAGTCGTGTCGTGCCTGAGAGCGCAGCTGTGCTCCTGGGCACGCGCAGTC
CGCCCCGCGGCTCCTGGCCAGACCACCCCTAGGACCCCCTGCCCCAAGTCGCAGCCGTTGGATCAGGTAA
GTATCAAGGTTACAAGACAGGTTTAAGGAGACCAATAGAAACTGGGCTTGTCGAGACAGAGAAGACTCTTG
CGTTTCTGATAGGCACCTATTGGTCTTACTGACATCCACTTTGCCTTTCTCTCCACAGGTGATGATATCAC
TAGTGCTAGCGCCACCATGCGCTGTTCTCCAGGCGGCGTGTGGCTCGCCCTGGCTGCTTCCCTTCTGCACG
TTAGCCTGCAGGGTGAGTTCCAGCGCAAACTGTATAAGGAGCTTGTTAAGAATTATAACCCCCTGGAGCGG
CCGGTCGCAAATGATTCCCAGCCACTGACAGTGTACTTCAGCCTCTCCTTGCTGCAGATCATGGACGTGGA
TGAAAAGAACCAGGTGCTGACCACTAATATTTGGTTGCAGATGTCCTGGACCGATCACTACTTGCAGTGGA
ATGTGAGCGAATACCCAGGTGTAAAGACTGTAAGATTCCCTGACGGCCAAATCTGGAAACCAGATATCCTG
CTGTACAACAGCGCAGACGAAAGGTTTGATGCAACATTTCACACCAACGTGGGAGTCAATTCTTCAGGCCA
CTGCCTGTACCTGCCCCCTGGAATCTTCAAGTCCTCATGCTATATCGACGTCCGCTGGTTTCCCTTCGACG
TCCAGCACTGCAAACTCAAATTCGGGAGCTGGAGCTACGGCGGATGGAGCCTGGATCTGCAAATGCAGGAG
GCTGACATCTCTGGTTACATCCCGAATGGGGAGTGGGACCTTGTGGGAATCCCCGGTAAAAGAAGCGAGCG
ATTTTATGAATGCTGCAAAGAGCCCTTCCCAGATGTCACCTTCACAGTGACCATGCGGAGACGCATGGGTT
ATTATCTGATCCAAATGTATATCCCAAGCTTGCTTATAGTGATTTTGTCATGGATCTCCTTCTGGATTAAT
ATGGACGCCGCTCCAGCTAGGGTCGGACTGGGCATCACCACAGTGCTGACAATGACTACTCAGAGCTCAGG
CAGCCGAGCCAGCTTGCCCAAGGTTTCTTACGTGAAGGCCATCGATATCTGGATGGCTGTCTGCCTTCTGT
TTGTCTTCAGCGCACTGCTGGAATACGCCGCTGTCAATTTTGTGTCTCGACAGCATAAAGAGCTGTTGCGG
TTCAGAAGAAAACGACGCCACCACAAAGAGGATGAGGCAGGAGAAGGACGCTTCAACTTTAGCGCCTATGG
TATGGGACCTGCTTGCCTCCAGGCTAAAGACGGAATTTCCGTGAAGGGAGCCAACAATAGCAACACAACCA
ACCCACCCCCTGCTCCATCTAAGAGCCCGGAGGAAATGCGCAAACTCTTTATTCAGAGAGCGAAAAAGATC
GACAAAATCTCCCGGATCGGATTCCCCATGGCTTTCCTGATTTTCAACATGTTTTATTGGATCATCTACAA
GATTGTGCGAAGGGAGGACGTACACAACCAGTAAGCGGCCGCAATTCCCCCGCCCCCCCCCCCCCCCCCT
CACCCTCCCCCCCCCCTAACGTTACTGGCCGAAGCCGCTTGGAATAAGGCCGGTGTGCGTTTGTCTATATG
TTATTTTCCACCATATTGCCGTCTTTTGGCAATGTGAGGGCCCGGAAACCTGGCCCTGTCTTCTTGACGAG
CATTCCTAGGGGTCTTTCCCCTCTCGCCAAAGGAATGCAAGGTCTGTTGAATGTCGTGAAGGAAGCAGTTC
```

FIG. 19B-1

```
CTCTGGAAGCTTCTTGAAGACAAACAACGTCTGTAGCGACCCTTTGCAGGCAGCGGAACCCCCACCTGGC
GACAGGTGCCTCTGCGGCCAAAAGCCACGTGTATAAGATACACCTGCAAAGGCGGCACAACCCCAGTGCCA
CGTTGTGAGTTGGATAGTTGTGGAAAGAGTCAAATGGCTCTCCTAAGCGTATTCAACAAGGGGCTGAAGGA
TGCCCAGAAGGTACCCCATTGTATGGGATCTGATCTGGGGCCTCGGTGCACATGCTTTACATGTGTTTAGT
CGAGGTTAAAAAAACGTCTAGGCCCCCCGAACCACGGGGACGTGGTTTTCCTTTGAAAAACACGATGATAA
TATGGCCACAACCATGGGAGATCCGGTGAGCAAGGGCGAGGAGCTGTTCACCGGGGTGGTGCCCATCCTGG
TCGAGCTGGACGGCGACGTAAACGGCCACAAGTTCAGCGTGTCCGGCGAGGGCGAGGGCGATGCCACCTAC
GGCAAGCTGACCCTGAAGTTCATCTGCACCACCGGCAAGCTGCCCGTGCCCTGGCCCACCCTCGTGACCAC
CCTGACCTACGGCGTGCAGTGCTTCAGCCGCTACCCCGACCACATGAAGCAGCACGACTTCTTCAAGTCCG
CCATGCCCGAAGGCTACGTCCAGGAGCGCACCATCTTCTTCAAGGACGACGGCAACTACAAGACCCGCGCC
GAGGTGAAGTTCGAGGGCGACACCCTGGTGAACCGCATCGAGCTGAAGGGCATCGACTTCAAGGAGGACGG
CAACATCCTGGGGCACAAGCTGGAGTACAACTACAACAGCCACAACGTCTATATCATGGCCGACAAGCAGA
AGAACGGCATCAAGGTGAACTTCAAGATCCGCCACAACATCGAGGACGGCAGCGTGCAGCTCGCCGACCAC
TACCAGCAGAACACCCCCATCGGCGACGGCCCCGTGCTGCTGCCCGACAACCACTACCTGAGCACCCAGTC
CAAGCTGAGCAAAGACCCCAACGAGAAGCGCGATCACATGGTCCTGCTGGAGTTCGTGACCGCCGCCGGGA
TCACTCTCGGCATGGACGAGCTGTACAAGTAAACCGGTAATCAACCTCTGGATTACAAAATTTGTGAAAGA
TTGACTGGTATTCTTAACTATGTTGCTCCTTTTACGCTATGTGGATACGCTGCTTTAATGCCTTTGTATCA
TGCTATTGCTTCCCGTATGGCTTTCATTTTCTCCTCCTTGTATAAATCCTGGTTGCTGTCTCTTTATGAGG
AGTTGTGGCCCGTTGTCAGGCAACGTGGCGTGGTGTGCACTGTGTTTGCTGACGCAACCCCCACTGGTTGG
GGCATTGCCACCACCTGTCAGCTCCTTTCCGGGACTTTCGCTTTCCCCCTCCCTATTGCCACGGCGGAACT
CATCGCCGCCTGCCTTGCCCGCTGCTGGACAGGGGCTCGGCTGTTGGGCACTGACAATTCCGTGGTGTTGT
CGGGGAAATCATCGTCCTTTCCTTGGCTGCTCGCCTGTGTTGCCACCTGGATTCTGCGCGGGACGTCCTTC
TGCTACGTCCCTTCGGCCCTCAATCCAGCGGACCTTCCTTCCCGCGGCCTGCTGCCGGCTCTGCGGCCTCT
TCCGCGTCTTCGCCTTCGCCCTCAGACGAGTCGGATCTCCCTTTGGGCCGCCTCCCCGCCGCTTCGAGCAG
ACATGATAAGATACATTGATGAGTTTGGACAAACCACAACTAGAATGCAGTGAAAAAAATGCTTTATTTGT
GAAATTTGTGATGCTATTGCTTTATTTGTAACCATTATAAGCTGCAATAAACAAGTTAACAACAACAATTG
CATTCATTTTATGTTTCAGGTTCAGGGGGAGATGTGGGAGGTTTTTTAAAGCAAGTAAAACCTCTACAAAT
GTGGTAAAATCGATAAGGATCTTCCTAGAGCATGGCTACGTAGATAAGTAGCATGGCGGGTTAATCATTAA
CTACAAGGAACCCCTAGTGATGGAGTTGGCCACTCCCTCTCTGCGCGCTCGCTCGCTCACTGAGGCCGGGC
GACCAAAGGTCGCCCGACGCCCGGGCTTTGCCCGGGCGGCCTCAGTGAGCGAGCGAGCGCGCAGCTGGCGT
AATAGCGAAGAGGCCCGCACCGATCGCCCTTCCCAACAGTTGCGCAGCCTGAATGGCGAATGGGACGCGCC
CTGTAGCGGCGCATTAAGCGCGGCGGGTGTGGTGGTTACGCGCAGCGTGACCGCTACACTTGCCAGCGCCC
TAGCGCCCGCTCCTTTCGCTTTCTTCCCTTCCTTTCTCGCCACGTTCGCCGGCTTTCCCCGTCAAGCTCTA
AATCGGGGGCTCCCTTTAGGGTTCCGATTTAGTGCTTTACGGCACCTCGACCCCAAAAAACTTGATTAGGG
```

FIG. 19B-2

```
TGATGGTTCACGTAGTGGGCCATCGCCCTGATAGACGGTTTTTCGCCCTTTGACGTTGGAGTCCACGTTCT
TTAATAGTGGACTCTTGTTCCAAACTGGAACAACACTCAACCCTATCTCGGTCTATTCTTTTGATTTATAA
GGGATTTTGCCGATTTCGGCCTATTGGTTAAAAAATGAGCTGATTTAACAAAAATTTAACGCGAATTTTAA
CAAAATATTAACGCTTACAATTTAGGTGGCACTTTTCGGGGAAATGTGCGCGGAACCCCTATTTGTTTATT
TTTCTAAATACATTCAAATATGTATCCGCTCATGAGACAATAACCCTGATAAATGCTTAATAATATTGAA
AAAGGAAGAGTATGAGTATTCAACATTTCCGTGTCGCCCTTATTCCCTTTTTTGCGGCATTTTGCCTTCCT
GTTTTTGCTCACCCAGAAACGCTGGTGAAAGTAAAAGATGCTGAAGATCAGTTGGGTGCACGAGTGGGTTA
CATCGAACTGGATCTCAACAGCGGTAAGATCCTTGAGAGTTTTCGCCCCGAAGAACGTTTTCCAATGATGA
GCACTTTTAAAGTTCTGCTATGTGGCGCGGTATTATCCCGTATTGACGCCGGGCAAGAGCAACTCGGTCGC
CGCATACACTATTCTCAGAATGACTTGGTTGAGTACTCACCAGTCACAGAAAAGCATCTTACGGATGGCAT
GACAGTAAGAGAATTATGCAGTGCTGCCATAACCATGAGTGATAACACTGCGGCCAACTTACTTCTGACAA
CGATCGGAGGACCGAAGGAGCTAACCGCTTTTTTGCACAACATGGGGGATCATGTAACTCGCCTTGATCGT
TGGGAACCGGAGCTGAATGAAGCCATACCAAACGACGAGCGTGACACCACGATGCCTGTAGCAATGGCAAC
AACGTTGCGCAAACTATTAACTGGCGAACTACTTACTCTAGCTTCCCGGCAACAATTAATAGACTGGATGG
AGGCGGATAAAGTTGCAGGACCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGATGGTAAGCCCTCCCGTATCGT
AGTTATCTACACGACGGGGAGTCAGGCAACTATGGATGAACGAAATAGACAGATCGCTGAGATAGGTGCCT
CACTGATTAAGCATTGGTAACTGTCAGACCAAGTTTACTCATATATACTTTAGATTGATTTAAAACTTCAT
TTTTAATTTAAAAGGATCTAGGTGAAGATCCTTTTTGATAATCTCATGACCAAAATCCCTTAACGTGAGTT
TTCGTTCCACTGAGCGTCAGACCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGTTTGCCGGATCAAGAGCTACCA
ACTCTTTTTCCGAAGGTAACTGGCTTCAGCAGAGCGCAGATACCAAATACTGTTCTTCTAGTGTAGCCGTA
GTTAGGCCACCACTTCAAGAACTCTGTAGCACCGCCTACATACCTCGCTCTGCTAATCCTGTTACCAGTGG
CTGCTGCCAGTGGCGATAAGTCGTGTCTTACCGGGTTGGACTCAAGACGATAGTTACCGGATAAGGCGCAG
CGGTCGGGCTGAACGGGGGGTTCGTGCACACAGCCCAGCTTGGAGCGAACGACCTACACCGAACTGAGATA
CCTACAGCGTGAGCTATGAGAAAGCGCCACGCTTCCCGAAGGGAGAAAGGCGGACAGGTATCCGGTAAGCG
GCAGGGTCGGAACAGGAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGCGGAGCCTATGGAAAAA
CGCCAGCAACGCGGCCTTTTTACGGTTCCTGGCCTTTTGCTGGCCTTTTGCTCACATGTTCTTTCCTGCGT
TATCCCCTGATTCTGTGGATAACCGTATTACCGCCTTTGAGTGAGCTGATACCGCTCGCCGCAGCCGAACG
ACCGAGCGCAGCGAGTCAGTGAGCGAGGAAGCGGAAG
```

FIG. 19B-3

AAV-CamkII::PSAM4-GlyR-IRES-EGFP-WPRE

AAV-CamkII::PSAM4-GlyR-IRES-EGFP-WPRE

```
CCTGCAGGCAGCTGCGCGCTCGCTCGCTCACTGAGGCCGCCCGGGCAAAGCCCGGGCGTCGGGCGACCTTT
GGTCGCCCGGCCTCAGTGAGCGAGCGAGCGCGCAGAGAGGGAGTGGCCAACTCCATCACTAGGGGTTCCTG
CGGCCGCACGCGTTTAACATTATGGCCTTAGGTCACTTCATCTCCATGGGGTTCTTCTTCTGATTTTCTAG
AAAATGAGATGGGGGTGCAGAGAGCTTCCTCAGTGACCTGCCCAGGGTCACATCAGAAATGTCAGAGCTAG
AACTTGAACTCAGATTACTAATCTTAAATTCCATGCCTTGGGGCATGCAAGTACGATATACAGAAGGAGT
GAACTCATTAGGGCAGATGACCAATGAGTTTAGGAAAGAAGAGTCCAGGGCAGGGTACATCTACACCACCC
GCCCAGCCCTGGGTGAGTCCAGCCACGTTCACCTCATTATAGTTGCCTCTCTCCAGTCCTACCTTGACGGG
AAGCACAAGCAGAAACTGGGACAGGAGCCCCAGGAGACCAAATCTTCATGGTCCCTCTGGGAGGATGGGTG
GGGAGAGCTGTGGCAGAGGCCTCAGGAGGGGCCCTGCTGCTCAGTGGTGACAGATAGGGGTGAGAAAGCAG
ACAGAGTCATTCCGTCAGCATTCTGGGTCTGTTTGGTACTTCTTCTCACGCTAAGGTGGCGGTGTGATATG
CACAATGGCTAAAAAGCAGGGAGAGCTGGAAAGAAACAAGGACAGAGACAGAGGCCAAGTCAACCAGACCA
ATTCCCAGAGGAAGCAAAGAAACCATTACAGAGACTACAAGGGGGAAGGGAAGGAGAGATGAATTAGCTTC
CCCTGTAAACCTTAGAACCCAGCTGTTGCCAGGGCAACGGGGCAATACCTGTCTCTTCAGAGGAGATGAAG
TTGCCAGGGTAACTACATCCTGTCTTTCTCAAGGACCATCCCAGAATGTGGCACCCACTAGCCGTTACCAT
AGCAACTGCCTCTTTGCCCCACTTAATCCCATCCCGTCTGTTAAAAGGGCCCTATAGTTGGAGGTGGGGGA
GGTAGGAAGAGCGATGATCACTTGTGGACTAAGTTTGTTCGCATCCCCTTCTCCAACCCCCTCAGTACATC
ACCCTGGGGGAACAGGGTCCACTTGCTCCTGGGCCCACACAGTCCTGCAGTATTGTGTATATAAGGCCAGG
GCAAAGAGGAGCAGGTTTTAAAGTGAAAGGCAGGCAGGTGTTGGGGAGGCAGTTACCGGGGCAACGGGAAC
AGGGCGTTTCGGAGGTGGTTGCCATGGGGACCTGGATGCTGACGAAGGCTCGCGAGGCTGTGAGCAGCCAC
AGTGCCCTGCTCAGAAGCCCCAAGCTCGTCAGTCAAGCCGGTTCTCCGTTTGCACTCAGGAGCACGGGCAG
GCGAGTGGCCCCTAGTTCTGGGGGCAGCTCTAGAGCGGTACCGGATCCAGGTAAGTATCAAGGTTACAAGA
CAGGTTTAAGGAGACCAATAGAAACTGGGCTTGTCGAGACAGAGAAGACTCTTGCGTTTCTGATAGGCACC
TATTGGTCTTACTGACATCCACTTTGCCTTTCTCTCCACAGGTGATGAATTCGCTAGCGCCACCATGCGCT
GTTCTCCAGGCGGCGTGTGGCTCGCCCTGGCTGCTTCCCTTCTGCACGTTAGCCTGCAGGGTGAGTTCCAG
CGCAAACTGTATAAGGAGCTTGTTAAGAATTATAACCCCCTGGAGCGGCCGGTCGCAAATGATTCCCAGCC
ACTGACAGTGTACTTCAGCCTCTCCTTGCTGCAGATCATGGACGTGGATGAAAAGAACCAGGTGCTGACCA
CTAATATTTGGTTGCAGATGTCCTGGACCGATCACTACTTGCAGTGGAATGTGAGCGAATACCCAGGTGTA
AAGACTGTAAGATTCCCTGACGGCCAAATCTGGAAACCAGATATCCTGCTGTACAACAGCGCAGACGAAAG
GTTTGATGCAACATTTCACACCAACGTGGGAGTCAATTCTTCAGGCCACTGCCTGTACCTGCCCCCTGGAA
TCTTCAAGTCCTCATGCTATATCGACGTCCGCTGGTTTCCCTTCGACGTCCAGCACTGCAAACTCAAATTC
GGGAGCTGGAGCTACGGCGGATGGAGCCTGGATCTGCAAATGCAGGAGGCTGACATCTCTGGTTACATCCC
GAATGGGGAGTGGGACCTTGTGGGAATCCCCGGTAAAAGAAGCGAGCGATTTTATGAATGCTGCAAAGAGC
CCTTCCCAGATGTCACCTTCACAGTGACCATGCGGAGACGCATGGGTTATTATCTGATCCAAATGTATATC
CCAAGCTTGCTTATAGTGATTTTGTCATGGATCTCCTTCTGGATTAATATGGACGCCGCTCCAGCTAGGGT
CGGACTGGGCATCACCACAGTGCTGACAATGACTACTCAGAGCTCAGGCAGCCGAGCCAGCTTGCCCAAGG
TTTCTTACGTGAAGGCCATCGATATCTGGATGGCTGTCTGCCTTCTGTTTGTCTTCAGCGCACTGCTGGAA
TACGCCGCTGTCAATTTTGTGTCTCGACAGCATAAAGAGCTGTTGCGGTTCAGAAGAAAACGACGCCACCA
CAAAGAGGATGAGGCAGGAGAAGGACGCTTCAACTTTAGCGCCTATGGTATGGGACCTGCTTGCCTCCAGG
CTAAAGACGGAATTTCCGTGAAGGGAGCCAACAATAGCAACACAACCAACCCACCCCCTGCTCCATCTAAG
AGCCCGGAGGAAATGCGCAAACTCTTTATTCAGAGAGCGAAAAAGATCGACAAAATCTCCCGGATCGGATT
CCCCATGGCTTTCCTGATTTTCAACATGTTTTATTGGATCATCTACAAGATTGTGCGAAGGGAGGACGTAC
ACAACCAGTAAGCGGCCGCAATTCCCCCGCCCCCCCCCCCCCCCCTCACCCTCCCCCCCCCCCTAACGTT
ACTGGCCGAAGCCGCTTGGAATAAGGCCGGTGTGCGTTTGTCTATATGTTATTTTCCACCATATTGCCGTC
TTTTGGCAATGTGAGGGCCCGGAAACCTGGCCCTGTCTTCTTGACGAGCATTCCTAGGGGTCTTTCCCCTC
```

FIG. 20B-1

```
TCGCCAAAGGAATGCAAGGTCTGTTGAATGTCGTGAAGGAAGCAGTTCCTCTGGAAGCTTCTTGAAGACAA
ACAACGTCTGTAGCGACCCTTTGCAGGCAGCGGAACCCCCCACCTGGCGACAGGTGCCTCTGCGGCCAAAA
GCCACGTGTATAAGATACACCTGCAAAGGCGGCACAACCCCAGTGCCACGTTGTGAGTTGGATAGTTGTGG
AAAGAGTCAAATGGCTCTCCTAAGCGTATTCAACAAGGGGCTGAAGGATGCCCAGAAGGTACCCCATTGTA
TGGGATCTGATCTGGGGCCTCGGTGCACATGCTTTACATGTGTTTAGTCGAGGTTAAAAAAACGTCTAGGC
CCCCCGAACCACGGGGACGTGGTTTTCCTTTGAAAAACACGATGATAATATGGCCACAACCATGGGAGATC
CGGTGAGCAAGGGCGAGGAGCTGTTCACCGGGGTGGTGCCCATCCTGGTCGAGCTGGACGGCGACGTAAAC
GGCCACAAGTTCAGCGTGTCCGGCGAGGGCGAGGGCGATGCCACCTACGGCAAGCTGACCCTGAAGTTCAT
CTGCACCACCGGCAAGCTGCCCGTGCCCTGGCCCACCCTCGTGACCACCCTGACCTACGGCGTGCAGTGCT
TCAGCCGCTACCCCGACCACATGAAGCAGCACGACTTCTTCAAGTCCGCCATGCCCGAAGGCTACGTCCAG
GAGCGCACCATCTTCTTCAAGGACGACGGCAACTACAAGACCCGCGCCGAGGTGAAGTTCGAGGGCGACAC
CCTGGTGAACCGCATCGAGCTGAAGGGCATCGACTTCAAGGAGGACGGCAACATCCTGGGGCACAAGCTGG
AGTACAACTACAACAGCCACAACGTCTATATCATGGCCGACAAGCAGAAGAACGGCATCAAGGTGAACTTC
AAGATCCGCCACAACATCGAGGACGGCAGCGTGCAGCTCGCCGACCACTACCAGCAGAACACCCCCATCGG
CGACGGCCCCGTGCTGCTGCCCGACAACCACTACCTGAGCACCCAGTCCAAGCTGAGCAAAGACCCCAACG
AGAAGCGCGATCACATGGTCCTGCTGGAGTTCGTGACCGCCGCCGGGATCACTCTCGGCATGGACGAGCTG
TACAAGTAAACCGGTGTCGACAAGCTTATCGATAATCAACCTCTGGATTACAAAATTTGTGAAAGATTGAC
TGGTATTCTTAACTATGTTGCTCCTTTTACGCTATGTGGATACGCTGCTTTAATGCCTTTGTATCATGCTA
TTGCTTCCCGTATGGCTTTCATTTTCTCCTCCTTGTATAAATCCTGGTTGCTGTCTCTTTATGAGGAGTTG
TGGCCCGTTGTCAGGCAACGTGGCGTGGTGTGCACTGTGTTTGCTGACGCAACCCCCACTGGTTGGGGCAT
TGCCACCACCTGTCAGCTCCTTTCCGGAACTTTCGCTTTCCCCCTCCCTATTGCCACGGCGGAACTCATCG
CCGCCTGCCTTGCCCGCTGCTGGACAGGGGCTCGGCTGTTGGGCACTGACAATTCCGTGGTGTTGTCGGGG
AAATCATCGTCCTTTCCTTGGCTGCTCGCCTGTGTTGCCACCTGGATTCTGCGCGGGACGTCCTTCTGCTA
CGTCCCTTCGGCCCTCAATCCAGCGGACCTTCCTTCCCGCGGCCTGCTGCCGGCTCTGCGGCCTCTTCCGC
GTCTTCGCCTTCGCCCTCAGACGAGTCGGATCTCCCTTTGGGCCGCCTCCCCGCATCGATACCGAGCGCTG
CTCGAGAGATCTACGGGTGGCATCCCTGTGACCCCTCCCCAGTGCCTCTCCTGGCCCTGGAAGTTGCCACT
CCAGTGCCCACCAGCCTTGTCCTAATAAAATTAAGTTGCATCATTTTGTCTGACTAGGTGTCCTTCTATAA
TATTATGGGGTGGAGGGGGGTGGTATGGAGCAAGGGGCAAGTTGGGAAGACAACCTGTAGGGCCTGCGGGG
TCTATTGGGAACCAAGCTGGAGTGCAGTGGCACAATCTTGGCTCACTGCAATCTCCGCCTCCTGGGTTCAA
GCGATTCTCCTGCCTCAGCCTCCCGAGTTGTTGGGATTCCAGGCATGCATGACCAGGCTCAGCTAATTTTT
GTTTTTTTGGTAGAGACGGGGTTTCACCATATTGGCCAGGCTGGTCTCCAACTCCTAATCTCAGGTGATCT
ACCCACCTTGGCCTCCCAAATTGCTGGGATTACAGGCGTGAACCACTGCTCCCTTCCCTGTCCTTCTGATT
TTGTAGGTAACCACGTGCGGACCGAGCGGCCGCAGGAACCCCTAGTGATGGAGTTGGCCACTCCCTCTCTG
CGCGCTCGCTCGCTCACTGAGGCCGGGCGACCAAAGGTCGCCCGACGCCCGGGCTTTGCCCGGGCGGCCTC
AGTGAGCGAGCGAGCGCGCAGCTGCCTGCAGGGGCGCCTGATGCGGTATTTTCTCCTTACGCATCTGTGCG
GTATTTCACACCGCATACGTCAAAGCAACCATAGTACGCGCCCTGTAGCGGCGCATTAAGCGCGGCGGGTG
TGGTGGTTACGCGCAGCGTGACCGCTACACTTGCCAGCGCCCTAGCGCCCGCTCCTTTCGCTTTCTTCCCT
TCCTTTCTCGCCACGTTCGCCGGCTTTCCCCGTCAAGCTCTAAATCGGGGCTCCCTTTAGGGTTCCGATT
TAGTGCTTTACGGCACCTCGACCCCAAAAAACTTGATTTGGGTGATGGTTCACGTAGTGGGCCATCGCCCT
GATAGACGGTTTTTCGCCCTTTGACGTTGGAGTCCACGTTCTTTAATAGTGGACTCTTGTTCCAAACTGGA
ACAACACTCAACCCTATCTCGGGCTATTCTTTTGATTTATAAGGGATTTTGCCGATTTCGGCCTATTGGTT
AAAAAATGAGCTGATTTAACAAAAATTTAACGCGAATTTTAACAAAATATTAACGTTTACAATTTTATGGT
GCACTCTCAGTACAATCTGCTCTGATGCCGCATAGTTAAGCCAGCCCCGACACCCGCCAACACCCGCTGAC
```

FIG. 20B-2

```
GCGCCCTGACGGGCTTGTCTGCTCCCGGCATCCGCTTACAGACAAGCTGTGACCGTCTCCGGGAGCTGCAT
GTGTCAGAGGTTTTCACCGTCATCACCGAAACGCGCGAGACGAAAGGGCCTCGTGATACGCCTATTTTTAT
AGGTTAATGTCATGATAATAATGGTTTCTTAGACGTCAGGTGGCACTTTTCGGGGAAATGTGCGCGGAACC
CCTATTTGTTTATTTTTCTAAATACATTCAAATATGTATCCGCTCATGAGACAATAACCCTGATAAATGCT
TCAATAATATTGAAAAAGGAAGAGTATGAGTATTCAACATTTCCGTGTCGCCCTTATTCCCTTTTTTGCGG
CATTTTGCCTTCCTGTTTTTGCTCACCCAGAAACGCTGGTGAAAGTAAAAGATGCTGAAGATCAGTTGGGT
GCACGAGTGGGTTACATCGAACTGGATCTCAACAGCGGTAAGATCCTTGAGAGTTTTCGCCCCGAAGAACG
TTTTCCAATGATGAGCACTTTTAAAGTTCTGCTATGTGGCGCGGTATTATCCCGTATTGACGCCGGGCAAG
AGCAACTCGGTCGCCGCATACACTATTCTCAGAATGACTTGGTTGAGTACTCACCAGTCACAGAAAAGCAT
CTTACGGATGGCATGACAGTAAGAGAATTATGCAGTGCTGCCATAACCATGAGTGATAACACTGCGGCCAA
CTTACTTCTGACAACGATCGGAGGACCGAAGGAGCTAACCGCTTTTTTGCACAACATGGGGGATCATGTAA
CTCGCCTTGATCGTTGGGAACCGGAGCTGAATGAAGCCATACCAAACGACGAGCGTGACACCACGATGCCT
GTAGCAATGGCAACAACGTTGCGCAAACTATTAACTGGCGAACTACTTACTCTAGCTTCCCGGCAACAATT
AATAGACTGGATGGAGGCGGATAAAGTTGCAGGACCACTTCTGCGCTCGGCCCTTCCGGCTGGCTGGTTTA
TTGCTGATAAATCTGGAGCCGGTGAGCGTGGGTCTCGCGGTATCATTGCAGCACTGGGGCCAGATGGTAAG
CCCTCCCGTATCGTAGTTATCTACACGACGGGGAGTCAGGCAACTATGGATGAACGAAATAGACAGATCGC
TGAGATAGGTGCCTCACTGATTAAGCATTGGTAACTGTCAGACCAAGTTTACTCATATATACTTTAGATTG
ATTTAAAACTTCATTTTTAATTTAAAAGGATCTAGGTGAAGATCCTTTTTGATAATCTCATGACCAAAATC
CCTTAACGTGAGTTTTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGTGGTTTGTTTGCCGG
ATCAAGAGCTACCAACTCTTTTTCCGAAGGTAACTGGCTTCAGCAGAGCGCAGATACCAAATACTGTCCTT
CTAGTGTAGCCGTAGTTAGGCCACCACTTCAAGAACTCTGTAGCACCGCCTACATACCTCGCTCTGCTAAT
CCTGTTACCAGTGGCTGCTGCCAGTGGCGATAAGTCGTGTCTTACCGGGTTGGACTCAAGACGATAGTTAC
CGGATAAGGCGCAGCGGTCGGGCTGAACGGGGGGTTCGTGCACACAGCCCAGCTTGGAGCGAACGACCTAC
ACCGAACTGAGATACCTACAGCGTGAGCTATGAGAAAGCGCCACGCTTCCCGAAGGGAGAAAGGCGGACAG
GTATCCGGTAAGCGGCAGGGTCGGAACAGGAGAGCGCACGAGGGAGCTTCCAGGGGGAAACGCCTGGTATC
TTTATAGTCCTGTCGGGTTTCGCCACCTCTGACTTGAGCGTCGATTTTTGTGATGCTCGTCAGGGGGCGG
AGCCTATGGAAAAACGCCAGCAACGCGGCCTTTTTACGGTTCCTGGCCTTTTGCTGGCCTTTTGCTCACAT
GT
```

FIG. 20B-3

MODIFIED LIGAND-GATED ION CHANNELS AND METHODS OF USE

CROSS-REFERENCE TO RELATED APPLICATIONS

This application is a continuation of U.S. application Ser. No. 16/186,122, filed Nov. 9, 2018, now allowed, which is a claims the benefit of U.S. Patent Application Ser. No. 62/584,428, filed on Nov. 10, 2017, and U.S. Patent Application Ser. No. 62/729,716, filed on Sep. 11, 2018. The disclosures of the prior applications are considered part of (and are incorporated by reference in) the disclosure of this application.

BACKGROUND

1. Technical Field

This document relates to materials and methods for modulating ligand gated ion channel (LGIC) activity. For example, this document provides modified LGICs including at least one LGIC subunit having a modified ligand binding domain (LBD) and/or a modified ion pore domain (IPD). Also provided are exogenous LGIC ligands that can bind to and activate the modified LGIC. In some cases, a modified LGIC and an exogenous ligand can be used to treat a mammal having a channelopathy (e.g., a neural channelopathy or a muscle channelopathy). In some cases, a modified LGIC and an exogenous LGIC ligand can be used to modulate (e.g., activate or inhibit) ion transport across the membrane of a cell of a mammal. In some cases, a modified LGIC and an exogenous LGIC ligand can be used to modulate (e.g., increase or decrease) the excitability of a cell in a mammal.

2. Background Information

Ion channels mediate ionic flux in cells, which profoundly affects their biological function. A prominent instance of this is in neurons, where ion channels control electrical signaling within and/or between neurons to influence physiology, sensation, behavior, mood, and cognition.

Different LGICs have distinct ligand binding properties as well as specific ion conductance properties (Hille 2001 Ion Channels of Excitable Membranes. pp. 814. Sunderland, MA: Sinauer Associates; Kandel et al 2000 Principles of Neural Science. USA: McGraw-Hill Co. 1414 pp). For example, nicotinic acetylcholine receptors (nAChRs) bind the endogenous ligand acetylcholine (ACh), which activates conductances for cations and typically depolarizes cells, thereby increasing cellular excitability. In contrast, the glycine receptor (GlyR) binds the endogenous ligand glycine, which activates chloride anion conductance and typically reduces the excitability of cells by hyperpolarization and/or by an electrical shunt of the cellular membrane resistance.

SUMMARY

Levels of endogenous LGIC ligands (e.g., agonists) such as ACh are not readily controlled.

This document provides materials and methods for modulating LGIC activity (e.g., increasing the sensitivity of LGICs to exogenous ligands and/or reducing sensitivity to endogenous ligands such as ACh. For example, this document provides modified LGICs including at least one modified LGIC subunit having a LBD and an IPD, and having at least one modified amino acid (e.g., an amino acid substitution). Also provided are exogenous LGIC ligands that can bind to and modulate (e.g., activate) the modified LGIC. In some cases, a modified LGIC and an exogenous ligand can be used to treat a mammal having a channelopathy (e.g., a neural channelopathy or a muscle channelopathy). In some cases, a modified LGIC and an exogenous LGIC ligand can be used to modulate (e.g., activate or inhibit) ion transport across the membrane of a cell of a mammal. In some cases, a modified LGIC and an exogenous LGIC ligand can be used to modulate (e.g., increase or decrease) the excitability of a cell in a mammal.

Having the ability to control LGIC activity provides a unique and unrealized opportunity to control ion transport in cells. For example, modified LGICs having increased sensitivity for one or more exogenous LGIC ligands can be used to provide temporal and spatial control of ion transport and/or cellular excitability based on delivery of the exogenous LGIC ligand. For example, modified LGICs with reduced sensitivity for endogenous LGIC ligands prevent unwanted activation of modified LGICs and allow for selective control over the modified LGIC by exogenous ligands. Further, exogenous LGIC ligands having increased potency for a modified LGIC improve selectivity of targeting of the modified LGIC over endogenous ion channels. Thus, the modified LCIGs and exogenous LGIC ligands provided herein are useful to achieve a therapeutic effect while reducing side effects from the small molecules on unintended targets.

As described herein, one or more mutations in a modified LGIC can enhance potency for exogenous LGIC ligands. Mutation of the α7 LBD of α7-GlyR at residue L131 (e.g., substituting Leu with Gly or Ala) increased potency for varenicline (16-fold) and tropisetron (3.6-fold) while reducing ACh potency (−6.4-fold) relative to α7-GlyR. Mutation of α7 LBD of α7-GlyR at residue G175 (e.g., G175K) or P216 (e.g., P216I) enhanced potency for ACh, nicotine, tropisetron, varenicline, as well as other quinuclidine and tropane agonists. Combining the mutation at residue G175K with mutations that reduce potency of the endogenous agonist ACh (e.g. Y115F) produced α7-GlyR Y115F G175K with increased potency for tropisetron (5.5-fold) and reduced potency from ACh (−8-fold). In addition, combining mutations in the α7 LBD at residues 77 (e.g., substituting Trp with Phe or Tyr) and/or 79 (e.g., substituting Gln with Gly, Ala, or Ser) and/or 131 (e.g., substituting Leu with Gly or Ala) and/or 141 (e.g., substituting Leu with Phe or Pro) in these chimeric channels with potency enhancing mutations at residues G175 (e.g., G175K) or P216 (e.g., P216I) increase potency for distinct ligands and/or reduce ACh potency. For example, a chimeric α7-GlyR LGIC with a α7 nAChR LBD (α7 LBD) having a mutation at residue 79 (e.g., substituting Gln with Gly), a mutation at residue 115 (e.g., substituting Tyr with Phe), and a mutation at residue 175 (e.g., substituting Gly with Lys) has greater than 100-fold increased sensitivity to an exogenous tropane LGIC ligand compound 723 (a tropane), and reduced ACh sensitivity (−15-fold) relative to the unmodified chimeric α7-GlyR LGIC. Furthermore, a modified LGIC including at least one chimeric LGIC subunit having an α7 nAChR LBD (α7 LBD) having a mutation at residue 79 (e.g., substituting Gln with Ala, Gly, or Ser) and a GlyR IPD having a mutation at residue 298 (e.g., substituting Ala with Gly) has nearly 20-fold increased sensitivity for an exogenous LGIC ligand, such as a quinuclidine or a tropane. Additional mutations at residue 27 (e.g., substituting Arg with Asp) and 41 (e.g., substituting Glu with Arg) of the α7 LBD reduced the association of the modified chimeric LGIC with an unmodified ion channels. Additional mutations at residue 115 (e.g., substituting Tyr with Phe), 139 (e.g., substituting Gln with Gly or Leu), 210 (e.g., substituting Tyr with Phe) 217 (e.g., substituting Tyr with Phe), and/or 219 (e.g., substituting Asp with Ala) of the α7 LBD reduced sensitivity of the chimeric LGIC to the endogenous ligand ACh. These chimeric LGICs allow for highly selective control over cellular function in cells of a mammal while minimizing cross-reactivity with endogenous signaling systems in the mammal.

In general, one aspect of this document features a modified LGIC having at least one modified LGIC subunit which includes a LBD having an amino acid modification, and an IPD, where an exogenous LGIC ligand activates the modified LGIC. The modified LGIC can be a chimeric LGIC having a LBD from a first LGIC and an IPD from a second LGIC. The LBD can be an alpha7 nicotinic acetylcholine receptor (α7-nAChR) LBD. The modified LGIC, wherein the at least one modified amino acid in the α7-nAChR LBD comprises an amino acid substitution at an amino acid residue selected from the group consisting of residues 77, 79, 131, 139, 141, 175, and 216 of the α7-nAChR LBD. The amino acid substitution can be at residue 79 of the α7 LBD, and the amino acid substitution can be Q79A, Q79G, or Q79S. For example, the amino acid substitution at residue 79 of the α7 LBD can be Q79G. The IPD can be a serotonin 3 receptor (5HT3) IPD, a glycine receptor (GlyR) IPD, a gamma-aminobutyric acid (GABA) receptor IPD, or an α7-nAChR IPD. The IPD can be a GlyR IPD, and the GlyR IPD can include an amino acid substitution at residue 298 (e.g., a A298G substitution) of the chimeric LGIC. The IPD can be a GABA IPD, and the GABA IPD can include an amino acid substitution at residue 298 (e.g., a W298A substitution) of the modified LGIC. The modified LGIC can be a chimeric LGIC including an α7 LBD having a Q79G amino acid substitution, and a GlyR IPD having a A298G amino acid substitution. The exogenous LGIC ligand can be a synthetic exogenous LGIC ligand selected from the group consisting of a quinuclidine, a tropane, a 9-azabicyclo[3.3.1]nonane, a 6,7,8,9-tetrahydro-6,10-methano-6H-pyrazino(2,3-h)benzazepine, and a 1,4-diazabicyclo[3.2.2]nonane. When the synthetic exogenous LGIC ligand is a tropane, the tropane can be tropisetron, pseudo-tropisetron, nortropisetron, compound 723, compound 725, compound 737, or compound 745. When the synthetic exogenous LGIC ligand is a quinuclidine, the quinuclidine can be PNU-282987, PHA-543613, compound 0456, compound 0434, compound 0436, compound 0354, compound 0353, compound 0295, compound 0296, compound 0536, compound 0676, or compound 702. When the synthetic exogenous LGIC ligand is a 6,7,8,9-tetrahydro-6,10-methano-6H-pyrazino(2,3-h)benzazepine, the ligand can be compound 765 or compound 770. When the synthetic exogenous LGIC ligand is a 1,4-diazabicyclo[3.2.2]nonane, the ligand can be compound 773 or compound 774. In some cases, the LBD can be an α7 LBD, and the α7 LBD can also include at least one modified amino acid that confers selective binding to another α7 LBD having the at least one modified amino acid over binding to an unmodified LGIC. The unmodified LGIC can be an endogenous LGIC (e.g., an endogenous α7-nAChR). The at least one modified amino acid in the α7 LBD that confers reduced binding to the unmodified LGIC can include an amino acid substitution at residue 27 (e.g., a R27D substitution) and/or residue 41 (e.g., an E41R substitution). In some cases, the IPD can be a 5HT3 IPD, and the 5HT3 IPD can include at least one modified amino acid that confers increased ion conductance to the modified LGIC. The at least one modified amino acid in the 5HT3 IPD that confers increased ion conductance to the modified LGIC can include an amino acid substitution at an amino acid residue at residue 425 (e.g., a R425Q substitution), 429 (e.g., a R429D substitution), and/or 433 (e.g., a R433A substitution).

In another aspect, this document features a modified LGIC having at least one modified LGIC subunit including a LBD having at least one modified amino acid, and an IPD, where the at least one modified amino acid in the LBD reduces binding with an endogenous LGIC ligand. The modified LGIC can be a chimeric LGIC having a LBD from a first LGIC and an IPD from a second LGIC. The endogenous LGIC ligand can be ACh. The modified LGIC can have an EC50 of greater than 20 µM for Ach. The at least one modified amino acid can include an amino acid substitution at residue 115, 139, 210, 217, and/or 219. When the at least one modified amino acid includes an amino acid substitution at residue 115, the amino acid substitution can be a Y115F substitution. When the at least one modified amino acid includes an amino acid substitution at residue 139, the amino acid substitution can be a Q139G or a Q139L substitution. When the at least one modified amino acid includes an amino acid substitution at residue 210, the amino acid substitution can be a Y210F substitution. When the at least one modified amino acid includes an amino acid substitution at residue 217, the amino acid substitution can be a Y217F substitution. When the at least one modified amino acid includes an amino acid substitution at residue 219, the amino acid substitution can be a D219A substitution. In some cases, a modified LGIC can include a modified α7-nAChR LBD having a L131G amino acid substitution, a Q139L amino acid substitution, and a Y217F amino acid substitution. A modified LGIC (e.g., a modified LGIC including a modified α7-nAChR LBD having a L131G amino acid substitution, a Q139L amino acid substitution, and a Y217F amino acid substitution) also can include an endoplasmic reticulum export sequence. The endoplasmic reticulum export sequence can include the amino acid sequence FCYENEV (SEQ ID NO:16). For example, a modified LGIC including a modified α7-nAChR LBD having a L131G amino acid substitution, a Q139L amino acid substitution, and a Y217F amino acid substitution, and also including an endoplasmic reticulum export sequence can include the amino acid sequence set forth in SEQ ID NO:13. A modified LGIC (e.g., a modified LGIC including a modified α7-nAChR LBD having a L131G amino acid substitution, a Q139L amino acid substitution, and a Y217F amino acid substitution) also can include a signal sequence (e.g., a CHRNB4 signal sequence). The CHRNB4 signal sequence can include the amino acid sequence MRRAPSLVLFFLVALCGRGNC (SEQ ID NO:17). For example, a modified LGIC including a modified α7-nAChR LBD having a L131G amino acid substitution, a Q139L amino acid substitution, and a Y217F amino acid substitution, and also including a CHRNB4 signal sequence can include the amino acid sequence set forth in SEQ ID NO:14. A modified LGIC (e.g., a modified LGIC including a modified α7-nAChR LBD having a L131G amino acid substitution, a Q139L amino acid substitution, and a Y217F amino acid substitution) also can include a somatic targeting sequence (e.g., a KCNB1 somatic targeting sequence). The KCNB1 somatic targeting sequence can include the amino acid sequence (SEQ ID NO: 18)
QSQPILNTKEMAPQSKPPEELEMSSMPSPVAPLPARTEGVIDMRSMSSI

DSFISCATDFPEATRF.

For example, a modified LGIC including a modified α7-nAChR LBD having a L131G amino acid substitution, a Q139L amino acid substitution, and a Y217F amino acid substitution, and also including a KCNB1 somatic targeting sequence can include the amino acid sequence set forth in SEQ ID NO:15.

In another aspect, this document features a ligand having increased potency for a modified ligand gated ion channel (LGIC), wherein the ligand comprises Formula I:

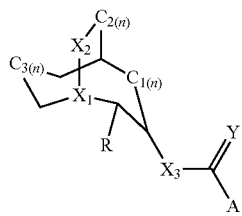

where each of X1, X2, and X3 can independently be CH, CH2, O, NH, or NMe; where each n can independently be 0 or 1; where Y=O or S; where A=an aromatic substituent; and where R=H or pyridinylmethylene. The aromatic substituent can be 1H-indole, 4-(trifluoromethyl) benzene, 2,5-dimethoxy benzene, 4-chloroaniline, aniline, 5-(trifluoromethyl) pyridin-2-yl, 6-(trifluoromethyl) nicotinic, or 4-chloro-benzene.

In some cases, a LGIC ligand can be a quinuclidine and can have a structure shown in Formula II:

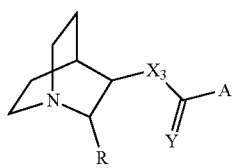

where X3=O, NH, or CH2; where Y=O or S; where A=an aromatic substituent; and where R=H or pyridinylmethylene. The aromatic substituent can be 1H-indole, 4-(trifluoromethyl) benzene, 4-chloro benzene, 2,5-dimethoxy benzene, 4-(trifluoromethyl) benzene, 4-chloroaniline, aniline, 5-(trifluoromethyl) pyridin-2-yl, 6-(trifluoromethyl) nicotinic, 3-chloro-4-fluoro benzene, or 1H-indole. The quinuclidine can be PNU-282987, PHA-543613, compound 0456, compound 0434, compound 0436, compound 0354, compound 0353, compound 0295, compound 0296, compound 0536, compound 0676, or compound 702.

In some cases, a LGIC ligand can be a tropane and can have a structure shown in Formula III:

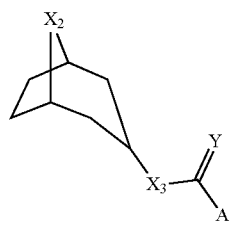

where X2=NH or NMe; where X3=O, NH, or CH2; where Y=O or S; and where A=an aromatic substituent. The aromatic substituent can be 1H-indole, 7-methoxy-1H-indole, 7-methyl-1H-indole, 5-chloro-1H-indole, or 1H-indazole. The tropane can be tropisetron, pseudo-tropisetron, nortropisetron, compound 723, compound 725, compound 737, or compound 745.

In some cases, a LGIC ligand can be a 9-azabicyclo[3.3.1]nonane and can have a structure shown in Formula IV:

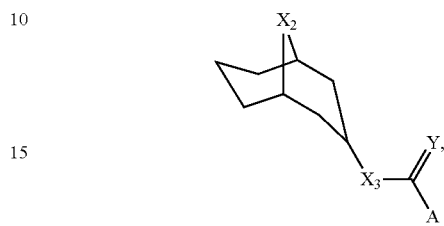

where X1 can be CH, X2 can be NH or NMe, X3 can be O, NH, or CH; Y can be O or S, and A can be an aromatic substituent. The aromatic substituent can be 4-chloro-benzene. The 9-azabicyclo[3.3.1]nonane can be compound 0536.

In another aspect, this document features a ligand having increased potency for a modified LGIC, where the ligand can be a 6,7,8,9-tetrahydro-6,10-methano-6H-pyrazino(2,3-h)benzazepine and can have a structure shown in Formula V:

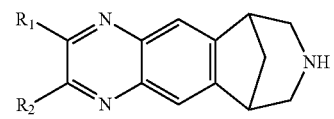

where R1 can be H, phenyl 2-toluyl; 3-pyridyl; 4-pyridyl; trifluoromethyl; methoxy; N,N-dimethylamino; N,N-diethylamino; imidazole, pyrrole, pyrazole, triazole, or isoxazole-3-amine, and where R2 can be H, methyl, or phenyl. The 6,7,8,9-tetrahydro-6,10-methano-6H-pyrazino(2,3-h)benzazepine can be varenicline, compound 0765, compound 0770, compound 0780, compound 0782, compound 0785, compound 0788, compound 0782, compound 0789, compound 0791, compound 0793, compound 0794, compound 0795, compound 0798, compound 0799, compound 0800, compound 0801, compound 0802, compound 0803, compound 0804, compound 0805, compound 0807, compound 0808, compound 0812, compound 0813, compound 815, and compound 817.

In another aspect, this document features a ligand having increased potency for a modified LGIC, where the ligand can be a 2-(pyridin-3-yl)-1,5,6,7,8,9-hexahydro-5,9-methanoimidazo[4',5':4,5]benzo[1,2-d]azepine (e.g., compound 0786):

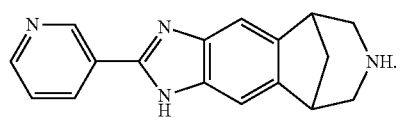 [SMILES: c1cncc(-c2nc3cc4c(cc3[nH]2)C2CNCC4C2)c1]

In another aspect, this document features a ligand having increased potency for a modified LGIC, where the ligand can be 7,8,9,10-tetrahydro-1H-6,10-methanoazepino[4,5-g]quinoxalin-2(6H)-one and can have a structure shown in Formula VI:

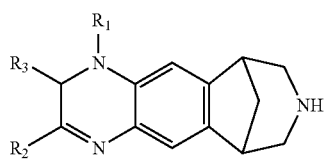

where R1 can be H or CH3, where R2 can be H, CH3, or an aromatic substituent, and where R3 can be O or S. The 7,8,9,10-tetrahydro-1H-6,10-methanoazepino[4,5-g]quinoxalin-2(6H)-one can be compound 0783, compound 0784, compound 0790, or compound 0792.

In another aspect, this document features a ligand having increased potency for a modified LGIC, where the ligand can be a 1,4-diazabicyclo[3.2.2]nonane and can have a structure shown in Formula VII:

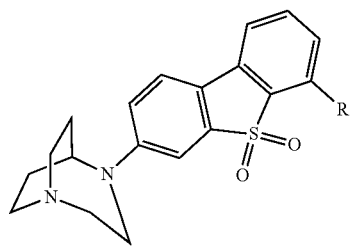

where R can be H, F, or NO$_2$. The 1,4-diazabicyclo[3.2.2]nonane can be 3-(1,4-diazabicyclo[3.2.2]nonan-4-yl)dibenzo[b,d]thiophene 5,5-dioxide, compound 0773, or compound 0774.

In another aspect, this document features methods of treating a channelopathy in a mammal. The methods include, or consist essentially of, administering to a cell in the mammal a modified LGIC, where an exogenous LGIC ligand selectively binds the modified LGIC. The modified LGIC has at least one modified LGIC subunit including a LBD including at least one modified amino acid, and an IPD; and administering the exogenous ligand to the mammal. The channelopathy can be Bartter syndrome, Brugada syndrome, catecholaminergic polymorphic ventricular tachycardia (CPVT), congenital hyperinsulinism, cystic fibrosis, Dravet syndrome, episodic ataxia, erythromelalgia, generalized epilepsy (e.g., with febrile seizures), familial hemiplegic migraine, fibromyalgia, hyperkalemic periodic paralysis, hypokalemic periodic paralysis, Lambert-Eaton myasthenic syndrome, long QT syndrome (e.g., Romano-Ward syndrome), short QT syndrome, malignant hyperthermia, mucolipidosis type IV, myasthenia gravis, myotonia congenital, neuromyelitis optica, neuromyotonia, nonsyndromic deafness, paramyotonia congenital, retinitis pigmentosa, timothy syndrome, tinnitus, seizure, trigeminal neuralgia, or multiple sclerosis.

In another aspect, this document features methods of modulating ion transport across a cell membrane of a mammal. The methods include, or consist essentially of, administering to the cell a modified LGIC, where an exogenous LGIC ligand selectively binds the modified LGIC. The modified LGIC has at least one modified LGIC subunit including a LBD including at least one modified amino acid, and an IPD; and administering the exogenous ligand to the mammal. The modulating can include activating or inhibiting ion transport. The cell can be a neuron, a glial cell, a myocyte, a stem cell, an endocrine cell, or an immune cell. The administering the modified LGIC to the cell can be an in vivo administration or an ex vivo administration. The administering the modified LGIC to the cell can include administering a nucleic acid encoding the modified LGIC.

In another aspect, this document features methods of modulating the excitability of a cell in a mammal. The methods include, or consist essentially of, administering to the cell from the mammal a modified LGIC, where an exogenous LGIC ligand selectively binds the modified LGIC. The modified LGIC has at least one modified LGIC subunit including a LBD including at least one modified amino acid, and an IPD; and administering the exogenous ligand to the mammal. The modulating can include increasing the excitability of the cell or decreasing the excitability of the cell. The cell can be an excitable cell. The cell can be a neuron, a glial cell, a myocyte, a stem cell, an endocrine cell, or an immune cell. The administering the modified LGIC to the cell can be an in vivo administration or an ex vivo administration. The administering the modified LGIC to the cell can include administering a nucleic acid encoding the modified LGIC.

In another aspect, this document features methods of modulating the activity of a cell in a mammal. The methods include, or consist essentially of, administering to the cell a modified LGIC, where an exogenous LGIC ligand selectively binds the modified LGIC. The modified LGIC has at least one modified LGIC subunit including a LBD including at least one modified amino acid, and an IPD; and administering the exogenous ligand to the mammal. The modulating can include increasing the activity of the cell or decreasing the activity of the cell. The activity can be ion transport, passive transport, excitation, inhibition, or exocytosis. The cell can be a neuron, a glial cell, a myocyte, a stem cell, an endocrine cell, or an immune cell. The administering the modified LGIC to the cell can be an in vivo administration or an ex vivo administration. The administering the modified LGIC to the cell can include administering a nucleic acid (e.g., via a viral vector such as an adeno-associated virus, a herpes simplex virus, or a lentivirus) encoding the modified LGIC.

In another aspect, this document features a method for identifying a ligand that selectively binds to a modified LGIC. The method includes, or consists essentially of, providing one or more candidate ligands to the modified LGIC described herein, and detecting binding between the candidate ligand and the modified LGIC, thereby identifying a ligand that selectively binds the modified LGIC. The modified LGIC can be a homomeric modified LGIC.

In another aspect, this document features a method for detecting a modified LGIC. The method includes, or consists essentially of, providing one or more modified LGIC subunits described herein, providing an agent that selectively binds the modified LGIC, and detecting binding between the modified LGIC and the agent that selectively binds the modified LGIC, thereby detecting the modified LGIC. The agent that selectively binds the modified LGIC comprises can be antibody, a protein (e.g., bungarotoxin), or a small molecule (e.g., a positron emission tomography (PET) ligand). The agent that selectively binds the modified LGIC can include a detectable label (e.g., a fluorescent label, a radioactive label, or a positron emitting label).

In another aspect, this document features synthetic nucleic acid constructs including a nucleic acid sequence having at least 75 percent sequence identity to the sequence set forth in SEQ ID NO:27. The nucleic acid sequence having at least 75 percent sequence identity to the sequence set forth in SEQ ID NO:27 can include a nucleic acid sequence that can encode a LBD having an amino acid modification. The modified LBD can be an α7-nAChR LBD having an amino acid substitution residue 77, 79, 115, 131, 139, 141, 175, 210, 216, 217, and/or 219 of the α7-nAChR LBD. The nucleic acid sequence having at least 75 percent sequence identity to the sequence set forth in SEQ ID NO:27 can include a nucleic acid sequence that can encode an IPD. The IPD can be a 5HT3 IPD, a GlyR IPD, a GABA receptor IPD, or an α7-nAChR IPD. The IPD can be a 5HT3 IPD.

In another aspect, this document features synthetic nucleic acid constructs including a nucleic acid sequence having at least 75 percent sequence identity to the sequence set forth in SEQ ID NO:28.

The nucleic acid sequence having at least 75 percent sequence identity to the sequence set forth in SEQ ID NO:28 can include a nucleic acid sequence that can encode a LBD having an amino acid modification. The modified LBD can be an α7-nAChR LBD having an amino acid substitution residue 77, 79, 115, 131, 139, 141, 175, 210, 216, 217, and/or 219 of the α7-nAChR LBD. The nucleic acid sequence having at least 75 percent sequence identity to the sequence set forth in SEQ ID NO:28 can include a nucleic acid sequence that can encode an IPD. The IPD can be a 5HT3 IPD, a GlyR IPD, a GABA receptor IPD, or an α7-nAChR IPD. The IPD can be a GlyR IPD having an amino acid modification. The modified GlyR IPD can have an amino acid substitution at amino acid residue 298 of the GlyR IPD.

In another aspect, this document features synthetic nucleic acid constructs including a nucleic acid sequence having at least 75 percent sequence identity to the sequence set forth in SEQ ID NO:29. The nucleic acid sequence having at least 75 percent sequence identity to the sequence set forth in SEQ ID NO:29 can include a nucleic acid sequence that can encode a LBD having an amino acid modification. The modified LBD can be a α7-nAChR LBD having an amino acid substitution residue 77, 79, 115, 131, 139, 141, 175, 210, 216, 217, and/or 219 of the α7-nAChR LBD. The nucleic acid sequence having at least 75 percent sequence identity to the sequence set forth in SEQ ID NO:29 can include a nucleic acid sequence that can encode an IPD. The IPD can be a 5HT3 IPD, a GlyR IPD, a GABA receptor IPD, or an α7-nAChR IPD. The IPD can be a GABA IPD having an amino acid modification. The modified GABA IPD can have an amino acid substitution at amino acid residue 298 of the GABA IPD.

In another aspect, this document features synthetic nucleic acid constructs having the sequence set forth in SEQ ID NO:33.

In another aspect, this document features synthetic nucleic acid constructs having the sequence set forth in SEQ ID NO:34.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 1A-1E show exemplary amino acid sequences of chimeric LGICs. Mutation of amino acid residue 77 (e.g., W77F or W77Y) resulted in sensitivity to granisetron and tropisetron. Mutation of amino acid residue 79 (e.g., Q79G) was most effective for several agonists. Mutations of amino acid residue 131 (e.g., L131G, L131A, L131M, or L131N) altered sensitivity to varenicline, tropisetron, granisetron, and ACh. Potency was considerably enhanced when LBD mutations were combined with mutation at amino acid residue 298 in the GlyR or GABAC IPD. Potency was also enhanced when α7 nAChR LBD mutations were combined with mutation at amino acid residue G175 and P216. FIG. 1A) An amino acid sequence of α7-5HT3 chimeric receptor (SEQ ID NO:6) including a human α7 nAChR LBD (SEQ ID NO:1) and a murine 5HT3 IPD (SEQ ID NO:3) components. FIG. 1B) An amino acid sequence of α7-GlyR chimeric receptor (SEQ ID NO:7), including a human α7 nAChR LBD (SEQ ID NO:2) and a human GlyR IPD (SEQ ID NO:5) components. FIG. 1C) An amino acid sequence of α7-5HT3 chimeric receptor (SEQ ID NO:8) including human α7 nAChR LBD (SEQ ID NO:1) and a human 5HT3 IPD (SEQ ID NO:4) components. FIG. 1D) An amino acid sequence of α7-GABAc chimeric receptor (SEQ ID NO:10) including a human α7 nAChR LBD (SEQ ID NO:11) and a human GABAc IPD (SEQ ID NO:9) components. FIG. 1E) An amino acid sequence of rat nAChR sequence (SEQ ID NO:12).

FIG. 3 shows the relative potency of known nAChR agonists for α7-5HT3 chimeric LGICs.

FIGS. 4A-4C show the relative potency of known nAChR agonists for α7-GlyR chimeric LGICs. FIG. 4A) A graph of EC50s for Q79 LBD mutants normalized to the unmodified α7-GlyR chimeric channel (log scale). FIG. 4B) A graph of EC50s for A298G IPD mutation normalized to the unmodified α7-GlyR chimeric channel (log scale). FIG. 4C) A graph of EC50s for α7-GlyR$^{A298G}$ normalized to the unmodified α7-GlyR chimeric channel and compared to the double mutant channel α7Q79G-GlyR$^{A298G}$ (log scale). *P<0.05, statistically significant potency changes are noted (ANOVA followed by Dunn's test).

FIGS. 5A-5C show schematic structures of LGIC agonists with substitution patterns most compatible with potency enhancement for α7$^{Q79G}$-5HT3 and α7$^{Q79G}$-GlyR$^{A298G}$. FIG. 5A generalized structure showing attributes associated with enhanced potency. FIG. 5B) Specific pharmacophores represented in (FIG. 5A) are quinuclidine, tropane, and 9-azabicyclo[3.3.1]nonane core structures. FIG. 5C) Exemplary synthetic molecules that show high potency for α7$^{Q79G}$-GlyR$^{A298G}$, α7$^{Q79G,Y115F,G175K}$-GlyR, α7$^{W77F,Q79G,G175K}$-GlyR.

FIG. 6A) Charge reversal schematic potential configurations of transfecting two epitope tagged (HA and V5) constructs encoding α7-5HT3 (top) or two constructs encoding α7-5HT3-HA and α7$^{R21D,E41R}$-5HT3-V5 where association between the two different epitope tagged subunits would be unfavored due to charge reversal mutations at the subunit interfaces. FIG. 6B) Whole cell recordings in HEK cells expressing α7$^{R21D,E41R}$-5HT3 with a V5 epitope tag shows potent responses to PNU-282987. FIG. 6C) Association of α7-5HT3 LGICs with HA and V5 epitope tags in HEK cells was probed by HA immunoprecipitation (left) or total lysate isolation followed by western blotting with either anti-HA (top) or anti-V5 antibodies (bottom). In cells co-expressing channels with the HA and V5 epitopes, anti-HA IP followed by anti-V5 immunoblotting shows the co-immunoprecipitation of unmodified channels of each type, but charge reversal mutations in the LBD α7$^{R21D,E41R}$-5HT3-V5 was not immunoprecipitated. MW of α7-5HT3 is ~48 kD (arrow).

FIGS. 8A-8C show activity of agonists on chimeric LGICs with a G175K mutation. FIG. 8A) A graph of EC50s for Q79G G175K LBD mutants against known agonists normalized to the unmodified α7-GlyR chimeric channel (log scale). FIG. 8B) A graph of EC50s for ACh and tropisetron for channels with mutations in α7-GlyR chimeric LGICs. Mutations that result in channels with high potency for tropisetron and low potency for the endogenous ligand, acetylcholine (ACh) are optimal (grey shading). Unmod.: unmodified α7-GlyR chimeric LGIC. FIG. 8C) Action potentials of cortical neurons from a mouse brain transduced with α7$^{Q79G,Y115F,G175K}$-GlyR chimeric LGIC. Neurons fire in response to current injection (PRE) and are potently suppressed by 100 nM tropisetron. After washout (WASH) of tropisetron, neuron firing is restored.

FIG. 9A) A graph of EC50s for L131 LBD mutants against known agonists normalized to the unmodified α7-GlyR chimeric channel (log scale). FIG. 9B) A graph of EC50s for ACh and tropisetron for channels with mutations in α7$^{L131G}$-GlyR chimeric LGICs. FIG. 9C) A graph showing mutations that result in channels with high potency for varenicline and low potency for the endogenous ligand, acetylcholine (ACh) are optimal (grey shading). Unmod.: unmodified α7-GlyR chimeric LGIC. FIG. 9D) A graph showing activation of channels with mutations in α7L131G-GlyR by Ach and varenicline after brief channel antagonism by picrotoxin (PTX). Solid lines represent duration of molecule administration. FIG. 9E) Action potentials of a cortical neuron from a mouse brain transduced with α7$^{L131G,Q139L,Y217F}$-GlyR chimeric LGIC. Neuron fires in response to current injection (PRE) and are potently suppressed by 10 nM varenicline, even with >6-fold greater injected current. After washout (WASH) of varenicline, neuron firing is restored.

FIGS. 11A-11C show chemical structures of exemplary LGIC agonists. FIG. 11A) Chemical structures of LGIC agonists with substitution patterns most compatible with potency enhancement for α7$^{Q79G,Y115F,G175K}$-GlyR. FIG. 11B) Chemical structures of LGIC agonists with substitution patterns most compatible with potency enhancement for α7$^{L131G,Q139L,Y217F}$-GlyR, α7$^{L131G,Q139L,Y217F}$-5HT3, or α7$^{L131G,Q139L,Y217F}$-5HT3 HC. FIG. 11C) Chemical structures of LGIC agonists with substitution patterns most compatible with potency enhancement for α7$^{L131G,Q139L,Y217F}$-GlyR or α7$^{L131G,Q139L,Y217F}$-5HT3 HC.

FIGS. 12A-12F show chemogenetic perturbation of cortical neuron activity. FIG. 12A-FIG. 12B) Action potential firing was strongly suppressed by varenicline strongly in neurons expressing PSAM$^4$-GlyR due to reduced input resistance (FIG. 12A) and elevated rheobase (FIG. 12B). FIG. 12C) Cortical layer 2/3 neuron membrane properties were similar in PSAM$^4$-GlyR expressing neurons and intermingled untransfected control neurons. FIG. 12D-FIG. 12E) Varenicline depolarizes (FIG. 12D) and elicits firing (FIG. 12E) in neurons expressing PSAM$^4$-5HT3 HC. FIG. 12F) Cortical layer 2/3 neuron membrane properties are similar in PSAM$^4$-5HT3 HC expressing neurons and intermingled untransfected control neurons. Data are mean±SEM. Mann Whitney U-test, n.s. P>0.05, ***P<0.001.

FIG. 13A) PSAM$^4$-GlyR-IRES-EGFP targeted unilaterally to the SNr. Inset: schematic of unilateral SNr transduction were silencing results in contraversive rotation. Asterisk: nonspecific immunofluorescence. FIG. 13B) Low doses of intraperitoneal varenicline elicit contraversive rotation for mice expressing PSAM$^4$-GlyR but not sham operated or EGFP-alone expressing mice. FIG. 13C) Two doses of varenicline separated by 5 h give similar proportion of total rotation, indicating no tachyphylaxis of the chemogenetic response. FIG. 13D) Duration of chemogenetic silencing monitored by the timecourse of rotation response normalized to maximum rotation for each mouse. Pink (narrow) arrows: amphetamine injections, cyan (wide) arrow: varenicline injection. Mann-Whitney U-test, n.s. P>0.05, **P<0.01.

FIGS. 14A-14J show ultrapotent chemogenetic agonists (uPSEMs). FIG. 14A) Comparison of uPSEM agonist EC50s at PSAM$^4$ channels and endogenous varenicline targets, as well as IC50 for α4β2 nAChR with 1 μM ACh. LED: lowest effective dose for mice in SNr rotation assay. Units: nM; parentheses: SEM. Selectivity relative to PSAM$^4$-GlyR in bold. FIG. 14B, FIG. 14C) Dose response curves for PSAM$^4$-GlyR, α4β2 nAChR, 5HT3-R. uPSEM$^{792}$ (FIG. 14B) is a 10% partial agonist of α4β2 nAChR and uPSEM$^{817}$ (FIG. 14C) inhibits α4β2 nAChR. FIG. 14D) Current response to uPSEMs (2 μM) and Ach (10 μM) in a HEK cell expressing α7 nAChRs. uPSEMs do not activate α7 nAChR, while ACh does. (FIG. 14E) Response amplitude normalized to ACh. FIG. 14F-FIG. 14J) uPSEM$^{792}$, uPSEM$^{793}$, uPSEM$^{815}$, and uPSEM$^{817}$ strongly suppress firing in cortical neurons expressing PSAM$^4$-GlyR by reducing the current required to fire an action potential (rheobase) (FIG. 14G-FIG. 14J).

FIG. 16 shows an exemplary amino acid sequence for PSAM⁴-GlyR-KirM3M4 (SEQ ID NO:13). PSAM⁴ mutations are highlighted. A sequence for a Kir2.1 (KCNJ2) endoplasmic reticulum (ER) export sequence is underlined and in blue.

FIG. 17 shows an exemplary amino acid sequence for PSAM⁴-GlyR-B4sig (SEQ ID NO:14). PSAM⁴ mutations are highlighted. A sequence for a β4 nAChR subunit (CHRNB4) signal sequence is underlined and in blue.

FIG. 18 shows an exemplary amino acid sequence for PSAM⁴-GlyR-Kv2M3M4-soma (SEQ ID NO:15). PSAM⁴ mutations are highlighted. Sequence for Kv2.1 (KCNB1) somatic targeting sequence underlined and in blue.

FIGS. 19A-19B show an exemplary construct including a nucleic acid sequence encoding a modified LGIC subunit. (FIG. 19A) A plasmid map of an AAV-Syn::PSAM4-GlyR-IRES-EGFP-WPRE construct including a nucleic acid sequence (SEQ ID NO:33) encoding a modified LGIC subunit. (FIG. 19B) A nucleic acid sequence of an AAV-Syn::PSAM4-GlyR-IRES-EGFP-WPRE construct including a nucleic acid sequence encoding a modified LGIC subunit.

FIGS. 20A-20B show an exemplary construct including a nucleic acid sequence encoding a modified LGIC subunit. (FIG. 20A) A plasmid map of an AAV-CamkII:PSAM4-GlyR-IRES-EGFP-WPRE construct including a nucleic acid sequence (SEQ ID NO:34) encoding a modified LGIC subunit. (FIG. 20B) A nucleic acid sequence of an AAV-CamkII::PSAM4-GlyR-IRES-EGFP-WPRE construct including a nucleic acid sequence encoding a modified LGIC subunit.

DETAILED DESCRIPTION

Figure 2:
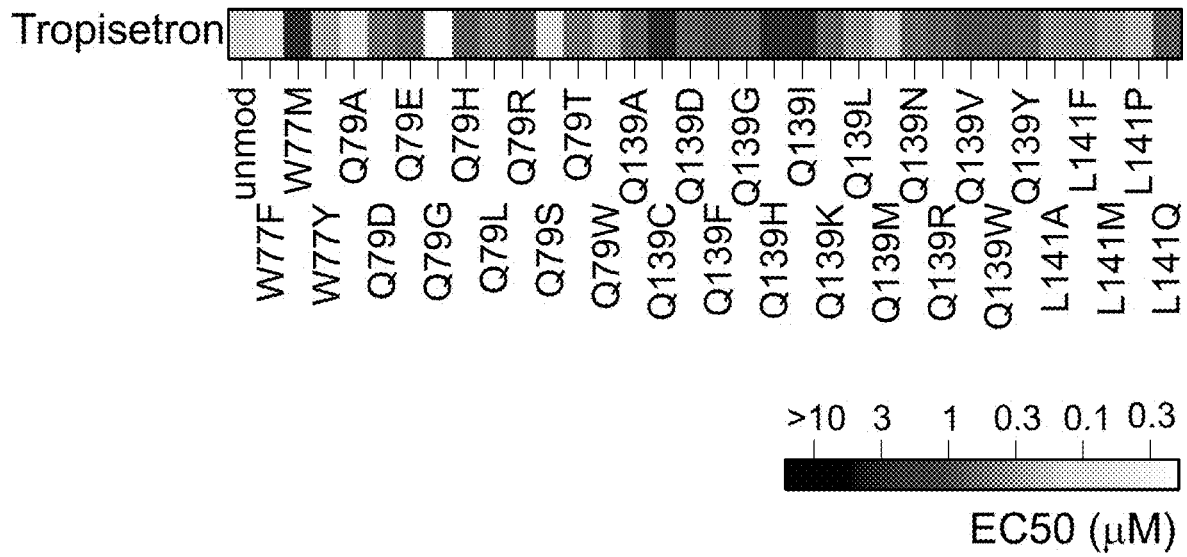
FIG. 2 shows EC50s for tropisetron against a α7-5HT3 chimeric LGIC and variants of the chimeric LGIC with LBD mutations at positions noted in FIG. 1. Multiple mutations at Gln79 showed similar or improved potency relative to the unmodified α7-5HT3 channel (arrows).

This document provides modified LGICs and methods of using them. For example, this document provides modified LGICs including at least one modified LGIC subunit having a LBD and an IPD, and having at least one modified amino acid (e.g., an amino acid substitution). In some cases, a modified LGIC can be a chimeric LGIC. For example, a chimeric LGIC can include a LBD from a first LGIC and an IPD from a second LGIC. In some cases, the modified amino acid can confer pharmacological selectivity to the modified LGIC. For example, the modified amino acid can confer the modified LGIC with selective binding of an exogenous LGIC ligand. For example, the modified amino acid can confer the modified LGIC with reduced (e.g., minimized or eliminated) binding of an unmodified LGIC subunit (e.g., an LGIC subunit lacking the modification and/or an endogenous LGIC subunit). For example, the modified amino acid can confer the modified LGIC with reduced (e.g., minimized or eliminated) binding of an endogenous LGIC ligand.

Modified LGICs provided herein can be used, for example, in methods for treating channelopathies (e.g., a neural channelopathy or a muscle channelopathy). For example, a modified LGIC, and an exogenous LGIC ligand that can bind to and activate the modified LGIC, can be used to treat a mammal having a channelopathy. In some cases, a modified LGIC and an exogenous LGIC ligand can be used to modulate (e.g., activate or inhibit) ion transport across the membrane of a cell of a mammal. In some cases, a modified LGIC and an exogenous LGIC ligand can be used to modulate (e.g., increase or decrease) the excitability of a cell in a mammal.

Modified LGICs

As used herein a "modified" LGIC is an LGIC that includes at least one LGIC subunit. Modified LGIC can also be referred to as pharmacologically selective actuator modules (PSAMs). A modified LGIC subunit can include at least one modified amino acid (e.g., an amino acid substitution) in the LBD and/or at least one modified amino acid (e.g., an amino acid substitution) in the IPD. A modified LGIC subunit described herein can be a modification of an LGIC from any appropriate species (e.g., human, rat, mouse, dog, cat, horse, cow, goat, pig, or monkey). In some cases, a modified LGIC can include at least one chimeric LGIC subunit having a non-naturally occurring combination of a LBD from a first LGIC and an IPD from a second LGIC.

A modified LGIC (e.g., an LGIC including one or more modified LGIC subunits) can be a homomeric (e.g., having any number of the same modified LGIC subunits) or heteromeric (e.g., having at least one modified LGIC subunit and any number of different LGIC subunits). In some cases, a modified LGIC described herein can be a homomeric modified LGIC. A modified LGIC described herein can include any suitable number of modified LGIC subunits. In some cases, a modified LGIC can be a trimer, a tetramer, a pentamer, or a hexamer. For example, a modified LGIC described herein can be a pentamer.

A modified LGIC subunit described herein can be a modification of any appropriate LGIC. The LGIC can conduct anions, cations, or both through a cellular membrane in response to the binding of a ligand. For example, the LGIC can transport sodium (Na+), potassium (K+), calcium (Ca2+), and/or chloride (Cl−) ions through a cellular membrane in response to the binding of a ligand. Examples of LGICs include, without limitation, Cys-loop receptors (e.g., AChR such as a nAChR (e.g., a muscle-type nAChR or a neuronal-type nAChR), gamma-aminobutyric acid (GABA; such as $GABA_A$ and $GABA_A$-ρ (also referred to as GABAc) receptors, GlyR, GluCl receptors, and 5HT3 receptors), ionotropic glutamate receptors (iGluR; such as AMPA receptors, kainate receptors, NMDA receptors, and delta receptors), ATP-gated channels (e.g., P2X), and phosphatidylinositol 4,5-bisphosphate (PIP2)-gated channels. In cases where a modified LGIC described herein is a chimeric LGIC, the chimeric LGIC can include a LBD selected from any appropriate LGIC and an IPD selected from any appropriate LGIC. In cases where a LGIC includes multiple different subunits (for example, a neuronal-type nAChR includes α4, β2, and α7 subunits), the LBD and/or IPD can be selected from any of the subunits. For example, a LBD from a nAChR can be a α7 LBD. A representative rat α7 nAChR amino acid sequence (including both a LBD and an IPD) is as follows.

SEQ ID NO: 12
MGGGRGGIWLALAAALLHVSLQGEFQRRLYKELVKNYNPLERPVANDSQP

LTVYFSLSLLQIMDVDEKNQVLTTNIWLQMSWTDHYLQWNMSEYPGVKNV

RFPDGQIWKPDILLYNSADERFDATFHTNVLVNASGHCQYLPPGIFKSSC

YIDVRWFPFDVQQCKLKFGSWSYGGWSLDLQMQEADISSYIPNGEWDLMG

IPGKRNEKFYECCKEPYPDVTYTVTMRRRTLYYGLNLLIPCVLISALALL

VFLLPADSGEKISLGITVLLSLTVFMLLVAEIMPATSDSVPLIAQYFAST

MIIVGLSVVVTVIVLRYHHHDPDGGKMPKWTRIILLNWCAWFLRMKRPGE

DKVRPACQHKPRRCSLASVELSAGAGPPTSNGNLLYIGFRGLEGMHCAPT

PDSGVVCGRLACSPTHDEHLMHGAHPSDGDPDLAKILEEVRYIANRNRCQ

DESEVICSEWKFAACVVDPLCLMAFSVFTIICTIGILMSAPNFVEAVSKD

FA

In some cases, a modified LGIC subunit described herein can include a LBD from a α7 nAChR. Examples of α7 nAChR LBDs include, without limitation, a human α7 nAChR LBD having the amino acid sequence set forth in SEQ ID NO:1, a human α7 nAChR LBD having the amino acid sequence set forth in SEQ ID NO:2, and a human α7 nAChR LBD having the amino acid sequence set forth in SEQ ID NO:11. In some cases, a α7 nAChR LBD can be a homolog, orthologue, or paralog of the human α7 nAChR LBD set forth in SEQ ID NO:1, SEQ ID NO:2, or SEQ ID NO:11. In some cases, a α7 nAChR LBD can be have at least 75 percent sequence identity (e.g., at least 80%, at least 82%, at least 85%, at least 88%, at least 90%, at least 93%, at least 95%, at least 97% or at least 99% sequence identity) to SEQ ID NO:1, SEQ ID NO:2, or SEQ ID NO:11.

SEQ ID NO: 1
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTV

SEQ ID NO: 2
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTVTMRRR

SEQ ID NO: 11
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTVTMRRRTLYY

In some cases, a modified LGIC subunit described herein can include a IPD from a 5HT3 receptor. Examples of 5HT3 IPDs include, without limitation, a murine 5HT3 IPD having the amino acid sequence set forth in SEQ ID NO:3, and a human 5HT3 IPD having the amino acid sequence set forth in SEQ ID NO:4. In some cases, a 5HT3 IPD can be a homolog, orthologue, or paralog of a 5HT3 IPD set forth in SEQ ID NO:3 or SEQ ID NO:4. In some cases, a 5HT3 IPD can be have at least 75 percent sequence identity (e.g., at least 80%, at least 82%, at least 85%, at least 88%, at least 90%, at least 93%, at least 95%, at least 97% or at least 99% sequence identity) to SEQ ID NO:3 of SEQ ID NO:4.

SEQ ID NO: 3
IIRRRPLFYAVSLLLPSIFLMVVDIVGFCLPPDSGERVSFKITLLLGYSV

FLIIVSDTLPATIGTPLIGVYFVVCMALLVISLAETIFIVRLVHKQDLQR

PVPDWLRHLVLDRIAWILCLGEQPMAHRPPATFQANKTDDCSGSDLLPAM

GNHCSHVGGPQDLEKTPRGRGSPLPPPREASLAVRGLLQELSSIRHFLEK

RDEMREVARDWLRVGYVLDRLLFRIYLLAVLAYSITLVTLWSIWHYS

SEQ ID NO: 4
IIRRRPLFYVVSLLLPSIFLMVMDIVGFYLPPNSGERVSFKITLLLGYSV

FLIIVSDTLPATAIGTPLIGVYFVVCMALLVISLAETIFIVRLVHKQDLQ

QPVPAWLRHLVLERIAWLLCLREQSTSQRPPATSQATKTDDCSAMGNHCS

HMGGPQDFEKSPRDRCSPPPPPREASLAVCGLLQELSSIRQFLEKRDEIR

EVARDWLRVGSVLDKLLFHIYLLAVLAYSITLVMLWSIWQYA

In some cases, a modified LGIC subunit described herein can include an IPD from a GlyR. Examples of GlyR IPDs include, without limitation, a murine GlyR IPD having the amino acid sequence set forth in SEQ ID NO:5. In some cases, a GlyR IPD can be a homolog, orthologue, or paralog of the human GlyR IPD set forth in SEQ ID NO:5. In some cases, a GlyR IPD can be have at least 75 percent sequence identity (e.g., at least 80%, at least 82%, at least 85%, at least 88%, at least 90%, at least 93%, at least 95%, at least 97% or at least 99% sequence identity) to SEQ ID NO:5.

SEQ ID NO: 5
MGYYLIQMYIPSLLIVILSWISFWINMDAAPARVGLGITTVLTMTTQSSG

SRASLPKVSYVKAIDIWMAVCLLFVFSALLEYAAVNFVSRQHKELLRFRR

KRRHHKEDEAGEGRFNFSAYGMGPACLQAKDGISVKGANNSNTTNPPPAP

SKSPEEMRKLFIQRAKKIDKISRIGFPMAFLIFNMFYWIIYKIVRREDVH

NQ

In some cases, a modified LGIC subunit described herein can include an IPD from a GABA receptor (e.g., GABA$_A$-ρ, also referred to as GABAc). Examples of GABA$_A$-ρ IPDs include, without limitation, a human GABA$_A$-ρ IPD having the amino acid sequence set forth in SEQ ID NO:9. In some cases, a GABA$_A$-ρ IPD can be a homolog, orthologue, or paralog of the human GABA$_A$-ρ IPD set forth in SEQ ID NO:9. In some cases, a GABA$_A$-ρ IPD can be have at least 75 percent sequence identity (e.g., at least 80%, at least 82%, at least 85%, at least 88%, at least 90%, at least 93%, at least 95%, at least 97% or at least 99% sequence identity) to SEQ ID NO:9.

SEQ ID NO: 9
LLQTYFPATLMVMLSWVSFWIDRRAVPARVPLGITTVLTMSTIITGVNAS

MPRVSYIKAVDIYLWVSFVFVFLSVLEYAAVNYLTTVQERKEQKLREKLP

CTSGLPPPRTAMLDGNYSDGEVNDLDNYMPENGEKPDRMMVQLTLASERS

SPQRKSQRSSYVSMRIDTHAIDKYSRIIFPAAYILFNLIYWSIFS

In calculating percent sequence identity, two sequences are aligned and the number of identical matches of amino acid residues between the two sequences is determined. The number of identical matches is divided by the length of the aligned region (i.e., the number of aligned amino acid residues) and multiplied by 100 to arrive at a percent sequence identity value. It will be appreciated that the length of the aligned region can be a portion of one or both sequences up to the full-length size of the shortest sequence.

It also will be appreciated that a single sequence can align with more than one other sequence and hence, can have different percent sequence identity values over each aligned region. The alignment of two or more sequences to determine percent sequence identity can be performed using the computer program ClustalW and default parameters, which calculates the best match between a query and one or more subject sequences, and aligns them so that identities, similarities and differences can be determined. See, e.g., Chenna et al., 2003, Nucleic Acids Res., 31(13):3497-500.

In cases where a modified LGIC subunit described herein is a chimeric LGIC subunit, the chimeric LGIC subunit can include a LBD and IPD from the same species or a LBD and IPD from different species. In some cases, a chimeric LGIC subunit can include a LBD from a human LGIC protein and an IPD from a human LGIC protein. For example, a chimeric LGIC subunit can include a human α7 LBD and a human GlyR IPD. In some cases, a chimeric LGIC subunit can include a LBD from a human LGIC protein and an IPD from a murine LGIC protein. For example, a chimeric LGIC subunit can include a human α7 LBD and a murine 5HT3 IPD.

In cases where a modified LGIC subunit described herein is a chimeric LGIC subunit, the chimeric LGIC subunit can include varied fusion points connecting the LBD and the IPD such that the number of amino acids in a LBD may vary when the LBD is fused with different IPDs to form a chimeric channel subunit. For example, the length of an α7 nAChR LBD used to form a chimeric LGIC subunit with a 5HT3 IPD is different from the length of an α7 nAChR LBD used to form a chimeric LGIC subunit with a GlyR IPD (compare, for example, FIGS. 1A and 1C to FIG. 1B).

A modified LGIC subunit described herein can include a LBD having at least one modified amino acid and/or an IPD having at least one modified amino acid. For example, a modified LGIC subunit described herein can include a α7 LBD having at least 75 percent sequence identity to SEQ ID NO:1, SEQ ID NO:2, SEQ ID NO:11, or SEQ ID NO:12, and an amino acid substitution at amino acid residue 27, 41, 77, 79, 131, 139, 141, 175, 210, 216, 217, and/or 219. For example, a modified LGIC subunit described herein can include a GlyR IPD having at least 75 percent sequence identity to a sequence set forth in SEQ ID NO:5, and an amino acid substitution at amino acid residue 298 of an α7-GlyR chimeric receptor (e.g., SEQ ID NO:7). For example, a modified LGIC subunit described herein can include a GABAc IPD having at least 75 percent sequence identity to SEQ ID NO:9, and an amino acid substitution at amino acid residue 298 of an α7-GABAc chimeric receptor (e.g., SEQ ID NO:10). In some cases, a modified LGIC subunit described herein can include more than one (e.g., two, three, four, five, six, seven, eight, nine, ten, eleven, twelve, or more) amino acid modifications. The modification can be an amino acid substitution. In some cases, the modified amino acid can confer pharmacological selectivity to the modified LGIC. For example, the modified amino acid can confer the modified LGIC with selective binding of an exogenous LGIC ligand. For example, the modified amino acid can confer the modified LGIC with reduced (minimized or eliminated) binding of an unmodified LGIC subunit (an LGIC subunit lacking the modification and/or an endogenous LGIC subunit). For example, the modified amino acid can confer the modified LGIC with reduced (minimized or eliminated) binding of an endogenous LGIC ligand.

In some aspects, a modified LGIC subunit described herein can include at least one modified amino acid that confers the modified LGIC with selective binding (e.g., enhanced binding or increased potency) with an exogenous LGIC ligand. The binding with an exogenous LGIC ligand can be selective over the binding with an endogenous LGIC ligand. A modified LGIC subunit with selective binding with an exogenous LGIC ligand can include any appropriate LDB (e.g., a α7 LBD). In some aspects, the modified LGIC subunit can include a α7 LBD set forth in SEQ ID NO:1, SEQ ID NO:2, SEQ ID NO:11, or SEQ ID NO:12, and the amino acid modification can be a substitution at amino acid residue 77, 79, 131 139, 141, 175, and/or 216. In some cases, the tryptophan at amino acid residue 77 of SEQ ID NO:1, SEQ ID NO:2, SEQ ID NO:11, or SEQ ID NO:12 can be substituted with a hydrophobic amino acid residue such as phenylalanine (e.g., W77F), tyrosine (e.g., W77Y), or methionine (e.g., W77M). For example, a modified LGIC subunit described herein can include a α7 LBD set forth in SEQ ID NO:1, SEQ ID NO:2, SEQ ID NO:11, or SEQ ID NO:12 and having a W77F substitution. In some cases, the glutamine at amino acid residue 79 of SEQ ID NO:1, SEQ ID NO:2, SEQ ID NO:11, or SEQ ID NO:12 can be substituted with an amino acid residue such as alanine (e.g., Q79A), glycine (e.g., Q79G), or serine (e.g., Q79S). For example, a modified LGIC subunit described herein can include a α7 LBD having a Q79G substitution. In some cases, the leucine at amino acid residue 131 of SEQ ID NO:1, SEQ ID NO:2, SEQ ID NO:11, or SEQ ID NO:12 can be substituted with an amino acid residue such as alanine (e.g., L131A), glycine (e.g., L131G), methionine (e.g., L131M), asparagine (e.g., L131N), glutamine (e.g., L131Q), valine (e.g., L131V), or phenylalanine (e.g., L131F). In some cases, the glycine at amino acid residue 175 of SEQ ID NO:1, SEQ ID NO:2, SEQ ID NO:11, or SEQ ID NO:12 can be substituted with an amino acid residue such as lysine (e.g., G175K), alanine (e.g., G175A), phenylalanine (e.g., G175F), histidine (e.g., G175H), methionine (e.g., G175m), arginine (e.g., G175R), serine (e.g., G175S), valine (e.g., G175V). In some cases, the proline at amino acid residue 216 of SEQ ID NO:1, SEQ ID NO:2, SEQ ID NO:11, or SEQ ID NO:12 can be substituted with an amino acid residue such as isoleucine (e.g., P216I). A modified LGIC subunit with selective binding with an exogenous LGIC ligand can include any appropriate IPD (e.g., a GlyR IPD or a $GABA_A$-ρ IPD). In some aspects, the modified LGIC subunit can include a GlyR IPD set forth in SEQ ID NO:5, and the amino acid modification can be a substitution at amino acid residue 298 of an α7-GlyR chimeric receptor (e.g., SEQ ID NO:7). In some cases, the alanine at amino acid residue 298 of SEQ ID NO:7 can be substituted with an amino acid residue such as glycine (e.g., A298G). In some aspects, the modified LGIC subunit can include the a $GABA_A$-ρ IPD set forth in SEQ ID NO:9, and the amino acid modification can be a substitution at amino acid residue 298 of an α7-$GABA_A$-ρ chimeric receptor (e.g., SEQ ID NO:10). In some cases, the tryptophan at amino acid residue 298 of SEQ ID NO:10 can be substituted with an amino acid residue such as alanine (e.g., W298A).

In some cases, a modified LGIC subunit described herein can include more than one (e.g., two, three, four, five, six, seven, eight, nine, ten, eleven, twelve, or more) amino acid modifications. For example, a modified LGIC subunit described herein can have at least 75 percent sequence identity to SEQ ID NO:7 and can include a Q79G substitution and a A298G substitution. Additional examples of modifications that can confer the modified LGIC with selective binding of an exogenous LGIC ligand include modifications described elsewhere (see, e.g., U.S. Pat. No. 8,435, 762).

A modified LGIC subunit that selectively binds (e.g., enhanced binding or increased potency) an exogenous LGIC ligand over an endogenous (e.g., a canonical) LGIC ligand can also be described as having enhanced potency for an exogenous ligand. In some cases, a modified LGIC subunit described herein that selectively binds an exogenous LGIC ligand can have at least 4 fold (e.g., at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, or at least 20 fold) enhanced potency for an exogenous ligand. In some cases, a modified LGIC subunit described herein that selectively binds an exogenous LGIC ligand can have about 4 fold to about 200 fold (e.g., about 4 fold to about 200 fold, about 5 fold to about 180 fold, about 6 fold to about 175 fold, about 7 fold to about 150 fold, about 8 fold to about 125 fold, about 9 fold to about 100 fold, about 10 fold to about 90 fold, about 11 fold to about 75 fold, about 12 fold to about 65 fold, about 13 fold to about 50 fold, about 14 fold to about 40 fold, or about 15 fold to about 30 fold) enhanced potency for an exogenous ligand. For example, a modified LGIC subunit described herein that selectively binds an exogenous LGIC ligand can have about 10 fold to about 100 fold enhanced potency for an exogenous ligand. For example, a modified LGIC subunit described herein that selectively binds an exogenous LGIC ligand can have about 10 fold to about 20 fold enhanced potency for an exogenous ligand.

In some aspects, a modified LGIC subunit described herein can include at least one modified amino acid that confers the modified LGIC with reduced (e.g., minimized or eliminated) binding with an unmodified LGIC subunit. The binding with a modified LGIC subunit having the same modification can be selective over the binding with an unmodified LGIC subunit. An unmodified LGIC subunit can be a LGIC subunit lacking the modification that confers the modified LGIC with reduced binding with an unmodified LGIC subunit or an unmodified LGIC can be an endogenous LGIC subunit. The modification that confers the modified LGIC with reduced binding with an unmodified LGIC subunit can be a charge reversal modification. A modified LGIC subunit with reduced binding with an unmodified LGIC subunit can include any appropriate LBD (e.g., a α7 LBD). In some aspects, the modified LGIC subunit can include a α7 LBD set forth in SEQ ID NO:1, SEQ ID NO:2, SEQ ID NO:11, or SEQ ID NO:12, and the amino acid modification can be a substitution at amino acid residue 27 and/or 41. For example, the arginine at amino acid residue 27 of SEQ ID NO:1, SEQ ID NO:2, SEQ ID NO:11, or SEQ ID NO:12 can be substituted with an aspartic acid (e.g., R27D). For example, the glutamic acid at amino acid residue 41 of SEQ ID NO:1, SEQ ID NO:2, SEQ ID NO:11, or SEQ ID NO:12 can be substituted with an arginine (e.g., E41R). In some cases, a modified LGIC subunit described herein can include a α7 LBD having a R27D substitution and a E41R.

In some aspects, a modified LGIC subunit described herein can include at least one modified amino acid that confers the modified LGIC with reduced (e.g., minimized or eliminated) binding of an endogenous LGIC ligand. The endogenous LGIC ligand can be ACh. A modified LGIC subunit with reduced binding of an endogenous LGIC ligand can include any appropriate IPD (e.g., a GlyR LBD). For example, the modified LGIC subunit can include a α7 LBD set forth in SEQ ID NO:1, SEQ ID NO:2, SEQ ID NO:11, or SEQ ID NO:12, and the amino acid modification can be a substitution at amino acid residue 115, 131, 139, 210, 217 and/or 219. In some cases, the tyrosine at amino acid residue 115 of SEQ ID NO:1, SEQ ID NO:2, SEQ ID NO:11, or SEQ ID NO:12 can be substituted with a phenylalanine (e.g., Y115F). In some cases, the leucine at amino acid residue 131 of SEQ ID NO:1, SEQ ID NO:2, SEQ ID NO:11, or SEQ ID NO:12 can be substituted with an amino acid residue such as alanine (e.g., L131A), glycine (e.g., L131G), methionine (e.g., L131M), asparagine (e.g., L131N), glutamine (e.g., L131Q), valine (e.g., L131V), or phenylalanine (e.g., L131F). In some cases, the glutamine at amino acid residue 139 of SEQ ID NO:1, SEQ ID NO:2, SEQ ID NO:11, or SEQ ID NO:12 can be substituted with a glycine (e.g., Q139G) or a leucine (e.g., Q139L). In some cases, the tyrosine at amino acid residue 210 of SEQ ID NO:1, SEQ ID NO:2, SEQ ID NO:11, or SEQ ID NO:12 can be substituted with a phenylalanine (e.g., Y210F). In some cases, the tyrosine at amino acid residue 217 of SEQ ID NO:1, SEQ ID NO:2, SEQ ID NO:11, or SEQ ID NO:12 can be substituted with a phenylalanine (e.g., Y217F). In some cases, the aspartate at amino acid residue 219 of SEQ ID NO:1, SEQ ID NO:2, SEQ ID NO:11, or SEQ ID NO:12 can be substituted with an alanine (e.g., D219A).

In some aspects, a modified LGIC subunit described herein can include at least one modified amino acid that confers the modified LGIC with increased ion conductance. In some cases, the modified LGIC subunit can include a 5HT3 IPD set forth in SEQ ID NO:3, and the amino acid modification can be a substitution at amino acid residue 425, 429, and/or 433. For example, a modified LGIC subunit described herein can include a 5HT3 IPD having a R425Q substitution, a R429D substitution, and a R433A substitution. In some cases, the modified LGIC subunit can include a 5HT3 IPD set forth in SEQ ID NO:4, and the amino acid modification can be a substitution at amino acid residue 420, 424, and/or 428. For example, a modified LGIC subunit described herein can include a 5HT3 IPD having a R420Q substitution, a R424D substitution, and a R428A substitution.

In some cases, a modified LGIC described herein can include at least one chimeric α7-5HT3 LGIC subunit (SEQ ID NO:6) having a human α7 nAChR LBD (SEQ ID NO:1) with a Q79G amino acid substitution and a Y115F amino acid substitution, and a murine 5HT3 IPD (SEQ ID NO:3).

In some cases, a modified LGIC described herein can include at least one chimeric α7-5HT3 LGIC subunit (SEQ ID NO:6) having a human α7 nAChR LBD (SEQ ID NO:1) with a Q79G amino acid substitution and a Q139G amino acid substitution, and a murine 5HT3 IPD (SEQ ID NO:3).

In some cases, a modified LGIC described herein can include at least one chimeric α7-GlyR LGIC subunit (SEQ ID NO:7) having a human α7 nAChR LBD (SEQ ID NO:2) with a Q79G amino acid substitution and a Y115F amino acid substitution, and a human GlyR IPD (SEQ ID NO:5) with a A298G amino acid substitution.

In some cases, a modified LGIC described herein can include at least one chimeric α7-GlyR LGIC subunit (SEQ ID NO:7) having a human α7 nAChR LBD (SEQ ID NO:2) with a Q79G amino acid substitution and a Q139G amino acid substitution, and a human GlyR IPD (SEQ ID NO:5) with a A298G amino acid substitution.

In some cases, a modified LGIC described herein can include at least one chimeric α7-GlyR LGIC subunit (SEQ ID NO:7) having a human α7 nAChR LBD (SEQ ID NO:2) with a R27D amino acid substitution, a E41R amino acid substitution, a Q79G amino acid substitution, and a Y115F amino acid substitution, and a human GlyR IPD (SEQ ID NO:5) with a A298G amino acid substitution.

In some cases, a modified LGIC described herein can include at least one chimeric α7-GlyR LGIC subunit (SEQ ID NO:7) having a human α7 nAChR LBD (SEQ ID NO:2) with a substitution at amino acid residue 131 (e.g., L131G, L131A, L131M, or L131N), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 131 (e.g., L131G, L131A, L131M, or L131N) and Y115 (e.g., Y115F), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 131 (e.g., L131G, L131A, L131M, or L131N) and 139 (e.g., Q139L), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 131 (e.g., L131G, L131A, L131M, or L131N) and 217 (e.g., Y217F), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 131 (e.g., L131G, L131A, L131M, or L131N), 139 (e.g., Q139L), and 217 (e.g., Y217F), and a human GlyR IPD (SEQ ID NO:5).

In some cases, a modified LGIC described herein can include at least one chimeric α7-5HT3 LGIC subunit having a human α7 nAChR LBD (SEQ ID NO:2) with a substitution at amino acid residue 131 (e.g., L131G, L131A, L131M, or L131N), and a human 5HT3 IPD (SEQ ID NO:4).

In some cases, a modified LGIC described herein can include at least one chimeric α7-GlyR LGIC subunit (SEQ ID NO:7) having a human α7 nAChR LBD (SEQ ID NO:2) with a substitution at amino acid residue 175 (e.g., G175K), and a human GlyR IPD (SEQ ID NO:5).

In some cases, a modified LGIC described herein can include at least one chimeric α7-5HT3 LGIC subunit having a human α7 nAChR LBD (SEQ ID NO:2) with a substitution at amino acid residue 131 (e.g., L131G, L131A, L131M, or L131N) and 139 (e.g., Q139L), and a human 5HT3 IPD (SEQ ID NO:4) with a R420Q substitution, a R424D substitution, and a R428A substitution.

In some cases, a modified LGIC described herein can include at least one chimeric α7-5HT3 LGIC subunit having a human α7 nAChR LBD (SEQ ID NO:2) with a substitution at amino acid residue 131 (e.g., L131G, L131A, L131M, or L131N) and 139 (e.g., Q139L) and 217 (e.g., Y217F), and a human 5HT3 IPD (SEQ ID NO:4) with a R420Q substitution, a R424D substitution, and a R428A substitution.

In some cases, a modified LGIC described herein can include at least one chimeric α7-GlyR LGIC subunit (SEQ ID NO:7) having a human α7 nAChR LBD (SEQ ID NO:2) with a substitution at amino acid residues 175 (e.g., G175K) and 115 (e.g., Y115F), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2)

with a substitution at amino acid residues 175 (e.g., G175K) and 115 (e.g., Y115F) and 79 (e.g., Q79G), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 175 (e.g., G175K) and 77 (e.g., W77F) and 79 (e.g., Q79G), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residue 216 (e.g., P216I), and a human GlyR IPD (SEQ ID NO:5).

In some cases, a modified LGIC described herein can include at least one chimeric α7-GlyR LGIC subunit (SEQ ID NO:7) having a human α7 nAChR LBD (SEQ ID NO:2) with a substitution at amino acid residues 216 (e.g., P216I) and 79 (e.g., Q79G), and a human GlyR IPD (SEQ ID NO:5).

In some cases, a modified LGIC described herein can include at least one chimeric α7-GlyR LGIC subunit (SEQ ID NO:10) having a human α7 nAChR LBD (SEQ ID NO:2) with a substitution at amino acid residue 131 (e.g., L131A, L131G, L131M, L131N, L131Q, L131V, or L131F), and a human GABAc IPD (SEQ ID NO:9).

In some cases, a modified LGIC described herein can include one or more additional polypeptide sequences. A polypeptide sequence can be a transport sequence (e.g., an export sequence and/or a signal sequence). Examples of export sequences include, without limitation, ER export sequences (e.g., FCYENEV (SEQ ID NO:16)). Examples of signal sequences include, without limitation, CHRNB4 signal sequences (e.g., MRRAPSLVLFFLVALCGRGNC (SEQ ID NO:17)). A polypeptide sequence can be a targeting sequence. Examples of targeting sequences include, without limitation, KCNB1 somatic targeting sequences (e.g.,

QSQPILNTKEMAPQSKPPEELEMSSMPSPVAPLPARTEGVIDMRSMSSI

DSFISCATDFPEATRF (SEQ ID NO:18)).

The one or more additional polypeptide sequences can be included in a modified LGIC in any appropriate location. In some cases, an additional polypeptide sequence can be a terminal (e.g., a C-terminal or an N-terminal) polypeptide sequence. In some cases, an additional polypeptide sequence can be an insertion. In some cases, an additional polypeptide sequence can be a substitution.

In some cases, a modified LGIC described herein can include an export sequence. For example, a modified LGIC can include an ER export sequence (e.g., FCYENEV (SEQ ID NO:16). An exemplary modified LGIC containing a α7 nAChR LBD having a L131G substitution, a Q139L substitution, and a Y217F (e.g., each of which is relative to the residue numbering set forth in SEQ ID NO:1, SEQ ID NO:2, SEQ ID NO:11, or SEQ ID NO:12), and a GlyR IPD having an ER export sequence inserted between residues 142 and 143 (e.g., relative to the residue numbering set forth in SEQ ID NO:5) is shown in FIG. 16.

In some cases, a modified LGIC described herein can include a signal sequence. for example, a modified LGIC can include a CHRNB4 signal sequence (e.g., (SEQ ID NO: 17)
MRRAPSLVLFFLVALCGRGNC.

An exemplary modified LGIC containing a α7 nAChR LBD having a CHRNB4 signal sequence substituting residues 1-22, a L131G substitution, a Q139L substitution, and a Y217F (e.g., each of which is relative to the residue numbering set forth in SEQ ID NO:1, SEQ ID NO:2, SEQ ID NO:11, or SEQ ID NO:12), and a GlyR IPD is shown in FIG. 17.

In some cases, a modified LGIC described herein can include a targeting sequence. For example, a modified LGIC can include a KCNB1 somatic targeting sequence (e.g., (SEQ ID NO: 18)
QSQPILNTKEMAPQSKPPEELEMSSMPSPVAPLPARTEGVIDMRSMSSI

DSFISCATDFPEATRF.

An exemplary modified LGIC containing a α7 nAChR LBD having a L131G substitution, a Q139L substitution, and a Y217F (e.g., each of which is relative to the residue numbering set forth in SEQ ID NO:1, SEQ ID NO:2, SEQ ID NO:11, or SEQ ID NO:12), and a GlyR IPD having a KCNB1 somatic targeting sequence inserted between residues 142 and 143 (e.g., relative to the residue numbering set forth in SEQ ID NO:5) is shown in FIG. 18. In cases where a LBD and/or a IPD is a homolog, orthologue, or paralog of a sequence set forth herein (e.g., SEQ ID NOs:1-5 and/or 9), it is understood that reference to a particular modified amino acid residue can shift to the corresponding amino acid in the homolog, orthologue, or paralog. For example, residues 425, 429, and 433 in a murine 5HT3 IPD set forth in SEQ ID NO:3 correspond to residues 420, 424, and 428 in a human 5HT3 IPD set forth in SEQ ID NO:4, and the R425Q, R429D, and R433A substitutions in a murine 5HT3 IPD correspond to R420Q, R424D, and R428A substitutions in a human 5HT3 IPD.

Any method can be used to obtain a modified LGIC subunit described herein. In some cases, peptide synthesis methods can be used to make a modified LGIC subunit described herein. Examples of methods of peptide synthesis include, without limitation, liquid-phase peptide synthesis, and solid-phase peptide synthesis. In some cases, protein biosynthesis methods can be used to make a modified LGIC subunit described herein. Examples of methods of protein biosynthesis include, without limitation, transcription and/or translation of nucleic acids encoding a phosphorylation-mimicking peptide provided herein. Similar modified LGIC subunits (e.g., modified subunits having essentially the same modifications and/or having essentially the same amino acid sequence) will self-assemble through interactions between the LBDs to form a modified LGIC.

This document also provides nucleic acids encoding modified LGIC subunits described herein as well as constructs (e.g., synthetic constructs such as plasmids, non-viral vectors, viral vectors (such as adeno-associated virus, a herpes simplex virus, or lentivirus vectors)) for expressing nucleic acids encoding modified LGIC subunits described herein.

A nucleic acid sequence encoding modified LGIC subunit described herein can encode any LGIC described herein. In some cases, a nucleic acid sequence provided herein can encode a LBD from any LGIC described herein. In some cases, a nucleic acid sequence provided herein can encode an IPD from any LGIC described herein. In cases where a nucleic acid sequence provided herein encodes a chimeric LGIC, the chimeric LGIC can include a LBD selected from any appropriate LGIC and an IPD selected from any appropriate LGIC.

In some cases, a nucleic acid sequence can encode a LGIC described herein. For example, a nucleic acid sequence can encode a nAChR (e.g., a α7 nAChR). A representative nucleic acid sequence encoding a rat α7 nAChR amino acid sequence (including both a LBD and an IPD) is as follows.

SEQ ID NO: 19
ATGGGCGGCGGGCGGGGAGGCATCTGGCTGGCTCTGGCCGCGGCGCTGCT

GCACGTGTCCCTGCAAGGCGAGTTCCAGAGGAGGCTGTACAAGGAGCTGG

TCAAGAACTACAACCCGCTGGAGAGGCCGGTGGCCAACGACTCGCAGCCG

CTCACCGTGTACTTCTCCCTGAGTCTCCTGCAGATCATGGATGTGGATGA

GAAGAACCAAGTTTTAACCACCAACATTTGGCTACAAATGTCTTGGACAG

ATCACTATTTGCAGTGGAACATGTCTGAGTACCCCGGAGTGAAGAATGTT

CGTTTTCCAGATGGCCAGATTTGGAAACCAGACATTCTCCTCTATAACAG

TGCTGATGAGCGCTTTGATGCCACGTTCCACACCAATGTTTTGGTGAATG

CATCTGGGCATTGCCAGTATCTCCCTCCAGGCATATTCAAGAGCTCCTGC

TACATTGACGTTCGCTGGTTCCCTTTTGATGTGCAGCAGTGCAAACTGAA

GTTTGGGTCCTGGTCCTATGGAGGGTGGTCACTGGACCTGCAAATGCAAG

AGGCAGATATCAGCAGCTATATCCCCAACGGAGAATGGGATCTCATGGGA

ATCCCTGGCAAAAGGAATGAGAAGTTCTATGAGTGCTGCAAAGAGCCATA

CCCAGATGTCACCTACACAGTAACCATGCGCCGTAGGACACTCTACTATG

GCCTCAATCTGCTCATCCCTTGTGTACTCATTTCAGCCCTGGCTCTGCTG

GTATTCTTGCTGCCTGCAGACTCTGGAGAGAAAATCTCTCTTGGAATAAC

TGTCTTACTTTCTCTGACTGTCTTCATGCTGCTTGTGGCTGAGATCATGC

CAGCAACATCTGATTCTGTGCCCTTGATAGCACAATACTTCGCCAGCACC

ATGATCATCGTGGGCCTCTCTGTAGTGGTGACAGTGATTGTGCTGAGATA

TCACCACCATGACCCTGATGGTGGCAAAATGCCTAAGTGGACCAGAATCA

TTCTCCTGAACTGGTGTGCATGGTTTCTGCGCATGAAGAGGCCCGGAGAG

GACAAGGTGCGGCCAGCTTGTCAGCACAAGCCTCGGCGCTGCAGCCTGGC

CAGTGTGGAGCTGAGTGCAGGTGCTGGGCCACCCACCAGCAATGGCAACC

TGCTCTACATTGGCTTCCGAGGCCTGGAGGGCATGCACTGTGCCCCAACT

CCAGACTCTGGGGTCGTATGTGGCCGTTTGGCCTGCTCCCCAACACATGA

TGAGCACCTCATGCACGGTGCACACCCCTCTGATGGGGACCCCGACCTGG

CCAAGATCCTGGAGGAGGTCCGCTACATCGCCAACCGCAACCGCTGCCAG

GACGAGAGTGAGGTGATCTGCAGTGAATGGAAGTTTGCAGCCTGCGTGGT

GGACCCGCTTTGCCTCATGGCCTTTTCGGTCTTTACCATCATCTGTACCA

TCGGCATCCTCATGTCAGCTCCAAACTTTGTGGAGGCTGTGTCCAAAGAC

TTTGCTTAA

In some cases, a nucleic acid sequence encoding a modified LGIC subunit described herein can encode a LBD from a α7 nAChR. Examples of nucleic acid sequences encoding α7 nAChR LBDs include, without limitation, a nucleic acid sequence set forth in SEQ ID NO:20, a nucleic acid sequence set forth in SEQ ID NO:21, and a nucleic acid sequence set forth in SEQ ID NO:22. In some cases, a nucleic acid sequence encoding α7 nAChR LBD can have at least 75 percent sequence identity (e.g., at least 80%, at least 82%, at least 85%, at least 88%, at least 90%, at least 93%, at least 95%, at least 97% or at least 99% sequence identity) to SEQ ID NO:20, SEQ ID NO:21, or SEQ ID NO:22.

SEQ ID NO: 20
ATGCGCTGTTCTCCAGGCGGCGTGTGGCTCGCCCTGGCTGCTTCCCTTCT
GCACGTTAGCCTGCAGGGTGAGTTCCAGCGCAAACTGTATAAGGAGCTTG
TTAAGAATTATAACCCCCTGGAGCGGCCGGTCGCAAATGATTCCCAGCCA
CTGACAGTGTACTTCAGCCTCTCCTTGCTGCAGATCATGGACGTGGATGA
AAAGAACCAGGTGCTGACCACTAATATTTGGTTGCAGATGTCCTGGACCG
ATCACTACTTGCAGTGGAATGTGAGCGAATACCCAGGTGTAAAGACTGTA
AGATTCCCTGACGGCCAAATCTGGAAACCAGATATCCTGCTGTACAACAG
CGCAGACGAAAGGTTTGATGCAACATTTCACACCAACGTGTTGGTCAATT
CTTCAGGCCACTGCCAGTACCTGCCCCCTGGAATCTTCAAGTCCTCATGC
TATATCGACGTCCGCTGGTTTCCCTTCGACGTCCAGCACTGCAAACTCAA
ATTCGGGAGCTGGAGCTACGGCGGATGGAGCCTGGATCTGCAAATGCAGG
AGGCTGACATCTCTGGTTACATCCCGAATGGGGAGTGGGACCTTGTGGGA
ATCCCCGGTAAAAGAAGCGAGCGATTTTATGAATGCTGCAAGGAACCCTA
CCCTGACGTAACATTCACAGTT

SEQ ID NO: 21
ATGCGCTGTTCTCCAGGCGGCGTGTGGCTCGCCCTGGCTGCTTCCCTTCT
GCACGTTAGCCTGCAGGGTGAGTTCCAGCGCAAACTGTATAAGGAGCTTG
TTAAGAATTATAACCCCCTGGAGCGGCCGGTCGCAAATGATTCCCAGCCA
CTGACAGTGTACTTCAGCCTCTCCTTGCTGCAGATCATGGACGTGGATGA
AAAGAACCAGGTGCTGACCACTAATATTTGGTTGCAGATGTCCTGGACCG
ATCACTACTTGCAGTGGAATGTGAGCGAATACCCAGGTGTAAAGACTGTA
AGATTCCCTGACGGCCAAATCTGGAAACCAGATATCCTGCTGTACAACAG
CGCAGACGAAAGGTTTGATGCAACATTTCACACCAACGTGTTGGTCAATT
CTTCAGGCCACTGCCAGTACCTGCCCCCTGGAATCTTCAAGTCCTCATGC
TATATCGACGTCCGCTGGTTTCCCTTCGACGTCCAGCACTGCAAACTCAA
ATTCGGGAGCTGGAGCTACGGCGGATGGAGCCTGGATCTGCAAATGCAGG
AGGCTGACATCTCTGGTTACATCCCGAATGGGGAGTGGGACCTTGTGGGA
ATCCCCGGTAAAAGAAGCGAGCGATTTTATGAATGCTGCAAAGAGCCCTA
CCCAGATGTCACCTTCACAGTGACCATGCGGAGACGC

SEQ ID NO: 22
ATGCGCTGTTCTCCAGGCGGCGTGTGGCTCGCCCTGGCTGCTTCCCTTCT
GCACGTTAGCCTGCAGGGTGAGTTCCAGCGCAAACTGTATAAGGAGCTTG
TTAAGAATTATAACCCCCTGGAGCGGCCGGTCGCAAATGATTCCCAGCCA
CTGACAGTGTACTTCAGCCTCTCCTTGCTGCAGATCATGGACGTGGATGA
AAAGAACCAGGTGCTGACCACTAATATTTGGTTGCAGATGTCCTGGACCG
ATCACTACTTGCAGTGGAATGTGAGCGAATACCCAGGTGTAAAGACTGTA
AGATTCCCTGACGGCCAAATCTGGAAACCAGATATCCTGCTGTACAACAG
CGCAGACGAAAGGTTTGATGCAACATTTCACACCAACGTGTTGGTCAATT
CTTCAGGCCACTGCCAGTACCTGCCCCCTGGAATCTTCAAGTCCTCATGC
TATATCGACGTCCGCTGGTTTCCCTTCGACGTCCAGCACTGCAAACTCAA
ATTCGGGAGCTGGAGCTACGGCGGATGGAGCCTGGATCTGCAAATGCAGG
AGGCTGACATCTCTGGTTACATCCCGAATGGGGAGTGGGACCTTGTGGGA
ATCCCCGGTAAAAGAAGCGAGCGATTTTATGAATGCTGCAAAGAGCCCTA
CCCAGATGTCACCTTCACAGTGACCATGCGGAGACGCACACTGTATTAC

In some cases, a nucleic acid sequence encoding a modified LGIC subunit described herein can encode an IPD from a 5HT3 receptor. Examples of nucleic acid sequences encoding 5HT3 IPDs include, without limitation, a nucleic acid sequence set forth in SEQ ID NO:23, and a nucleic acid sequence set forth in SEQ ID NO:24. In some cases, a nucleic acid sequence encoding a 5HT3 IPD can have at least 75 percent sequence identity (e.g., at least 80%, at least 82%, at least 85%, at least 88%, at least 90%, at least 93%, at least 95%, at least 97% or at least 99% sequence identity) to SEQ ID NO:23 or SEQ ID NO:24.

SEQ ID NO: 23
ATCATCAGAAGAAGGCCATTGTTCTACGCCGTTAGTTTGTTGCTCCCCAG
TATTTTTCTCATGGTCGTGGACATCGTGGGATTTTGTCTCCCACCTGATA
GCGGGGAGAGGGTCTCCTTTAAGATTACCTTGTTGCTCGGCTATTCTGTA
TTTCTGATCATCGTGTCCGATACCCTTCCTGCCACAATCGGCACTCCGCT
GATAGGAGTGTATTTCGTCGTGTGTATGGCACTCCTGGTGATAAGTCTGG
CGGAAACTATCTTCATTGTACGGCTGGTACATAAGCAGGACCTGCAAAGA
CCCGTGCCAGACTGGTTGCGACACCTTGTGCTGGACAGAATTGCATGGAT
TCTGTGTCTTGGCGAGCAACCTATGGCCCACCGGCCACCTGCAACCTTTC
AAGCCAACAAGACAGACGATTGTAGTGGGTCTGATCTGTTGCCTGCTATG
GGGAATCACTGCTCCCATGTTGGGGGACCACAAGATTTGGAAAAGACCCC
ACGGGGCGGGATCACCCCTTCCTCCTCCCCGAGAAGCCTCTCTCGCTG
TCCGGGGCTGCTCCAGGAACTGTCAAGCATCCGACATTTTCTGGAGAAG
CGGGACGAGATGAGGGAAGTCGCTAGAGACTGGCTGCGAGTGGGCTACGT
CCTTGACAGGCTGCTGTTTCGGATCTACTTGCTGGCGGTGCTGGCTTATT
CCATTACTCTGGTGACACTCTGGTCCATATGGCACTACAGTTAG

SEQ ID NO: 24
ATCATCCGTAGAAGGCCTCTGTTTTACGTGGTGAGCCTGCTGCTGCCATC
CATCTTCCTGATGGTCATGGACATCGTGGGCTTTTACCTGCCACCCAATT
CTGGCGAGCGCGTGAGCTTCAAGATCACACTGCTGCTGGGCTATAGCGTG
TTTCTGATCATCGTGTCCGATACCCTGCCTGCAACAGCAATCGGAACCCC
ACTGATCGGCGTGTATTTCGTGGTGTGCATGGCCCTGCTGGTCATCAGCC
TGGCCGAGACAATCTTTATCGTGCGGCTGGTGCACAAGCAGGACCTGCAG
CAGCCTGTGCCAGCATGGCTGAGGCACCTGGTGCTGGAGAGGATCGCATG
GCTGCTGTGCCTGAGAGAGCAGTCCACATCTCAGAGGCCTCCAGCCACCT
CTCAGGCCACCAAGACAGACGATTGCTCTGCCATGGGCAATCACTGTAGC
CACATGGGCGGCCCCCAGGACTTTGAGAAGTCCCCTCGCGATCGGTGCTC
TCCACCTCCACCACCTAGGGAGGCCAGCCTGGCCGTGTGCGCCTGCTGC

-continued

```
AGGAGCTGTCCTCTATCCGGCAGTTCCTGGAGAAGCGCGACGAGATCCGG

GAGGTGGCCAGAGATTGGCTGAGGGTGGGCAGCGTGCTGGATAAGCTGCT

GTTTCACATCTACCTGCTGGCAGTCCTGGCCTATTCTATTACCCTGGTCA

TGCTGTGGTCCATCTGGCAGTACGCC
```

In some cases, a nucleic acid sequence encoding a modified LGIC subunit described herein can encode an IPD from a GlyR. Examples of nucleic acid sequences encoding GlyR IPDs include, without limitation, a nucleic acid sequence set forth in SEQ ID NO:5. In some cases, a GlyR IPD can be a homolog, orthologue, or paralog of the human GlyR IPD set forth in SEQ ID NO:5. In some cases, a GlyR IPD can be have at least 75 percent sequence identity (e.g., at least 80%, at least 82%, at least 85%, at least 88%, at least 90%, at least 93%, at least 95%, at least 97% or at least 99% sequence identity) to SEQ ID NO:25.

```
                                    SEQ ID NO: 25
ATGGGTTATTATCTGATCCAAATGTATATCCCAAGCTTGCTTATAGTGAT

TTTGTCATGGATCTCCTTCTGGATTAATATGGACGCCGCTCCAGCTAGGG

TCGGACTGGGCATCACCACAGTGCTGACAATGACTACTCAGAGCTCAGGC

AGCCGAGCCAGCTTGCCCAAGGTTTCTTACGTGAAGGCCATCGATATCTG

GATGGCTGTCTGCCTTCTGTTTGTCTTCAGCGCACTGCTGGAATACGCCG

CTGTCAATTTTGTGTCTCGACAGCATAAAGAGCTGTTGCGGTTCAGAAGA

AAACGACGCCACCACAAAGAGGATGAGGCAGGAGAAGGACGCTTCAACTT

TAGCGCCTATGGTATGGGACCTGCTTGCCTCCAGGCTAAAGACGGAATTT

CCGTGAAGGGAGCCAACAATAGCAACACAACCAACCCACCCCCTGCTCCA

TCTAAGAGCCCGGAGGAAATGCGCAAACTCTTTATTCAGAGAGCGAAAAA

GATCGACAAAATCTCCCGGATCGGATTCCCCATGGCTTTCCTGATTTTCA

ACATGTTTTATTGGATCATCTACAAGATTGTGCGAAGGGAGGACGTACAC

AACCAGTAA
```

In some cases, a nucleic acid sequence encoding a modified LGIC subunit described herein can encode an IPD from a GABA receptor (e.g., GABA$_A$-ρ, also referred to as GABAc). Examples of nucleic acid sequences encoding GABA$_A$-ρ IPDs include, without limitation, a nucleic acid sequence set forth in SEQ ID NO:26. In some cases, a GABA$_A$-ρ IPD can be have at least 75 percent sequence identity (e.g., at least 80%, at least 82%, at least 85%, at least 88%, at least 90%, at least 93%, at least 95%, at least 97% or at least 99% sequence identity) to SEQ ID NO:26.

```
                                    SEQ ID NO: 26
CTTTTGCAAACTTACTTTCCAGCAACCCTCATGGTGATGCTTTCATGGGT

GTCCTTTTGGATCGACCGCCGAGCGGTCCCTGCACGGGTCCCCCTGGGGA

TTACGACGGTACTGACCATGAGCACCATAATCACTGGAGTCAATGCAAGC

ATGCCTAGAGTGTCTTACATAAAGGCCGTGGACATCTATCTGTGGGTTAG

TTTTGTGTTCGTATTCCTCTCCGTGCTGGAGTATGCAGCTGTGAACTATC

TGACAACAGTTCAAGAGCGGAAAGAGCAGAAGTTGAGGGAGAAGCTGCCA

TGCACTAGCGGACTGCCACCGCCCAGAACCGCTATGCTCGATGGTAACTA

TTCCGACGGCGAAGTTAATGACCTCGATAACTACATGCCTGAAAATGGCG

AAAAGCCCGACAGGATGATGGTCCAGCTGACACTGGCCTCAGAAAGGTCC

AGTCCACAGAGAAAGTCACAGCGATCCTCTTACGTCAGCATGCGCATCGA

TACACATGCCATCGACAAATACTCTCGCATTATCTTTCCGGCTGCTTACA

TATTGTTCAACCTTATCTATTGGAGCATTTTCAGTTGA
```

In calculating percent sequence identity, two sequences are aligned and the number of identical matches of amino acid residues between the two sequences is determined. The number of identical matches is divided by the length of the aligned region (i.e., the number of aligned nucleic acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. The alignment of two or more sequences to determine percent sequence identity can be performed using the computer program ClustalW and default parameters, which calculates the best match between a query and one or more subject sequences, and aligns them so that identities, similarities and differences can be determined. See, e.g., Chenna et al., 2003, Nucleic Acids Res., 31(13):3497-500.

A nucleic acid sequence encoding a modified LGIC described herein can include at least one modified nucleic acid such that the nucleic acid sequence can encode a LBD having at least one modified amino acid and/or an IPD having at least one modified amino acid. In some cases, a nucleic acid sequence encoding a modified LGIC described herein can include more than one (e.g., two, three, four, five, six, seven, eight, nine, ten, eleven, twelve, or more) modified nucleic acids. For example, a nucleic acid sequence can encode a modified LGIC subunit including a α7 LBD having at least 75 percent sequence identity to SEQ ID NO:1, SEQ ID NO:2, SEQ ID NO:11, or SEQ ID NO:12, and an amino acid substitution at amino acid residue 27, 41, 77, 79, 131, 139, 141, 175, 210, 216, 217, and/or 219. Examples of nucleic acid codons at codon numbers 27, 41, 77, 79, 131, 139, 141, 175, 210, 216, 217, and/or 219 that can results amino acid substitutions at amino acid residues 27, 41, 77, 79, 131, 139, 141, 175, 210, 216, 217, and/or 219 can be as shown below.

TABLE 12

Codon usage resulting in LBD amino acid substitutions

| WT amino acid residue | Modified amino acid: Modified nucleic acid codon |
|---|---|
| R27 | D: GAC |
| E41 | R: AGG |
| W77 | F: TTC, Y: TAC |
| Q79 | A: GCA, G: GGC, S: TCG |
| Y115 | F: TTC |
| L131 | A: GCG, F: TTC, G: GGA, I: ATA, M: ATG, N: AAC, Q: CAA, V: GTG |
| Q139 | G: GGC, L: CTG |

TABLE 12-continued

Codon usage resulting in LBD amino acid substitutions

| WT amino acid residue | Modified amino acid: Modified nucleic acid codon |
|---|---|
| L141 | F: TTC or TTT |
| G175 | A: GCA, F: TTC, H: CAC, K: AAA, M: ATG, R: CGA, S: TCA, V: GTA |
| Y210 | F: TTT |
| P216 | I: ATC |
| Y217 | F: TTC |
| D219 | A: GCT |
| W298 | A: GCG |

For example, a nucleic acid sequence can encode a modified LGIC subunit including a GlyR IPD having at least 75 percent sequence identity to a sequence set forth in SEQ ID NO:5, and an amino acid substitution at amino acid residue 298 of an α7-GlyR IPD. Examples of nucleic acid codons at codon number 298 that can result in an amino acid substitution at amino acid residue 298 can be as shown below.

TABLE 13

Codon usage resulting in GlyR IPD amino acid substitutions

| WT amino acid residue | Modified amino acid: Modified nucleic acid codon |
|---|---|
| A298 | G: GGT |

* numbering is relative to the residue numbering set forth in SEQ ID NO: 7

For example, a nucleic acid sequence can encode a modified LGIC subunit including a GABAC IPD having at least 75 percent sequence identity to SEQ ID NO:9, and an amino acid substitution at amino acid residue 298 of an α7-GABAC chimeric receptor. Examples of nucleic acid codons at codon number 298 that can result in an amino acid substitution at amino acid residue 298 can be as shown below

TABLE 14

Codon usage resulting in GABAC IPD amino acid substitutions

| WT amino acid residue | Modified amino acid: Modified nucleic acid codon |
|---|---|
| W298* | A: GCG |

*numbering is relative to the residue numbering set forth in SEQ ID NO: 10

In some cases, a nucleic acid sequence encoding a modified LGIC described herein can encode a α7-5HT3 chimeric receptor as set forth in SEQ ID NO:6 (e.g., including a human α7 nAChR LBD (SEQ ID NO:1) and a murine 5HT3 IPD (SEQ ID NO:3) components). Examples of nucleic acid sequences encoding a α7-5HT3 chimeric receptor including a human α7 nAChR LBD and a murine 5HT3 IPD include, without limitation, a nucleic acid sequence set forth in SEQ ID NO:27.

SEQ ID NO: 27
ATGCGCTGTTCTCCAGGCGGCGTGTGGCTCGCCCTGGCTGCTTCCCTTCT

GCACGTTAGCCTGCAGGGTGAGTTCCAGCGCAAACTGTATAAGGAGCTTG

TTAAGAATTATAACCCCCTGGAGCGGCCGGTCGCAAATGATTCCCAGCCA

CTGACAGTGTACTTCAGCCTCTCCTTGCTGCAGATCATGGACGTGGATGA

AAAGAACCAGGTGCTGACCACTAATATTTGGTTGCAGATGTCCTGGACCG

ATCACTACTTGCAGTGGAATGTGAGCGAATACCCAGGTGTAAAGACTGTA

AGATTCCCTGACGGCCAAATCTGGAAACCAGATATCCTGCTGTACAACAG

CGCAGACGAAAGGTTTGATGCAACATTTCACACCAACGTGTTGGTCAATT

CTTCAGGCCACTGCCAGTACCTGCCCCCTGGAATCTTCAAGTCCTCATGC

TATATCGACGTCCGCTGGTTTCCCTTCGACGTCCAGCACTGCAAACTCAA

ATTCGGGAGCTGGAGCTACGGCGGATGGAGCCTGGATCTGCAAATGCAGG

AGGCTGACATCTCTGGTTACATCCCGAATGGGGAGTGGGACCTTGTGGGA

ATCCCCGGTAAAAGAAGCGAGCGATTTTATGAATGCTGCAAGGAACCCTA

CCCTGACGTAACATTCACAGTTATCATCAGAAGAAGGCCATTGTTCTACG

CCGTTAGTTTGTTGCTCCCCAGTATTTTTCTCATGGTCGTGGACATCGTG

GGATTTTGTCTCCCACCTGATAGCGGGGAGAGGGTCTCCTTTAAGATTAC

CTTGTTGCTCGGCTATTCTGTATTTCTGATCATCGTGTCCGATACCCTTC

CTGCCACAATCGGCACTCCGCTGATAGGAGTGTATTTCGTCGTGTGTATG

GCACTCCTGGTGATAAGTCTGGCGGAAACTATCTTCATTGTACGGCTGGT

ACATAAGCAGGACCTGCAAAGACCCGTGCCAGACTGGTTGCGACACCTTG

TGCTGGACAGAATTGCATGGATTCTGTGTCTTGGCGAGCAACCTATGGCC

CACCGGCCACCTGCAACCTTTCAAGCCAACAAGACAGACGATTGTAGTGG

GTCTGATCTGTTGCCTGCTATGGGAATCACTGCTCCCATGTTGGGGGAC

CACAAGATTTGGAAAAGACCCCACGGGGCGGGGATCACCCCTTCCTCCT

CCCCGAGAAGCCTCTCTCGCTGTCCGGGGGCTGCTCCAGGAACTGTCAAG

CATCCGACATTTTCTGGAGAAGCGGGACGAGATGAGGGAAGTCGCTAGAG

ACTGGCTGCGAGTGGGCTACGTCCTTGACAGGCTGCTGTTTCGGATCTAC

TTGCTGGCGGTGCTGGCTTATTCCATTACTCTGGTGACACTCTGGTCCAT

ATGGCACTACAGTTAG

In some cases, a nucleic acid sequence encoding a modified LGIC described herein can encode a α7-GlyR chimeric receptor as set forth in SEQ ID NO:7 (e.g., including a human α7 nAChR LBD (SEQ ID NO:2) and a human GlyR IPD (SEQ ID NO:5)). Examples of nucleic acid sequences encoding a α7-GlyR chimeric receptor including a human α7 nAChR LBD and a human GlyR IPD include, without limitation, a nucleic acid sequence set forth in SEQ ID NO:28.

SEQ ID NO: 28
ATGCGCTGTTCTCCAGGCGGCGTGTGGCTCGCCCTGGCTGCTTCCCTTCT

GCACGTTAGCCTGCAGGGTGAGTTCCAGCGCAAACTGTATAAGGAGCTTG

TTAAGAATTATAACCCCCTGGAGCGGCCGGTCGCAAATGATTCCCAGCCA

CTGACAGTGTACTTCAGCCTCTCCTTGCTGCAGATCATGGACGTGGATGA

```
AAAGAACCAGGTGCTGACCACTAATATTTGGTTGCAGATGTCCTGGACCG

ATCACTACTTGCAGTGGAATGTGAGCGAATACCCAGGTGTAAAGACTGTA

AGATTCCCTGACGGCCAAATCTGGAAACCAGATATCCTGCTGTACAACAG

CGCAGACGAAAGGTTTGATGCAACATTTCACACCAACGTGTTGGTCAATT

CTTCAGGCCACTGCCAGTACCTGCCCCCTGGAATCTTCAAGTCCTCATGC

TATATCGACGTCCGCTGGTTTCCCTTCGACGTCCAGCACTGCAAACTCAA

ATTCGGGAGCTGGAGCTACGGCGGATGGAGCCTGGATCTGCAAATGCAGG

AGGCTGACATCTCTGGTTACATCCCGAATGGGGAGTGGGACCTTGTGGGA

ATCCCCGGTAAAAGAAGCGAGCGATTTTATGAATGCTGCAAAGAGCCCTA

CCCAGATGTCACCTTCACAGTGACCATGCGGAGACGCATGGGTTATTATC

TGATCCAAATGTATATCCCAAGCTTGCTTATAGTGATTTTGTCATGGATC

TCCTTCTGGATTAATATGGACGCCGCTCCAGCTAGGGTCGGACTGGGCAT

CACCACAGTGCTGACAATGACTACTCAGAGCTCAGGCAGCCGAGCCAGCT

TGCCCAAGGTTTCTTACGTGAAGGCCATCGATATCTGGATGGCTGTCTGC

CTTCTGTTTGTCTTCAGCGCACTGCTGGAATACGCCGCTGTCAATTTTGT

GTCTCGACAGCATAAAGAGCTGTTGCGGTTCAGAAGAAAACGACGCCACC

ACAAAGAGGATGAGGCAGGAGAAGGACGCTTCAACTTTAGCGCCTATGGT

ATGGGACCTGCTTGCCTCCAGGCTAAAGACGGAATTTCCGTGAAGGGAGC

CAACAATAGCAACACAACCAACCCACCCCCTGCTCCATCTAAGAGCCCGG

AGGAAATGCGCAAACTCTTTATTCAGAGAGCGAAAAAGATCGACAAAATC

TCCCGGATCGGATTCCCCATGGCTTTCCTGATTTTCAACATGTTTTATTG

GATCATCTACAAGATTGTGCGAAGGGAGGACGTACACAACCAGTAA
```

In some cases, a nucleic acid sequence encoding a modified LGIC described herein can encode a α7-GABAC chimeric receptor set forth in SEQ ID NO:10 (e.g., including a human α7 nAChR LBD (SEQ ID NO:2) and a human GABAC IPD (SEQ ID NO:9)). Examples of nucleic acid sequences encoding a including a human α7 nAChR LBD (SEQ ID NO:2) and a human GABAC IPD (SEQ ID NO:9) chimeric receptor including a human α7 nAChR LBD and a human GABAC IPD include, without limitation, a nucleic acid sequence set forth in SEQ ID NO:29.

```
                                           SEQ ID NO: 29
ATGCGCTGTTCTCCAGGCGGCGTGTGGCTCGCCCTGGCTGCTTCCCTTCT

GCACGTTAGCCTGCAGGGTGAGTTCCAGCGCAAACTGTATAAGGAGCTTG

TTAAGAATTATAACCCCCTGGAGCGGCCGGTCGCAAATGATTCCCAGCCA

CTGACAGTGTACTTCAGCCTCTCCTTGCTGCAGATCATGCGACGTGGATGA

AAAGAACCAGGTGCTGACCACTAATATTTGGTTGCAGATGTCCTGGACCG

ATCACTACTTGCAGTGGAATGTGAGCGAATACCCAGGTGTAAAGACTGTA

AGATTCCCTGACGGCCAAATCTGGAAACCAGATATCCTGCTGTACAACAG

CGCAGACGAAAGGTTTGATGCAACATTTCACACCAACGTGTTGGTCAATT

CTTCAGGCCACTGCCAGTACCTGCCCCCTGGAATCTTCAAGTCCTCATGC

TATATCGACGTCCGCTGGTTTCCCTTCGACGTCCAGCACTGCAAACTCAA

ATTCGGGAGCTGGAGCTACGGCGGATGGAGCCTGGATCTGCAAATGCAGG

AGGCTGACATCTCTGGTTACATCCCGAATGGGGAGTGGGACCTTGTGGGA

ATCCCCGGTAAAAGAAGCGAGCGATTTTATGAATGCTGCAAAGAGCCCTA

CCCAGATGTCACCTTCACAGTGACCATGCGGAGACGCACACTGTATTACC

TTTTGCAAACTTACTTTCCAGCAACCCTCATGGTGATGCTTTCATGGGTG

TCCTTTTGGATCGACCGCCGAGCGGTCCCTGCACGGGTCCCCCTGGGGAT

TACGACGGTACTGACCATGAGCACCATAATCACTGGAGTCAATGCAAGCA

TGCCTAGAGTGTCTTACATAAAGGCCGTGGACATCTATCTGTGGGTTAGT

TTTGTGTTCGTATTCCTCTCCGTGCTGGAGTATGCAGCTGTGAACTATCT

GACAACAGTTCAAGAGCGGAAAGAGCAGAAGTTGAGGGAGAAGCTGCCAT

GCACTAGCGGACTGCCACCGCCCAGAACCGCTATGCTCGATGGTAACTAT

TCCGACGGCGAAGTTAATGACCTCGATAACTACATGCCTGAAAATGGCGA

AAAGCCCGACAGGATGATGGTCCAGCTGACACTGGCCTCAGAAAGGTCCA

GTCCACAGAGAAAGTCACAGCGATCCTCTTACGTCAGCATGCGCATCGAT

ACACATGCCATCGACAAATACTCTCGCATTATCTTTCCGGCTGCTTACAT

ATTGTTCAACCTTATCTATTGGAGCATTTTCAGTTGA
```

In some cases, a nucleic acid sequence encoding a modified LGIC described herein can include a nucleic acid sequence encoding one or more additional polypeptide sequences (e.g., a transport sequence such as an export sequence and/or a signal sequence, or a targeting sequence). Examples of nucleic acid sequences encoding export sequences include, without limitation, a nucleic acid sequence encoding an ER export sequence (e.g.,

```
          TTTTGCTATGAAAACGAAGTC; SEQ ID NO: 30).
```

Examples of nucleic acid sequences encoding signal sequences include, without limitation, a nucleic acid sequence encoding a CHRNB4 signal sequence (e.g.,

```
ATGAGAAGGGCCCCATCCCTGGTATTGTTTTTTTTGGTAGCTTTGTGCG

GGAGGGGGAACTGC; SEQ ID NO: 31).
```

Examples of nucleic acid sequences encoding targeting sequences include, without limitation, a nucleic acid sequence encoding a KCNB1 somatic targeting sequence (e.g.,

```
CAAAGCCAACCTATCCTTAACACTAAAGAGAGCGCCGCTCAATCCAAAC

CCAAAGAAGAGTTGGAAATGGAGTCTATACCTTCACCTGTTGCACCTCT

CCCTACTAGGACCGAAGGCGTGATTGACATGCGCTCTATGTCTAGTATA

GATAGCTTTATATCCTGCGCCACAGACTTTCCCGAAGCCACTAGGTTC;

SEQ ID NO: 32).
```

In some cases, a nucleic acid encoding a modified LGIC subunit described herein can be linked (e.g., operably linked) to one or more regulatory elements. For example, nucleic acids encoding modified LGIC subunits described herein can be operably linked to any appropriate promoter. A promoter can be a native (i.e., minimal) promoter or a composite promoter. A promoter can be a ubiquitous (i.e., constitutive) promoter or a regulated promoter (e.g., inducible, tissue specific, cell-type specific (e.g., neuron specific, muscle specific, glial specific), and neural subtype-specific). Examples of promoters that can be used to drive expression of nucleic acids encoding modified LGIC subunits described herein include, without limitation, synapsin (SYN), CAM-KII, CMV, CAG, enolase, TRPV1, POMC, NPY, AGRP, MCH, and Orexin promoters. In some cases, a nucleic acid encoding a modified LGIC subunit described herein can be operably linked to a neuron specific promoter.

Figure 19A:
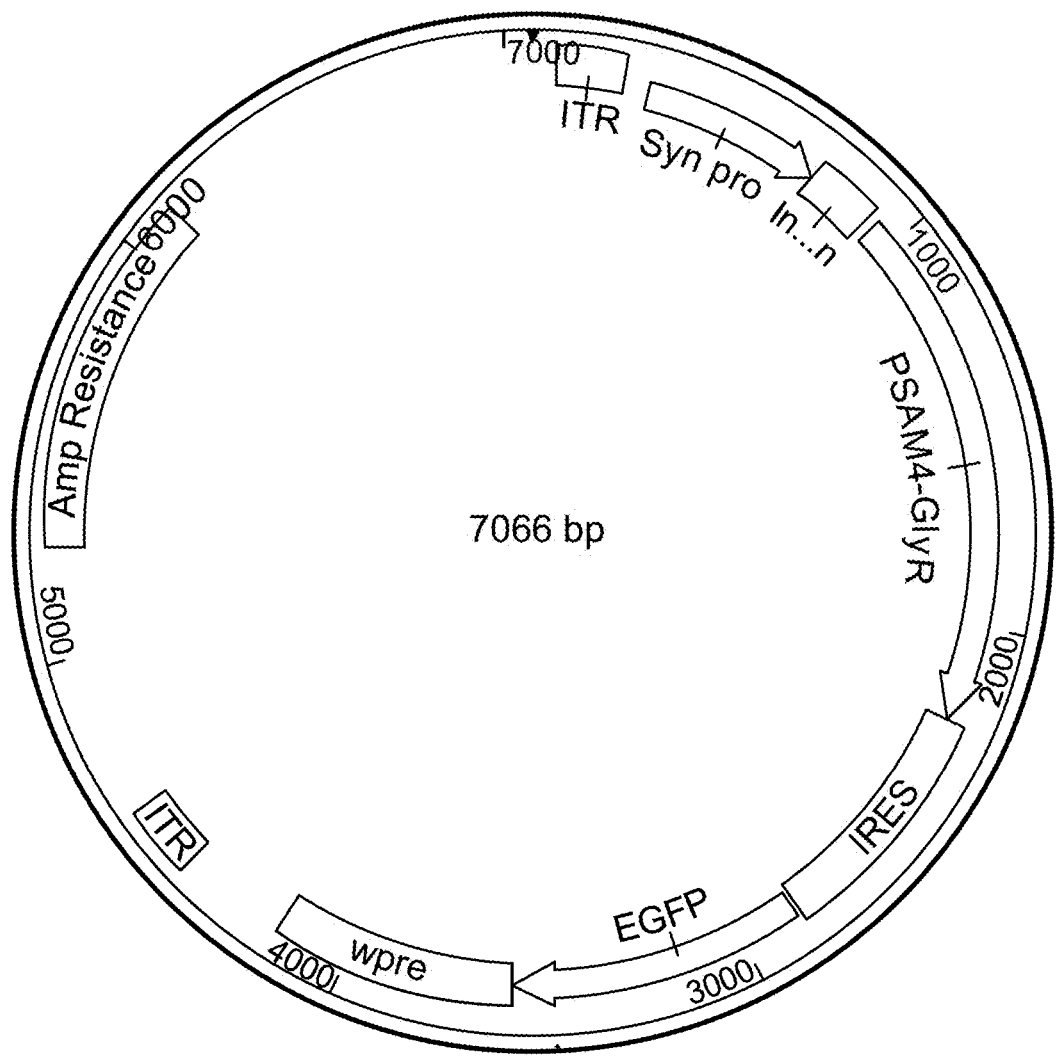
Figure 20A:
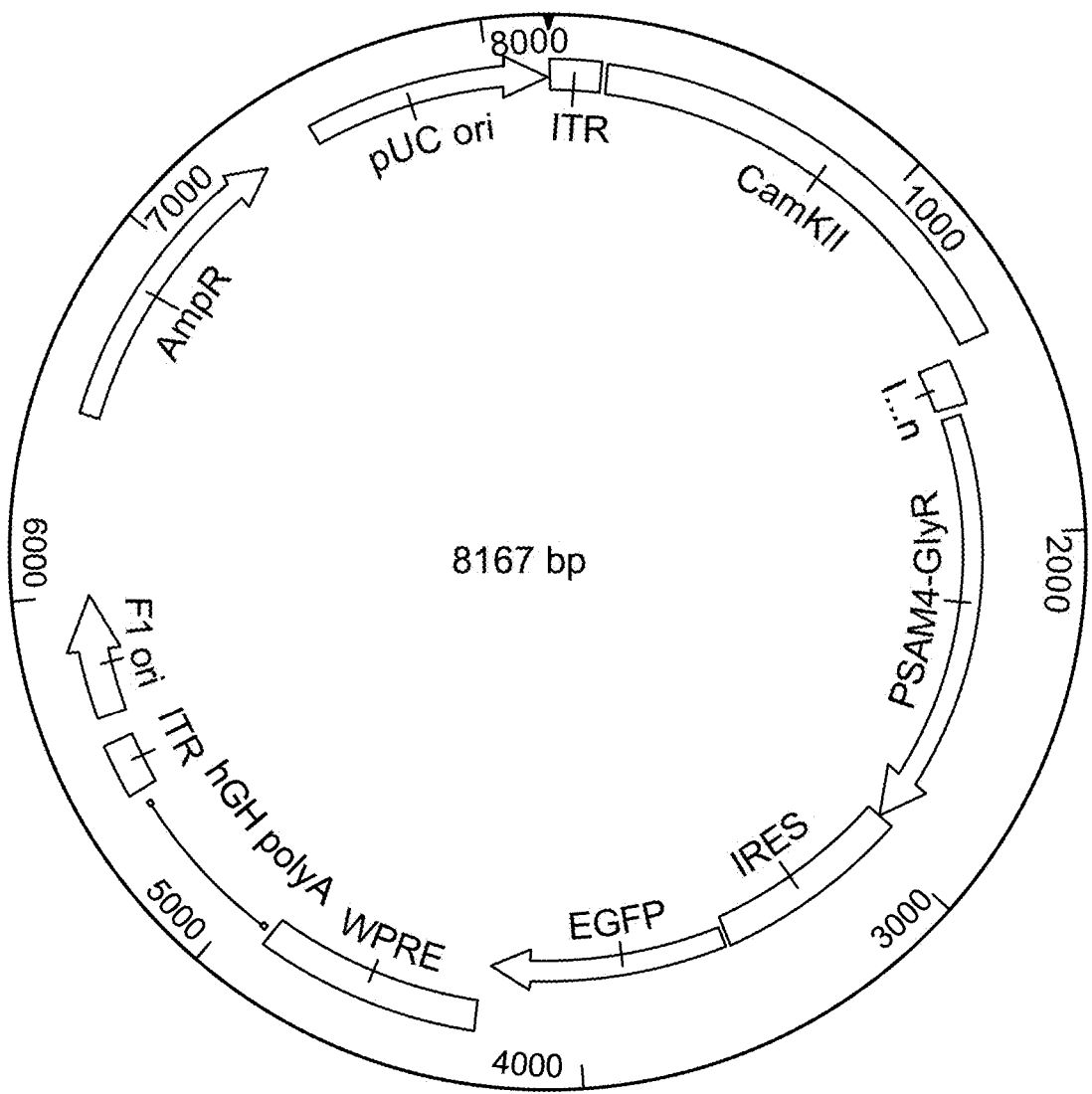

In cases where nucleic acids encoding modified LGIC subunits described herein are present in a construct, the construct can be any appropriate construct. A construct can be a nucleic acid (e.g., DNA, RNA, or a combination thereof) construct. Examples of constructs include, without limitation, plasmids, non-viral vectors, viral vectors (e.g., adeno-associated virus vectors, herpes simplex virus vectors, or lentivirus vectors). In some cases, a construct including a nucleic acid encoding a modified LGIC subunit described herein can express the modified LGIC subunit. In some cases, a construct can include an internal ribosome entry site (IRES; e.g., a bicistronic IRES). In some cases, a construct can include a nucleic acid sequence encoding a detectable marker (e.g., a fluorescent polypeptide such as a green fluorescent polypeptide (GFP; e.g., an enhanced GFP (EGFP))). In some cases, a construct can include a nucleic acid sequence providing the construct with a selectable marker (e.g., an antibiotic resistance marker such as ampicillin resistance). An exemplary plasmid map and nucleic acid sequence of a construct including a nucleic acid sequence encoding modified LGIC subunit described herein are shown in FIG. 19. Another exemplary plasmid map and nucleic acid sequence of a construct including a nucleic acid sequence encoding modified LGIC subunit described herein are shown in FIG. 20.

This document also provides cells (e.g., mammalian cells) having a modified LGIC described herein. Mammalian cells having a modified LGIC described herein can be obtained by any appropriate method. In some cases, a pre-assembled modified LGIC can be provided to the cell. In some cases, a nucleic acid encoding a modified LGIC subunit described herein can be provided to the cell under conditions in which a modified LGIC subunit is translated and under conditions in which multiple (e.g., three, four, five, six, or more) modified LGIC subunits can assemble into a modified LGIC described herein.

LGIC Ligands

This document also provides LGIC ligands that can bind to and activate modified LGICs described herein. LGIC ligands can also be referred to as pharmacologically selective effector molecules (PSEMs). A LGIC ligand that can bind to and activate modified LGICs described herein can be exogenous or endogenous. A LGIC ligand that can bind to and activate modified LGICs described herein can be naturally occurring or synthetic. A LGIC ligand that can bind to and activate modified LGICs described herein can be canonical or non-canonical. A LGIC ligand that can bind to and activate modified LGICs described herein can be an agonist or an antagonist. In some cases, an LGIC ligand is an exogenous LGIC agonist. Examples of LGIC ligands include, without limitation, ACh, nicotine, epibatatine, cytisine, RS56812, tropisetron, nortropisetron, PNU-282987, PHA-543613, compound 0353, compound 0354, compound 0436, compound 0676, compound 702, compound 723, compound 725, granisetron, ivermectin, mequitazine, promazine, varenicline, compound 765, compound 770, 3-(1,4-diazabicyclo[3.2.2]nonan-4-yl)dibenzo [b,d]thiophene 5,5-dioxide, compound 773, and compound 774 (see, e.g., FIG. 3B, FIG. 5C, FIG. 11A, FIG. 11B, and FIG. 11C).

A LGIC ligand that can bind to and activate modified LGICs described herein can have selective binding (e.g., enhanced binding or increased potency) for a modified LGIC described herein (e.g., relative to an unmodified LGIC). In some cases, a LGIC ligand that can bind to and activate modified LGICs described herein does not bind to and activate endogenous receptors (e.g., endogenous LGICs). A LGIC ligand that selectively binds to and activates a modified LGIC (e.g., a modified LGIC having at least one amino acid modification that confers pharmacological selectivity to the modified LGIC) described herein over an unmodified LGIC ligand can also be described as having enhanced potency for a modified LGIC. In some cases, a modified LGIC subunit described herein that selectively binds an exogenous LGIC ligand can have at least 5 fold (e.g., at least 10 fold, at least 15 fold, at least 20 fold, at least 25 fold, at least 30 fold, at least 35 fold, at least 40 fold, at least 45 fold, at least 50 fold, at least 55 fold, at least 60 fold, at least 65 fold, at least 70 fold, at least 75 fold, at least 80 fold, at least 85 fold, at least 95 fold, at least 100 fold, at least 125 fold, at least 150 fold, at least 200 fold, at least 250 fold, or at least 300 fold) enhanced potency for a modified LGIC. For example, a LGIC ligand that selectively binds to and activates a modified LGIC can have about 10 fold to about 300 fold (e.g., about 10 fold to about 250 fold, about 10 fold to about 200 fold, about 10 fold to about 150 fold, about 10 fold to about 100 fold, about 25 fold to about 300 fold, about 50 fold to about 300 fold, about 100 fold to about 300 fold, about 200 fold to about 300 fold, about 25 fold to about 250 fold, about 50 fold to about 200 fold, or about 100 fold to about 150 fold) enhanced potency for a modified LGIC. In some cases, a LGIC ligand that binds to and activates a modified LGIC described herein can have a ligand potency of less than 25 nM (e.g., less than 22 nM, less than 20 nM, less than 17 nM, less than 15 nM, less than 13 nM, less than 12 nM, less than 11 nM, less than 10 nM, less than 5 nM, less, than 2 nM, or less than 1 nM). For example, a LGIC ligand that binds to and activates a modified LGIC described herein can have a ligand potency of less than 15 nM. In some cases, a LGIC ligand can have an EC50 of less than 25 nM (e.g., less than 22 nM, less than 20 nM, less than 17 nM, less than 15 nM, less than 13 nM, less than 12 nM, less than 11 nM, or less than 10 nM) for a modified LGIC subunit described herein. For example, a LGIC ligand (e.g., tropisetron) can have an EC50 of about 11 nM for a modified LGIC subunit described herein (e.g., $\alpha 7^{Q79G}$-GlyR$^{A298G}$). For example, a LGIC ligand (e.g., nortropisetron) can have an EC50 of about 13 nM for a modified LGIC subunit described herein (e.g., $\alpha 7^{Q79G,Y115F}$-GlyR$^{A298G}$). In some cases, a LGIC ligand can have an EC50 of greater than 20 µM (e.g., greater than 22 µM, greater than 25 µM, greater than 35 µM, greater than 50, greater than 65 µM, greater than 80 µM, or greater than 100 µM) for a modified LGIC subunit described herein. For example, a LGIC ligand (e.g., ACh) can have an EC50 of greater than 100 µM for a modified LGIC subunit described herein (e.g., $\alpha 7^{Q79G,Y115F}$-GlyR$^{A298G}$).

In some aspects, a LGIC ligand can be a synthetic ligand that can bind to and activate modified LGICs described herein can be a quinuclidine, a tropane, a 9-azabicyclo[3.3.1]nonane, or a 2-phenyl-7,8,9,10-tetrahydro-6H-6,10-methanoazepino[4,5-g]quinoxaline.

A LGIC ligand that can be to and activate a modified LGIC described herein can have Formula I:

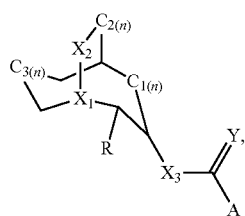

where X1 and X2 can independently be CH, CH2, O, NH, or NMe; each n can independently be 0 or 1; Y can be O or S; A can be an aromatic substituent; and R can be H or pyridinymethylene. Examples of aromatic substituents include, without limitation, 4-chloro-benzene, 1H-indole, 4-(trifluoromethyl) benzene, 4-chloro benzene, 2,5-dimethoxy benzene, 4-chloroaniline, aniline, 5-(trifluoromethyl) pyridin-2-yl, 6-(trifluoromethyl) nicotinic, and 4-chlorobenzene.

A LGIC ligand that can bind to and activate a modified LGIC described herein can be a quinuclidine. A quinuclidine can have the structure of Formula II:

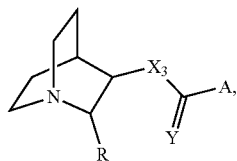

where X3 can be O, NH, or CH2; Y can be O or S; A can be an aromatic substituent; and R can be H or pyridinylmethylene. Examples of aromatic substituents include without limitation, 1H-indole, 4-(trifluoromethyl) benzene, 4-chloro benzene, 2,5-dimethoxy benzene, 4-(trifluoromethyl) benzene, 4-chloroaniline, aniline, 5-(trifluoromethyl) pyridin-2-yl, 6-(trifluoromethyl) nicotinic, 3-chloro-4-fluoro benzene, 4-chloro-benzene, and 1H-indole. Examples of quinuclidines include, without limitation, compounds PNU-282987, PHA-543613, 0456, 0434, 0436, 0354, 0353, 0295, 0296, and 0676 (see, e.g., FIG. 5C, Table 3, and Table 6).

A LGIC ligand that can bind to and activate a modified LGIC described herein can be a tropane. A tropane can have the structure of Formula III:

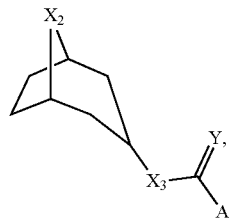

where X2 can be NH or NMe; X3 can be O, NH, or CH2; Y can be O or S; and A can be an aromatic substituent. Example of aromatic substituents include, without limitation, 1H-indole, 7-methoxy-1H-indole, 7-methyl-1H-indole, 5-chloro-1H-indole, and 1H-indazole. Examples of tropanes include, without limitation, tropisetron, pseudo-tropisetron, nortropisetron, compound 737, and compound 745 (see, e.g., FIG. 5C, Table 3, and Table 6).

A LGIC ligand that can bind to and activate a modified LGIC described herein can be a 9-azabicyclo[3.3.1]nonane. A 9-azabicyclo[3.3.1]nonane can have the structure of Formula IV:

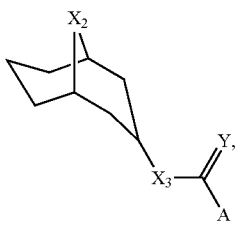

where X1 can be CH, X2 can be NH or NMe, X3 can be O, NH, or CH; Y can be O or S; and A can be an aromatic substituent. An example of an aromatic substituent is, without limitation, 4-chloro-benzene. Examples of 9-azabicyclo[3.3.1]nonanes include, without limitation, compound 0536, compound 0749, compound 0751, compound 0760, and compound 0763 (see, e.g., FIG. 5C, Table 3, and Table 6).

Figure 14B:
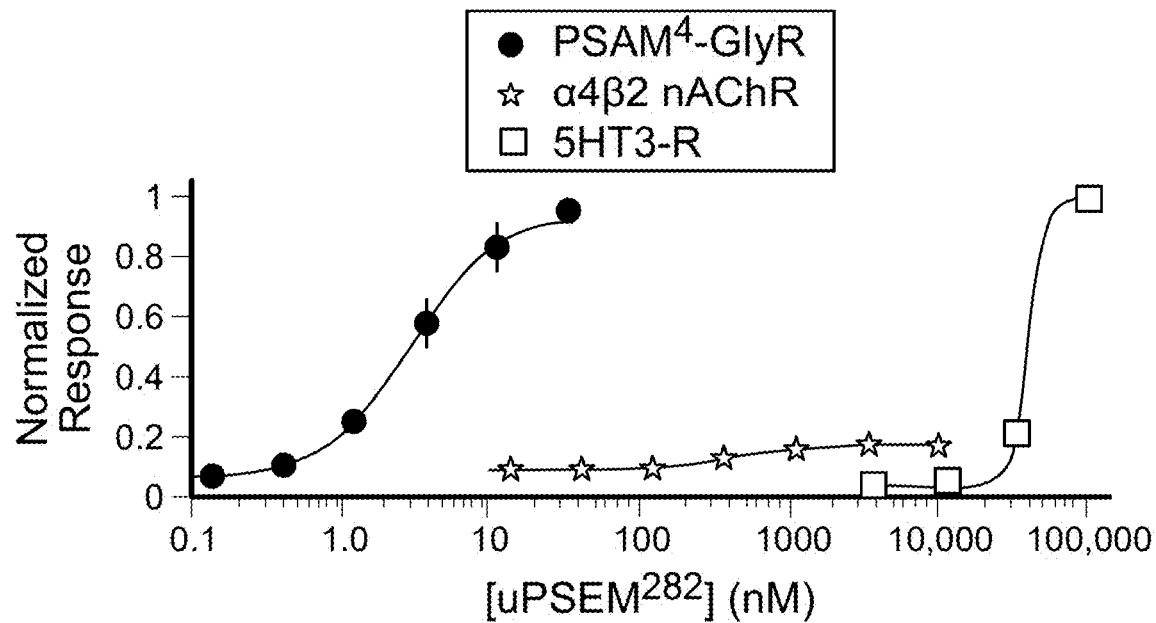
Figure 14C:
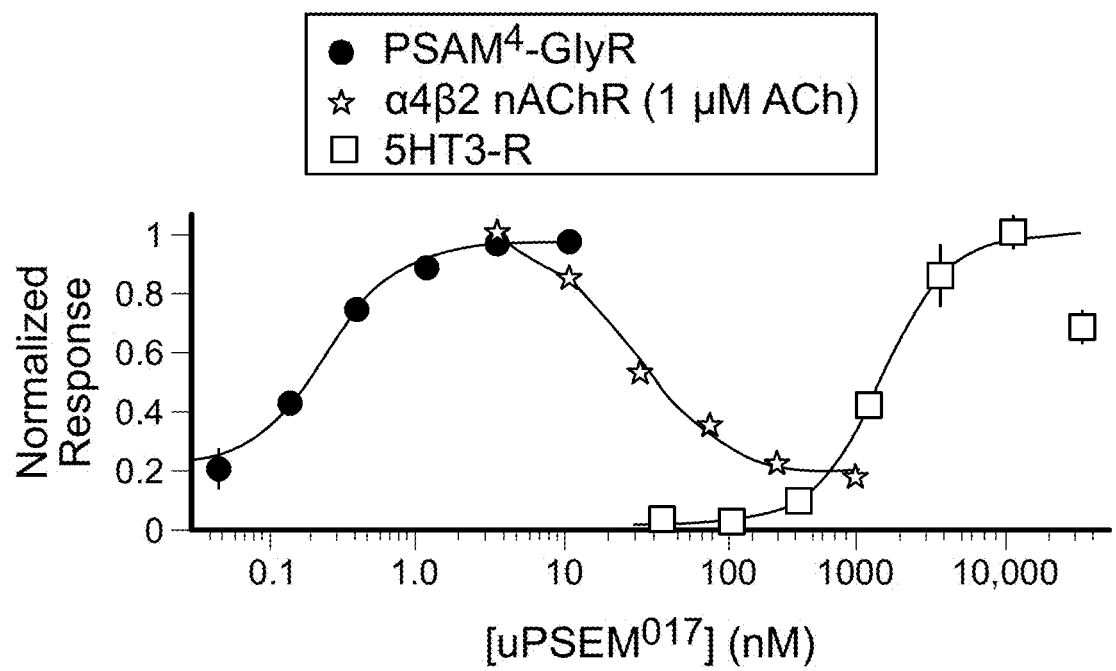
Figure 14D:
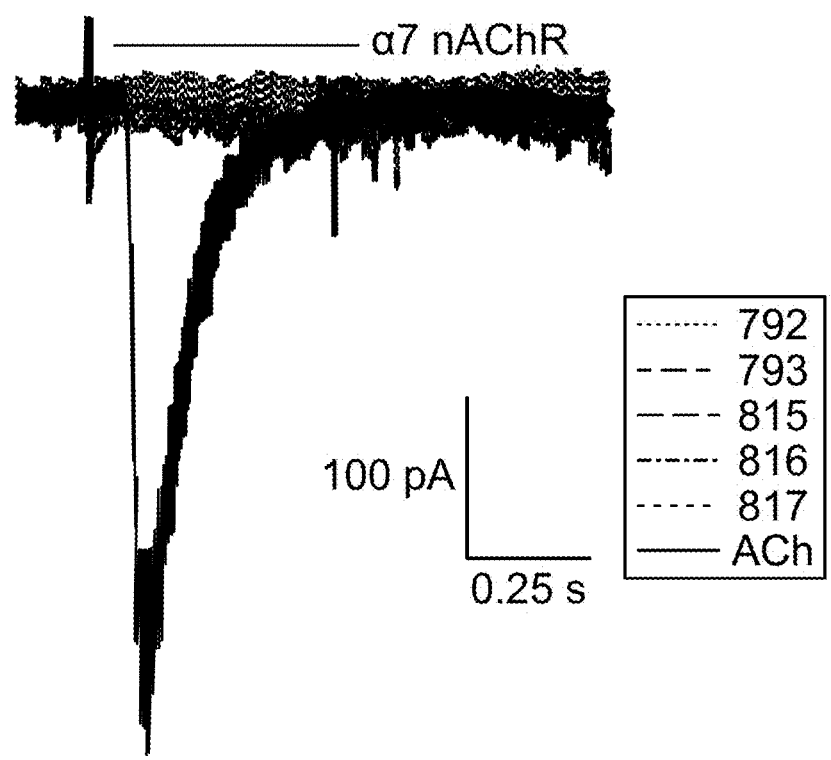
Figure 14E:
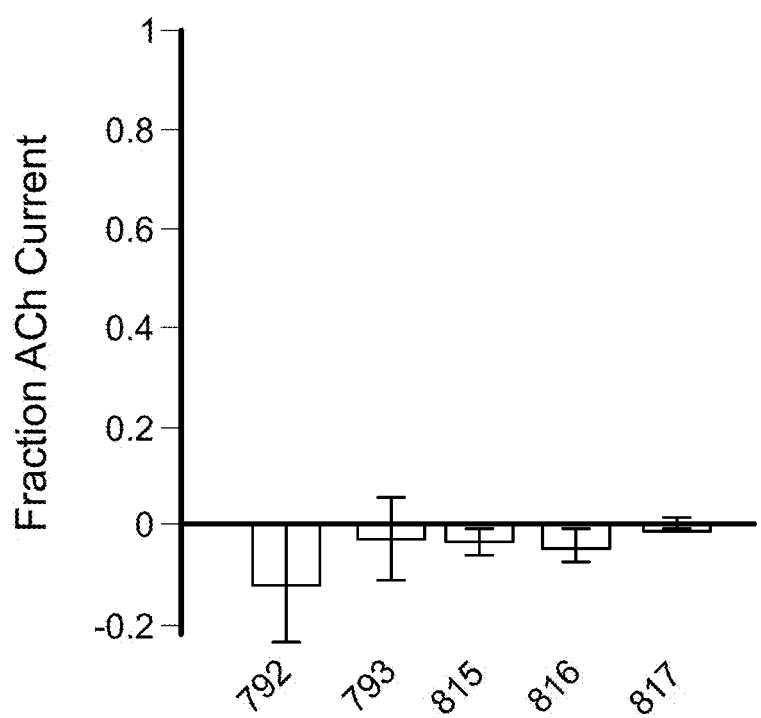
Figure 14F:
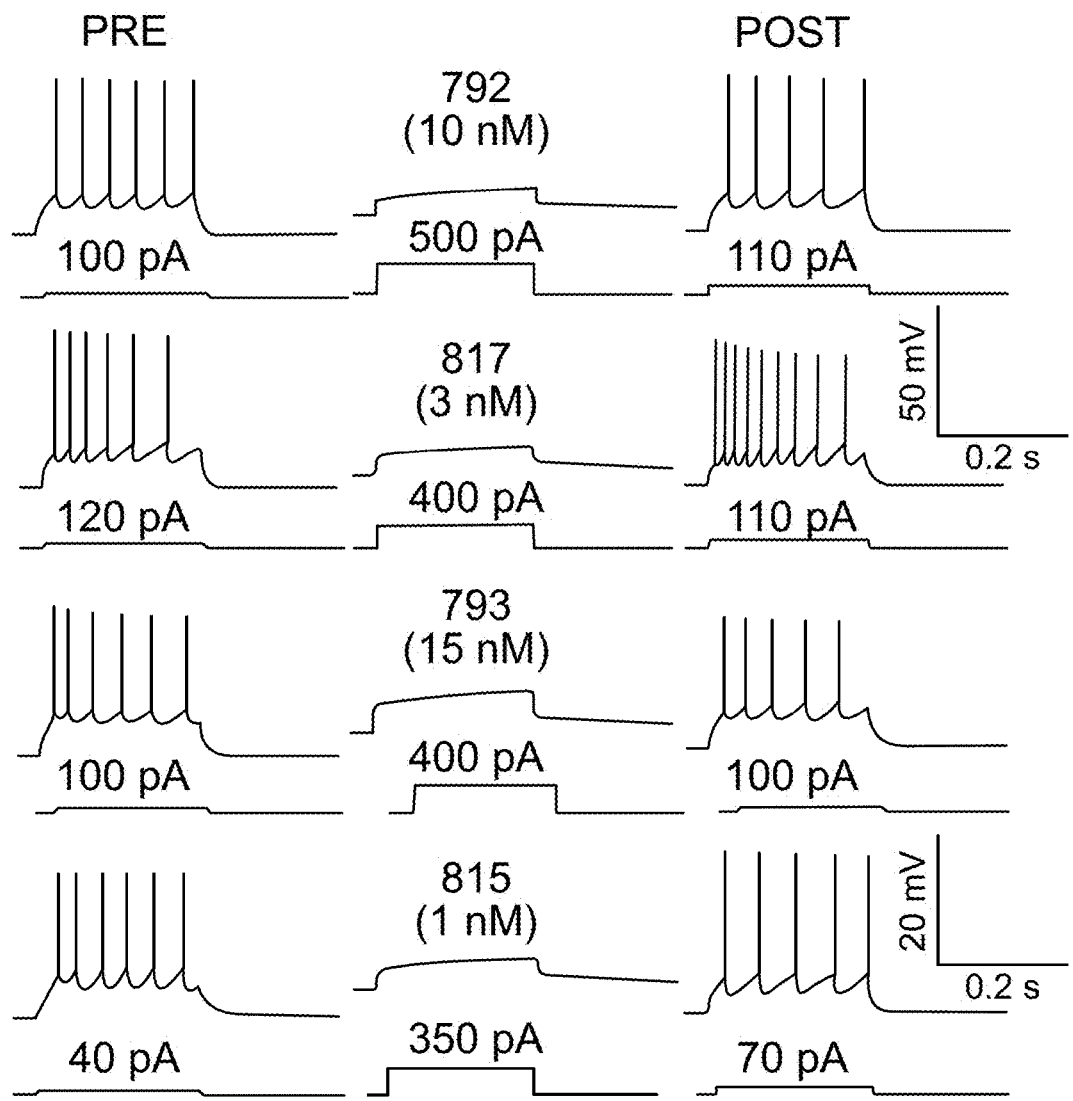
Figure 14G:
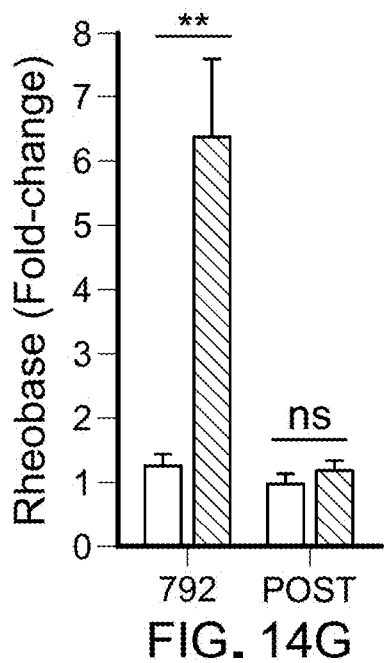
Figure 14H:
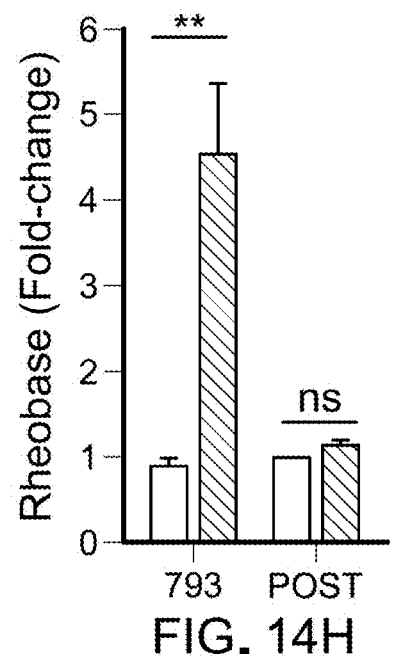
Figure 14I:
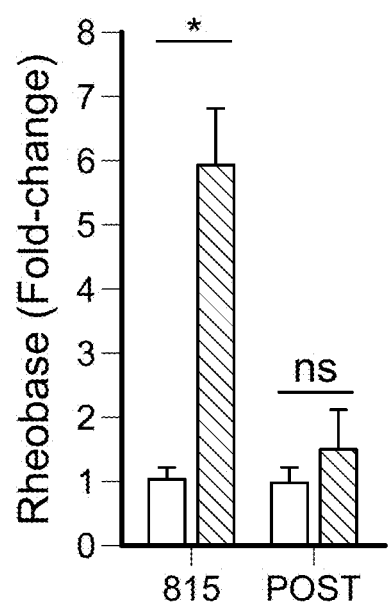
Figure 14J:
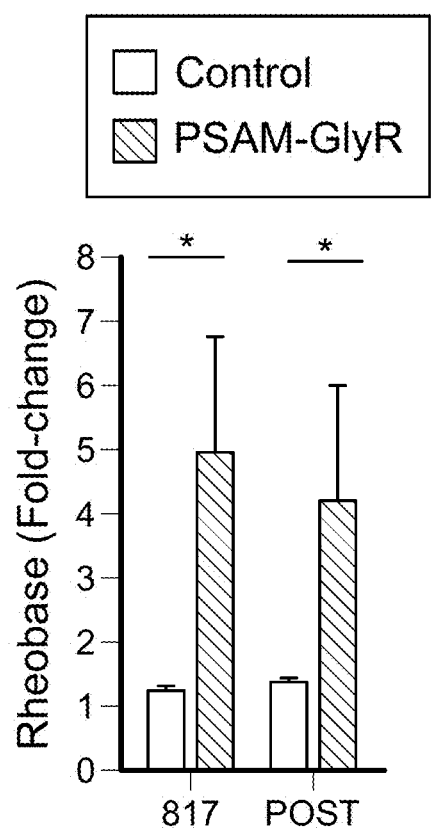
Figures 15A, 15B:
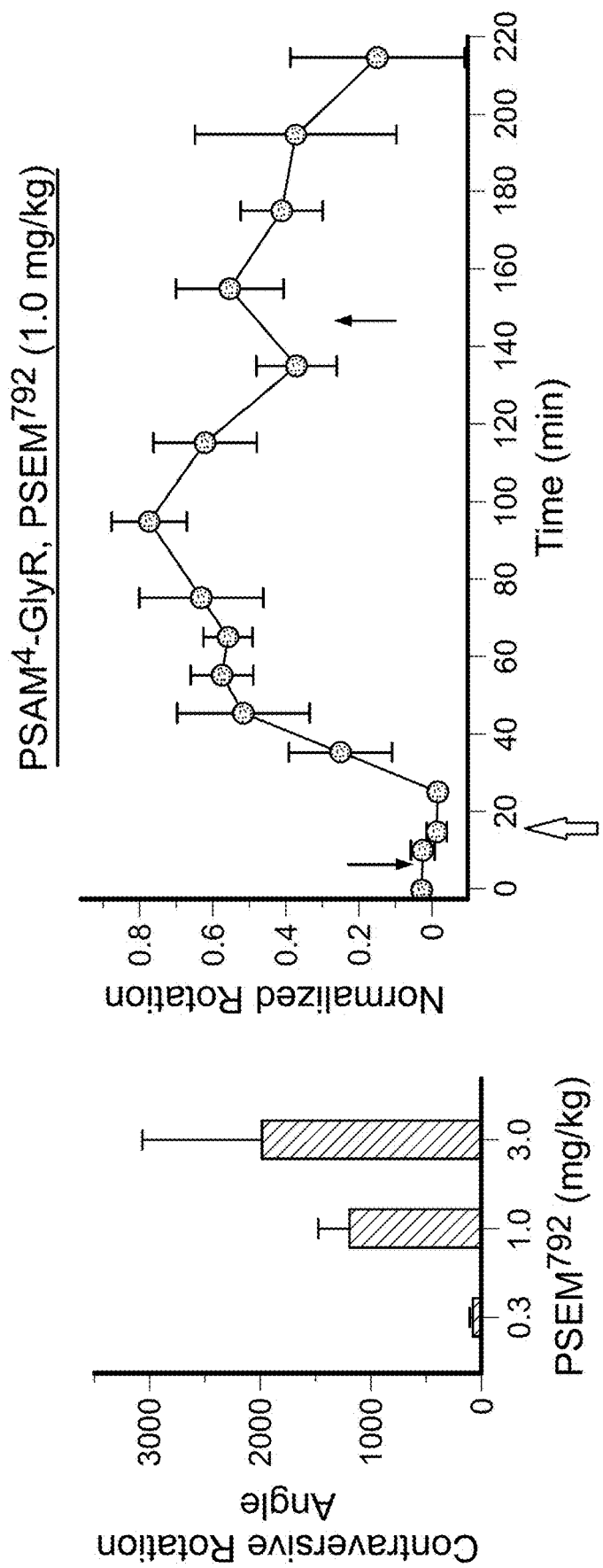
FIGS. 15A-15H show in vivo uPSEM dose responses for mice expressing PSAM$^4$-GlyR unilaterally in SNr. Behavioral response and timecourse for uPSEM$^{792}$ (FIG. 15A, FIG. 15B), uPSEM$^{793}$ (FIG. 15C, FIG. 15D), uPSEM$^{815}$ (FIG. 15E, FIG. 15F), uPSEM$^{817}$ (FIG. 15G, FIG. 15H). Timecourse of rotation response normalized to maximum rotation for each mouse. Pink (narrow) arrows: amphetamine injections, blue (wide) arrows: uPSEM injection.
Figure 15D:
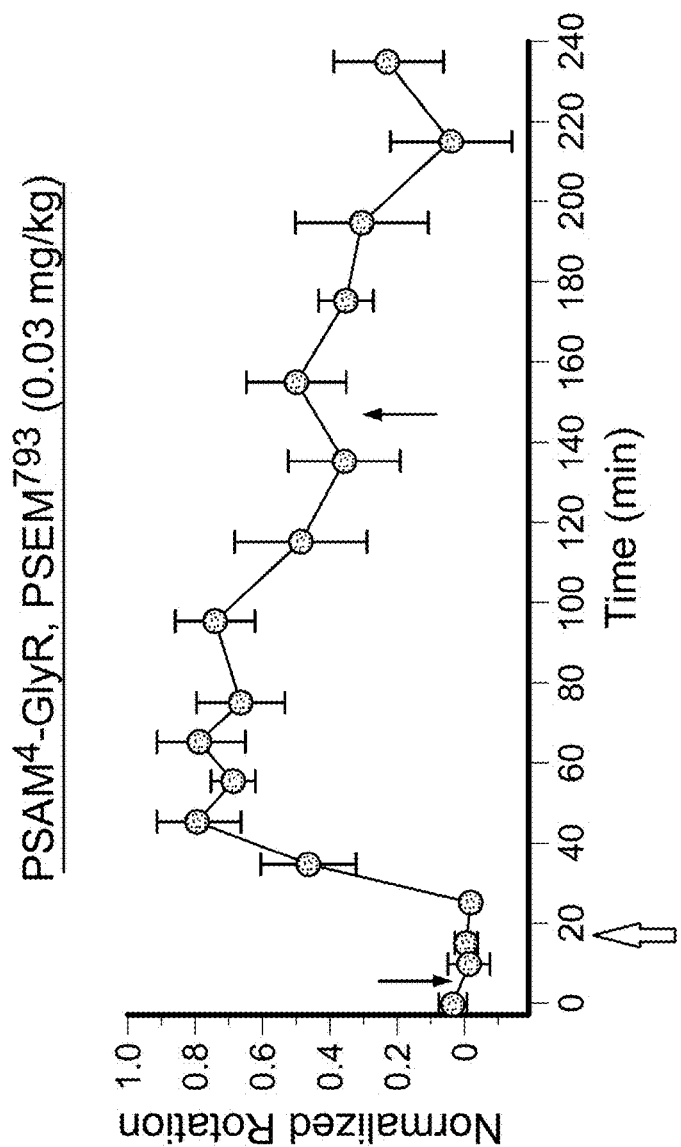
Figure 15C:
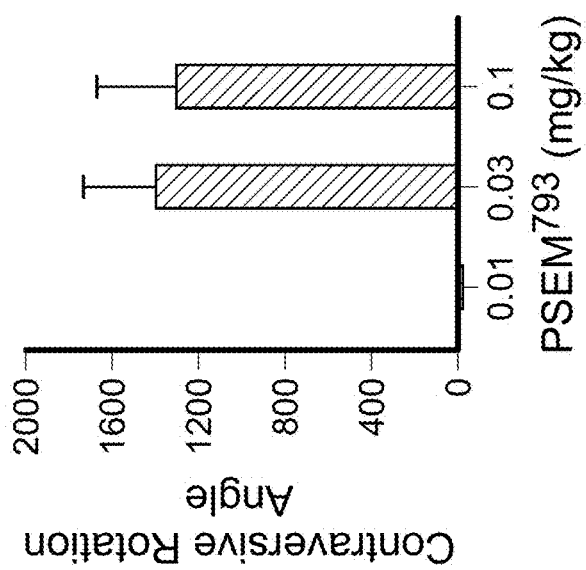
Figures 15E, 15F:
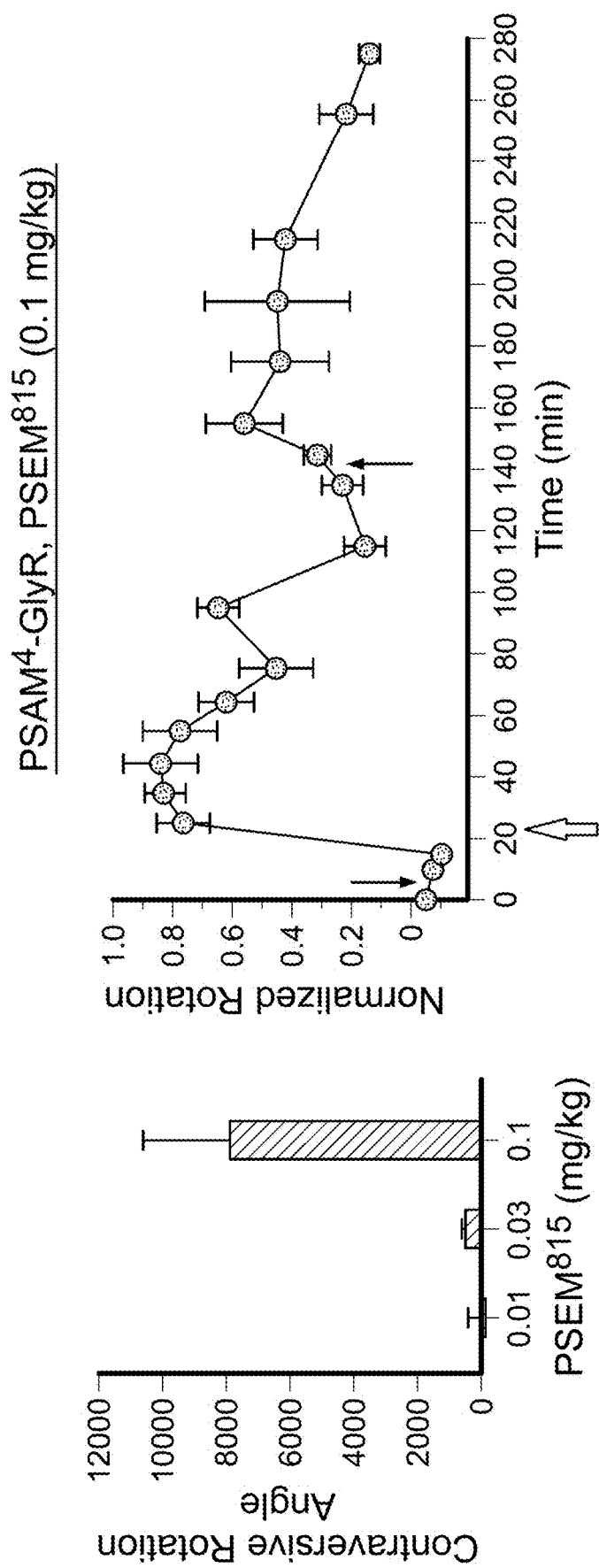
Figures 15G, 15H:
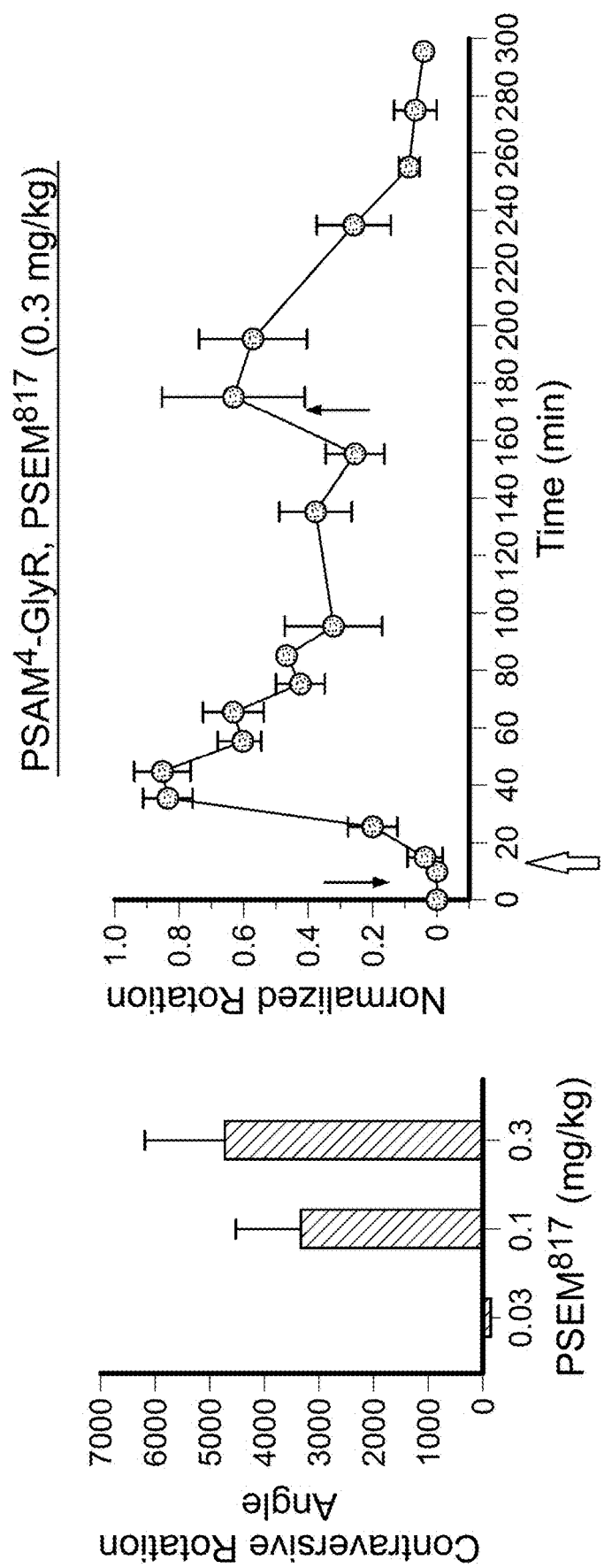

In some cases, a LGIC ligand can be an a 6,7,8,9-tetrahydro-6,10-methano-6H-pyrazino(2,3-h)benzazepine and can have a structure shown in Formula V:

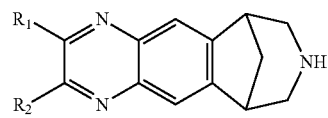

where R1=H, an aromatic substituent, a methyl containing group, an ethyl containing group, or other aliphatic groups, an alkoxy-containing group (e.g., methoxy-containing groups, ethoxy-containing groups, propoxy-containing groups, and isopropoxy-containing groups); or an amino-containing group; and R2=H, an aliphatic substituent (e.g., methyl), or an aromatic substituent (e.g., phenyl). Examples of R1 groups include, without limitation, phenyl, 2-toluyl, 3-pyridyl, 4-pyridyl, imidazole, pyrrole, pyrazole, triazole, isoxazole-3-amine, trifluoromethyl, methoxy, N,N-dimethylamino, and N,N-diethylamino. In some cases, R1 and R2 can be connected to form a ring. Examples of 6,7,8,9-tetrahydro-6,10-methano-6H-pyrazino(2,3-h)benzazepines include, without limitation, varenicline, compound 0765, compound 0770, compound 0780, compound 0782, compound 0785, compound 0788, compound 0782, compound 0789, compound 0791, compound 0793, compound 0794, compound 0795, compound 0798, compound 0799, compound 0800, compound 0801, compound 0802, compound 0803, compound 0804, compound 0805, compound 0807, compound 0808, compound 0812, compound 0813, compound 815, compound 816, and compound 817 (see, e.g., FIG. 11A, FIG. 14A, Table 3, Table 9, Table 10, and Table 11).

In some cases, a LGIC ligand can be a 2-(pyridin-3-yl)-1,5,6,7,8,9-hexahydro-5,9-methanoimidazo[4',5':4,5]benzo[1,2-d]azepine:

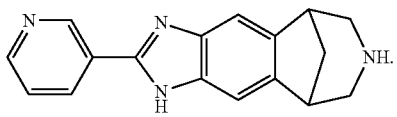 [SMILES: c1cncc(-c2nc3cc4c(cc3[nH]2)C2CNCC4C2)c1]

Examples of 2-(pyridin-3-yl)-1,5,6,7,8,9-hexahydro-5,9-methanoimidazo[4',5':4,5]benzo[1,2-d]azepines include compound 0786 (see, e.g., Table 10 and Table 11).

In some cases, a LGIC ligand can be a 7,8,9,10-tetrahydro-1H-6,10-methanoazepino[4,5-g]quinoxalin-2(6H)-one and can have a structure shown in formula VI:

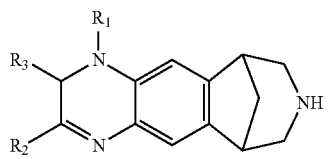

where R1=H or an aliphatic substituent (e.g., methyl); where R2=H, an aliphatic substituent (e.g., methyl), or an aromatic substituent; and where R3=O or S. Examples of 7,8,9,10-tetrahydro-1H-6,10-methanoazepino[4,5-g]quinoxalin-2(6H)-ones include, without limitation, compound 0783, compound 0784, compound 0790, or compound 0792 (see, e.g., FIG. 11B, Table 10, and Table 11). For example, a LGIC can be a 7,8,9,10-tetrahydro-1H-6,10-methanoazepino[4,5-g]quinoxalin-2(6H)-one having a structure of:

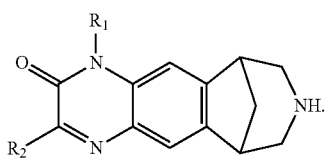

In some cases, a LGIC ligand can be a 1,4-diazabicyclo[3.2.2]nonane and can have a structure shown in Formula VII:

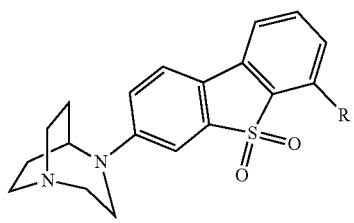

where R=H, F, NO$_2$. Examples of 1,4-diazabicyclo[3.2.2]nonanes include, without limitation, 3-(1,4-diazabicyclo[3.2.2]nonan-4-yl)dibenzo[b,d]thiophene 5,5-dioxide, compound 0773, and compound 0774 (see, e.g., FIG. 11C, Table 6, and Table 9).

Methods of Using

This document also provides methods of using a modified LGIC described herein and a LGIC ligand that can bind to and activate the modified LGIC as described herein. A LGIC ligand that can bind to and activate the modified LGIC can be used to activate a modified LGIC with temporal and/or spatial control based on delivery of the ligand.

In some aspects, a modified LGIC described herein and a LGIC ligand that can bind to and activate the modified LGIC as described herein can be used to identify a ligand that selectively binds to a modified LGIC described herein. For example, such screening methods can include providing one or more candidate ligands to a modified LGIC described herein, and detecting binding between the candidate ligand and the modified LGIC.

Any appropriate method can be used to detect binding between a candidate ligand and the modified LGIC and any appropriate method can be used to detect activity of a modified LGIC. For example, the ability of a ligand to bind to and activate a modified LGIC can be measured by assays including, but not limited to, membrane potential (MP) assay (e.g., a fluorescence MP assay), radioactive binding assays, and/or voltage clamp measurement of peak currents and sustained currents.

In some aspects, a modified LGIC described herein and a LGIC ligand that can bind to and activate the modified LGIC as described herein can be used to treat a mammal having a channelopathy (e.g., a neural channelopathy or a muscle channelopathy). For example, a mammal having a channelopathy can be treated by administering a modified LGIC described herein, and then administering a LGIC ligand that can bind to and activate the modified LGIC. For example, a mammal having a channelopathy can be treated by administering a modified LGIC described herein (e.g., including at least one chimeric α7-GlyR LGIC subunit (SEQ ID NO:6) having a human α7 nAChR LBD (SEQ ID NO:2) with a R27D amino acid substitution, a E41R amino acid substitution, a Q79G amino acid substitution, and a Y115F amino acid substitution, and a human GlyR IPD (SEQ ID NO:5) with a A298G amino acid substitution), and then administering tropisetron. For example, a mammal having a channelopathy can be treated by administering a modified LGIC described herein including a modified human α7 nAChR LBD (e.g., SEQ ID NO:1, SEQ ID NO:2, SEQ ID NO:11, or SEQ ID NO:12) with an L131 amino acid substitution (e.g., L131G, L131A, L131M, or L131N) and, optionally, a Q79S amino acid substitution, a Q139L amino acid substitution, and/or a Y217F amino acid substitution, and then administering varenicline, tropisetron, and/or compound 765.

Any type of mammal can be treated using a modified LGIC described herein and a LGIC ligand that can bind to and activate the modified LGIC as described herein. For example, humans and other primates such as monkeys can be treated using a modified LGIC described herein and a LGIC ligand that can bind to and activate the modified LGIC as described herein. In some cases, dogs, cats, horses, cows, pigs, sheep, rabbits, mice, and rats can be treated using a modified LGIC described herein and a LGIC ligand that can bind to and activate the modified LGIC as described herein.

Any appropriate method can be used to identify a mammal having a channelopathy and/or a mammal at risk of developing a channelopathy. For example, genetic testing can be used to identify a mammal having a channelopathy and/or a mammal at risk of developing a channelopathy.

Once identified as having a channelopathy and/or a mammal at risk of developing a channelopathy, the mammal can be administered or instructed to self-administer a modified LGIC described herein, and then administered or instructed to self-administer a LGIC ligand that can bind to and activate the modified LGIC as described herein. A modified LGIC described herein and a LGIC ligand that can bind to and activate the modified LGIC as described herein can be administered together or can be administered separately.

When treating a mammal having a channelopathy and/or a mammal at risk of developing a channelopathy using the materials and methods described herein, the channelopathy can be any channelopathy. As used herein, a channelopathy can be any disease or disorder caused by aberrant ion channel function and/or aberrant ligand function, or which could be alleviated by modulated ion channel function and/or altered cellular ion flux (e.g., calcium ion flux). A channelopathy can be congenital or acquired. Examples of channelopathies include, without limitation, Bartter syndrome, Brugada syndrome, catecholaminergic polymorphic ventricular tachycardia (CPVT), congenital hyperinsulinism, cystic fibrosis, Dravet syndrome, episodic ataxia, erythromelalgia, generalized epilepsy (e.g., with febrile seizures), familial hemiplegic migraine, fibromyalgia, hyperkalemic periodic paralysis, hypokalemic periodic paralysis, Lambert-Eaton myasthenic syndrome, long QT syndrome (e.g., Romano-Ward syndrome), short QT syndrome, malignant hyperthermia, mucolipidosis type IV, myasthenia gravis, myotonia congenital, neuromyelitis optica, neuromyotonia, nonsyndromic deafness, paramyotonia congenital, retinitis pigmentosa, timothy syndrome, tinnitus, seizure, trigeminal neuralgia, and multiple sclerosis. Alternatively, or in addition, the materials and methods described herein can be used in other applications including, without limitation, pain treatment, cancer cell therapies, appetite control, spasticity treatment, muscle dystonia treatment, tremor treatment, and movement disorder treatment.

In some cases, a modified LGIC described herein and a LGIC ligand that can bind to and activate the modified LGIC as described herein can be used to modulate the activity of a cell. The activity of the cell that is modulated using a modified LGIC described herein and a LGIC ligand that can bind to and activate the modified LGIC as described herein can be any cellular activity. Examples of cellular activities include, without limitation, active transport (e.g., ion transport), passive transport, excitation, inhibition, ion flux (e.g., calcium ion flux), and exocytosis. The cellular activity can be increased or decreased. For example, a modified LGIC described herein and a LGIC ligand that can bind to and activate the modified LGIC as described herein can be used to modulate (e.g., increase) ion transport across the membrane of a cell. For example, a modified LGIC described herein and a LGIC ligand that can bind to and activate the modified LGIC as described herein can be used to modulate (e.g., increase) the excitability of a cell.

A modified LGIC described herein and a LGIC ligand that can bind to and activate the modified LGIC as described herein can be used to modulate the activity of any type of cell in a mammal. The cell can be a neuron, a glial cell, a myocyte, an immune cell (e.g., neutrophils, eosinophils, basophils, lymphocytes, and monocytes), an endocrine cell, or a stem cell (e.g., an embryonic stem cell). In some cases, the cell can be an excitable cell. The cell can be in vivo or ex vivo.

A modified LGIC described herein can be administered by any appropriate method. A modified LGIC can be administered as modified LGIC subunits or as pre-assembled modified LGICs. A modified LGIC can be administered as a nucleic acid encoding a modified LGIC. A modified LGIC can be administered as a nucleic acid encoding a modified LGIC subunit described herein. For example, a nucleic acid can be delivered as naked nucleic acid or using any appropriate vector (e.g., a recombinant vector). Vectors can be a DNA based vector, an RNA based, or combination thereof. Vectors can express a nucleic acid in dividing cells or non-dividing cells. Examples of recombinant vectors include, without limitation, plasmids, viral vectors (e.g., retroviral vectors, adenoviral vectors, adeno-associated viral vectors, and herpes simplex vectors), cosmids, and artificial chromosomes (e.g., yeast artificial chromosomes or bacterial artificial chromosomes). In some cases, a nucleic acid encoding a modified LGIC subunit described herein can be expressed by an adeno-associated viral vector.

A modified LGIC described herein can be detected (e.g., to confirm its presence in a cell) by any appropriate method. In some cases, an agent that selectively binds a modified LGIC can be used to detect the modified LGIC. Examples of agents that can be used to bind to a modified LGIC described herein include, without limitation, antibodies, proteins (e.g., bungarotoxin), and small molecule ligands (e.g., PET ligands). An agent that selectively binds a modified LGIC can include a detectable label (e.g., fluorescent labels, radioactive labels, positron emitting labels, and enzymatic labels). Methods to detect LGIC expression in a cell can include fluorescence imaging, autoradiography, functional MRI, PET, and SPECT.

A modified LGIC described herein and a LGIC ligand that can bind to and activate the modified LGIC as described herein can be administered to a mammal having a channelopathy and/or at risk of developing a channelopathy as a combination therapy with one or more additional agents/ therapies used to treat a channelopathy. For example, a combination therapy used to treat a mammal having a channelopathy as described herein can include administering a modified LGIC described herein and a LGIC ligand that can bind to and activate the modified LGIC as described herein and treating with acetazolamide, dichlorphenamide, mexilitine, glucose, calcium gluconate, L-DOPA, muscle stimulation, spinal stimulation, brain stimulation, and/or nerve stimulation.

In embodiments where a modified LGIC described herein and a LGIC ligand that can bind to and activate the modified LGIC as described herein are used in combination with additional agents/therapies used to treat a channelopathy, the one or more additional agents can be administered at the same time or independently. For example, a modified LGIC described herein and a LGIC ligand that can bind to and activate the modified LGIC as described herein first, and the one or more additional agents administered second, or vice versa. In embodiments where a modified LGIC described herein and a LGIC ligand that can bind to and activate the modified LGIC as described herein are used in combination with one or more additional therapies used to treat a channelopathy, the one or more additional therapies can be performed at the same time or independently of the administration of a modified LGIC described herein and a LGIC ligand that can bind to and activate the modified LGIC as described herein. For example, a modified LGIC described herein and a LGIC ligand that can bind to and activate the modified LGIC as described herein can be administered before, during, or after the one or more additional therapies are performed.

In some cases, a modified LGIC described herein and/or a LGIC ligand that can bind to and activate the modified LGIC as described herein can be formulated into a pharmaceutically acceptable composition for administration to a mammal having a channelopathy or at risk of developing a channelopathy. For example, a therapeutically effective amount of a modified LGIC described herein (e.g., a nucleic acid encoding a modified LGIC described herein) and/or a LGIC ligand that can bind to and activate the modified LGIC as described herein can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing a modified LGIC described herein and/or a LGIC ligand that can bind to and activate the modified LGIC as described herein can be designed for oral, parenteral (including subcutaneous, intracranial, intraarterial, intramuscular, intravenous, intracoronary, intradermal, or topical), or inhaled administration. When being administered orally, a pharmaceutical composition containing a therapeutically effective amount of a modified LGIC described herein (e.g., a nucleic acid encoding a modified LGIC described herein) and/or a LGIC ligand that can bind to and activate the modified LGIC as described herein can be in the form of a pill, tablet, or capsule. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. Compositions for inhalation can be delivered using, for example, an inhaler, a nebulizer, and/or a dry powder inhaler. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

A pharmaceutically acceptable composition including a therapeutically effective amount of a modified LGIC described herein (e.g., a nucleic acid encoding a modified LGIC described herein) and/or a LGIC ligand that can bind to and activate the modified LGIC as described herein can be administered locally or systemically. In some cases, a composition containing a therapeutically effective amount of a modified LGIC described herein (e.g., a nucleic acid encoding a modified LGIC described herein) and/or a LGIC ligand that can bind to and activate the modified LGIC as described herein can be administered systemically by venous or oral administration to, or inhalation by a mammal (e.g., a human). In some cases, a composition containing a therapeutically effective amount of a modified LGIC described herein (e.g., a nucleic acid encoding a modified LGIC described herein) and/or a LGIC ligand that can bind to and activate the modified LGIC as described herein can be administered locally by percutaneous, subcutaneous, intramuscular, intracranial, or open surgical administration (e.g., injection) to a target tissue of a mammal (e.g., a human).

Effective doses can vary depending on the severity of the channelopathy, the route of administration, the age and general health condition of the subject, excipient usage, the possibility of co-usage with other therapeutic treatments such as use of other agents, and the judgment of the treating physician.

The frequency of administration can be any frequency that improves symptoms of a channelopathy without producing significant toxicity to the mammal. For example, the frequency of administration can be from about once a week to about three times a day, from about twice a month to about six times a day, or from about twice a week to about once a day. The frequency of administration can remain constant or can be variable during the duration of treatment. A course of treatment with a composition containing a therapeutically effective amount of a modified LGIC described herein (e.g., a nucleic acid encoding a modified LGIC described herein) and/or a LGIC ligand that can bind to and activate the modified LGIC as described herein can include rest periods. For example, a composition containing a therapeutically effective amount of a modified LGIC described herein (e.g., a nucleic acid encoding a modified LGIC described herein) and/or a LGIC ligand that can bind to and activate the modified LGIC as described herein can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the channelopathy may require an increase or decrease in administration frequency.

An effective duration for administering a composition containing a therapeutically effective amount of a modified LGIC described herein (e.g., a nucleic acid encoding a modified LGIC described herein) and/or a LGIC ligand that can bind to and activate the modified LGIC as described herein can be any duration that improves symptoms of a channelopathy without producing significant toxicity to the mammal. For example, the effective duration can vary from several days to several weeks, months, or years. In some cases, the effective duration for the treatment of a channelopathy can range in duration from about one month to about 10 years. Multiple factors can influence the actual effective duration used for a particular treatment. For example, an effective duration can vary with the frequency of administration, effective amount, use of multiple treatment agents, route of administration, and severity of the channelopathy being treated.

In certain instances, a course of treatment and the symptoms of the mammal being treated for a channelopathy can be monitored. Any appropriate method can be used to monitor the symptoms of a channelopathy.

The invention will be further described in the following examples, which do not limit the scope of the invention described in the claims.

EXAMPLES

Example 1: Potency-Enhancing Ligand Binding Domain Mutations

Figure 3A:
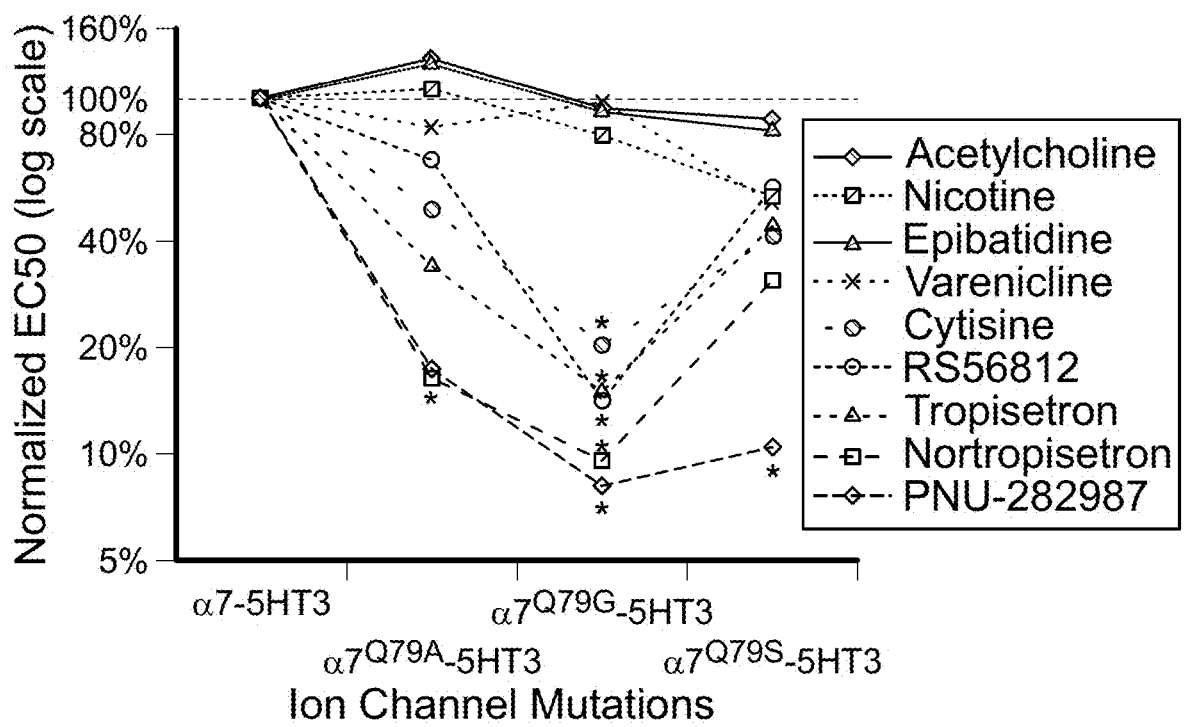
FIG. 3A) A graph of EC50s normalized to the unmodified α7-5HT3 chimeric channel (log scale). *P<0.05, statistically significant potency changes are noted (ANOVA followed by Dunn's test).
Figure 3B:
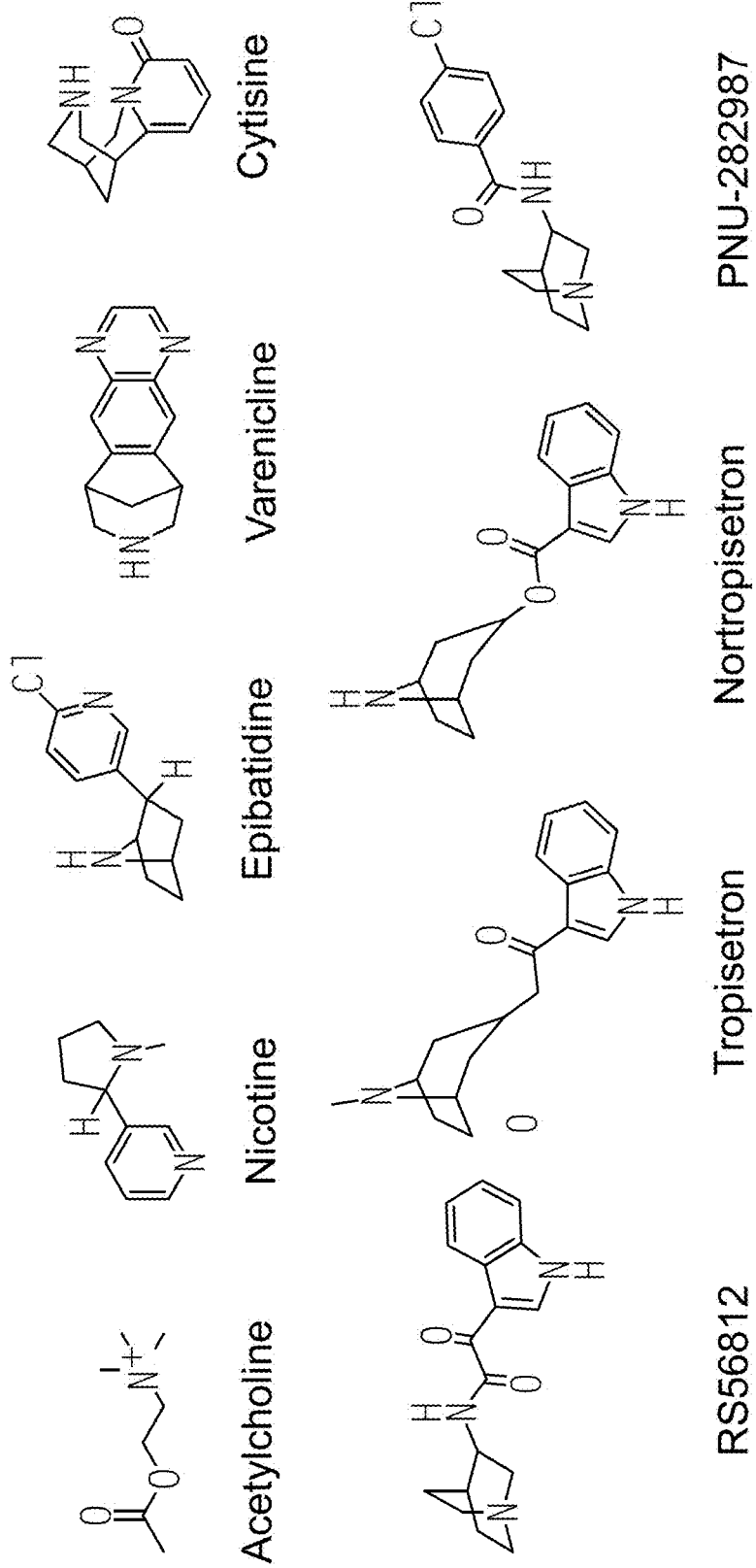
FIG. 3B) Chemical structures of know nAChR agonists.
Figure 5C:
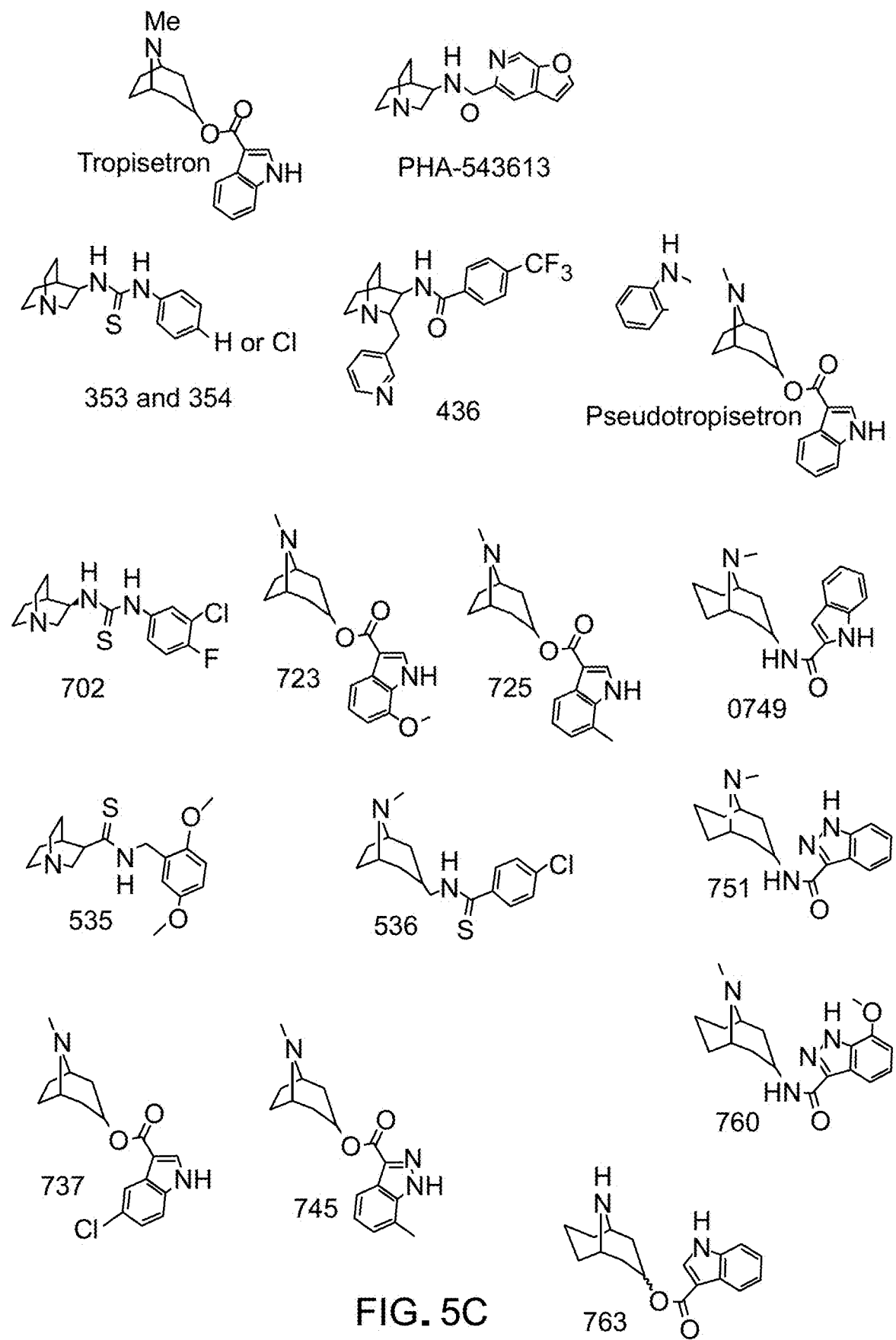

A screen was performed with a panel of 41 α7-5HT3 chimeric channels having mutant LBDs against a panel of 51 clinically used drugs with chemical similarity to nicotinic receptor agonists. Mutations were at residues highlighted in FIG. 1. The screen revealed mutations at Gln$^{79}$ in the α7 nAChR LBD that enhanced potency for the known nAChR agonist tropisetron (FIG. 2). These mutations (Q79A, Q79G, Q79S) reduce the size of the amino acid side chain. Some mutant ion channel-ligand combinations gave up to 12-fold improvement in potency (Table 1, FIG. 3). Canonical α7 nAChR agonists, ACh, nicotine, epibatidine, and the anti-smoking drug varenicline were not significantly affected by Q79A, Q79G, or Q79S mutations. However, a subset of α7 nAChR agonists showed enhanced potency with some of the mutations. Cytisine, RS56812, tropisetron, nortropisetron, and PNU-282987 showed significantly improved potency for $\alpha7^{Q79G}$-5HT3. Additionally, nortropisetron and PNU-282987 showed a significantly enhanced potency for $\alpha7^{Q79A}$-5HT3 and $\alpha7^{Q79S}$-5HT3, respectively. In general, agonists based on a quinuclidine or tropane pharmacophore with a linked aromatic structure that interacts with the complementary binding face of the ligand binding domain showed improved potency with Gln79 substitution with the smaller amino acid residues Ala, Gly, or Ser. For most agonists, $\alpha7^{Q79G}$-5HT3 was the most preferred mutant chimeric ion channel.

TABLE 1

Potency of nAChR agonists against chimeric cation channels mutated at Gln79 in HEK cells. Mean EC50, SEM in parentheses (μM).

| Agonist | α7-5HT3 | $\alpha7^{Q79A}$-5HT3 | $\alpha7^{Q79G}$-5HT3 | $\alpha7^{Q79S}$-5HT3 |
|---|---|---|---|---|
| Acetylcholine | 7.0 (0.8) | 9.2 (1.8) | 6.7 (0.6) | 6.2 (1.4) |
| Nicotine | 3.9 (0.4) | 4.1 (1.3) | 3.1 (0.5) | 2.1 (0.4) |
| Epibatidine | 0.053 (0.006) | 0.067 (0.022) | 0.050 (0.008) | 0.044 0.006) |
| Varenicline | 0.92 (0.16) | 0.76 (0.21) | 0.91 (0.12) | 0.47 (0.07) |
| Cytisine | 8.2 (0.3) | 4.0 (0.9) | 1.7 (0.2) | 4.4 (1.0) |
| RS56812 | 10 (1.8) | 6.8 (1.9) | 1.4 (0.2) | 5.7 (0.8) |
| Tropisetron | 0.24 (0.03) | 0.08 (0.02) | 0.035 (0.002) | 0.11 (0.02) |
| Nortropisetron | 0.061 (0.021) | 0.010 (0.002) | 0.006 (0.001) | 0.019 (0.007) |
| PNU-282987 | 0.22 (0.03) | 0.037 (0.009) | 0.018 (0.003) | 0.023 (0.004) |

These mutated LBDs were used to generate α7-GlyR chimeric channels having enhanced potency for most of these ligands up to 6-fold (FIG. 4A). Like mutations of α7-5HT3, these mutations at Gln79 did not significantly affect potency of ACh, nicotine, epibatidine, varenicline, or cytisine. However, tropisetron, nortropisetron, and RS56812 showed significantly enhanced potency for $\alpha7^{Q79G}$-GlyR. Similar to LBD mutations for α7-5HT3, nortropisetron had significantly enhanced potency for $\alpha7^{Q79A}$-GlyR, and PNU-282987 showed significantly enhanced potency for $\alpha7^{Q79S}$-GlyR. For most agonists, $\alpha7^{Q79G}$-GlyR was the most preferred mutant chimeric ion channel.

Another relationship that was observed in the small molecule screen was that mutations at Trp77 conferred agonist activity for the drug granisetron at the $\alpha7^{W77F}$-5HT3 (EC50: 1.2 μM), $\alpha7^{W77Y}$-5HT3 (EC50: 1.1 μM), and $\alpha7^{W77F}$-GlyR (EC50: 0.66 μM) receptors. Granisetron is a 5HT3 receptor antagonist granisetron, which does not activate α7-5HT3 or α7-GlyR.

These results show that mutation of Q79 (to A, G, or S) in the α7 nAChR LBD enhanced binding of known LGIC ligands to modified LGICs.

Example 2: Potency Enhancing Ion Pore Domain Mutations

α7-GlyR channels having IPD mutations previously established in full length glycine receptor channels (T258S and A288G, GlyR numbering; equivalent to T268S and A298G for α7-GlyR numbering) were examined for enhanced potency for the allosteric agonist ivermectin. Channels having $\alpha7\text{-GlyR}^{T268S}$ were found to have substantial ligand-free open probability, which rendered them unsuitable for ligand-controlled manipulations of cells. Mutations at $\alpha7\text{-GlyR}^{A298G}$, which were effective for enhancing ivermectin potency at the full length glycine receptor, led to modest change in open probability in the absence of the ligand; thus this channel was examined for activity against a panel of known agonists. For canonical agonists ACh, nicotine, and epibatidine, as well as for varenicline and tropisetron, the agonist potency was not significantly enhanced in $\alpha7\text{-GlyR}^{A298G}$. A subset of α7 nAChR agonists did show up to a modest 4-fold increase in potency: RS56812, cytisine, PNU-282987, and nortropisetron were significantly more potent. Therefore, the effect of the IPD A298G mutation improved ligand potency, but depended on ligand structure and was not as effective as mutations in the LBD.

The Q79G mutation in the LBD and the A298G IPD mutation for α7-GlyR was examined (Table 2). The double mutant chimeric channel, $\alpha7^{Q79G}\text{-GlyR}^{A298G}$, led to synergistic enhancement of potency showing up to 18-fold enhancement of potency relative to α7-GlyR to α7 nAChR agonists. The enhancement from this double mutant channel was greater than that from the individual mutations for agonists RS56812, tropisetron, nortropisetron, and PNU-282987. Further underscoring the unexpected structural sensitivity of this combination of mutations, multiple agonists, such as ACh, nicotine, epibatidine, varenicline, and cytisine were not significantly changed between α7-GlyR and $\alpha7^{Q79G}\text{-GlyR}^{A298G}$. Therefore, combination of the LBD mutation Q79G with the IPD mutation A298G led to a synergistic effect where potency for some but not all nicotinic agonists was greatly increased by ~10-20-fold.

TABLE 2

Potency of nAChR agonists against mutated chimeric chloride channels. Mean EC50 and SEM in parentheses (μM) for agonist activity in HEK cells expressing chimeric channels.

| Agonist | α7 GlyR | α7$^{Q79A}$-GlyR | α7$^{Q79G}$-GlyR | α7$^{Q79S}$-GlyR | α7-GlyR$^{A298G}$ | α7$^{Q79G}$-GlyR$^{A298G}$ |
|---|---|---|---|---|---|---|
| Acetylcholine | 6.4 (1.2) | 7.6 (1.7) | 7.1 (1.2) | 4.5 (1.2) | 6.4 (1.8) | 4.8 (0.5) |
| Nicotine | 5.0 (1.8) | 2.6 (0.7) | 4.1 (0.3) | 1.4 (0.4) | 3.1 (1.8) | 2.2 (0.6) |
| Epibatidine | 0.062 (0.021) | 0.038 (0.005) | 0.069 (0.011) | 0.024 (0.003) | 0.018 (0.001) | 0.032 (0.007) |
| Varenicline | 0.62 (0.2) | 0.48 (0.08) | 1.1 (0.25) | 0.28 (0.06) | 0.25 (0.04) | 0.33 (0.08) |
| Cytisine | 6.4 (2.0) | 4.5 (0.6) | 5.6 (2.1) | 2.5 (0.7) | 2.1 (0.28) | 2.8 (1.0) |
| RS56812 | 6.5 (1.8) | 3.5 (0.5) | 2.0 (0.15) | 2.8 (0.5) | 2.3 (0.1) | 0.61 (0.14) |
| Tropisetron | 0.15 (0.045) | 0.044 (0.008) | 0.038 (0.003) | 0.040 (0.009) | 0.065 (0.026) | 0.011 (0.002) |
| Nortropisetron | 0.022 (0.007) | 0.004 (0.001) | 0.008 (0.003) | 0.005 (0.001) | 0.005 (0.001) | 0.002 (0.001) |
| PNU-282987 | 0.13 (0.038) | 0.022 (0.004) | 0.026 (0.005) | 0.014 (0.002) | 0.035 (0.005) | 0.007 (0.001) |

These results show that mutation of Q79 (to A, G, or S) in the α7 nAChR LBD and/or mutation of A298 (to G) in the GlyR IPD further enhanced selective binding of known LGIC ligands to modified LGICs.

Example 3: Molecules Exhibiting Enhanced Potency

Based on the structure activity relationship of known agonists that showed enhanced potency with α7$^{Q79G}$-GlyR$^{A298G}$, a variety of synthetic molecules comprised of either quinuclidine, tropane, or 9-azabicyclo[3.3.1]nonane pharmacophores with one or more aromatic side chain substituents were tested. In addition, the known α7 nAChR agonist PHA-543613 (Walker et al 2006, Wishka et al 2006) was also tested and showed exceptional potency for α7$^{Q79G}$-GlyR$^{A298G}$. These molecules generally showed enhanced potency 10-fold to 100-fold (Table 3), indicating that, for these pharmacophores, a range of structural features were compatible with improved potency for α7$^{Q79G}$-GlyR$^{A298G}$.

These results show that modified LGICs can be activated by synthetic quinuclidine-containing and tropane-containing LGIC ligands.

TABLE 3

Potency of compounds against chimeric channels. Mean EC50 and SEM in parentheses (μM) for agonist activity in HEK cells expressing chimeric channels. Partial refers to partial agonist activity.

| Compound | $X_1$ | $X_2$ | $X_3$ | Y | $C_1$ n | $C_2$ n | $C_3$ n | C-X config | R | A | α7-5HT3 EC$_{50}$ (μM) | α7-GlyR EC$_{50}$ (μM) | α7$^{Q79G}$-GlyR$^{A298G}$ EC$_{50}$ (μM) |
|---|---|---|---|---|---|---|---|---|---|---|---|---|---|
| PNU-282987 | N | CH$_2$ | NH | O | 0 | 1 | 0 | R | H | 4-chloro-benzene | 0.22 | 0.13 | 0.007 |
| Tropisetron | C | NMe | O | O | 1 | 0 | 0 | Endo | H | 1H-indole | 0.24 | 0.15 | 0.011 |
| Pseudotropisetron | C | NMe | O | O | 1 | 0 | 0 | Exo | H | 1H-indole | 2 | 0.7 | <0.2 |
| Nortropisetron | C | NH | O | O | 1 | 0 | 0 | Endo | H | 1H-indole | 0.061 | 0.022 | 0.002 |
| PHA-543613 | N | CH$_2$ | NH | O | 0 | 1 | 0 | R | H | furo[2,3]pyridine | 0.046 | 0.039 | 0.004 |
| 0542 | C | NMe | NH | S | 1 | 0 | 0 | Endo | H | 1H-indole | 3.8 | 0.58 | 0.072 |
| 0026 | N | CH$_2$ | O | O | 0 | 1 | 0 | S | H | 4-(trifluoromethyl) benzene | — | 13.7 | 1.43 |
| 0456 | N | CH$_2$ | CH$_2$—NH | S | 0 | 1 | 0 | mix | H | 4-chloro benzene | — | 2.8 | 0.47 |
| 0434 | N | CH$_2$ | NH | O | 0 | 1 | 0 | mix | pyridin-3-ylmethyl | 2,5-dimethoxy benzene | >10 | >10 | 0.19 |
| 0436 | N | CH$_2$ | NH | O | 0 | 1 | 0 | mix | pyridin-3-ylmethyl | 4-(trifluoromethyl) benzene | 0.84 | 0.31 | 0.006 |
| 0354 | N | CH$_2$ | NH | S | 0 | 1 | 0 | R | H | 4-chloroaniline | 1.4 partial | 1.0 | 0.03 |
| 0353 | N | CH$_2$ | NH | O | 0 | 1 | 0 | S | H | aniline | 0.65 | 0.27 | 0.01 |
| 0295 | N | CH$_2$ | NH | O | 0 | 1 | 0 | S | H | 5-(trifluoromethyl) pyridin-2-yl) | >100 | >100 | 4.6 |
| 0296 | N | CH | NH | O | 0 | 1 | 0 | S | H | 6-(trifluoromethyl) nicotinic | >100 | — | 0.45 |
| 0536 | C | NMe | NH | S | 1 | 0 | 1 | Endo | H | 4-chloro-benzene | >33 | >100 | 9.1 |
| 0676 | N | CH$_2$ | NH | O | 0 | 1 | 0 | S | H | 1H-indole | 0.03 | 0.018 | 0.002 |

Example 4: Mutations that Reduce Acetylcholine Responsiveness

Figure 6A:
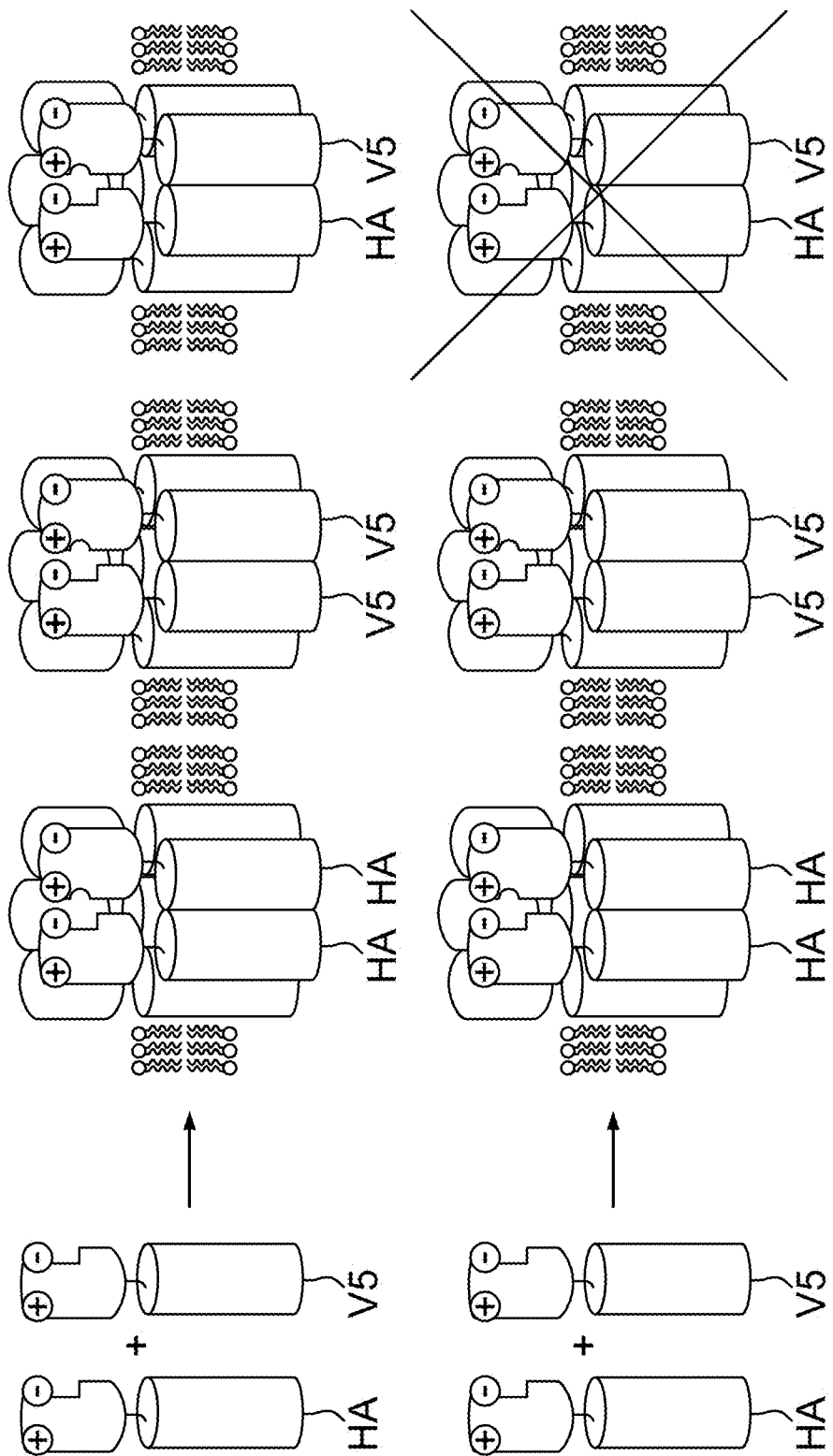
FIGS. 6A-6C show mutations that reduce association of chimeric LCIG α7 nAChR LBDs with unmodified LBDs.
Figure 6B:
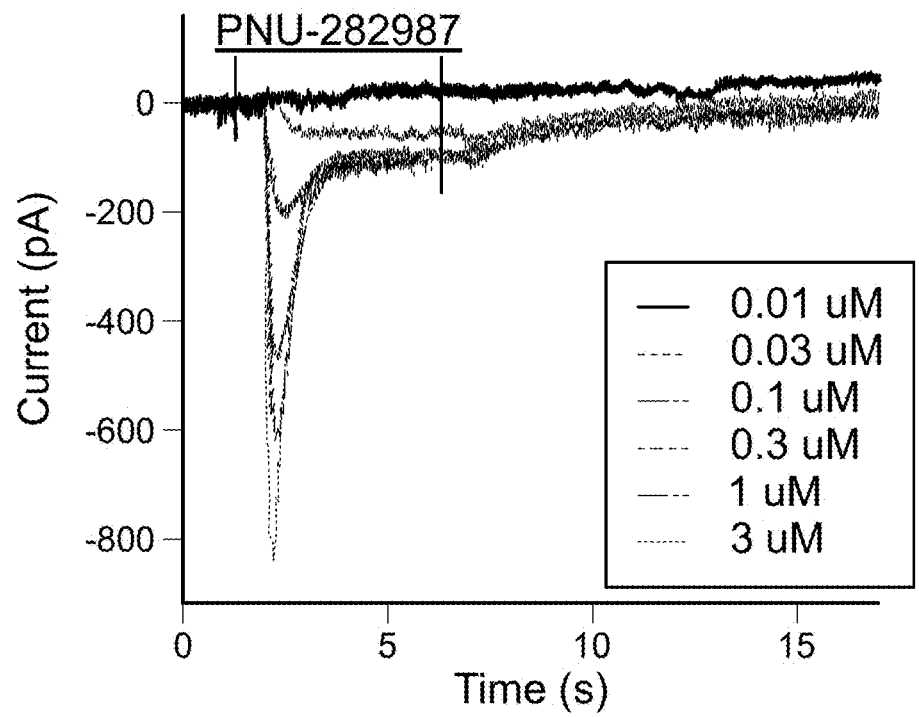
Figure 6C:
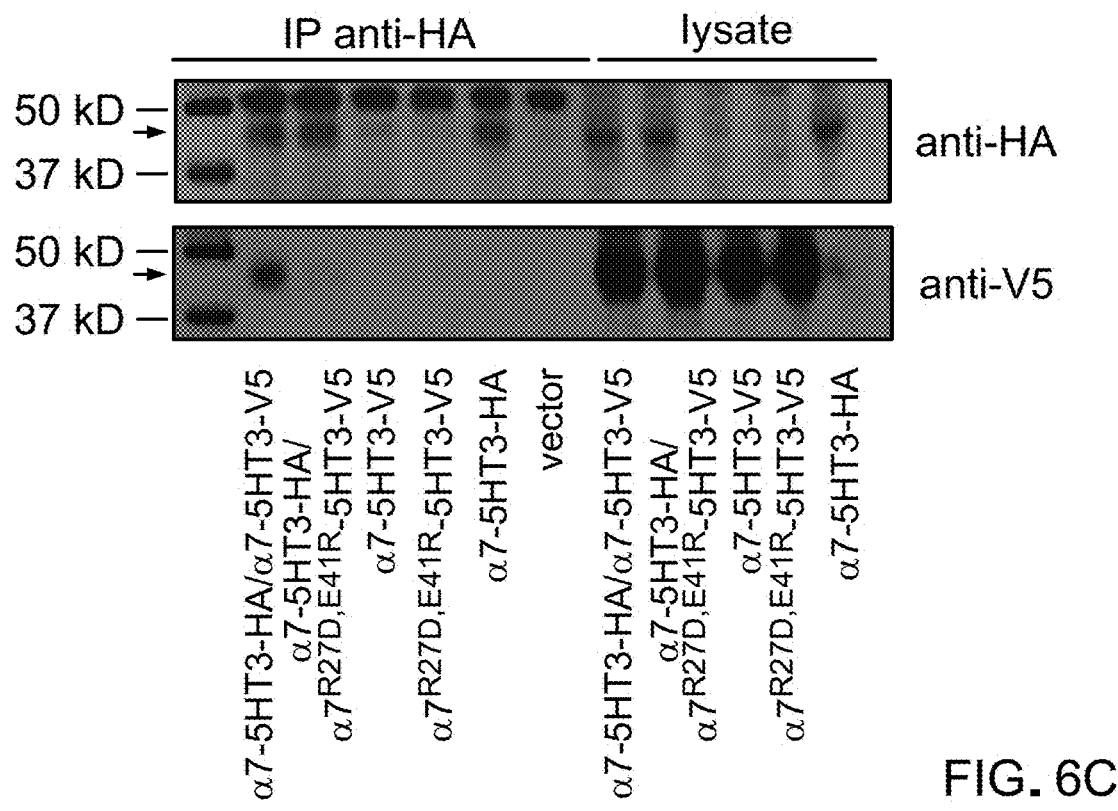

The α7 nAChR has relatively low sensitivity to ACh compared to other nAChR isoforms, and potency enhancing mutations for tropane and quinuclidine ligands did not substantially alter the potency of acetylcholine at these channels. Thus, the chimeric channels were further modified to reduce acetylcholine responsiveness of these channels. Acetylcholine responsiveness was considerably reduced to more than 100 µM in some cases with additional LBD mutations Y115F and Q139G that that only modestly reduced the potency of some agonists for α7$^{Q79G,Y115F}$-5HT3, α7$^{Q79G,Q139G}$-5HT3, α7$^{Q79G,Q139G}$-GlyR$^{A298}$, α7$^{Q79G,Y115F}$-GlyR$^{A298G}$. For example, α7$^{Q79G,Y115F}$-GlyR$^{A298G}$ has an EC50 of 13 nM for nortropisetron and >100 µM for ACh (Table 4).

subunits having charge reversal mutations were able to assemble selectively with each other without interacting with unmodified channels, e.g. endogenous α7 nAChR. The double mutation of R27D,E41R in the α7 nAChR LBD resulted in functional channels (FIG. 6B). Co-expression of these charge reversal channels with α7-5HT3 channels having an unmodified sequence showed that the charge reversal subunits did not co-immunoprecipitate with unmodified channels (FIG. 6C). Combination with potency enhancing mutations and acetylcholine blocking mutations to give the chimeric channel α7$^{R27D,E41R,Q79G,Y115F}$-GlyR$^{A298G}$ revealed that some agonists retained high potency for their cognate agonist (Table 4, right column).

These results show that R27D and E41R mutations in α7 nAChR LBD reduced association of the modified LGIC subunits with other modified and/or endogenous LGIC subunits.

TABLE 4

Potency of nAChR agonists against mutated chimeric chloride channels with low acetylcholine responsiveness. Mean EC50 and SEM in parentheses (µM) for activity in HEK cells expressing chimeric channels.

|  | α7$^{Q79G,Y115F}$-5HT3 | α7$^{Q79G,Q139G}$-5HT3 | α7$^{Q79G,Y115F}$-GlyRA298G | α7$^{Q79G,Q139G}$-GlyRA298G | α7$^{R27D,E41R,Q79G,Y115F}$-GlyRA298G |
|---|---|---|---|---|---|
| Acetylcholine | >100 | 36 (2) | >100 | 73 (27) | >100 |
| Nicotine | 34 (4) | 24 (4) | 22 (3) | 30 (8) | 7.5 (1.3) |
| Tropisetron | 0.10 (0.12) | 0.31 (0.06) | 0.086 (0.043) | 0.26 (0.04) | 0.035 (0.021) |
| Nortropisetron | 0.028 (0.005) | 0.047 (0.013) | 0.013 (0.001) | 0.031 (0.006) | 0.003 (0.001) |
| PNU-282987 | 0.35 (0.07) | 0.16 (0.04) | 0.22 (0.04) | 0.18 (0.04) | 0.066 (0.010) |

These results show that Y115F and/or Q139G mutations in the α7 nAChR LBD reduced binding of the endogenous LGIC ligand Ach to the modified LGIC.

Example 5: Mutations that Reduce Associations with Endogenous Receptor Subunits Assembly of α7 nAChRs is based on associations of five homomeric subunits through interactions between the LBDs (Celie et al 2004 Neuron 41: 907-14). To minimize undesired associations with endogenous α7 nAChR subunits and/or unwanted associations of chimeric channels, potential inter-subunit salt bridges were identified by examining the crystal structure of the acetylcholine binding protein and identifying nearby inter-subunit residues with opposite charge that also have homologous ionic amino acids in the α7 nAChR receptor LBD. Charge reversal mutations (switching the acidic member of a potential salt bridge to a basic residue and its basic partner to an acidic residue) were designed to disrupt inter-subunit interactions with unmodified subunits but preserve interactions between the subunits with charge reversal mutations (FIG. 6A). Chimeric LGIC

Example 6: LBD Mutations that Increase Ligand Potency

Mutations in Gly$^{175}$ and Pro$^{216}$ of the α7 nAChR LBD in α7-GlyR chimeric channels were tested. Mutation of Gly$^{175}$ to Lys (α7$^{G175K}$-GlyR) showed increased potency for ACh (5-fold) (Table 5). For α7$^{G175K}$-GlyR, it was also found that nicotine potency was enhanced 10-fold relative to the unmodified α7-GlyR chimeric channel (Table 5). Mutation of Pro$^{216}$ to Ile (α7$^{P216I}$-GlyR) did not substantially alter ACh potency (Table 5). However, α7$^{P216I}$-GlyR showed increased nicotine potency by >4-fold relative to unmodified α7-GlyR (Table 5). These potency enhancing mutations in α7$^{G175K}$-GlyR and α7$^{P216I}$-GlyR also affected potency of several other α7-GlyR agonists up to 30-fold (Table 5). For α7$^{G175K}$-GlyR, greater than 10-fold potency enhancement over α7-GlyR was seen for the clinically used drugs tropisetron, varenicline, cytisine, granisetron, and epibatidine. For α7$^{P216I}$-GlyR, potency enhancement was approximately 3-fold (Table 5).

TABLE 5

Agonist potency enhancement by G175K and P216I mutations at a7GlyR chimeric channels. Units: µM. Parentheses: SEM.

| Compound | a7GlyR | α7GlyR G175K | α7GlyR P216I | α7GlyR Y115F G175K | α7GlyR G175K Y210F | α7GlyR W77F G175K | α7GlyR Q79G G175K | α7GlyR W77F Q79G G175K |
|---|---|---|---|---|---|---|---|---|
| Acetylcholine | 6.4 (1.2) | 1.2 (0.41) | 4.0 (0.5) | 52 (6.6) | 93 (1.3) | 6.8 (1.6) | 4.5 (1.3) | 41 (3.1) |
| Nicotine | 5.0 (1.8) | 0.5 (0.25) | 1.4 (0.1) | 4.1 (1.4) | 6 (0.5) | 1.3 (0.4) | 1.1 (0.1) | 2.6 (0.7) |
| Epibatidine | 0.062 (0.021) | 0.005 (0.001) | 0.03 (0.01) | 0.036 (0.006) | 0.65 (0.11) | 0.04 (0) | 0.037 (0.013) | 2.6 (2.3) |

TABLE 5-continued

Agonist potency enhancement by G175K and P216I mutations at α7GlyR chimeric channels.
Units: μM. Parentheses: SEM.

| Compound | a7GlyR | α7GlyR G175K | α7GlyR P216I | α7GlyR Y115F G175K | α7GlyR G175K Y210F | α7GlyR W77F G175K | α7GlyR Q79G G175K | α7GlyR W77F Q79G G175K |
|---|---|---|---|---|---|---|---|---|
| Varenicline | 0.62 (0.2) | 0.056 (0.014) | 0.18 (0.06) | 5.0 (1.7) | 4.3 (0.6) | 0.57 (0.18) | 0.42 (0.1) | 3.3 (1.0) |
| Cytisine | 6.4 (2.0) | 0.4 (0.05) | 1.9 (0.2) | 7.1 (1.2) | >10 | 1.5 (0.6) | 2.5 (1.1) | 6.9 (1.2) |
| PNU-282987 | 0.13 (0.038) | 0.005 (0.001) | 0.04 (0.004) | 0.1 (0.01) | 0.7 (0.3) | 0.67 (0.35) | 0.06 (0.05) | 0.5 (0.2) |
| Tropisetron | 0.15 (0.045) | 0.011 (0.002) | 0.05 (0.003) | 0.027 (0.004) | 1.1 (0.2) | 0.04 (0.01) | 0.01 (0.001) | 0.024 (0.004) |
| Nortropisetron | 0.022 (0.007) | 0.003 (0.002) | 0.006 (0.0004) | 0.007 (0.001) | 0.28 (0.09) | 0.004 (0.001) | 0.0008 (0.0001) | 0.0026 (0.0004) |
| PHA-543613 | 0.03 (0.01) | 0.001 (0.0001) | 0.009 (0.001) | 0.02 (0.007) | 0.26 (0.08) | 0.041 (0.016) | 0.003 (0.0004) | 0.12 (0.04) |
| Granisetron | >100 | 3.3 (0.1) | 6.1 (0.9) | 1.6 (0.6) | 1.4 (0.1) | 0.18 (0.02) | >100 | 1.6 (0.4) |
| Ivermectin | nd | nd | nd | nd | nd | nd | nd | nd |

| Compound | α7GlyR W77F Q79G Y115F G175K | α7GlyR W77F G175K Y210F | α7GlyR Q79G G175K Y115F | α7GlyR Q79G Y115F G175K Y210F | α7GlyR Q79G Y115F G175K K322L | α7GlyR Y115F G175K L141F | α7GlyR Q79G Q139L G175K |
|---|---|---|---|---|---|---|---|
| Acetylcholine | 143 (13) | 80 (31) | 98 (10) | >1000 | >200 | 58 | 53 |
| Nicotine | 6.1 (2.0) | 4.2 | 13 (0.2) | >100 | 14.5 | 3 | 5.8 |
| Epibatidine | 0.33 | 0.38 | 0.22 (0.015) | >10 | 0.27 | 0.144 | 0.144 |
| Varenicline | >10 | >9 | >10 | >30 | >30 | >8.1 | 0.96 |
| Cytisine | 4.02 | 5.1 | >10 | >30 | >30 | 4.74 | 3.24 |
| PNU-282987 | >1 | >40 | 0.08 (0.01) | >1 | 0.018 | 0.51 | 0.05 |
| Tropisetron | 0.1 (0.04) | >1 | 0.027 (0.002) | 0.717 | 0.066 | 0.117 | 0.105 |
| Nortropisetron | 0.014 | >12 | 0.012 (0.001) | >0.3 | 0.069 | 0.075 | 0.001 |
| PHA-543613 | >0.3 | >3 | 0.036 (0.006) | >1 | 0.111 | 0.057 | 0.024 |
| Granisetron | 0.2 | 0.06 (0.01) | 6.8 (1.7) | 4.8 | >30 | 0.84 | >30 |
| Ivermectin | nd | nd | 0.21 | nd | nd | nd | nd | nd = not determined

For use in organisms that produce ACh, it is important to reduce the endogenous ACh potency at these channels comprised of the α7 nAChR LBD. Mutation G175K could be further combined with other mutations that reduced sensitivity to ACh, such as Y115F and Y210F. For $α7^{Y115F,G175K}$-GlyR, high potency for agonists based on tropane or quinuclidine core structures were found for tropisetron, granisetron, nortropisetron, PNU-282987, and PHA-543613, and greatly reduced potency for varenicline and cytisine (Table 5). For $α7^{G175K,Y210F}$-GlyR, potency for most agonists was considerably reduced, however potency enhancement for granisetron was observed (Table 5).

To develop channels with reduced ACh responsiveness but high potency for other agonists, $α7^{G175K}$-GlyR was combined with additional mutations that increase the potency of specific agonists. Combination with W77F reduced ACh potency, and $α7^{W77F,G175K}$-GlyR showed increased potency over α7-GlyR for granisetron, nortropisetron, and tropisetron but not for PNU282-987, varenicline, cytisine, or PHA-543613 (Table 5). Combination of G175K with Q79G reduced ACh potency, and $α7^{Q79G,G175K}$-GlyR showed increased potency for nortropisetron, PHA-543613, and tropisetron (Table 5). However, this potency enhancement was not observed for other agonists, such as PNU282-987, or varenicline. $α7^{G175K,Q139L}$-GlyR reduced ACh potency and increased potency for nortropisetron and tropisetron (Table 5).

Further reductions in ACh potency were achieved while maintaining high potency for with synthetic agonists, including those based on tropane and quinuclidine core structures, by incorporating mutations at W77F, Q79G, L141F, Y115F, G175K, and Y210F in various combinations. $α7^{Q79G,Y115F,G175K}$-GlyR reduced ACh responsiveness while maintaining potent responses to tropisetron (Table 5). These mutations also enhanced responsiveness to other tropane and quinuclidine core structures relative to $α7^{Y115F,G175K}$-GlyR as well as relative to α7-5HT3 (representative of endogenous α7 nAChR activity), especially quinuclidine thioureas 702 and 703 as well as tropane ester 723, 725, 726, 736, 737, 738, and 745 (Table 6). $α7^{Q79G,Y115F,G175K}$-GlyR also showed high sensitivity to ivermectin (Table 5). $α7^{W77F,Q79G,G175K}$-GlyR reduced ACh responsiveness while maintaining high potency responses to tropisetron, and nortropisetron (Table 5). $α7^{W77F,Q79G,G175K}$-GlyR also showed enhanced potency for additional tropane-based core structures, such as compounds 723 and 725, as well as the clinically used drugs mequitazine and promazine (Table 6). $α7^{W77F,G175K,Y210F}$-GlyR reduced ACh responsiveness but markedly improved potency to granisetron (Table 5). $\alpha7^{L141F,Y115F,G175K}$-GlyR reduced ACh responsiveness while conferring sensitivity to granisetron (Table 5). $\alpha7^{Q79G,Q139L,G175K}$-GlyR reduced ACh responsiveness but showed potent responses to nortropisetron (Table 5).

TABLE 6

Potency enhancement of tropane, quinuclidine agonists, 9-azabicyclo[3.3.1]nonane agonists, diazabicyclo[3.2.2]nonane agonists, and promazine by G175K and P216I α7GlyR chimeric channels. Indole and indazole aromatic (A) substituents attached at 3-position. Units: μM.

| Agonist class | $X_1$ | $X_2$ | $X_3$ | Y | $C_1$ n | $C_2$ n | $C_3$ n | C-X configuration | R | Aromatic substitution (A) | Compound | α7-5HT3 | α7-GlyR | α7GlyR G175K | α7GlyR Q79G G175K | α7GlyR Y115F G175K | α7Gly Q79G G175K Y115F | α7GlyR Q79G G175K Y115F R27D E41R | α7GlyR W77F Q79G G175K |
|---|---|---|---|---|---|---|---|---|---|---|---|---|---|---|---|---|---|---|---|
| Quinuclidine | N | CH₂ | NH | S | 0 | 1 | 0 | R | H | 3,5-dichloro-aniline | 677 | 10.6 | 4.4 | 0.66 (0.06) | 0.86 (0.004) | 3.7 (0.7) | 0.98 (0.09) | 0.58 (0.14) | nd |
| Quinuclidine | N | CH₂ | NH | S | 0 | 1 | 0 | R | H | 3,4-dichloro-aniline | 682 | >100 | 0.2 | 0.12 (0.1) | 0.013 (0.001) | 0.40 (0.01) | 0.13 (0.01) | 0.06 (0.012) | nd |
| Quinuclidine | N | CH₂ | NH | S | 0 | 1 | 0 | R | H | 4-(trifluoromethoxy)aniline | 684 | >100 | 1.6 | 0.23 (0.02) | 0.078 (0.022) | 3.0 (0.3) | 0.79 (0.04) | 0.4 (0.03) | nd |
| Quinuclidine | N | CH₂ | NH | S | 0 | 1 | 0 | R | H | 4-fluoroaniline | 699 | 2.8 | 3.6 | 0.26 (0.11) | 0.039 (0.009) | 2.9 | 0.52 (0.09) | 0.33 (0.1) | nd |
| Quinuclidine | N | CH₂ | NH | S | 0 | 1 | 0 | R | H | 3-chloro-aniline | 700 | 1.8 | 1.9 | 0.081 (0.009) | 0.012 (0.0002) | 1.5 | 0.21 (0.04) | 0.11 (0.02) | nd |
| Quinuclidine | N | CH₂ | NH | S | 0 | 1 | 0 | R | H | 3-chloro-2-fluoroaniline | 701 | >100 | nd | 0.47 (0.17) | 0.086 (0.014) | 5.46 | 1.0 (0.2) | 0.58 (0.03) | nd |
| Quinuclidine | N | CH₂ | NH | S | 0 | 1 | 0 | R | H | 3-chloro-4-fluoroaniline | 702 | >100 | 0.9 | 0.12 (0.004) | 0.018 (0.003) | 1.6 | 0.17 (0.03) | 0.12 (0.02) | nd |
| Quinuclidine | N | CH₂ | NH | S | 0 | 1 | 0 | R | H | 5-chloro-2-fluoroaniline | 703 | >100 | nd | 0.52 (0.08) | 0.03 (0.01) | 12.7 | 1.2 (0.06) | 1.1 (0.5) | nd |
| Quinuclidine | N | CH₂ | NH | S | 0 | 1 | 0 | R | H | 3-chloro-4-methylaniline | 704 | 0.7 | nd | 0.062 (0.008) | 0.018 (0.002) | 0.76 (0.01) | 0.24 (0.02) | 0.18 (0.06) | nd |
| Quinuclidine | N | CH₂ | NH | S | 0 | 1 | 0 | R | H | 5-chloro-2-methylaniline | 705 | >100 | nd | 9.6 | 0.67 (0.14) | >10 | 4.8 (1.4) | 4.5 (2.7) | nd |
| Quinuclidine | N | CH₂ | NH | S | 0 | 1 | 0 | R | H | 4-(trifluoromethoxy)aniline | 713 | >100 | nd | 2.1 (0.2) | 0.54 (0.06) | >10 | 23.9 | >10 | nd |
| Tropane | C | NMe | NH | S | 1 | 0 | 0 | Endo | H | 1-methyl-1H-indole | 622 | >100 | nd | 0.87 | 1.3 (0.2) | 2.5 (0.4) | 0.93 (0.02) | 1.0 (0.2) | 1.7 |
| Tropane | C | NMe | O | O | 1 | 0 | 0 | Endo | H | 4-methoxy-1H-indole | 721 | 0.5 | nd | 0.027 (0) | 0.015 (0.003) | 0.080 (0.002) | 0.020 (0.001) | 0.016 (0.001) | 0.04 |
| Tropane | C | NMe | O | O | 1 | 0 | 0 | Endo | H | 6-methoxy-1H-indole | 722 | 0.5 | nd | 0.02 (0.001) | 0.015 (0) | 0.052 (0.008) | 0.028 (0.008) | 0.016 (0.001) | 0.03 |
| Tropane | C | NMe | O | O | 1 | 0 | 0 | Endo | H | 7-methoxy-1H-indole | 723 | 12.8 | 4 | 0.31 (0.02) | 0.02 (0) | 0.71 (0.46) | 0.07 (0.01) | 0.024 (0.003) | 0.02 |
| Tropane | C | NMe | O | O | 1 | 0 | 0 | Endo | H | 4-methyl-1H-indole | 724 | 1.2 | nd | 0.036 (0.003) | 0.012 (0.002) | 0.091 (0.013) | 0.02 (0.006) | 0.012 (0.002) | 0.06 |
| Tropane | C | NMe | O | O | 1 | 0 | 0 | Endo | H | 7-methyl-1H-indole | 725 | 12.2 | 8.1 | | 0.022 (0.02) | 0.069 (0.33) | 0.042 (0.005) | 0.022 (0.0001) | 0.024 |
| Tropane | C | NMe | O | O | 1 | 0 | 0 | Endo | H | 4-chloro-1H-indole | 726 | 4.2 | nd | 0.58 (0.24) | 0.016 (0.001) | 0.51 (0.37) | 0.044 (0.006) | 0.018 (0) | 0.03 |
| Tropane | C | NMe | O | O | 1 | 0 | 0 | Endo | H | 5-methoxy-1H-indole | 736 | 0.83 | 0.9 | 0.2 (0.01) | 0.044 (0.002) | 0.57 (0.21) | 0.078 (0.018) | 0.078 (0.024) | 0.06 |
| Tropane | C | NMe | O | O | 1 | 0 | 0 | Endo | H | 5-chloro-1H-indole | 737 | 1 | nd | 0.082 (0.004) | 0.013 (0.001) | 0.16 (0.03) | 0.033 (0.004) | 0.016 (0.001) | 0.101 |
| Tropane | C | NMe | O | O | 1 | 0 | 0 | Endo | H | 6-chloro-1H-indole | 738 | 0.4 | nd | 0.015 | 0.016 | 0.04 | 0.025 | 0.012 | 0.033 |

TABLE 6-continued

Potency enhancement of tropane, quinuclidine agonists, 9-azabicyclo[3.3.1]nonane agonists, diazabicyclo[3.2.2]nonane agonists, and promazine by G175K and P216I α7GlyR chimeric channels. Indole and indazole aromatic (A) substituents attached at 3-position. Units: μM.

| Agonist class | $X_1$ | $X_2$ | $X_3$ | Y | $C_1$ n | $C_2$ n | $C_3$ n | C-X configuration | R | Aromatic substitution (A) | Compound | α7-5HT3 | α7-GlyR | α7GlyR G175K | α7GlyR Q79G G175K | α7GlyR Y115F G175K | α7Gly Q79G G175K Y115F | α7GlyR Q79G G175K Y115F R27D E41R | α7GlyR W77F Q79G G175K |
|---|---|---|---|---|---|---|---|---|---|---|---|---|---|---|---|---|---|---|---|
| Tropane | C | NMe | O | O | 1 | 0 | 0 | Endo | H | 1H-indazole | 745 | 1.2 | 1.3 | (0) 0.069 | (0.002) 0.026 (0.002) | (0.014) 0.26 (0.03) | (0.002) 0.089 (0.024) | (0.001) 0.043 (0.014) | 0.05 |
| 9-azabicyclo[3.3.1]nonane | CH | NMe | NH | O | 1 | 0 | 1 | Endo | H | 1H-indole | 749 | 6.6 | nd | nd | nd | nd | 1.3 | nd | 1.9 |
| 9-azabicyclo[3.3.1]nonane | CH | NMe | NH | O | 1 | 0 | 1 | Endo | H | 1H-indazole | 751 | 1.8 | 3.4 | nd | nd | nd | 3.2 | nd | 0.7 |
| 9-azabicyclo[3.3.1]nonane | CH | NMe | NH | O | 1 | 0 | 1 | Endo | H | 7-methoxy-1H-indazole | 760 | >100 | 9.8 | nd | nd | nd | 3 | nd | 1.3 |
| 9-azabicyclo[3.3.1]nonane | CH | NH | O | O | 1 | 0 | 1 | Endo | H | 1H-indole | 763 | 1.9 | 0.17 | nd | nd | nd | 0.3 | nd | 0.2 |
| 1,4-diazabicyclo[3.2.2]nonane | | | | | | | | | F | dibenzo[b,d]thiophene 5,5-dioxide | 773 | 0.135 | 0.001 | nd | nd | 0.0003 | 0.00042 | nd | 0.0014 |
| 1,4-diazabicyclo[3.2.2]nonane | | | | | | | | | $NO_2$ | dibenzo[b,d]thiophene 5,5-dioxide | 774 | 0.03 | 0.006 | nd | nd | 0.00078 | 0.03 | nd | 0.03 |
| Quinuclidine | N | $CH_2$ | $CH_2$ | | 0 | 1 | 0 | R | H | 10H-phenothiazine | Mequitazine | >30 | nd | nd | nd | nd | >10 | nd | 0.15 |
| N,N-dimethylpropyl amine | | | | | | | | | | 10H-phenothiazine | Promazine | >100 | nd | nd | nd | nd | >100 | nd | 1.6 | nd = not determined;
parentheses: SEM $\alpha7^{G175K}$-GlyR and $\alpha7^{P216I}$-GlyR along with mutations at Q79G, Y115F, and G175K were also compatible with non-association mutations R27D,E41R as well as the GlyR IPD mutation A298G, which further enhanced ligand potency for granisetron, epibatidine, varenicline, cytisine, PNU-282987, tropisetron, nortropisetron, and PHA-543613 (Table 7). Combination with non-association mutations to form $\alpha7^{R27D,E41R,Q79G,Y115F,G175K}$ further improved the potency for 702, 723, 725, and 726, with low ACh responsiveness (Table 6).

responsiveness (5-fold) and enhanced potency for varenicline (16-fold) and tropisetron (2.3-fold) (FIG. 9A and Table 9). $\alpha7^{L131G,Q139L}$-GlyR and $\alpha7^{L131G,Y217F}$-GlyR showed similar potency enhancement over α7-GlyR for varenicline (21-fold) but also reduced ACh sensitivity (−11-fold and −13-fold, respectively). $\alpha7^{Q79S,L131G}$-GlyR further improved potency over α7-GlyR for varenicline (89-fold) and tropisetron (15-fold). $\alpha7^{L131G,Q139L,Y217F}$-GlyR showed the greatest improvement in potency over α7-GlyR for varenicline (387-fold) and also showed reduced ACh

TABLE 7

Agonist potency enhancement by G175K and A298G mutations at α7GlyR chimeric channels as well as W298A at α7GABAc (also referred to as $GABA_A$-ρ) channels. Units: μM.

| Compound | α7GlyR Q79G W77F A298G | α7GlyR Q79G G175K A298G | α7GlyR Q79G A298G G175K Y115F | α7GlyR Q79G A298G P216I | α7GlyR Q79G A298G Y115F K395 K396A | a7GABAc Q79G L141F W298A | α7GlyR Q79G G175K Y115F R27D, E41R | α7GlyR R27D E41R Q79G Y115F |
|---|---|---|---|---|---|---|---|---|
| Acetylcholine | 45 | 0.66 | 31 | 5 | 90 | 52 | 52 (7.7) | >500 |
| Nicotine | 3.8 | 0.11 | 3.3 | 1.6 | 16.5 | 16.2 | 4.8 (0.4) | >39.8 |
| Epibatidine | 0.37 | 0.0023 | 0.011 | 0.05 | 0.15 | 0.42 | 0.059 (0.03) | 0.267 |
| Varenicline | 3.66 | 0.022 | 2.37 | 0.18 | >30 | 6.27 | 4.9 (0.3) | >30 |
| Cytisine | 14.1 | 0.134 | 4.6 | 5.5 | >30 | 13.3 | 4.8 (0.4) | >30 |
| PNU-282987 | 1.63 | 0.00036 | 0.009 | 0.25 | 0.11 | 0.12 | 0.05 (0.03) | 0.34 |
| Tropisetron | 0.018 | 0.0006 | 0.0028 | 0.009 | 0.021 | 0.111 | 0.013 (0.005) | >0.096 |
| Nortropisetron | 0.0024 | 0.00013 | 0.0084 | 0.0012 | 0.0063 | 0.009 | 0.003 (0.001) | 0.102 |
| PHA-543613 | 0.0066 | 0.00018 | 0.0039 | 0.003 | 0.0408 | 0.039 | 0.0054 | 0.156 |
| Granisetron | 1.2 | nd | nd | nd | >30 | >100 | 2.4 (0.3) | >30 | nd = not determined;
parentheses: SEM

Additional amino acid substitutions at Gly[175] of the α7 nAChR LBD in $\alpha7^{Y115F}$-GlyR chimeric channels are also enhanced agonist potency. Potency for tropisetron at $\alpha7^{Y115F}$-GlyR chimeric channels was enhanced with additional mutations, which include G175A (7.1-fold), G175F (2-fold), G175H (2.3-fold), G175K (5.6-fold), G175M (2.6-fold), G175R (5.8-fold), G175S (9.3-fold), G175V (16.7-fold).

potency (13-fold) (FIG. 9B and Table 9). $\alpha7^{L131G,Q139L,Y217F}$-GlyR also showed extremely high potency for compound 770 (0.001 μM), compound 773 (0.00034 μM), and compound 774 (0.00013 μM) (FIG. 11). $\alpha7^{Q79S,L131G,\ Q139L}$-GlyR also improved potency over α7-GlyR for varenicline (31-fold) and tropisetron (3-fold) but reduced ACh potency (9-fold) (FIG. 9B and Table 9). $\alpha7^{L131M}$-GlyR, $\alpha7^{L131Q}$-GlyR, and $\alpha7^{L131V}$-GlyR reduced

TABLE 8

Agonist potency enhancement by G175 mutations at α7GlyR Y115F chimeric channels. Units: μM.

| Compound | a7GlyR | α7GlyR Y115F G175K | α7GlyR Y115F G175A | α7GlyR Y115F G175F | α7GlyR Y115F G175H | α7GlyR Y115F G175M | α7GlyR Y115F G175R | α7GlyR Y115F G175S | α7GlyR Y115F G175V |
|---|---|---|---|---|---|---|---|---|---|
| Acetylcholine | 6.4 (1.2) | 52 (6.6) | 24 | 67 | 79 | 71 | 29.5 | 31.5 | 15 |
| Varenicline | 0.62 (0.2) | 5.0 (1.7) | 5.9 | 13.6 | 12.7 | 14.1 | 7.6 | 9.7 | 4.6 |
| Tropisetron | 0.15 (0.045) | 0.027 (0.004) | 0.021 | 0.074 | 0.064 | 0.057 | 0.024 | 0.016 | 0.009 |
| PHA-543613 | 0.03 (0.01) | 0.02 (0.007) | 0.027 | 0.173 | 0.12 | 0.25 | 0.11 | 0.12 | 0.037 | nd = not determined;
parentheses: SEM

Mutations for Leu[131] to smaller amino acids were found to reduce the potency of canonical agonists ACh and nicotine, while markedly increasing potency of varenicline, tropisetron and several other agonists. $\alpha7^{L131A}$-GlyR and $\alpha7^{L131G}$-GlyR had reduced ACh responsiveness (6-fold) and enhanced potency for varenicline (8-fold and 17-fold, respectively) and tropisetron (2.5-fold and 3.6-fold, respectively) (Table 9). $\alpha7^{L131G}$-5 HT3 HC had reduced ACh ACh potency but enhanced potency to tropisetron, nortropisetron, PHA-543613, and granisetron (Table 9). $\alpha7^{L131F}$-GlyR was found to substantially reduced ACh potency but did not improve potency for other agonists (Table 8). $\alpha7^{L131G}$-GABAc substantially reduced ACh potency but did not improve potency for other agonists (Table 9). $\alpha7^{L131G,Q139L,Y217F}$-5HT3 HC (Table 9) improved varenicline potency by 131-fold over α7-5HT3 (Table 1).

α7$^{L131G,Q139L,Y217F}$-5HT3 HC also showed high potency for compound 770 (0.007 μM), compound 773 (0.002 μM), and compound 774 (0.004 μM) (Table 8).

TABLE 9

Agonist potency enhancement by chimeric channels with L131 mutations. Units: μM.

| Compound | a7GlyR | α7GlyR L131A | α7GlyR L131G | α7GlyR L131G Q139L | α7GlyR L131G Y217F | α7GlyR L131G Q139L Y217F | α7GlyR Q79G L131G | α7GlyR Q79S L131G | α7GlyR Q79S L131G Q139L | α7GlyR L131G D219A |
|---|---|---|---|---|---|---|---|---|---|---|
| Acetylcholine | 6.4 (1.2) | 42 (21) | 41 (11) | 68 | 85 | 83 (20) | >500 | 21 (3.5) | 58 | 210 |
| Nicotine | 5.0 (1.8) | 8.0 (3.2) | 15 (3.5) | 26 | 28 | 55 (18) | >100 | 8.2 (0.8) | 25 | 36 |
| Epibatidine | 0.062 (0.021) | 0.027 | 0.009 (0.004) | 0.012 | 0.015 | 0.021 (0.002) | nd | 0.007 (0.001) | 0.012 | 0.16 |
| Varenicline | 0.62 (0.2) | 0.082 (0.068) | 0.037 (0.026) | 0.03 | 0.03 | 0.0016 (0.001) | >10 | 0.007 (0.001) | 0.02 | 0.78 |
| Cytisine | 6.4 (2.0) | 20.6 (9.4) | 13.1 (0.66) | 12 | 30 | nd | >30 | 8.1 (0.3) | 10 | >30 |
| PNU-282987 | 0.13 (0.038) | 0.055 (0.025) | 0.034 (0.008) | 0.063 | 0.054 | 0.16 (0.03) | 0.096 | 0.006 (0.002) | 0.018 | 0.41 |
| Tropisetron | 0.15 (0.045) | 0.06 (0.021) | 0.042 (0.01) | 0.13 | 0.087 | 0.31 (0.05) | 0.09 | 0.01 (0.003) | 0.045 | 0.36 |
| Nortropisetron | 0.022 (0.007) | 0.006 (0.003) | 0.004 (0.001) | 0.024 | 0.018 | 0.047 (0.006) | 0.012 | 0.004 (0.002) | 0.006 | 0.07 |
| PHA-543613 | 0.03 (0.01) | 0.012 (0.006) | 0.008 (0.002) | 0.021 | 0.016 | 0.045 (0.008) | 0.066 | 0.002 (0.0005) | 0.009 | 0.038 |
| Granisetron | >100 | 17.2 (12.8) | 6.7 (1.6) | 4 | 4 | nd | nd | 4.2 (0.8) | nd | >30 |
| 765 | >100 | nd | nd | nd | nd | 0.031 (0.02) | 0.027 | 0.024 | nd | nd |
| 770 | nd | nd | nd | nd | nd | 0.001 (0.0003) | nd | nd | nd | nd |
| 773 | 0.001 | nd | 0.00013 | 0.00004 | nd | 0.00034 | 0.00004 | nd | nd | nd |
| 774 | 0.006 | nd | 0.00004 | 0.00004 | nd | 0.00018 | 0.00004 | nd | nd | nd |

| Compound | α7GlyR L131F | α7GlyR Q79S L131G Q139L Y217F | α7GlyR L131M | α7GlyR Y115F L131M | α7GlyR L131N | α7GlyR L131Q | α7GlyR L131V | α75HT3 L131G HC | α75HT3 L131G Q139L Y217F HC | α7-GABA$_C$ L131G |
|---|---|---|---|---|---|---|---|---|---|---|
| Acetylcholine | 92 (32) | 67 (3) | 29 | >500 | 5 (0.5) | 58 | 16 (5) | 35 | 39 | >500 |
| Nicotine | 20 (6.3) | 41 (8) | 15 | nd | nd | 13 | 3.9 (0.7) | 15 | 20 | >500 |
| Epibatidine | 0.24 (0.05) | 0.022 (0.004) | 0.042 | nd | nd | 0.027 | 0.21 (0.04) | 0.009 | nd | |
| Varenicline | 2.6 (1.1) | 0.003 (0.001) | 0.53 | >100 | 0.069 (0.027) | 0.72 | 0.33 (0.21) | 0.04 | 0.007 | 0.3 |
| Cytisine | 10.5 (1.8) | nd | 7 | nd | nd | >30 | 4.3 (0.7) | 11 | nd | >500 |
| PNU-282987 | 0.20 (0.04) | 0.05 (0.01) | 0.021 | nd | nd | 0.048 | 0.064 (0.018) | 0.033 | 0.015 | 0.12 |
| Tropisetron | 0.39 (0.2) | 0.084 (0.009) | 0.024 | 0.035 | 0.025 (0.005) | 0.048 | 0.062 (0.013) | 0.066 | 0.04 | 0.18 |
| Nortropisetron | 0.027 (0.008) | 0.014 (0.002) | 0.006 | nd | nd | 0.009 | 0.003 (0.001) | 0.009 | nd | 0.021 |
| PHA-543613 | 0.04 (0.007) | 0.015 (0.001) | 0.009 | 0.028 | 0.02 | 0.015 | 0.011 (0.002) | 0.012 | 0.009 | 0.027 |
| Granisetron | >100 | nd | 4 | nd | nd | 4 | 5.4 (1.3) | 4 | nd | >500 |
| 765 | nd | 0.034 (0.013) | nd | nd | >10 | nd | nd | nd | 0.11 | nd |
| 770 | 0.034 | 0.001 (0.0001) | 0.03 | nd | >10 | >0.3 | nd | nd | 0.007 | nd |
| 773 | 0.0005 | nd | 0.00005 | nd | 0.0004 | 0.006 | nd | nd | 0.002 | nd |
| 774 | 0.0013 | nd | 0.001 | nd | 0.0006 | 0.002 | nd | nd | 0.004 | nd | nd: not determined;
parentheses: SEM

Example 7: Chimeric LGICs in Neurons

Figure 7:
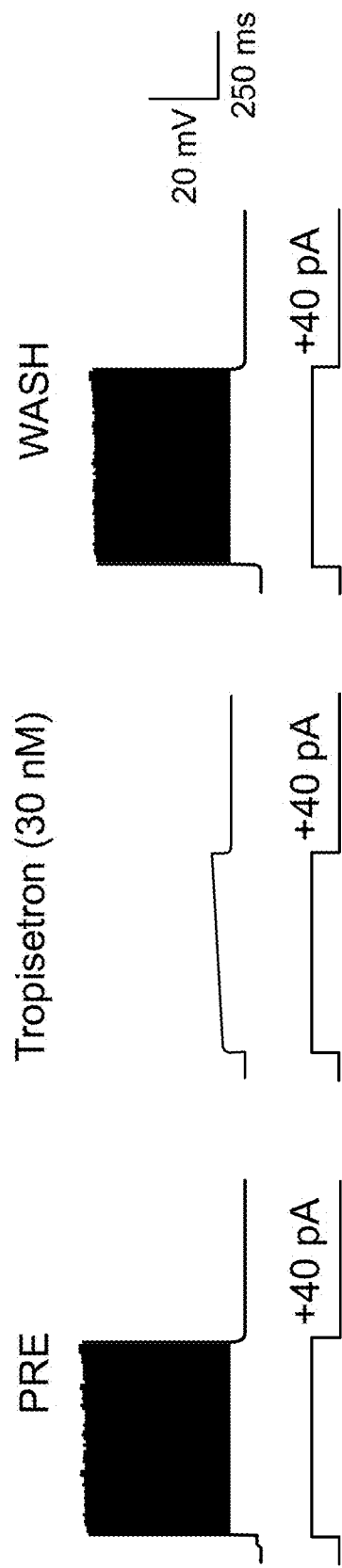
FIG. 7 shows that chimeric LGICs can be controlled using an exogenous ligand. Cortical neurons from a mouse brain transduced with α7$^{Q79G}$-GlyR$^{A298G}$ chimeric LGIC via adeno-associated virus (AAV) vectors fires action potentials in response to 40 pA current injection (PRE) that are potently suppressed by 30 nM tropisetron. After washout (WASH) of tropisetron, neuron firing is restored.
Figure 8C:
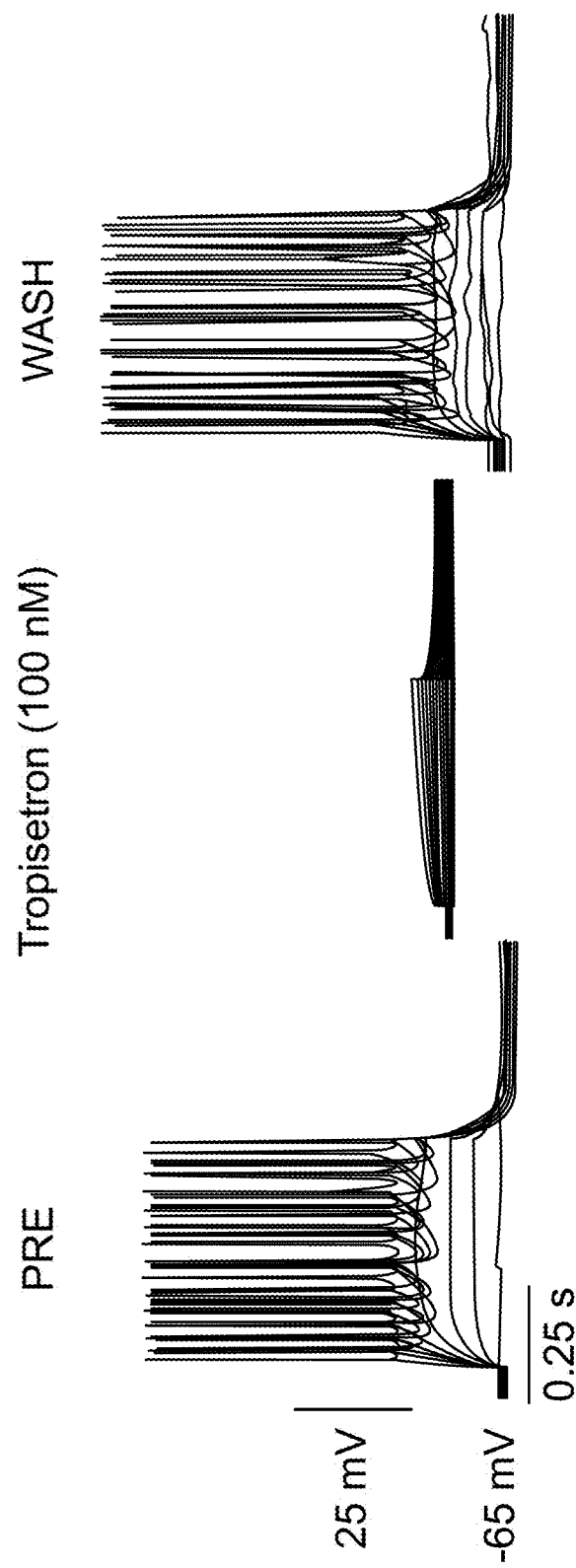

AAVs or DNA plasmids containing nucleic acids encoding a α7$^{Q79G}$-GlyR$^{A298G}$ or α7Q79G,Y115F,G175K-GlyR chimeric LGICs were transduced into mouse cortical neurons. A low concentration of tropisetron (30 nM or 100 nM) was administered to mouse cortical neurons. Neuron activity was silenced by application of low concentration of agonist (FIG. 7 and FIG. 8C).

Figure 9A:
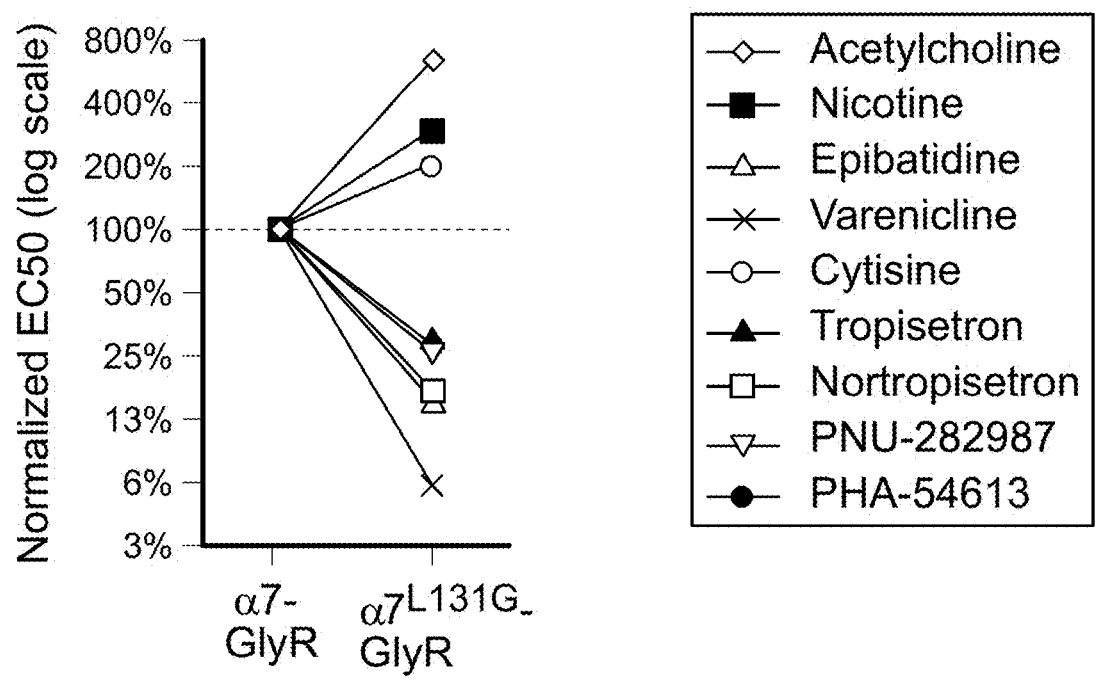
FIGS. 9A-9E show activity of agonists on chimeric LGICs with a L131G mutation.
Figure 9B:
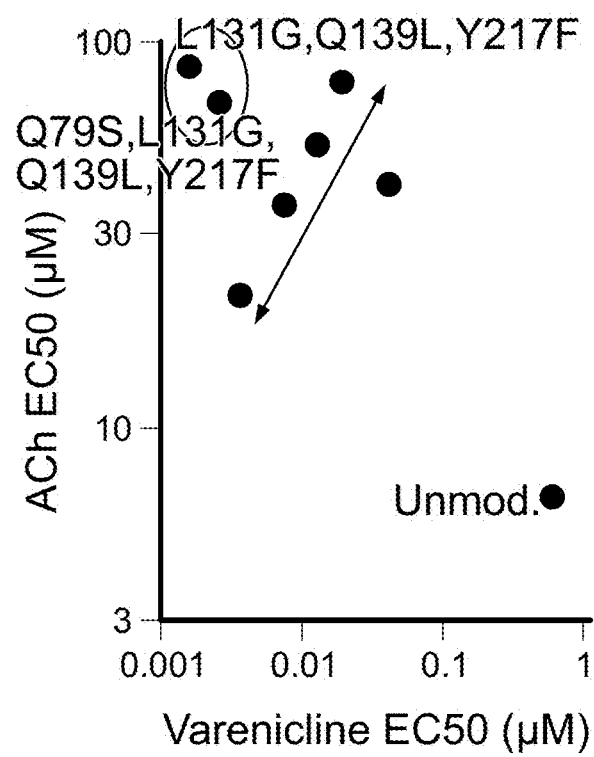
Figure 9C:
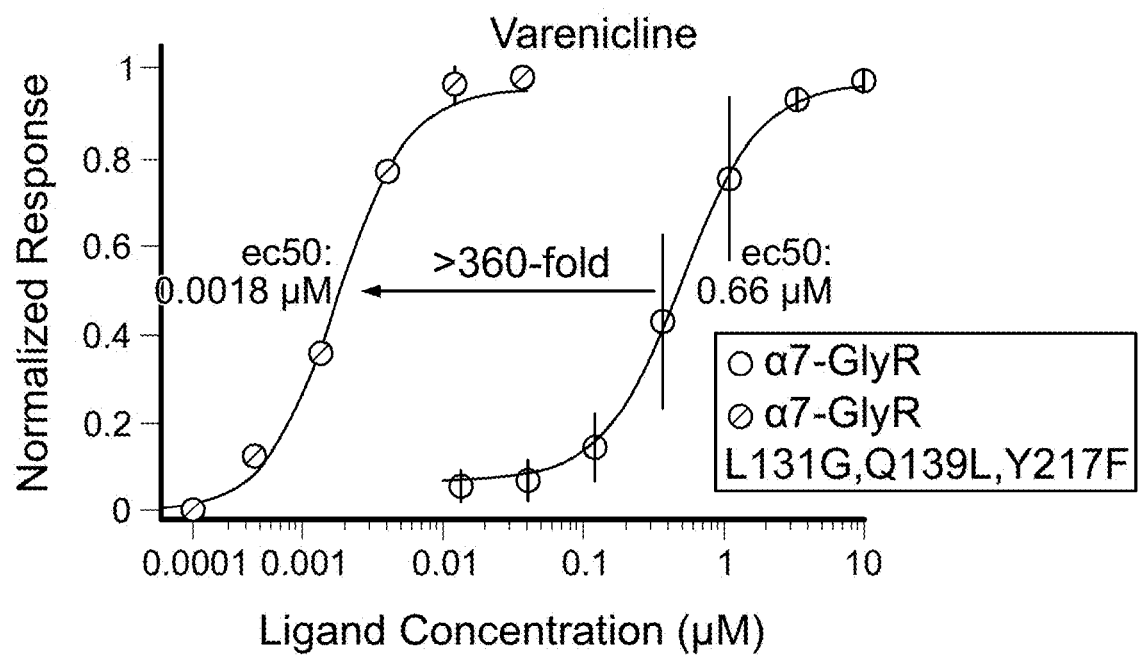

DNA plasmids containing nucleic acids encoding a α7L131G,Q139L,Y217F-GlyR chimeric LGICs were transfected into mouse cortical neurons. Low concentration of varenicline (10 nM) was administered to mouse cortical neurons. Neuron activity was silenced by application of low concentration of agonist (FIG. 9C).

These results show that modified LGIC activity can be controlled in neurons using low concentration of the LGIC ligands tropisetron and varenicline.

Example 8: Varenicline and Varenicline Derivatives and Chimeric LGICs in Therapy The anti-smoking drug varenicline is a potent partial a4b2 agonist. Varenicline is also a modest a7 nAChR agonist and an agonist at 5HT3. It has excellent brain penetrance.

The chimeric channels $\alpha7^{L131G,Q139L,Y217F}$-GlyR and $\alpha7^{L131G,Q139L,Y217F}$-5HT3 HC have enhanced potency binding for the ligand varenicline compared to the unmodified chimeric channels, α7-GlyR and α7-5HT3. However, varenicline activates endogenous ion channels, such as α7 nAChR, α4β2 nAChR, and serotonin receptor 3 (5HT3-R) and it is desirable to obtain varenicline derivatives with high potency at the engineered channels but lowered potency at these endogenous targets.

Using the crystal structure of varenicline bound to the acetylcholine binding protein, it was found that the molecule contacts reside V106, which is homologous to L131 in the α7 nAChR sequence. Mutation to L131G improved varenicline potency by 20-fold while reduce Ach potency 5-fold (FIG. 9A).

Figure 9D:
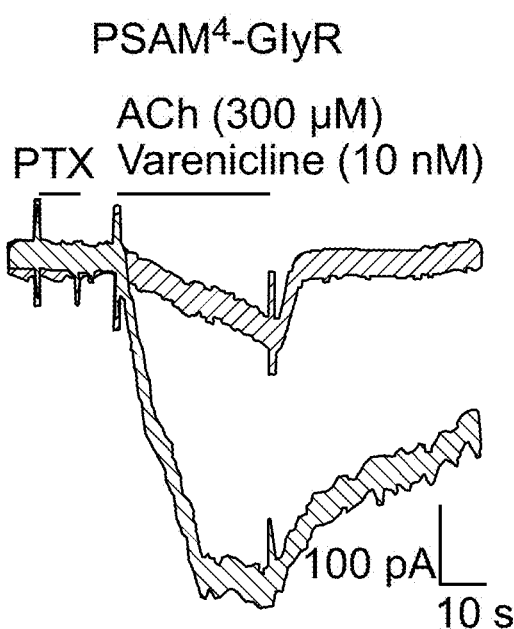
Figure 9E:
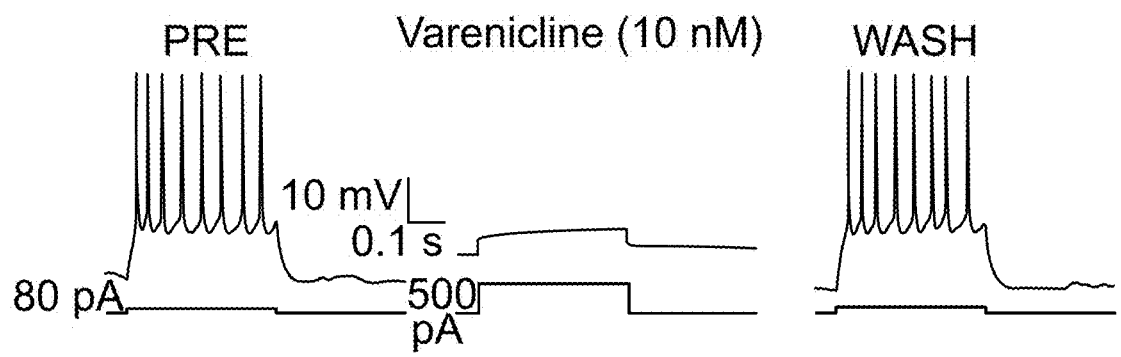

Additional mutations to L131G were made to further reduce Ach potency and to improve varenicline potency. In most cases the change in potency was related for both molecules but a subset of mutations selectively enhanced varenicline potency by 360-fold and reduced Ach potency by 20-fold (FIGS. 9B and 9C). You can see the response on the right to 10 nM varenicline compared to 300 uM Ach (FIG. 9D). These chimeric channels show a characteristically slow activation that acts as a low pass filter for transient fluctuations in Ach. Also note that despite the high potency of the channel, it does not have any ligand independent activity as shown by brief application of the channel antagonist picrotoxin before these ligands are added. Ligand independent activity would have registered as an outward current in this trace. When chimeric channels were expressed in cortical neurons, 10 nM varenicline induced ultrapotent neuron silencing (FIG. 9E).

Figure 10:
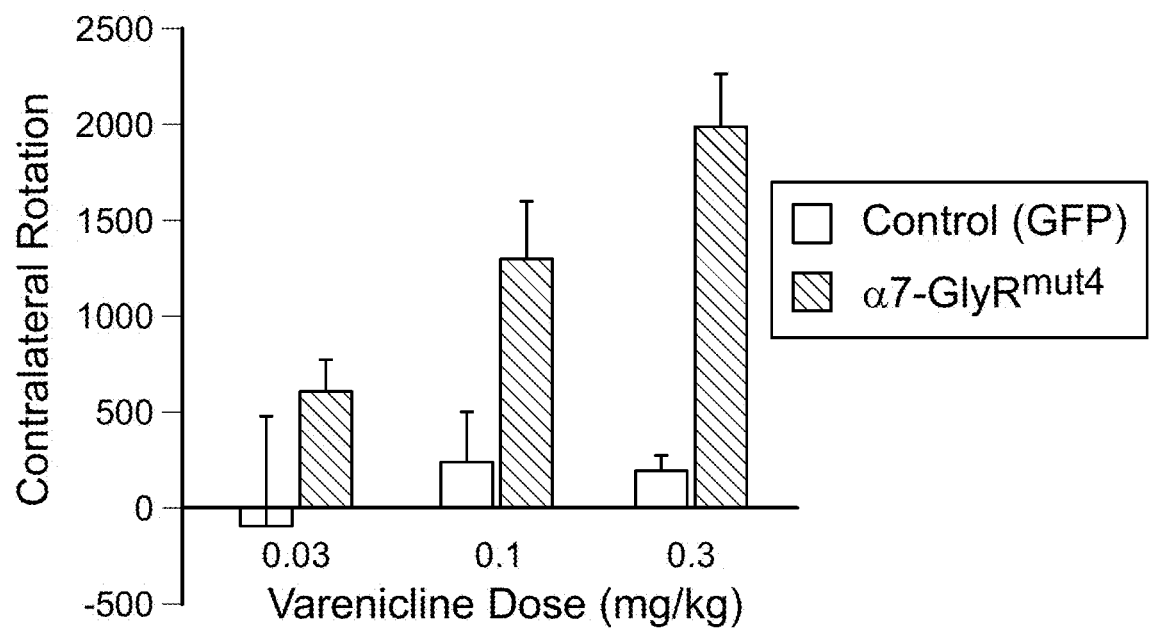
FIG. 10 contains a graph showing that varenicline can activate chimeric receptors in mice to induce a behavioral effect. In this case, expressing α7$^{L131G,Q139L,Y217F}$-GlyR in the VGAT-expressing neurons unilaterally in the substantia nigra reticulate followed by varenicline administration leads to contralateral rotation, consistent with varenicline-induced silencing the α7$^{L131G,Q139L,Y217F}$-GlyR expressing neurons.
Figure 13A:
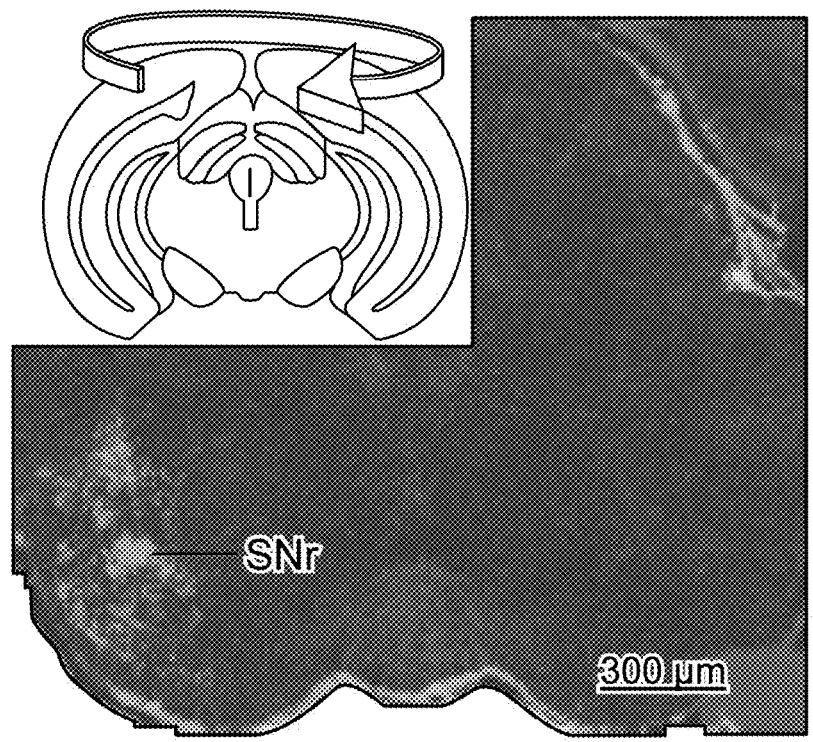
FIGS. 13A-13D show PSAM$^4$-GlyR neuron silencing in mice.
Figure 13B:
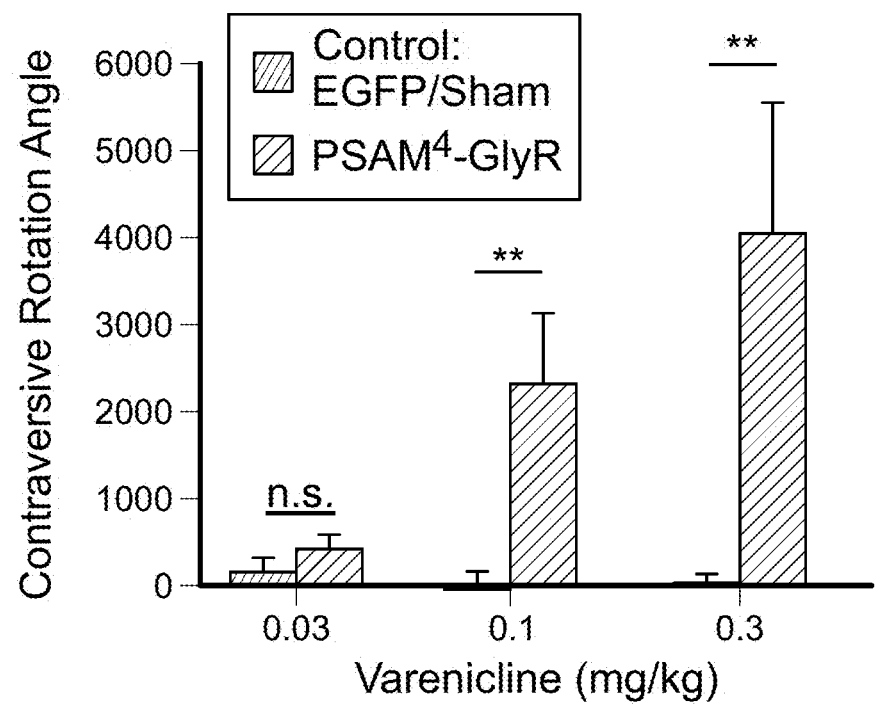
Figure 13C:
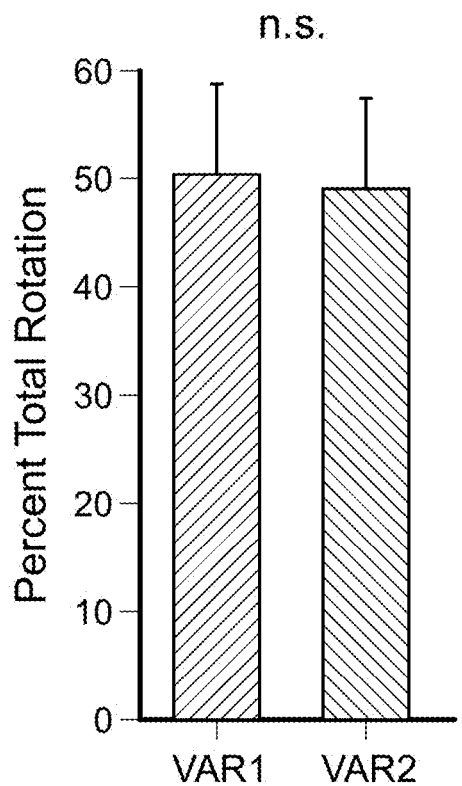
Figure 13D:
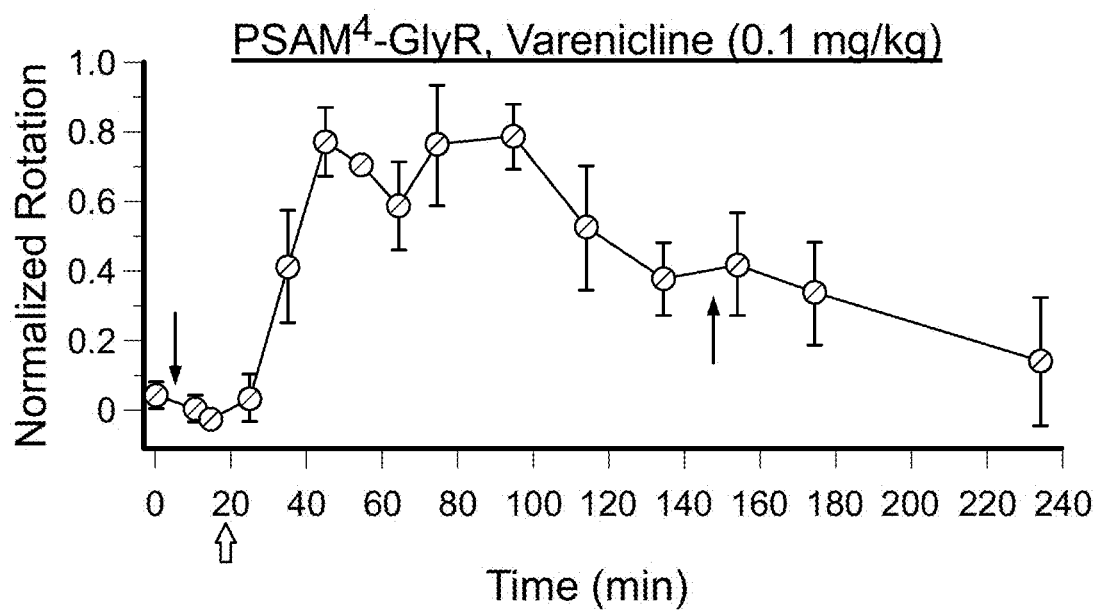

In vivo activity was also very potent in a unilateral substantia nigra (SNr) silencing experiment. Circling contralateral to the silenced SNr was seen at doses above 0.1 milligrams per kilograms (mpk). A 10-fold improvement was seen in varenicline potency over anti-nicotine activity (FIG. 10).

Varenicline derivatives were engineered to reduce or eliminate endogenous varenicline activity. The potency of varenicline and each varenicline derivative was determined for a variety of chimeric channels (Table 10).

TABLE 10

Potency (EC50, μM) of varenicline and varenicline derivatives at chimeric channels, and comparison to agonist potency at 5HT3-R and α4β2 nAChR.

| Compound structure | Number | α7-5HT3 | α7-GlyR | α7GlyR L131G Q139L Y217F | α75HT3 L131G Q139L Y217F | 5HT3-R | α4β2 nAChR |
|---|---|---|---|---|---|---|---|
| (structure) | Varenicline | 0.92 (0.15) | 0.62 (0.2) | 0.0016 (0.001) | 0.004 (0.002) | 1.4 (0.4) | 0.25 (0.06) |
| (structure) | 780 | 10.6 | >100 | 0.007 | nd | nd | nd |
| (structure) | 782 | >100 | >100 | 0.64 | 0.36 | >30 | nd |
| (structure) | 783 | >100 | >100 | 0.008 (0.002) | 0.01 | 0.43 (0.04) | 43 |

TABLE 10-continued
Potency (EC50, μM) of varenicline and varenicline derivatives at chimeric
channels, and comparison to agonist potency at 5HT3-R and α4β2 nAChR.
| Compound structure | Number | α7-5HT3 | α7-GlyR | α7GlyR L131G Q139L Y217F | α75HT3 L131G Q139L Y217F | 5HT3-R | α4β2 nAChR |
|---|---|---|---|---|---|---|---|
| 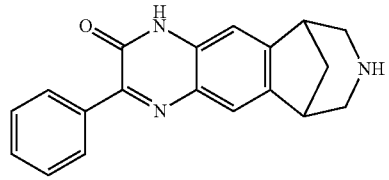 [SMILES: O=c1[nH]c2cc3c(cc2nc1-c1ccccc1)C1CNCC3C1] | 784 | >30 | >30 | 0.43 | 0.88 | 6.2 (0.8) | nd |
| 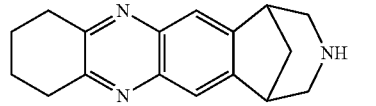 [SMILES: c1c2c(cc3nc4c(nc13)CCCC4)C1CNCC2C1] | 785 | >100 | >100 | 0.25 | 0.12 (0.04) | 10.2 (2.0) | nd |
| 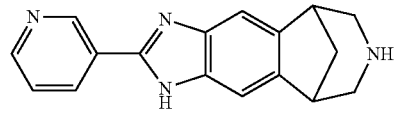 [SMILES: c1cncc(-c2nc3cc4c(cc3[nH]2)C2CNCC4C2)c1] | 786 | >100 | >100 | >10 | >10 | nd | nd |
| 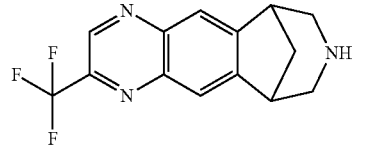 [SMILES: FC(F)(F)c1cnc2cc3c(cc2n1)C1CNCC3C1] | 788 | >100 | >100 | 0.16 (0.02) | 0.13 (0.02) | 41 (1.4) | >30 |
| 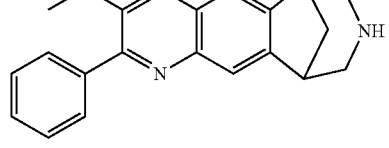 | 789 | >100 | >100 | 0.028 (0.001) | 0.031 (0.002) | 0.51 (0.21) | >30 |
| 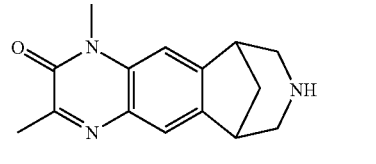 [SMILES: Cc1nc2cc3c(cc2n(C)c1=O)C1CNCC3C1] | 790 | >100 | >100 | 0.048 (0.002) | 0.015 (0.004) | 4.3 (1.1) | >30 |
| 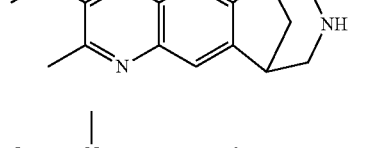 | 791 | >30 | >30 | 0.010 (0.003) | 0.003 (0.0005) | 0.17 (0.04) | >30 |
| 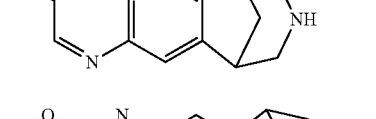 | 792 | >30 | >30 | 0.0023 (0.0003) | 0.0016 (0.0002) | 40.5 (0.5) | 0.52 (0.1) |
| 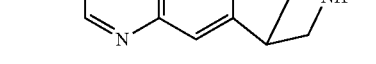 | 793 | 20 | 19 | 0.0007 (0.0004) | 0.001 (0.0005) | 0.19 (0.055) | 18 (6.1) |

TABLE 10-continued
Potency (EC50, μM) of varenicline and varenicline derivatives at chimeric channels, and comparison to agonist potency at 5HT3-R and α4β2 nAChR.
| Compound structure | Number | α7-5HT3 | α7-GlyR | α7GlyR L131G Q139L Y217F | α75HT3 L131G Q139L Y217F | 5HT3-R | α4β2 nAChR |
|---|---|---|---|---|---|---|---|
| 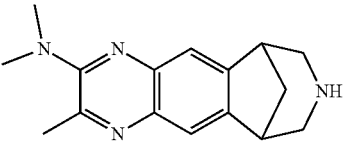 [SMILES: Cc1nc2cc3c(cc2nc1N(C)C)C1CNCC3C1] | 794 | >30 | >30 | 0.071 (0.011) | 0.034 (0.003) | 1.7 (0.37) | >30 |
| 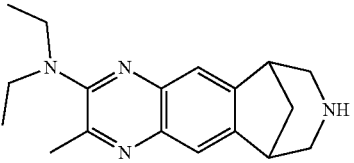 [SMILES: CCN(CC)c1nc2cc3c(cc2nc1C)C1CNCC3C1] | 795 | >30 | >30 | 0.021 (0.004) | 0.016 (0.003) | 1.1 (0.2) | >30 |
| 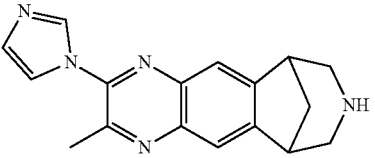 [SMILES: Cc1nc2cc3c(cc2nc1-n1ccnc1)C1CNCC3C1] | 798 | >30 | >30 | 0.020 (0.001) | 0.006 (0.001) | 1.1 (0.24) | 28 (2) |
| 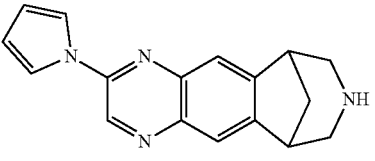 [SMILES: c1ccn(-c2cnc3cc4c(cc3n2)C2CNCC4C2)c1] | 799 | >100 | >100 | 0.74 | 0.42 | 11.7 | 3.5 (1.9) |
| 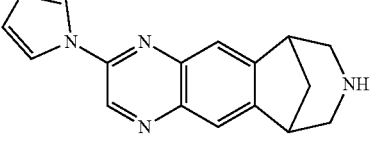 | 800 | >30 | >30 | 0.11 (0.04) | 0.041 (0.016) | 3.5 (1.9) | 13.9 |
| 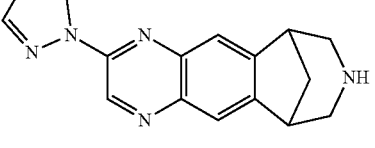 | 801 | >30 | >30 | 0.074 (0.022) | 0.060 (0.006) | 4.4 (0.9) | 26 (7.4) |
| 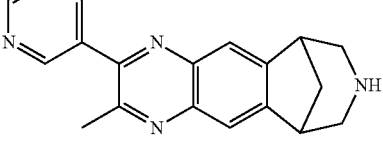 | 802 | >30 | >30 | 0.003 (0.0006) | 0.001 (0.0004) | 1.5 (0.5) | >30 |
| 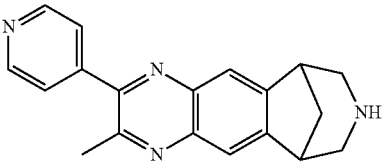 [SMILES: Cc1nc2cc3c(cc2nc1-c1ccncc1)C1CNCC3C1] | 803 | >30 | >30 | 0.007 (0.002) | 0.002 (0.001) | 0.75 (0.22) | 14 (5) |

TABLE 10-continued

Potency (EC50, µM) of varenicline and varenicline derivatives at chimeric channels, and comparison to agonist potency at 5HT3-R and α4β2 nAChR.

| Compound structure | Number | α7-5HT3 | α7-GlyR | α7GlyR L131G Q139L Y217F | α75HT3 L131G Q139L Y217F | 5HT3-R | α4β2 nAChR |
|---|---|---|---|---|---|---|---|
| 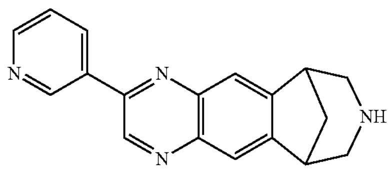 [SMILES: c1cncc(-c2cnc3cc4c(cc3n2)C2CNCC4C2)c1] | 804 | >30 | >30 | 0.020 (0.001) | 0.017 (0.002) | 2.0 (0.48) | 4.8 |
| 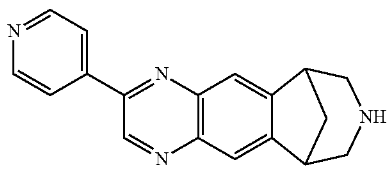 [SMILES: c1cc(-c2cnc3cc4c(cc3n2)C2CNCC4C2)ccn1] | 805 | >30 | >30 | 0.026 (0.003) | 0.030 (0.010) | 1.0 | 4.9 |
| 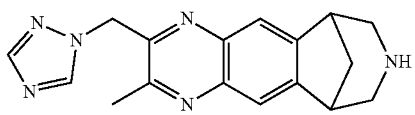 [SMILES: Cc1nc2cc3c(cc2nc1Cn1cncn1)C1CNCC3C1] | 807 | >30 | >30 | 0.007 (0.004) | 0.002 (0.001) | 0.57 | >30 |
| 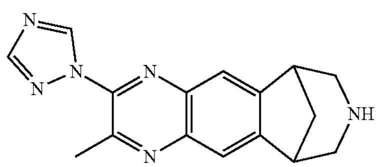 | 808 | >30 | >30 | 0.015 (0.006) | 0.005 (0.0006) | 12.5 (0.5) | >30 |
| 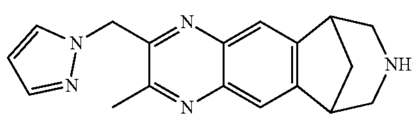 [SMILES: Cc1nc2cc3c(cc2nc1Cn1cccn1)C1CNCC3C1] | 812 | >100 | >100 | 0.03 (0.006) | 0.013 (0.006) | 11 (1) | >100 |
| | 813 | >100 | >100 | 0.017 (0.001) | 0.006 (0.0003) | 3.3 (0.7) | 16.5 (13.5) |

Table 10 shows specific chemical structures of LGIC agonists with substitution patterns compatible with high potency for $\alpha7^{L131G,Q139L,Y217F}$-GlyR or $\alpha7^{L131G,Q139L,Y217F}$-5 HT3 HC.

All molecules in Table 10 show reduced sensitivity for α7-GlyR and α7-5HT3 (which serve as proxies for α7 nAChR potency). Compound 780, compound 783, compound 789, compound 790, compound 791, compound 792, compound 793, compound 795, compound 798, compound 802, compound 803, compound 804, compound 805, compound 807, compound 808, compound 812, and compound 813 show potency less than 30 nM for either $\alpha7^{L131G,Q139L,Y217F}$-GlyR or $\alpha7^{L131G,Q139L,Y217F}$-5 HT3 HC. Compound 780, compound 783, compound 791, compound 792, compound 793, compound 798, compound 802, compound 803, compound 807, or compound 808 show potency less than 10 nM for either $\alpha7^{L131G,Q139L,Y217F}$-GlyR or $\alpha7^{L131G,Q139L,Y217F}$-5 HT3 HC. Compound 792, compound 795, compound 802, compound 808 show potency less than 10 nM for either $\alpha7^{L131G,Q139L,Y217F}$-GlyR or $\alpha7^{L131G,Q139L,Y217F}$-5 HT3 HC and potency >1 µM for 5HT3-R, and >10 µM for α4β2 nAChR.

Chemogenetic perturbation of cortical neuron activity was evaluated. Action potential firing was strongly suppressed by varenicline strongly in neurons expressing PSAM[4]-GlyR due to reduced input resistance and elevated rheobase. Cortical layer 2/3 neuron membrane properties were similar in PSAM[4]-GlyR expressing neurons and intermingled untransfected control neurons. Varenicline depolarizes and elicits firing in neurons expressing PSAM[4]-5HT3 HC. Cortical layer 2/3 neuron membrane properties are similar in PSAM[4]-5HT3 HC expressing neurons and intermingled untransfected control neurons. See, e.g., FIG. 12.

PSAM[4]-GlyR neuron silencing was evaluated in mice. PSAM[4]-GlyR-IRES-EGFP targeted unilaterally to the SNr. Low doses of intraperitoneal varenicline elicit contraversive rotation for mice expressing PSAM[4]-GlyR but not sham operated or EGFP-alone expressing mice. Two doses of varenicline separated by 5 hours give similar proportion of total rotation, indicating no tachyphylaxis of the chemogenetic response. Duration of chemogenetic silencing monitored by the timecourse of rotation response normalized to maximum rotation for each mouse. See, e.g., FIG. 13.

Ultrapotent chemogenetic agonists were evaluated. uPSEM agonist EC50s were compared at PSAM[4] channels and endogenous varenicline targets, as well as IC50 for α4β2 nAChR with 1 µM ACh. uPSEM[792] was a 10% partial agonist of α4β2 nAChR and uPSEM[817], and inhibited α4β2 nAChR. uPSEM[792], uPSEM[793], uPSEM[815], and uPSEM[817] strongly suppressed firing in cortical neurons expressing PSAM$^4$-GlyR by reducing the current required to fire an action potential (rheobase). See, e.g., FIG. 14.

In vivo uPSEM dose responses were evaluated for mice expressing PSAM$^4$-GlyR unilaterally in SNr. See, e.g., FIG. 15.

Varenicline derivatives were engineered to reduce or eliminate endogenous varenicline activity. The potency of varenicline and each varenicline derivative was determined for a variety of chimeric channels (Table 11).

TABLE 11

EC50$_{MP}$ (μM) of varenicline and derivatives at chimeric channels along with comparison of agonist potency at 5HT3-R and α4β2 nAChR. In vivo potency determined in SNr silencing rotation assay in mice.

| Structure | Compound | α7-5HT3 | α7-GlyR | PSAM$^4$-GlyR | PSAM$^4$-5HT3 | 5HT3-R | α4β2 nAChR | In vivo potency |
|---|---|---|---|---|---|---|---|---|
| 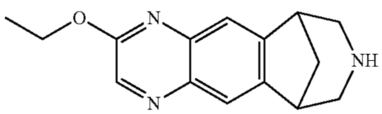 [SMILES: CCOc1cnc2cc3c(cc2n1)C1CNCC3C1] | 815 | >100 | >100 | 0.0005 ± 0.0001 | 0.0008 ± 0.0004 | 1.3 ± 0.0 | >30 | 0.1 mpk |
| 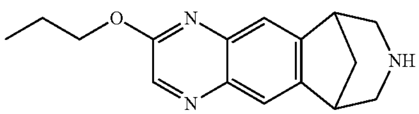 [SMILES: CCCOc1cnc2cc3c(cc2n1)C1CNCC3C1] | 817 | >100 | >100 | 0.0003 ± 0.0001 | 0.0005 ± 0.0002 | 1.5 ± 1.0 | >30 | 0.1 mpk |
| | 816 | 33 ± 4 | 52 ± 25 | 0.0005 ± 0.0001 | 0.0009 ± 0.0003 | >100 | 0.56 ± 0.32 | nd | nd: not determined.
nr: no response.
Values are mean ± SEM.

Ethoxy and propoxy compounds (uPSEMs) 815 and 817 resulted in sub-nanomolar potencies at PSAM$^4$-GlyR. uPSEM[817] agonist selectivity was excellent, having 5000-fold to 10,000-fold selectivity for PSAM$^4$-GlyR over α7-GlyR, α7-5HT3, and 5HT3-R. uPSEM[815] and uPSEM[817] do not show evident α4β2 nAChR agonism up to 30 μM, and uPSEM 815 has >2000-fold selectivity for PSAM$^4$-GlyR over 5HT3-R.

Example 9: Chimeric LGICs in Therapy

Chemogenetic tools offer an attractive strategy for combined drug and gene therapy. This is because cellular function can be modulated in a consistent manner across different cell types in various indications using the same ion channels and ligands by use of an exogenously delivered ion channel that is selectively engaged by administration of a drug. Identification of ion channels that are gated by well tolerated, clinically used drugs are especially attractive for potentially extending chemogenetics to human therapeutic use.

For the drug tropisetron, we have found that it activates α7$^{Q79G}$-GlyR$^{T298G}$ with an EC50 of 11 nM, which is similar to the reported IC50 of 10 nM tropisetron for its therapeutic target, the 5HT3 receptor (Combrink et al 2009 Pharmacological reports: PR 61: 785-97).

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method for treating a mammal having a neural channelopathy, said method comprising:
   administering a nucleic acid sequence encoding a modified ligand gated ion channel (LGIC) subunit to said mammal under conditions in which said modified LGIC subunit can assemble into a modified LGIC comprising said modified LGIC subunit in a cell within said mammal, wherein each of said modified LGIC subunits comprises:
   a human alpha7 nicotinic acetylcholine receptor (α7-nAChR) ligand binding domain (LBD) comprising a L131G amino acid substitution, a Q139L amino acid substitution, and/or a Y217F amino acid substitution as numbered in SEQ ID NO:1, SEQ ID NO:2, or SEQ ID NO:11, and
   an ion pore domain (IPD), wherein the IPD is an IPD from a receptor selected from the group consisting of a serotonin 3 receptor (5HT3) IPD, a glycine receptor (GlyR) IPD, a gamma-aminobutyric acid (GABA) receptor IPD, and an alpha7 nicotinic acetylcholine receptor (α7-nAChR) IPD; and
   administering to the subject a LGIC ligand, wherein the LGIC ligand acts as an agonist of said modified LGIC subunit.

2. The method of claim 1, wherein said mammal is a human.

3. The method of claim 1, wherein said cell is a neuron or a glial cell.

4. The method of claim 1, wherein said nucleic acid sequence encoding said modified LGIC subunit is in the form of a nucleic acid vector.

5. The method of claim 4, wherein said nucleic acid vector is a viral vector.

6. The method of claim 5, wherein said viral vector is selected from the group consisting of a retroviral vector, an adenoviral vector, an adeno-associated viral vector, and a herpes simplex viral vector.

7. The method of claim 4, wherein said nucleic acid vector comprises a promoter operably linked to said nucleic acid sequence encoding said modified LGIC subunit.

8. The method of claim 7, wherein said promoter is a neuron specific promoter.

9. The method of claim 7, wherein said promoter is selected from the group consisting of synapsin (SYN), calcium/calmodulin-dependent protein kinase II (CAMKII), cytomegalovirus (CMV), cytomegalovirus immediate-early enhancer/chicken β-actin (CAG), enolase, transient receptor potential vanilloid type 1 (TRPV1), pro-opiomelanocortin (POMC), neuropeptide Y gene (NPY), agouti-related protein (AGRP), melanin-concentrating hormone (MCH), and Orexin promoters.

10. The method of claim 1, wherein said nucleic acid sequence encoding said modified LGIC subunit comprises a nucleic acid sequence encoding an endoplasmic reticulum (ER) export sequence.

11. The method of claim 10, wherein said nucleic acid sequence encoding said ER export sequence comprises the sequence set forth in SEQ ID NO:30.

12. The method of claim 1, wherein said nucleic acid sequence encoding said modified LGIC subunit comprises a nucleic acid sequence encoding a signal sequence.

13. The method of claim 12, wherein said nucleic acid sequence encoding said signal sequence comprises the sequence set forth in SEQ ID NO:31.

14. The method of claim 1, wherein said nucleic acid sequence encoding said modified LGIC subunit comprises a nucleic acid sequence encoding a targeting sequence.

15. The method of claim 14, wherein said nucleic acid sequence encoding said targeting sequence comprises the sequence set forth in SEQ ID NO:32.

16. The method of claim 1, wherein said LGIC ligand is a synthetic LGIC ligand.

17. The method of claim 1, wherein said LGIC ligand is a quinuclidine, a tropane, a 9-azabicyclo[3.3.1]nonane, a 2-phenyl-7,8,9,10-tetrahydro-6H-6,10-methanoazepino[4,5-g]quinoxaline, or a 1,4-diazabicyclo[3.2.2]nonane.

18. The method of claim 1, wherein said LGIC ligand is selected from the group consisting of acetylcholine, nicotine, tropisetron, PNU-282987, PHA-543613, and 3-(1,4-diazabicyclo[3.2.2]nonan-4-yl)dibenzo[b,d]thiophene 5,5-dioxide.

19. The method of claim 1, wherein said neural channelopathy is generalized epilepsy or seizure.

20. The method of claim 1, wherein the modified LGIC subunit comprises any one of the amino acid sequences set forth in SEQ ID NOs: 13, 14, or 15.

21. The method of claim 1, wherein said LGIC ligand is selected from the group consisting of varenicline 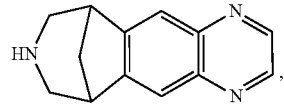, compound 765 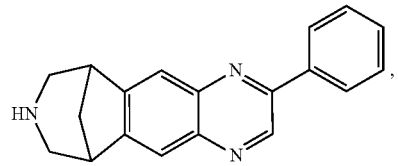 [SMILES: Cc1nc2cc3c(cc2nc1-c1ccccc1)C1CNCC3C1], compound 770 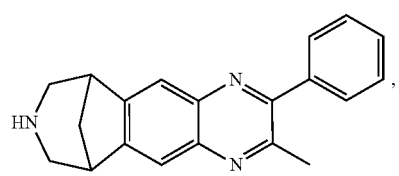, -continued
| | | |
|---|---|---|
| compound 793 | 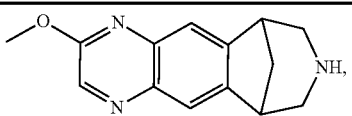 | |
| compound 807 | 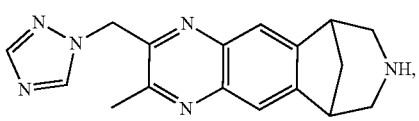 [SMILES: Cc1nc2cc3c(cc2nc1Cn1cncn1)C1CNCC3C1] | |
| compound 815 | 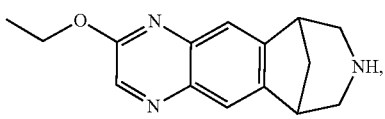 [SMILES: CCOc1cnc2cc3c(cc2n1)C1CNCC3C1] | |
| compound 816 | 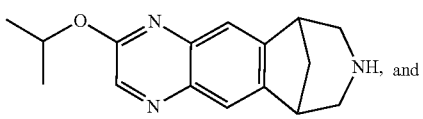 [SMILES: CC(C)Oc1cnc2cc3c(cc2n1)C1CNCC3C1] | and |
| compound 817 | 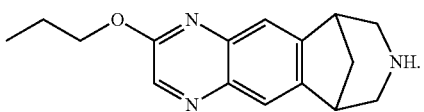 [SMILES: CCCOc1cnc2cc3c(cc2n1)C1CNCC3C1] | |
* * * * *

SEQUENCE LISTING

<160> NUMBER OF SEQ ID NOS: 34

<210> SEQ ID NO 1
<211> LENGTH: 224
<212> TYPE: PRT
<213> ORGANISM: Homo sapiens

<400> SEQUENCE: 1

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
        50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

<210> SEQ ID NO 2
<211> LENGTH: 229
<212> TYPE: PRT
<213> ORGANISM: Homo sapiens

<400> SEQUENCE: 2

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
        50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
130                 135                 140

```
Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
210                 215                 220

Thr Met Arg Arg Arg
225

<210> SEQ ID NO 3
<211> LENGTH: 247
<212> TYPE: PRT
<213> ORGANISM: Mus musculus

<400> SEQUENCE: 3

Ile Ile Arg Arg Pro Leu Phe Tyr Ala Val Ser Leu Leu Leu Pro
1               5                   10                  15

Ser Ile Phe Leu Met Val Val Asp Ile Val Gly Phe Cys Leu Pro Pro
                20                  25                  30

Asp Ser Gly Glu Arg Val Ser Phe Lys Ile Thr Leu Leu Gly Tyr
            35                  40                  45

Ser Val Phe Leu Ile Ile Val Ser Asp Thr Leu Pro Ala Thr Ile Gly
50                  55                  60

Thr Pro Leu Ile Gly Val Tyr Phe Val Val Cys Met Ala Leu Leu Val
65                  70                  75                  80

Ile Ser Leu Ala Glu Thr Ile Phe Ile Val Arg Leu Val His Lys Gln
                85                  90                  95

Asp Leu Gln Arg Pro Val Pro Asp Trp Leu Arg His Leu Val Leu Asp
            100                 105                 110

Arg Ile Ala Trp Ile Leu Cys Leu Gly Glu Gln Pro Met Ala His Arg
        115                 120                 125

Pro Pro Ala Thr Phe Gln Ala Asn Lys Thr Asp Asp Cys Ser Gly Ser
130                 135                 140

Asp Leu Leu Pro Ala Met Gly Asn His Cys Ser His Val Gly Gly Pro
145                 150                 155                 160

Gln Asp Leu Glu Lys Thr Pro Arg Gly Arg Gly Ser Pro Leu Pro Pro
                165                 170                 175

Pro Arg Glu Ala Ser Leu Ala Val Arg Gly Leu Leu Gln Glu Leu Ser
            180                 185                 190

Ser Ile Arg His Phe Leu Glu Lys Arg Asp Glu Met Arg Glu Val Ala
        195                 200                 205

Arg Asp Trp Leu Arg Val Gly Tyr Val Leu Asp Arg Leu Leu Phe Arg
210                 215                 220

Ile Tyr Leu Leu Ala Val Leu Ala Tyr Ser Ile Thr Leu Val Thr Leu
225                 230                 235                 240

Trp Ser Ile Trp His Tyr Ser
                245

<210> SEQ ID NO 4
<211> LENGTH: 242
<212> TYPE: PRT
```

<213> ORGANISM: Homo sapiens

<400> SEQUENCE: 4

```
Ile Ile Arg Arg Arg Pro Leu Phe Tyr Val Val Ser Leu Leu Leu Pro
1               5                   10                  15

Ser Ile Phe Leu Met Val Met Asp Ile Val Gly Phe Tyr Leu Pro Pro
            20                  25                  30

Asn Ser Gly Glu Arg Val Ser Phe Lys Ile Thr Leu Leu Gly Tyr
        35                  40                  45

Ser Val Phe Leu Ile Ile Val Ser Asp Thr Leu Pro Ala Thr Ala Ile
    50                  55                  60

Gly Thr Pro Leu Ile Gly Val Tyr Phe Val Val Cys Met Ala Leu Leu
65                  70                  75                  80

Val Ile Ser Leu Ala Glu Thr Ile Phe Ile Val Arg Leu Val His Lys
                85                  90                  95

Gln Asp Leu Gln Gln Pro Val Pro Ala Trp Leu Arg His Leu Val Leu
            100                 105                 110

Glu Arg Ile Ala Trp Leu Leu Cys Leu Arg Glu Gln Ser Thr Ser Gln
        115                 120                 125

Arg Pro Pro Ala Thr Ser Gln Ala Thr Lys Thr Asp Asp Cys Ser Ala
    130                 135                 140

Met Gly Asn His Cys Ser His Met Gly Gly Pro Gln Asp Phe Glu Lys
145                 150                 155                 160

Ser Pro Arg Asp Arg Cys Ser Pro Pro Pro Arg Glu Ala Ser
                165                 170                 175

Leu Ala Val Cys Gly Leu Leu Gln Glu Leu Ser Ser Ile Arg Gln Phe
            180                 185                 190

Leu Glu Lys Arg Asp Glu Ile Arg Glu Val Ala Arg Asp Trp Leu Arg
        195                 200                 205

Val Gly Ser Val Leu Asp Lys Leu Leu Phe His Ile Tyr Leu Leu Ala
    210                 215                 220

Val Leu Ala Tyr Ser Ile Thr Leu Val Met Leu Trp Ser Ile Trp Gln
225                 230                 235                 240

Tyr Ala
```

<210> SEQ ID NO 5
<211> LENGTH: 202
<212> TYPE: PRT
<213> ORGANISM: Homo sapiens

<400> SEQUENCE: 5

```
Met Gly Tyr Tyr Leu Ile Gln Met Tyr Ile Pro Ser Leu Leu Ile Val
1               5                   10                  15

Ile Leu Ser Trp Ile Ser Phe Trp Ile Asn Met Asp Ala Ala Pro Ala
            20                  25                  30

Arg Val Gly Leu Gly Ile Thr Thr Val Leu Thr Met Thr Thr Gln Ser
        35                  40                  45

Ser Gly Ser Arg Ala Ser Leu Pro Lys Val Ser Tyr Val Lys Ala Ile
    50                  55                  60

Asp Ile Trp Met Ala Val Cys Leu Leu Phe Val Phe Ser Ala Leu Leu
65                  70                  75                  80

Glu Tyr Ala Ala Val Asn Phe Val Ser Arg Gln His Lys Glu Leu Leu
                85                  90                  95

Arg Phe Arg Arg Lys Arg Arg His His Lys Glu Asp Glu Ala Gly Glu
            100                 105                 110
```

```
Gly Arg Phe Asn Phe Ser Ala Tyr Gly Met Gly Pro Ala Cys Leu Gln
            115                 120                 125

Ala Lys Asp Gly Ile Ser Val Lys Gly Ala Asn Asn Ser Asn Thr Thr
130                 135                 140

Asn Pro Pro Ala Pro Ser Lys Ser Pro Glu Glu Met Arg Lys Leu
145                 150                 155                 160

Phe Ile Gln Arg Ala Lys Lys Ile Asp Lys Ile Ser Arg Ile Gly Phe
                165                 170                 175

Pro Met Ala Phe Leu Ile Phe Asn Met Phe Tyr Trp Ile Ile Tyr Lys
            180                 185                 190

Ile Val Arg Arg Glu Asp Val His Asn Gln
            195                 200

<210> SEQ ID NO 6
<211> LENGTH: 471
<212> TYPE: PRT
<213> ORGANISM: Artificial Sequence
<220> FEATURE:
<223> OTHER INFORMATION: alpha7-5HT3 chimeric receptor sequence

<400> SEQUENCE: 6

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
                35                  40                  45

Gln Pro Leu Thr Val Tyr Phe Ser Leu Ser Leu Leu Gln Ile Met Asp
50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
            85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
            130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
    210                 215                 220

Ile Ile Arg Arg Arg Pro Leu Phe Tyr Ala Val Ser Leu Leu Leu Pro
225                 230                 235                 240

Ser Ile Phe Leu Met Val Val Asp Ile Val Gly Phe Cys Leu Pro Pro
            245                 250                 255

Asp Ser Gly Glu Arg Val Ser Phe Lys Ile Thr Leu Leu Leu Gly Tyr
            260                 265                 270
```

```
Ser Val Phe Leu Ile Ile Val Ser Asp Thr Leu Pro Ala Thr Ile Gly
            275                 280                 285

Thr Pro Leu Ile Gly Val Tyr Phe Val Val Cys Met Ala Leu Leu Val
290                 295                 300

Ile Ser Leu Ala Glu Thr Ile Phe Ile Val Arg Leu Val His Lys Gln
305                 310                 315                 320

Asp Leu Gln Arg Pro Val Pro Asp Trp Leu Arg His Leu Val Leu Asp
                325                 330                 335

Arg Ile Ala Trp Ile Leu Cys Leu Gly Glu Gln Pro Met Ala His Arg
            340                 345                 350

Pro Pro Ala Thr Phe Gln Ala Asn Lys Thr Asp Cys Ser Gly Ser
            355                 360                 365

Asp Leu Leu Pro Ala Met Gly Asn His Cys Ser His Val Gly Gly Pro
370                 375                 380

Gln Asp Leu Glu Lys Thr Pro Arg Gly Arg Gly Ser Pro Leu Pro Pro
385                 390                 395                 400

Pro Arg Glu Ala Ser Leu Ala Val Arg Gly Leu Leu Gln Glu Leu Ser
                405                 410                 415

Ser Ile Arg His Phe Leu Glu Lys Arg Asp Glu Met Arg Glu Val Ala
            420                 425                 430

Arg Asp Trp Leu Arg Val Gly Tyr Val Leu Asp Arg Leu Leu Phe Arg
            435                 440                 445

Ile Tyr Leu Leu Ala Val Leu Ala Tyr Ser Ile Thr Leu Val Thr Leu
450                 455                 460

Trp Ser Ile Trp His Tyr Ser
465                 470

<210> SEQ ID NO 7
<211> LENGTH: 431
<212> TYPE: PRT
<213> ORGANISM: Artificial Sequence
<220> FEATURE:
<223> OTHER INFORMATION: alpha7-GlyR chimeric receptor sequence

<400> SEQUENCE: 7

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
130                 135                 140

Ile Phe Lys Ser Ser Cys Tyr Ile Asp Val Arg Trp Phe Pro Phe Asp
145                 150                 155                 160
```

Val Gln His Cys Lys Leu Lys Phe Gly Ser Trp Ser Tyr Gly Gly Trp
            165                 170                 175

Ser Leu Asp Leu Gln Met Gln Glu Ala Asp Ile Ser Gly Tyr Ile Pro
        180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
        210                 215                 220

Thr Met Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
            245                 250                 255

Asp Ala Ala Pro Ala Arg Val Gly Leu Gly Ile Thr Thr Val Leu Thr
        260                 265                 270

Met Thr Thr Gln Ser Ser Gly Ser Arg Ala Ser Leu Pro Lys Val Ser
            275                 280                 285

Tyr Val Lys Ala Ile Asp Ile Trp Met Ala Val Cys Leu Leu Phe Val
        290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg Arg His His Lys Glu
            325                 330                 335

Asp Glu Ala Gly Glu Gly Arg Phe Asn Phe Ser Ala Tyr Gly Met Gly
        340                 345                 350

Pro Ala Cys Leu Gln Ala Lys Asp Gly Ile Ser Val Lys Gly Ala Asn
            355                 360                 365

Asn Ser Asn Thr Thr Asn Pro Pro Ala Pro Ser Lys Ser Pro Glu
        370                 375                 380

Glu Met Arg Lys Leu Phe Ile Gln Arg Ala Lys Lys Ile Asp Lys Ile
385                 390                 395                 400

Ser Arg Ile Gly Phe Pro Met Ala Phe Leu Ile Phe Asn Met Phe Tyr
            405                 410                 415

Trp Ile Ile Tyr Lys Ile Val Arg Arg Glu Asp Val His Asn Gln
        420                 425                 430

<210> SEQ ID NO 8
<211> LENGTH: 466
<212> TYPE: PRT
<213> ORGANISM: Artificial Sequence
<220> FEATURE:
<223> OTHER INFORMATION: alpha7-5HT3 chimeric receptor sequence

<400> SEQUENCE: 8

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
            85                  90                  95

```
Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
            130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                    165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Ile Ile Arg Arg Arg Pro Leu Phe Tyr Val Val Ser Leu Leu Leu Pro
225                 230                 235                 240

Ser Ile Phe Leu Met Val Met Asp Ile Val Gly Phe Tyr Leu Pro Pro
                    245                 250                 255

Asn Ser Gly Glu Arg Val Ser Phe Lys Ile Thr Leu Leu Leu Gly Tyr
            260                 265                 270

Ser Val Phe Leu Ile Ile Val Ser Asp Thr Leu Pro Ala Thr Ala Ile
            275                 280                 285

Gly Thr Pro Leu Ile Gly Val Tyr Phe Val Val Cys Met Ala Leu Leu
            290                 295                 300

Val Ile Ser Leu Ala Glu Thr Ile Phe Ile Val Arg Leu Val His Lys
305                 310                 315                 320

Gln Asp Leu Gln Gln Pro Val Pro Ala Trp Leu Arg His Leu Val Leu
                    325                 330                 335

Glu Arg Ile Ala Trp Leu Leu Cys Leu Arg Glu Gln Ser Thr Ser Gln
            340                 345                 350

Arg Pro Pro Ala Thr Ser Gln Ala Thr Lys Thr Asp Asp Cys Ser Ala
            355                 360                 365

Met Gly Asn His Cys Ser His Met Gly Gly Pro Gln Asp Phe Glu Lys
            370                 375                 380

Ser Pro Arg Asp Arg Cys Ser Pro Pro Pro Pro Arg Glu Ala Ser
385                 390                 395                 400

Leu Ala Val Cys Gly Leu Leu Gln Glu Leu Ser Ser Ile Arg Gln Phe
                    405                 410                 415

Leu Glu Lys Arg Asp Glu Ile Arg Glu Val Ala Arg Asp Trp Leu Arg
            420                 425                 430

Val Gly Ser Val Leu Asp Lys Leu Leu Phe His Ile Tyr Leu Leu Ala
            435                 440                 445

Val Leu Ala Tyr Ser Ile Thr Leu Val Met Leu Trp Ser Ile Trp Gln
            450                 455                 460

Tyr Ala
465

<210> SEQ ID NO 9
<211> LENGTH: 195
<212> TYPE: PRT
<213> ORGANISM: Homo sapiens
```

```
<400> SEQUENCE: 9

Leu Leu Gln Thr Tyr Phe Pro Ala Thr Leu Met Val Met Leu Ser Trp
1               5                   10                  15

Val Ser Phe Trp Ile Asp Arg Arg Ala Val Pro Ala Arg Val Pro Leu
            20                  25                  30

Gly Ile Thr Thr Val Leu Thr Met Ser Thr Ile Ile Thr Gly Val Asn
        35                  40                  45

Ala Ser Met Pro Arg Val Ser Tyr Ile Lys Ala Val Asp Ile Tyr Leu
    50                  55                  60

Trp Val Ser Phe Val Phe Val Phe Leu Ser Val Leu Glu Tyr Ala Ala
65              70                  75                  80

Val Asn Tyr Leu Thr Thr Val Gln Glu Arg Lys Glu Gln Lys Leu Arg
                85                  90                  95

Glu Lys Leu Pro Cys Thr Ser Gly Leu Pro Pro Arg Thr Ala Met
            100                 105                 110

Leu Asp Gly Asn Tyr Ser Asp Gly Glu Val Asn Asp Leu Asp Asn Tyr
                115                 120                 125

Met Pro Glu Asn Gly Glu Lys Pro Asp Arg Met Met Val Gln Leu Thr
    130                 135                 140

Leu Ala Ser Glu Arg Ser Ser Pro Gln Arg Lys Ser Gln Arg Ser Ser
145                 150                 155                 160

Tyr Val Ser Met Arg Ile Asp Thr His Ala Ile Asp Lys Tyr Ser Arg
                165                 170                 175

Ile Ile Phe Pro Ala Ala Tyr Ile Leu Phe Asn Leu Ile Tyr Trp Ser
                180                 185                 190

Ile Phe Ser
        195

<210> SEQ ID NO 10
<211> LENGTH: 428
<212> TYPE: PRT
<213> ORGANISM: Artificial Sequence
<220> FEATURE:
<223> OTHER INFORMATION: alpha7- GABAC chimeric receptor sequence

<400> SEQUENCE: 10

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65              70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
    130                 135                 140
```

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Thr Leu Tyr Tyr Leu Leu Gln Thr Tyr Phe Pro
225                 230                 235                 240

Ala Thr Leu Met Val Met Leu Ser Trp Val Ser Phe Trp Ile Asp Arg
                245                 250                 255

Arg Ala Val Pro Ala Arg Val Pro Leu Gly Ile Thr Thr Val Leu Thr
            260                 265                 270

Met Ser Thr Ile Ile Thr Gly Val Asn Ala Ser Met Pro Arg Val Ser
        275                 280                 285

Tyr Ile Lys Ala Val Asp Ile Tyr Leu Trp Val Ser Phe Val Phe Val
    290                 295                 300

Phe Leu Ser Val Leu Glu Tyr Ala Ala Val Asn Tyr Leu Thr Thr Val
305                 310                 315                 320

Gln Glu Arg Lys Glu Gln Lys Leu Arg Glu Lys Leu Pro Cys Thr Ser
                325                 330                 335

Gly Leu Pro Pro Pro Arg Thr Ala Met Leu Asp Gly Asn Tyr Ser Asp
            340                 345                 350

Gly Glu Val Asn Asp Leu Asp Asn Tyr Met Pro Glu Asn Gly Glu Lys
        355                 360                 365

Pro Asp Arg Met Met Val Gln Leu Thr Leu Ala Ser Glu Arg Ser Ser
    370                 375                 380

Pro Gln Arg Lys Ser Gln Arg Ser Ser Tyr Val Ser Met Arg Ile Asp
385                 390                 395                 400

Thr His Ala Ile Asp Lys Tyr Ser Arg Ile Ile Phe Pro Ala Ala Tyr
                405                 410                 415

Ile Leu Phe Asn Leu Ile Tyr Trp Ser Ile Phe Ser
            420                 425

<210> SEQ ID NO 11
<211> LENGTH: 233
<212> TYPE: PRT
<213> ORGANISM: Homo sapiens

<400> SEQUENCE: 11

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
        50                  55                  60

Val Asp Glu Lys Asn Gln Val Leu Thr Thr Asn Ile Trp Leu Gln Met
65                  70                  75                  80

```
Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Thr Leu Tyr Tyr
225                 230

<210> SEQ ID NO 12
<211> LENGTH: 502
<212> TYPE: PRT
<213> ORGANISM: Rattus norvegicus

<400> SEQUENCE: 12

Met Gly Gly Gly Arg Gly Gly Ile Trp Leu Ala Leu Ala Ala Ala Leu
1               5                   10                  15

Leu His Val Ser Leu Gln Gly Glu Phe Gln Arg Arg Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Met Ser Glu Tyr Pro Gly
                85                  90                  95

Val Lys Asn Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ala Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln Gln Cys Lys Leu Lys Phe Gly Ser Trp Ser Tyr Gly Gly Trp
                165                 170                 175

Ser Leu Asp Leu Gln Met Gln Glu Ala Asp Ile Ser Ser Tyr Ile Pro
            180                 185                 190

Asn Gly Glu Trp Asp Leu Met Gly Ile Pro Gly Lys Arg Asn Glu Lys
        195                 200                 205
```

-continued

Phe Tyr Glu Cys Cys Lys Glu Pro Tyr Pro Asp Val Thr Tyr Thr Val
            210                 215                 220

Thr Met Arg Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                245                 250                 255

Asp Ser Gly Glu Lys Ile Ser Leu Gly Ile Thr Val Leu Leu Ser Leu
            260                 265                 270

Thr Val Phe Met Leu Leu Val Ala Glu Ile Met Pro Ala Thr Ser Asp
        275                 280                 285

Ser Val Pro Leu Ile Ala Gln Tyr Phe Ala Ser Thr Met Ile Ile Val
        290                 295                 300

Gly Leu Ser Val Val Thr Val Ile Val Leu Arg Tyr His His His
305                 310                 315                 320

Asp Pro Asp Gly Gly Lys Met Pro Lys Trp Thr Arg Ile Ile Leu Leu
            325                 330                 335

Asn Trp Cys Ala Trp Phe Leu Arg Met Lys Arg Pro Gly Glu Asp Lys
            340                 345                 350

Val Arg Pro Ala Cys Gln His Lys Pro Arg Arg Cys Ser Leu Ala Ser
            355                 360                 365

Val Glu Leu Ser Ala Gly Ala Gly Pro Pro Thr Ser Asn Gly Asn Leu
370                 375                 380

Leu Tyr Ile Gly Phe Arg Gly Leu Glu Gly Met His Cys Ala Pro Thr
385                 390                 395                 400

Pro Asp Ser Gly Val Val Cys Gly Arg Leu Ala Cys Ser Pro Thr His
                405                 410                 415

Asp Glu His Leu Met His Gly Ala His Pro Ser Asp Gly Asp Pro Asp
            420                 425                 430

Leu Ala Lys Ile Leu Glu Glu Val Arg Tyr Ile Ala Asn Arg Asn Arg
            435                 440                 445

Cys Gln Asp Glu Ser Glu Val Ile Cys Ser Glu Trp Lys Phe Ala Ala
        450                 455                 460

Cys Val Val Asp Pro Leu Cys Leu Met Ala Phe Ser Val Phe Thr Ile
465                 470                 475                 480

Ile Cys Thr Ile Gly Ile Leu Met Ser Ala Pro Asn Phe Val Glu Ala
                485                 490                 495

Val Ser Lys Asp Phe Ala
            500

<210> SEQ ID NO 13
<211> LENGTH: 438
<212> TYPE: PRT
<213> ORGANISM: Artificial Sequence
<220> FEATURE:
<223> OTHER INFORMATION: PSAM4-GlyR-KirM3M4 sequence

<400> SEQUENCE: 13

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
            85                  90                  95

Val Lys Thr Val Arg Phe Pro Asp Gly Gln Ile Trp Lys Pro Asp Ile
        100                 105                 110

Leu Leu Tyr Asn Ser Ala Asp Glu Arg Phe Asp Ala Thr Phe His Thr
            115                 120                 125

Asn Val Gly Val Asn Ser Ser Gly His Cys Leu Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
            165                 170                 175

Ser Leu Asp Leu Gln Met Gln Glu Ala Asp Ile Ser Gly Tyr Ile Pro
        180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Phe Pro Asp Val Thr Phe Thr Val
210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
            245                 250                 255

Asp Ala Ala Pro Ala Arg Val Gly Leu Gly Ile Thr Thr Val Leu Thr
        260                 265                 270

Met Thr Thr Gln Ser Ser Gly Ser Arg Ala Ser Leu Pro Lys Val Ser
275                 280                 285

Tyr Val Lys Ala Ile Asp Ile Trp Met Ala Val Cys Leu Leu Phe Val
290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg Arg His His Lys Glu
            325                 330                 335

Asp Glu Ala Gly Glu Gly Arg Phe Asn Phe Ser Ala Tyr Gly Met Gly
        340                 345                 350

Pro Ala Cys Leu Gln Ala Lys Asp Gly Ile Ser Val Lys Gly Ala Asn
        355                 360                 365

Asn Ser Asn Phe Cys Tyr Glu Asn Glu Val Thr Thr Asn Pro Pro Pro
        370                 375                 380

Ala Pro Ser Lys Ser Pro Glu Glu Met Arg Lys Leu Phe Ile Gln Arg
385                 390                 395                 400

Ala Lys Lys Ile Asp Lys Ile Ser Arg Ile Gly Phe Pro Met Ala Phe
            405                 410                 415

Leu Ile Phe Asn Met Phe Tyr Trp Ile Ile Tyr Lys Ile Val Arg Arg
            420                 425                 430

Glu Asp Val His Asn Gln
            435

<210> SEQ ID NO 14
<211> LENGTH: 437
<212> TYPE: PRT
<213> ORGANISM: artificial
<220> FEATURE:

<223> OTHER INFORMATION: PSAM4-GlyR-B4sig sequence

<400> SEQUENCE: 14

```
Met Arg Arg Ala Pro Ser Leu Val Leu Phe Leu Val Ala Leu Cys
1               5                   10                  15

Gly Arg Gly Asn Cys Gly Glu Phe Gln Arg Lys Leu Tyr Lys Glu Leu
            20                  25                  30

Val Lys Asn Tyr Asn Pro Leu Glu Arg Pro Val Ala Asn Asp Ser Gln
            35                  40                  45

Pro Leu Thr Val Tyr Phe Ser Leu Ser Leu Leu Gln Ile Met Asp Val
        50                  55                  60

Asp Glu Lys Asn Gln Val Leu Thr Thr Asn Ile Trp Leu Gln Met Ser
65                  70                  75                  80

Trp Thr Asp His Tyr Leu Gln Trp Asn Val Ser Glu Tyr Pro Gly Val
                85                  90                  95

Lys Thr Val Arg Phe Pro Asp Gly Gln Ile Trp Lys Pro Asp Ile Leu
            100                 105                 110

Leu Tyr Asn Ser Ala Asp Glu Arg Phe Asp Ala Thr Phe His Thr Asn
        115                 120                 125

Val Gly Val Asn Ser Ser Gly His Cys Leu Tyr Leu Pro Pro Gly Ile
    130                 135                 140

Phe Lys Ser Ser Cys Tyr Ile Asp Val Arg Trp Phe Pro Phe Asp Val
145                 150                 155                 160

Gln His Cys Lys Leu Lys Phe Gly Ser Trp Ser Tyr Gly Gly Trp Ser
                165                 170                 175

Leu Asp Leu Gln Met Gln Glu Ala Asp Ile Ser Gly Tyr Ile Pro Asn
            180                 185                 190

Gly Glu Trp Asp Leu Val Gly Ile Pro Gly Lys Arg Ser Glu Arg Phe
        195                 200                 205

Tyr Glu Cys Cys Lys Glu Pro Phe Pro Asp Val Thr Phe Thr Val Thr
    210                 215                 220

Met Arg Arg Arg Met Gly Tyr Tyr Leu Ile Gln Met Tyr Ile Pro Ser
225                 230                 235                 240

Leu Leu Ile Val Ile Leu Ser Trp Ile Ser Phe Trp Ile Asn Met Asp
                245                 250                 255

Ala Ala Pro Ala Arg Val Gly Leu Gly Ile Thr Thr Val Leu Thr Met
            260                 265                 270

Thr Thr Gln Ser Ser Gly Ser Arg Ala Ser Leu Pro Lys Val Ser Tyr
        275                 280                 285

Val Lys Ala Ile Asp Ile Trp Met Ala Val Cys Leu Leu Phe Val Phe
    290                 295                 300

Ser Ala Leu Leu Glu Tyr Ala Ala Val Asn Phe Val Ser Arg Gln His
305                 310                 315                 320

Lys Glu Leu Leu Arg Phe Arg Arg Lys Arg Arg His His Lys Glu Asp
                325                 330                 335

Glu Ala Gly Glu Gly Arg Phe Asn Phe Ser Ala Tyr Gly Met Gly Pro
            340                 345                 350

Ala Cys Leu Gln Ala Lys Asp Gly Ile Ser Val Lys Gly Ala Asn Asn
        355                 360                 365

Ser Asn Phe Cys Tyr Glu Asn Glu Val Thr Thr Asn Pro Pro Ala
    370                 375                 380

Pro Ser Lys Ser Pro Glu Glu Met Arg Lys Leu Phe Ile Gln Arg Ala
385                 390                 395                 400
```

```
Lys Lys Ile Asp Lys Ile Ser Arg Ile Gly Phe Pro Met Ala Phe Leu
            405                 410                 415

Ile Phe Asn Met Phe Tyr Trp Ile Ile Tyr Lys Ile Val Arg Arg Glu
            420                 425                 430

Asp Val His Asn Gln
            435

<210> SEQ ID NO 15
<211> LENGTH: 496
<212> TYPE: PRT
<213> ORGANISM: Artificial Sequence
<220> FEATURE:
<223> OTHER INFORMATION: PSAM4-GlyR-Kv2M3M4-soma sequence

<400> SEQUENCE: 15

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Gly Val Asn Ser Ser Gly His Cys Leu Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Phe Pro Asp Val Thr Phe Thr Val
            210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285

Tyr Val Lys Ala Ile Asp Ile Trp Met Ala Val Cys Leu Leu Phe Val
        290                 295                 300

Phe Ser Ala Leu Leu Glu Tyr Ala Ala Val Asn Phe Val Ser Arg Gln
305                 310                 315                 320
```

```
His Lys Glu Leu Leu Arg Phe Arg Arg Lys Arg His His Lys Glu
            325                 330                 335

Asp Glu Ala Gly Glu Gly Arg Phe Asn Phe Ser Ala Tyr Gly Met Gly
        340                 345                 350

Pro Ala Cys Leu Gln Ala Lys Asp Gly Ile Ser Val Lys Gly Ala Asn
            355                 360                 365

Asn Ser Asn Gln Ser Gln Pro Ile Leu Asn Thr Lys Glu Met Ala Pro
    370                 375                 380

Gln Ser Lys Pro Pro Glu Leu Glu Met Ser Ser Met Pro Ser Pro
385                 390                 395                 400

Val Ala Pro Leu Pro Ala Arg Thr Glu Gly Val Ile Asp Met Arg Ser
            405                 410                 415

Met Ser Ser Ile Asp Ser Phe Ile Ser Cys Ala Thr Asp Phe Pro Glu
            420                 425                 430

Ala Thr Arg Phe Thr Thr Asn Pro Pro Ala Pro Ser Lys Ser Pro
            435                 440                 445

Glu Glu Met Arg Lys Leu Phe Ile Gln Arg Ala Lys Lys Ile Asp Lys
    450                 455                 460

Ile Ser Arg Ile Gly Phe Pro Met Ala Phe Leu Ile Phe Asn Met Phe
465                 470                 475                 480

Tyr Trp Ile Ile Tyr Lys Ile Val Arg Glu Asp Val His Asn Gln
            485                 490                 495

<210> SEQ ID NO 16
<211> LENGTH: 7
<212> TYPE: PRT
<213> ORGANISM: Artificial Sequence
<220> FEATURE:
<223> OTHER INFORMATION: endoplasmic reticulum export sequence

<400> SEQUENCE: 16

Phe Cys Tyr Glu Asn Glu Val
1               5

<210> SEQ ID NO 17
<211> LENGTH: 21
<212> TYPE: PRT
<213> ORGANISM: Artificial Sequence
<220> FEATURE:
<223> OTHER INFORMATION: CHRNB4 signal sequence

<400> SEQUENCE: 17

Met Arg Arg Ala Pro Ser Leu Val Leu Phe Phe Leu Val Ala Leu Cys
1               5                   10                  15

Gly Arg Gly Asn Cys
            20

<210> SEQ ID NO 18
<211> LENGTH: 65
<212> TYPE: PRT
<213> ORGANISM: Artificial Sequence
<220> FEATURE:
<223> OTHER INFORMATION: KCNB1 somatic targeting sequence

<400> SEQUENCE: 18

Gln Ser Gln Pro Ile Leu Asn Thr Lys Glu Met Ala Pro Gln Ser Lys
1               5                   10                  15

Pro Pro Glu Glu Leu Glu Met Ser Ser Met Pro Ser Pro Val Ala Pro
            20                  25                  30
```

Leu Pro Ala Arg Thr Glu Gly Val Ile Asp Met Arg Ser Met Ser Ser
            35                  40                  45

Ile Asp Ser Phe Ile Ser Cys Ala Thr Asp Phe Pro Glu Ala Thr Arg
    50                  55                  60

Phe
65

<210> SEQ ID NO 19
<211> LENGTH: 1509
<212> TYPE: DNA
<213> ORGANISM: Rattus norvegicus

<400> SEQUENCE: 19

| | | | | | | |
|---|---|---|---|---|---|---|
| atgggcggcg | ggcggggagg | catctggctg | gctctggccg | cggcgctgct | gcacgtgtcc | 60 |
| ctgcaaggcg | agttccagag | gaggctgtac | aaggagctgg | tcaagaacta | caacccgctg | 120 |
| gagaggccgg | tggccaacga | ctcgcagccg | ctcaccgtgt | acttctccct | gagtctcctg | 180 |
| cagatcatgg | atgtggatga | gaagaaccaa | gttttaacca | ccaacatttg | gctacaaatg | 240 |
| tcttggacag | atcactattt | gcagtggaac | atgtctgagt | accccggagt | gaagaatgtt | 300 |
| cgttttccag | atggccagat | ttggaaacca | gacattctcc | tctataacag | tgctgatgag | 360 |
| cgctttgatg | ccacgttcca | caccaatgtt | ttggtgaatg | catctgggca | ttgccagtat | 420 |
| ctccctccag | gcatattcaa | gagctcctgc | tacattgacg | ttcgctggtt | ccttttgat | 480 |
| gtgcagcagt | gcaaactgaa | gtttgggtcc | tggtcctatg | gagggtggtc | actggacctg | 540 |
| caaatgcaag | aggcagatat | cagcagctat | atccccaacg | gagaatggga | tctcatggga | 600 |
| atccctggca | aaaggaatga | gaagttctat | gagtgctgca | aagagccata | cccagatgtc | 660 |
| acctacacag | taaccatgcg | ccgtaggaca | ctctactatg | cctcaatct | gctcatccct | 720 |
| tgtgtactca | tttcagccct | ggctctgctg | gtattcttgc | tgcctgcaga | ctctggagag | 780 |
| aaaatctctc | ttggaataac | tgtcttactt | tctctgactg | tcttcatgct | gcttgtggct | 840 |
| gagatcatgc | cagcaacatc | tgattctgtg | cccttgatag | cacaatactt | cgccagcacc | 900 |
| atgatcatcg | tgggcctctc | tgtagtggtg | acagtgattg | tgctgagata | tcaccaccat | 960 |
| gaccctgatg | gtggcaaaat | gcctaagtgg | accagaatca | ttctcctgaa | ctggtgtgca | 1020 |
| tggtttctgc | gcatgaagag | gcccggagag | gacaaggtgc | ggccagcttg | tcagcacaag | 1080 |
| cctcggcgct | gcagcctggc | cagtgtggag | ctgagtgcag | gtgctgggcc | acccaccagc | 1140 |
| aatggcaacc | tgctctacat | tggcttccga | ggcctggagg | gcatgcactg | tgccccaact | 1200 |
| ccagactctg | gggtcgtatg | tggccgtttg | gcctgctccc | caacacatga | tgagcacctc | 1260 |
| atgcacggtg | cacaccccctc | tgatggggac | cccgacctgg | ccaagatcct | ggaggaggtc | 1320 |
| cgctacatcg | ccaaccgcaa | ccgctgccag | gacgagagtg | aggtgatctg | cagtgaatgg | 1380 |
| aagtttgcag | cctgcgtggt | ggacccgctt | tgcctcatgg | ccttttcggt | ctttaccatc | 1440 |
| atctgtacca | tcggcatcct | catgtcagct | ccaaactttg | tggaggctgt | gtccaaagac | 1500 |
| tttgcttaa | | | | | | 1509 |

<210> SEQ ID NO 20
<211> LENGTH: 672
<212> TYPE: DNA
<213> ORGANISM: Homo sapiens

<400> SEQUENCE: 20

```
atgcgctgtt ctccaggcgg cgtgtggctc gccctggctg cttcccttct gcacgttagc     60
ctgcagggtg agttccagcg caaactgtat aaggagcttg ttaagaatta taaccccctg    120
gagcggccgg tcgcaaatga ttcccagcca ctgacagtgt acttcagcct ctccttgctg    180
cagatcatgg acgtggatga aaagaaccag gtgctgacca ctaatatttg gttgcagatg    240
tcctggaccg atcactactt gcagtggaat gtgagcgaat acccaggtgt aaagactgta    300
agattccctg acggccaaat ctggaaacca gatatcctgc tgtacaacag cgcagacgaa    360
aggtttgatg caacatttca caccaacgtg ttggtcaatt cttcaggcca ctgccagtac    420
ctgcccctg  aatcttcaa  gtcctcatgc tatatcgacg tccgctggtt tcccttcgac    480
gtccagcact gcaaactcaa attcgggagc tggagctacg gcggatggag cctggatctg    540
caaatgcagg aggctgacat ctctggttac atcccgaatg gggagtggga ccttgtggga    600
atccccggta aaagaagcga gcgatttat gaatgctgca aggaacccta ccctgacgta    660
acattcacag tt                                                        672
```

<210> SEQ ID NO 21
<211> LENGTH: 687
<212> TYPE: DNA
<213> ORGANISM: Homo sapiens

<400> SEQUENCE: 21

```
atgcgctgtt ctccaggcgg cgtgtggctc gccctggctg cttcccttct gcacgttagc     60
ctgcagggtg agttccagcg caaactgtat aaggagcttg ttaagaatta taaccccctg    120
gagcggccgg tcgcaaatga ttcccagcca ctgacagtgt acttcagcct ctccttgctg    180
cagatcatgg acgtggatga aaagaaccag gtgctgacca ctaatatttg gttgcagatg    240
tcctggaccg atcactactt gcagtggaat gtgagcgaat acccaggtgt aaagactgta    300
agattccctg acggccaaat ctggaaacca gatatcctgc tgtacaacag cgcagacgaa    360
aggtttgatg caacatttca caccaacgtg ttggtcaatt cttcaggcca ctgccagtac    420
ctgcccctg  aatcttcaa  gtcctcatgc tatatcgacg tccgctggtt tcccttcgac    480
gtccagcact gcaaactcaa attcgggagc tggagctacg gcggatggag cctggatctg    540
caaatgcagg aggctgacat ctctggttac atcccgaatg gggagtggga ccttgtggga    600
atccccggta aaagaagcga gcgatttat gaatgctgca aagagcccta cccagatgtc    660
accttcacag tgaccatgcg gagacgc                                        687
```

<210> SEQ ID NO 22
<211> LENGTH: 699
<212> TYPE: DNA
<213> ORGANISM: Homo sapiens

<400> SEQUENCE: 22

```
atgcgctgtt ctccaggcgg cgtgtggctc gccctggctg cttcccttct gcacgttagc     60
ctgcagggtg agttccagcg caaactgtat aaggagcttg ttaagaatta taaccccctg    120
gagcggccgg tcgcaaatga ttcccagcca ctgacagtgt acttcagcct ctccttgctg    180
cagatcatgg acgtggatga aaagaaccag gtgctgacca ctaatatttg gttgcagatg    240
tcctggaccg atcactactt gcagtggaat gtgagcgaat acccaggtgt aaagactgta    300
agattccctg acggccaaat ctggaaacca gatatcctgc tgtacaacag cgcagacgaa    360
```

| | |
|---|---:|
| aggtttgatg caacatttca caccaacgtg ttggtcaatt cttcaggcca ctgccagtac | 420 |
| ctgcccctg gaatcttcaa gtcctcatgc tatatcgacg tccgctggtt tcccttcgac | 480 |
| gtccagcact gcaaactcaa attcgggagc tggagctacg gcggatggag cctggatctg | 540 |
| caaatgcagg aggctgacat ctctggttac atcccgaatg gggagtggga ccttgtggga | 600 |
| atccccggta aagaagcga gcgatttat gaatgctgca agagccta cccagatgtc | 660 |
| accttcacag tgaccatgcg agacgcaca ctgtattac | 699 |

<210> SEQ ID NO 23
<211> LENGTH: 744
<212> TYPE: DNA
<213> ORGANISM: Mus musculus

<400> SEQUENCE: 23

| | |
|---|---:|
| atcatcagaa aaggccatt gttctacgcc gttagtttgt tgctccccag tatttttctc | 60 |
| atggtcgtgg acatcgtggg attttgtctc ccacctgata gcggggagag ggtctccttt | 120 |
| aagattacct tgttgctcgg ctattctgta tttctgatca tcgtgtccga tacccttcct | 180 |
| gccacaatcg gcactccgct gataggagtg tatttcgtcg tgtgtatggc actcctggtg | 240 |
| ataagtctgg cggaaactat cttcattgta cggctgtac ataagcagga cctgcaaaga | 300 |
| cccgtgccag actggttgcg acaccttgtg ctggacagaa ttgcatggat tctgtgtctt | 360 |
| ggcgagcaac ctatggccca ccggccacct gcaacctttc aagccaacaa gacagacgat | 420 |
| tgtagtgggt ctgatctgtt gcctgctatg gggaatcact gctcccatgt tgggggacca | 480 |
| caagatttgg aaaagacccc acgggggcgg ggatcacccc ttcctcctcc ccgagaagcc | 540 |
| tctctcgctg tccgggggct gctccaggaa ctgtcaagca tccgacattt tctggagaag | 600 |
| cgggacgaga tgagggaagt cgctagagac tggctgcgag tgggctacgt ccttgacagg | 660 |
| ctgctgttc ggatctactt gctggcggtg ctggcttatt ccattactct ggtgacactc | 720 |
| tggtccatat ggcactacag ttag | 744 |

<210> SEQ ID NO 24
<211> LENGTH: 726
<212> TYPE: DNA
<213> ORGANISM: Homo sapiens

<400> SEQUENCE: 24

| | |
|---|---:|
| atcatccgta gaaggcctct gttttacgtg gtgagcctgc tgctgccatc catcttcctg | 60 |
| atggtcatgg acatcgtggg cttttacctg ccacccaatt ctggcgagcg cgtgagcttc | 120 |
| aagatcacac tgctgctggg ctatagcgtg tttctgatca tcgtgtccga tacccttgcct | 180 |
| gcaacagcaa tcggaacccc actgatcggc gtgtatttcg tggtgtgcat ggccctgctg | 240 |
| gtcatcagcc tggccgagac aatctttatc gtgcggctgg tgcacaagca ggacctgcag | 300 |
| cagcctgtgc cagcatggct gaggcacctg gtgctggaga ggatcgcatg gctgctgtgc | 360 |
| ctgagagagc agtccacatc tcagaggcct ccagccacct ctcaggccac caagacagac | 420 |
| gattgctctg ccatgggcaa tcactgtagc cacatgggcg gcccccagga ctttgagaag | 480 |
| tcccctcgcg atcggtgctc tccacctcca ccacctaggg aggccagcct ggccgtgtgc | 540 |
| ggcctgctgc aggagctgtc ctctatccgg cagttcctgg agaagcgcga cgagatccgg | 600 |
| gaggtggcca gagattggct gagggtgggc agcgtgctgg ataagctgct gtttcacatc | 660 |
| tacctgctgg cagtcctggc ctattctatt accctggtca tgctgctggtc catctggcag | 720 |
| tacgcc | 726 |

<210> SEQ ID NO 25
<211> LENGTH: 609
<212> TYPE: DNA
<213> ORGANISM: Mus musculus

<400> SEQUENCE: 25

| | | | | | |
|---|---|---|---|---|---|
| atgggttatt | atctgatcca | aatgtatatc | ccaagcttgc | ttatagtgat | tttgtcatgg | 60 |
| atctccttct | ggattaatat | ggacgccgct | ccagctaggg | tcggactggg | catcaccaca | 120 |
| gtgctgacaa | tgactactca | gagctcaggc | agccgagcca | gcttgcccaa | ggtttcttac | 180 |
| gtgaaggcca | tcgatatctg | gatggctgtc | tgccttctgt | ttgtcttcag | cgcactgctg | 240 |
| gaatacgccg | ctgtcaattt | tgtgtctcga | cagcataaag | agctgttgcg | gttcagaaga | 300 |
| aaacgacgcc | accacaaaga | ggatgaggca | ggagaaggac | gcttcaactt | tagcgcctat | 360 |
| ggtatgggac | ctgcttgcct | ccaggctaaa | gacggaattt | ccgtgaaggg | agccaacaat | 420 |
| agcaacacaa | ccaacccacc | ccctgctcca | tctaagagcc | cggaggaaat | gcgcaaactc | 480 |
| tttattcaga | gagcgaaaaa | gatcgacaaa | atctcccgga | tcggattccc | catggctttc | 540 |
| ctgattttca | acatgtttta | ttggatcatc | tacaagattg | tgcgaaggga | ggacgtacac | 600 |
| aaccagtaa | | | | | | 609 |

<210> SEQ ID NO 26
<211> LENGTH: 588
<212> TYPE: DNA
<213> ORGANISM: Homo sapiens

<400> SEQUENCE: 26

| | | | | | |
|---|---|---|---|---|---|
| cttttgcaaa | cttactttcc | agcaaccctc | atggtgatgc | tttcatgggt | gtccttttgg | 60 |
| atcgaccgcc | gagcggtccc | tgcacgggtc | cccctgggga | ttacgacggt | actgaccatg | 120 |
| agcaccataa | tcactggagt | caatgcaagc | atgcctagag | tgtcttacat | aaaggccgtg | 180 |
| gacatctatc | tgtgggttag | ttttgtgttc | gtattcctct | ccgtgctgga | gtatgcagct | 240 |
| gtgaactatc | tgacaacagt | tcaagagcgg | aaagagcaga | agttgaggga | gaagctgcca | 300 |
| tgcactagcg | gactgccacc | gcccagaacc | gctatgctcg | atggtaacta | ttccgacggc | 360 |
| gaagttaatg | acctcgataa | ctacatgcct | gaaaatggcg | aaaagcccga | caggatgatg | 420 |
| gtccagctga | cactggcctc | agaaaggtcc | agtccacaga | gaaagtcaca | gcgatcctct | 480 |
| tacgtcagca | tgcgcatcga | tacacatgcc | atcgacaaat | actctcgcat | tatctttccg | 540 |
| gctgcttaca | tattgttcaa | ccttatctat | tggagcattt | tcagttga | | 588 |

<210> SEQ ID NO 27
<211> LENGTH: 1416
<212> TYPE: DNA
<213> ORGANISM: Artificial Sequence
<220> FEATURE:
<223> OTHER INFORMATION: alpha7-5HT3 chimeric receptor sequence

<400> SEQUENCE: 27

| | | | | | |
|---|---|---|---|---|---|
| atgcgctgtt | ctccaggcgg | cgtgtggctc | gccctggctg | cttcccttct | gcacgttagc | 60 |
| ctgcagggtg | agttccagcg | caaactgtat | aaggagcttt | taagaattaa | taccccctg | 120 |
| gagcggccgg | tcgcaaatga | ttcccagcca | ctgacagtgt | acttcagcct | ctccttgctg | 180 |
| cagatcatgg | acgtggatga | aaagaaccag | gtgctgacca | ctaatatttg | gttgcagatg | 240 |
| tcctggaccg | atcactactt | gcagtggaat | gtgagcgaat | acccaggtgt | aaagactgta | 300 |

| | |
|---|---|
| agattccctg acggccaaat ctggaaacca gatatcctgc tgtacaacag cgcagacgaa | 360 |
| aggtttgatg caacatttca caccaacgtg ttggtcaatt cttcaggcca ctgccagtac | 420 |
| ctgcccctg aatcttcaa gtcctcatgc tatatcgacg tccgctggtt tcccttcgac | 480 |
| gtccagcact gcaaactcaa attcgggagc tggagctacg gcggatggag cctggatctg | 540 |
| caaatgcagg aggctgacat ctctggttac atcccgaatg gggagtggga ccttgtggga | 600 |
| atccccggta aagaagcga gcgattttat gaatgctgca aggaaccta ccctgacgta | 660 |
| acattcacag ttatcatcag aagaaggcca ttgttctacg ccgttagttt gttgctcccc | 720 |
| agtattttc tcatggtcgt ggacatcgtg ggattttgtc tcccacctga tagcggggag | 780 |
| agggtctcct ttaagattac cttgttgctc ggctattctg tatttctgat catcgtgtcc | 840 |
| gataccttc ctgccacaat cggcactccg ctgataggag tgtatttcgt cgtgtgtatg | 900 |
| gcactcctgg tgataagtct ggcggaaact atcttcattg tacggctggt acataagcag | 960 |
| gacctgcaaa gacccgtgcc agactggttg cgacaccttg tgctggacag aattgcatgg | 1020 |
| attctgtgtc ttggcgagca acctatggcc caccggccac ctgcaacctt tcaagccaac | 1080 |
| aagacagacg attgtagtgg gtctgatctg ttgcctgcta tggggaatca ctgctcccat | 1140 |
| gttggggac acaagatttt ggaaaagacc ccacgggggc ggggatcacc ccttcctcct | 1200 |
| ccccgagaag cctctctcgc tgtccggggg ctgctccagg aactgtcaag catccgacat | 1260 |
| tttctgagaa gcgggacga gatgagggaa gtcgctagag actggctgcg agtgggctac | 1320 |
| gtccttgaca ggctgctgtt tcggatctac ttgctggcgg tgctggctta ttccattact | 1380 |
| ctggtgacac tctggtccat atggcactac agttag | 1416 |

<210> SEQ ID NO 28
<211> LENGTH: 1296
<212> TYPE: DNA
<213> ORGANISM: Artificial Sequence
<220> FEATURE:
<223> OTHER INFORMATION: alpha7-GlyR chimeric receptor sequence

<400> SEQUENCE: 28

| | |
|---|---|
| atgcgctgtt ctccaggcgg cgtgtggctc gccctggctg cttcccttct gcacgttagc | 60 |
| ctgcagggtg agttccagcg caaactgtat aaggagcttg ttaagaatta taccccctg | 120 |
| gagcggccgg tcgcaaatga ttcccagcca ctgacagtgt acttcagcct ctccttgctg | 180 |
| cagatcatgg acgtggatga aagaaccag gtgctgacca ctaatatttg gttgcagatg | 240 |
| tcctggaccg atcactactt gcagtggaat gtgagcgaat acccaggtgt aaagactgta | 300 |
| agattccctg acggccaaat ctggaaacca gatatcctgc tgtacaacag cgcagacgaa | 360 |
| aggtttgatg caacatttca caccaacgtg ttggtcaatt cttcaggcca ctgccagtac | 420 |
| ctgcccctg aatcttcaa gtcctcatgc tatatcgacg tccgctggtt tcccttcgac | 480 |
| gtccagcact gcaaactcaa attcgggagc tggagctacg gcggatggag cctggatctg | 540 |
| caaatgcagg aggctgacat ctctggttac atcccgaatg gggagtggga ccttgtggga | 600 |
| atccccggta aagaagcga gcgattttat gaatgctgca agagcccta cccagatgtc | 660 |
| accttcacag tgaccatgcg agacgcatg gttattatc tgatccaaat gtatatccca | 720 |
| agcttgctta tagtgatttt gtcatggatc tccttctgga ttaatatgga cgccgctcca | 780 |
| gctagggtcg gactgggcat caccacagtg ctgacaatga ctactcagag ctcaggcagc | 840 |
| cgagccagct tgcccaaggt ttcttacgtg aaggccatcg atatctggat ggctgtctgc | 900 |
| cttctgtttg tcttcagcgc actgctggaa tacgccgctg tcaattttgt gtctcgacag | 960 |

| | | |
|---|---|---|
| cataaagagc tgttgcggtt cagaagaaaa cgacgccacc acaaagagga tgaggcagga | 1020 | |
| gaaggacgct tcaactttag cgcctatggt atgggacctg cttgcctcca ggctaaagac | 1080 | |
| ggaatttccg tgaagggagc aacaatagc aacacaacca acccacccc tgctccatct | 1140 | |
| aagagcccgg aggaaatgcg caaactcttt attcagagag cgaaaaagat cgacaaaatc | 1200 | |
| tcccggatcg gattccccat ggctttcctg attttcaaca tgttttattg gatcatctac | 1260 | |
| aagattgtgc gaagggagga cgtacacaac cagtaa | 1296 | |

<210> SEQ ID NO 29
<211> LENGTH: 1287
<212> TYPE: DNA
<213> ORGANISM: Artificial Sequence
<220> FEATURE:
<223> OTHER INFORMATION: alpha7- GABAC chimeric receptor sequence

<400> SEQUENCE: 29

| | | |
|---|---|---|
| atgcgctgtt ctccaggcgg cgtgtggctc gccctggctg cttcccttct gcacgttagc | 60 | |
| ctgcagggtg agttccagcg caaactgtat aaggagcttg ttaagaatta taccccctg | 120 | |
| gagcggccgt cgcaaatga ttcccagcca ctgacagtgt acttcagcct ctccttgctg | 180 | |
| cagatcatgg acgtggatga aaagaaccag gtgctgacca ctaatatttg gttgcagatg | 240 | |
| tcctggaccg atcactactt gcagtggaat gtgagcgaat acccaggtgt aaagactgta | 300 | |
| agattccctg acggccaaat ctggaaacca gatatcctgc tgtacaacag cgcagacgaa | 360 | |
| aggtttgatg caacatttca caccaacgtg ttggtcaatt cttcaggcca ctgccagtac | 420 | |
| ctgcccctg gaatcttcaa gtcctcatgc tatatcgacg tccgctggtt tccttcgac | 480 | |
| gtccagcact gcaaactcaa attcgggagc tggagctacg gcggatggag cctggatctg | 540 | |
| caaatgcagg aggctgacat ctctggttac atcccgaatg gggagtggga ccttgtggga | 600 | |
| atccccggta aagaagcga gcgatttat gaatgctgca agagcccta cccagatgtc | 660 | |
| accttcacag tgaccatgcg agacgcaca ctgtattacc ttttgcaaac ttactttcca | 720 | |
| gcaaccctca tggtgatgct ttcatgggtg tccttttgga tcgaccgccg agcggtccct | 780 | |
| gcacgggtcc ccctggggat tacgacgta ctgaccatga gcaccataat cactggagtc | 840 | |
| aatgcaagca tgcctagagt gtcttacata aaggccgtgg acatctatct gtgggttagt | 900 | |
| tttgtgttcg tattcctctc cgtgctggag tatgcagctg tgaactatct gacaacagtt | 960 | |
| caagagcgga aagagcagaa gttgagggag aagctgccat gcactagcgg actgccaccg | 1020 | |
| cccagaaccg ctatgctcga tggtaactat tccgacggcg aagttaatga cctcgataac | 1080 | |
| tacatgcctg aaaatggcga aaagcccgac aggatgatgg tccagctgac actggcctca | 1140 | |
| gaaaggtcca gtccacagag aaagtcacag cgatcctctt acgtcagcat gcgcatcgat | 1200 | |
| acacatgcca tcgacaaata ctctcgcatt atctttccgg ctgcttacat attgttcaac | 1260 | |
| cttatctatt ggagcatttt cagttga | 1287 | |

<210> SEQ ID NO 30
<211> LENGTH: 21
<212> TYPE: DNA
<213> ORGANISM: Artificial Sequence
<220> FEATURE:
<223> OTHER INFORMATION: endoplasmic reticulum export sequence

<400> SEQUENCE: 30

| | | |
|---|---|---|
| ttttgctatg aaaacgaagt c | 21 | |

<210> SEQ ID NO 31
<211> LENGTH: 63
<212> TYPE: DNA
<213> ORGANISM: Artificial Sequence
<220> FEATURE:
<223> OTHER INFORMATION: CHRNB4 signal sequence

<400> SEQUENCE: 31

```
atgagaaggg cccccatccct ggtattgttt tttttggtag ctttgtgcgg gagggggaac    60
tgc                                                                  63
```

<210> SEQ ID NO 32
<211> LENGTH: 195
<212> TYPE: DNA
<213> ORGANISM: Artificial Sequence
<220> FEATURE:
<223> OTHER INFORMATION: KCNB1 somatic targeting sequence

<400> SEQUENCE: 32

```
caaagccaac ctatccttaa cactaaagag agcgccgctc aatccaaacc caaagaagag    60
ttggaaatgg agtctatacc ttcacctgtt gcacctctcc ctactaggac cgaaggcgtg   120
attgacatgc gctctatgtc tagtatagat agctttatat cctgcgccac agactttccc   180
gaagccacta ggttc                                                    195
```

<210> SEQ ID NO 33
<211> LENGTH: 7066
<212> TYPE: DNA
<213> ORGANISM: Artificial Sequence
<220> FEATURE:
<223> OTHER INFORMATION: AAV-Syn::PSAM4-GlyR-IRES-EGFP-WPRE sequence

<400> SEQUENCE: 33

```
agcgcccaat acgcaaaccg cctctccccg cgcgttggcc gattcattaa tgcagctgcg    60
cgctcgctcg ctcactgagg ccgcccgggc aaagcccggg cgtcgggcga cctttggtcg   120
cccggcctca gtgagcgagc gagcgcgcag agagggagtg gccaactcca tcactagggg   180
ttccttgtag ttaatgatta acccgccatg ctacttatct acgtagccat gctctaggaa   240
gatccgagct ccagtgtgct ggaattcgcc ttttcagta tttaaattga cgaccgaccc   300
cgacccactg gacaagcacc caaccccat tccccaaatt gcgcatcccc tatcagagag    360 ggggaggga aacaggatgc ggcgaggcgc gtgcgcactg ccagcttcag caccgcggac    420
agtgccttcg ccccgcctg gcggcgcgcg ccaccgccgc tcagcactg aaggcgcgct    480 gacgtcactc gccggtcccc cgcaaactcc ccttcccggc caccttggtc gcgtccgcgc   540
cgccgccggc ccagccggac cgcaccacgc gaggcgcgag ataggggggc acgggcgcga   600
ccatctgcgc tgcggcgccg cgactcagc gctgcctcag tctgcggtgg gcagcggagg   660
agtcgtgtcg tgcctgagag cgcagctgtg ctcctgggca ccgcgcagtc cgccccgcg    720 gctcctggcc agaccacccc taggaccccc tgccccaagt cgcagccgtt ggatcaggta   780
agtatcaagg ttacaagaca ggtttaagga gaccaataga aactgggctt gtcgagacag   840
agaagactct tgcgtttctg ataggcacct attggtctta ctgacatcca ctttgccttt   900
ctctccacag gtgatgatat cactagtgct agcgccacca tgcgctgttc tccaggcggc   960
gtgtggctcg ccctggctgc ttcccttctg cacgttagcc tgcagggtga gttcagcgc   1020 aaactgtata aggagcttgt taagaattat aacccctgg agcggccggt cgcaaatgat   1080
tcccagccac tgacagtgta cttcagcctc tccttgctgc agatcatgga cgtggatgaa   1140
```

```
aagaaccagg tgctgaccac taatatttgg ttgcagatgt cctggaccga tcactacttg    1200
cagtggaatg tgagcgaata cccaggtgta aagactgtaa gattccctga cggccaaatc    1260
tggaaaccag atatcctgct gtacaacagc gcagacgaaa ggtttgatgc aacatttcac    1320
accaacgtgg gagtcaattc ttcaggccac tgcctgtacc tgcccccctgg aatcttcaag    1380 tcctcatgct atatcgacgt ccgctggttt cccttcgacg tccagcactg caaactcaaa    1440
ttcgggagct ggagctacgg cggatggagc ctggatctgc aaatgcagga ggctgacatc    1500
tctggttaca tcccgaatgg ggagtgggac cttgtgggaa tccccggtaa agaagcgag    1560 cgattttatg aatgctgcaa agagcccttc ccagatgtca ccttcacagt gaccatgcgg    1620
agacgcatgg gttattatct gatccaaatg tatatcccaa gcttgcttat agtgattttg    1680
tcatggatct ccttctggat taatatggac gccgctccag ctagggtcgg actgggcatc    1740
accacagtgc tgacaatgac tactcagagc tcaggcagcc gagccagctt gcccaaggtt    1800
tcttacgtga aggccatcga tatctggatg gctgtctgcc ttctgtttgt cttcagcgca    1860
ctgctggaat acgccgctgt caattttgtg tctcgacagc ataaagagct gttgcggttc    1920
agaagaaaac gacgccacca caaagaggat gaggcaggag aaggacgctt caactttagc    1980
gcctatggta tgggacctgc ttgcctccag gctaaagacg gaatttccgt gaagggagcc    2040
aacaatagca cacaaccaa cccaccccct gctccatcta agagcccgga ggaaatgcgc    2100 aaactctttta ttcagagagc gaaaaagatc gacaaaatct cccggatcgg attccccatg    2160
gctttcctga ttttcaacat gtttttattgg atcatctaca agattgtgcg aagggaggac    2220
gtacacaacc agtaagcggc cgcaattccc ccgcccccc ccccccccc ctcaccctcc    2280 cccccccta acgttactgg ccgaagccgc ttggaataag gccggtgtgc gtttgtctat    2340
atgttatttt ccaccatatt gccgtctttt ggcaatgtga gggcccggaa acctggccct    2400
gtcttcttga cgagcattcc tagggtgtctt tccctctcg ccaaaggaat gcaaggtctg    2460
ttgaatgtcg tgaaggaagc agttcctctg gaagcttctt gaagacaaac aacgtctgta    2520
gcgacccttt gcaggcagcg gaaccccca cctggcgaca ggtgcctctg cggccaaaag    2580
ccacgtgtat aagatacacc tgcaaaggcg gcacaacccc agtgccacgt tgtgagttgg    2640
atagttgtgg aaaagagtcaa atggctctcc taagcgtatt caacaagggg ctgaaggatg    2700
cccagaaggt acccccattgt atgggatctg atctggggcc tcggtgcaca tgctttacat    2760
gtgtttagtc gaggttaaaa aaacgtctag gcccccgaa ccacggggac gtggttttcc    2820
tttgaaaaac acgatgataa tatggccaca accatgggag atccggtgag caagggcgag    2880
gagctgttca ccggggtggt gcccatcctg gtcgagctgg acggcgacgt aaacggccac    2940
aagttcagcg tgtccggcga gggcgagggc gatgccacct acggcaagct gaccctgaag    3000
ttcatctgca ccaccggcaa gctgcccgtg ccctggccca ccctcgtgac caccctgacc    3060
tacggcgtgc agtgcttcag ccgctacccc gaccacatga gcagcacga cttcttcaag    3120 tccgccatgc ccgaaggcta cgtccaggag cgcaccatct tcttcaagga cgacggcaac    3180
tacaagaccc gcgccgaggt gaagttcgag ggcgacaccc tggtgaaccg catcgagctg    3240
aagggcatcg acttcaagga ggacggcaac atcctggggc acaagctgga gtacaactac    3300
aacagccaca acgtctatat catggccgac aagcagaaga acggcatcaa ggtgaacttc    3360
aagatccgcc acaacatcga ggacggcagc gtgcagctcg ccgaccacta ccagcagaac    3420
acccccatcg gcgacggccc cgtgctgctg cccgacaacc actacctgag cacccagtcc    3480
```

-continued

```
aagctgagca aagaccccaa cgagaagcgc gatcacatgg tcctgctgga gttcgtgacc    3540
gccgccggga tcactctcgg catggacgag ctgtacaagt aaaccggtaa tcaacctctg    3600
gattacaaaa tttgtgaaag attgactggt attcttaact atgttgctcc ttttacgcta    3660
tgtggatacg ctgctttaat gcctttgtat catgctattg cttcccgtat ggctttcatt    3720
ttctcctcct tgtataaatc ctggttgctg tctctttatg aggagttgtg gcccgttgtc    3780
aggcaacgtg gcgtggtgtg cactgtgttt gctgacgcaa cccccactgg ttggggcatt    3840
gccaccacct gtcagctcct tccgggact ttcgctttcc cctccctat tgccacggcg    3900
gaactcatcg ccgcctgcct tgcccgctgc tggacagggg ctcggctgtt gggcactgac    3960
aattccgtgg tgttgtcggg gaaatcatcg tcctttcctt ggctgctcgc ctgtgttgcc    4020
acctggattc tgcgcgggac gtccttctgc tacgtccctt cggccctcaa tccagcggac    4080
cttccttccc gcggcctgct gccggctctg cggcctcttc cgcgtcttcg ccttcgccct    4140
cagacgagtc ggatctccct ttgggccgcc tccccgccgc ttcgagcaga catgataaga    4200
tacattgatg agtttggaca aaccacaact agaatgcagt gaaaaaaatg ctttatttgt    4260
gaaatttgtg atgctattgc tttatttgta accattataa gctgcaataa acaagttaac    4320
aacaacaatt gcattcattt tatgtttcag gttcaggggg agatgtggga ggttttttaa    4380
agcaagtaaa acctctacaa atgtggtaaa atcgataagg atcttcctag agcatggcta    4440
cgtagataag tagcatggcg ggttaatcat taactacaag gaaccctag tgatggagtt    4500
ggccactccc tctctgcgcg ctcgctcgct cactgaggcc gggcgaccaa aggtcgcccg    4560
acgcccgggc tttgcccggg cggcctcagt gagcgagcga gcgcgcagct ggcgtaatag    4620
cgaagaggcc cgcaccgatc gcccttccca acagttgcgc agcctgaatg gcgaatggga    4680
cgcgccctgt agcggcgcat taagcgcggc gggtgtggtg gttacgcgca gcgtgaccgc    4740
tacacttgcc agcgccctag cgcccgctcc tttcgctttc ttcccttcct ttctcgccac    4800
gttcgccggc tttccccgtc aagctctaaa tcggggctc cctttagggt tccgatttag    4860
tgctttacgg cacctcgacc ccaaaaaact tgattagggt gatggttcac gtagtgggcc    4920
atcgccctga tagacggttt ttcgcccttt gacgttggag tccacgttct ttaatagtgg    4980
actcttgttc caaactggaa caacactcaa ccctatctcg gtctattctt ttgatttata    5040
agggattttg ccgatttcgg cctattggtt aaaaaatgag ctgatttaac aaaaatttaa    5100
cgcgaatttt aacaaaatat taacgcttac aatttaggtg cacttttcg gggaaatgtg    5160
cgcggaaccc ctatttgttt attttctaa atacattcaa atatgtatcc gctcatgaga    5220
caataaccct gataaatgct tcaataatat tgaaaaagga agagtatgag tattcaacat    5280
ttccgtgtcg cccttattcc cttttttgcg gcattttgcc ttcctgtttt tgctcaccca    5340
gaaacgctgg tgaaagtaaa agatgctgaa gatcagttgg gtgcacgagt gggttacatc    5400
gaactggatc tcaacagcgg taagatcctt gagagttttc gccccgaaga acgttttcca    5460
atgatgagca cttttaaagt tctgctatgt ggcgcggtat tatcccgtat tgacgccggg    5520
caagagcaac tcggtcgccg catacactat tctcagaatg acttggttga gtactcacca    5580
gtcacagaaa agcatcttac ggatggcatg acagtaagag aattatgcag tgctgccata    5640
accatgagtg ataacactgc ggccaactta cttctgacaa cgatcggagg accgaaggag    5700
ctaaccgctt ttttgcacaa catgggggat catgtaactc gccttgatcg ttgggaaccg    5760
gagctgaatg aagccatacc aaacgacgag cgtgacacca cgatgcctgt agcaatggca    5820
acaacgttgc gcaaactatt aactggcgaa ctacttactc tagcttcccg gcaacaatta    5880
```

```
atagactgga tggaggcgga taaagttgca ggaccacttc tgcgctcggc ccttccggct    5940
ggctggttta ttgctgataa atctggagcc ggtgagcgtg ggtctcgcgg tatcattgca    6000
gcactggggc cagatggtaa gccctcccgt atcgtagtta tctacacgac ggggagtcag    6060
gcaactatgg atgaacgaaa tagacagatc gctgagatag gtgcctcact gattaagcat    6120
tggtaactgt cagaccaagt ttactcatat atactttaga ttgatttaaa acttcatttt    6180
taatttaaaa ggatctaggt gaagatcctt tttgataatc tcatgaccaa atcccttaa    6240 cgtgagtttt cgttccactg agcgtcagac cccgtagaaa agatcaaagg atcttcttga    6300
gatccttttt ttctgcgcgt aatctgctgc ttgcaaacaa aaaaaccacc gctaccagcg    6360
gtggtttgtt tgccggatca agagctacca actctttttc cgaaggtaac tggcttcagc    6420
agagcgcaga taccaaatac tgttcttcta gtgtagccgt agttaggcca ccacttcaag    6480
aactctgtag caccgcctac atacctcgct ctgctaatcc tgttaccagt ggctgctgcc    6540
agtggcgata agtcgtgtct taccgggttg gactcaagac gatagttacc ggataaggcg    6600
cagcggtcgg gctgaacggg gggttcgtgc acacagccca gcttggagcg aacgacctac    6660
accgaactga gatacctaca gcgtgagcta tgagaaagcg ccacgcttcc cgaagggaga    6720
aaggcggaca ggtatccggt aagcggcagg gtcggaacag gagagcgcac gagggagctt    6780
ccagggggaa acgcctggta tctttatagt cctgtcgggt ttcgccacct ctgacttgag    6840
cgtcgatttt tgtgatgctc gtcaggggggg cggagcctat ggaaaaacgc cagcaacgcg    6900
gcctttttac ggttcctggc cttttgctgg ccttttgctc acatgttctt tcctgcgtta    6960
tcccctgatt ctgtggataa ccgtattacc gcctttgagt gagctgatac cgctcgccgc    7020
agccgaacga ccgagcgcag cgagtcagtg agcgaggaag cggaag               7066
```

<210> SEQ ID NO 34
<211> LENGTH: 8167
<212> TYPE: DNA
<213> ORGANISM: Artificial Sequence
<220> FEATURE:
<223> OTHER INFORMATION: AAV-CamkII::PSAM4-GlyR-IRES-EGFP-WPRE sequence

<400> SEQUENCE: 34

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtttaac attatggcct taggtcactt     180
catctccatg gggttcttct tctgattttc tagaaaatga gatgggggtg cagagagctt     240
cctcagtgac ctgcccaggg tcacatcaga aatgtcagag ctagaacttg aactcagatt     300
actaatctta aattccatgc cttggggca tgcaagtacg atatacagaa ggagtgaact     360
cattagggca gatgaccaat gagtttagga agaagagtc cagggcaggg tacatctaca     420
ccacccgccc agccctgggt gagtccagcc acgttcacct cattatagtt gcctctctcc     480
agtcctacct tgacgggaag cacaagcaga aactgggaca ggagccccag gagaccaaat     540
cttcatggtc cctctgggag gatggtgggg gagagctgtg gcagaggcct caggaggggc     600
cctgctgctc agtggtgaca gataggggtg agaaagcaga cagagtcatt ccgtcagcat     660
tctgggtctg tttggtactt cttctcacgc taaggtggcg gtgtgatatg cacaatggct     720
aaaaagcagg gagagctgga agaaacaag acagagaca gaggccaagt caaccagacc     780
aattcccaga ggaagcaaag aaaccattac agagactaca aggggaagg gaaggagaga     840
```

```
tgaattagct tcccctgtaa accttagaac ccagctgttg ccagggcaac ggggcaatac    900
ctgtctcttc agaggagatg aagttgccag ggtaactaca tcctgtcttt ctcaaggacc    960
atcccagaat gtggcaccca ctagccgtta ccatagcaac tgcctctttg ccccacttaa   1020
tcccatcccg tctgttaaaa gggccctata gttggaggtg ggggaggtag gaagagcgat   1080
gatcacttgt ggactaagtt tgttcgcatc cccttctcca acccctcag tacatcaccc    1140 tgggggaaca gggtccactt gctcctgggc ccacacagtc ctgcagtatt gtgtatataa   1200
ggccagggca aagaggagca ggttttaaag tgaaaggcag gcaggtgttg gggaggcagt   1260
taccggggca acgggaacag ggcgtttcgg aggtggttgc catggggacc tggatgctga   1320
cgaaggctcg cgaggctgtg agcagccaca gtgccctgct cagaagcccc aagctcgtca   1380
gtcaagccgg ttctccgttt gcactcagga gcacgggcag gcgagtggcc cctagttctg   1440
ggggcagctc tagagcggta ccggatccag gtaagtatca aggttacaag acaggtttaa   1500
ggagaccaat agaaactggg cttgtcgaga cagagaagac tcttgcgttt ctgataggca   1560
cctattggtc ttactgacat ccactttgcc tttctctcca caggtgatga attcgctagc   1620
gccaccatgc gctgttctcc aggcggcgtg tggctcgccc tggctgcttc ccttctgcac   1680
gttagcctgc agggtgagtt ccagcgcaaa ctgtataagg agcttgttaa gaattataac   1740
cccctggagc ggccggtcgc aaatgattcc cagccactga cagtgtactt cagcctctcc   1800
ttgctgcaga tcatgacgt ggatgaaaag aaccaggtgc tgaccactaa tatttggttg    1860
cagatgtcct ggaccgatca ctacttgcag tggaatgtga gcgaataccc aggtgtaaag   1920
actgtaagat tccctgacgg ccaaatctgg aaaccagata tcctgctgta caacagcgca   1980
gacgaaaggt ttgatgcaac atttcacacc aacgtgggag tcaattcttc aggccactgc   2040
ctgtacctgc ccctggaat cttcaagtcc tcatgctata tcgacgtccg ctggtttccc   2100
ttcgacgtcc agcactgcaa actcaaattc gggagctgga gctacggcgg atggagcctg   2160
gatctgcaaa tgcaggaggc tgacatctct ggttacatcc cgaatgggga gtgggacctt   2220
gtgggaatcc ccggtaaaag aagcgagcga ttttatgaat gctgcaaaga gcccttccca   2280
gatgtcacct tcacagtgac catgcggaga cgcatgggtt attatctgat ccaaatgtat   2340
atcccaagct tgcttatagt gattttgtca tggatctcct tctggattaa tatggacgcc   2400
gctccagcta gggtcggact gggcatcacc acagtgctga caatgactac tcagagctca   2460
ggcagccgag ccagcttgcc caaggtttct tacgtgaagg ccatcgatat ctggatggct   2520
gtctgccttc tgtttgtctt cagcgcactg ctggaatacg ccgctgtcaa ttttgtgtct   2580
cgacagcata aagagctgtt gcggttcaga agaaaacgac gccaccacaa agaggatgag   2640
gcaggagaag gacgcttcaa ctttagcgcc tatggtatgg acctgcttg cctccaggct    2700 aaagacggaa tttccgtgaa gggagccaac aatagcaaca caaccaaccc accccctgct   2760
ccatctaaga gcccggagga aatgcgcaaa ctctttattc agagagcgaa aaagatcgac   2820
aaaatctccc ggatcggatt ccccatggct ttcctgattt tcaacatgtt ttattggatc   2880
atctacaaga ttgtgcgaag ggaggacgta cacaaccagt aagcggccgc aattccccccc   2940 gcccccccc cccccccctc accctccccc cccctaacg ttactggccg aagccgcttg    3000
gaataaggcc ggtgtgcgtt tgtctatatg ttattttcca ccatattgcc gtcttttggc   3060
aatgtgaggg cccggaaacc tggccctgtc ttcttgacga gcattcctag gggtcttttc   3120
cctctcgcca aaggaatgca aggtctgttg aatgtcgtga aggaagcagt tcctctggaa   3180
gcttcttgaa gacaaacaac gtctgtagcg accctttgca ggcagcggaa ccccccacct   3240
```

-continued

```
ggcgacaggt gcctctgcgg ccaaaagcca cgtgtataag atacacctgc aaaggcggca    3300
caaccccagt gccacgttgt gagttggata gttgtggaaa gagtcaaatg gctctcctaa    3360
gcgtattcaa caagggggctg aaggatgccc agaaggtacc ccattgtatg ggatctgatc   3420
tggggcctcg gtgcacatgc tttacatgtg tttagtcgag gttaaaaaaa cgtctaggcc    3480
ccccgaacca cggggacgtg gttttccttt gaaaaacacg atgataatat ggccacaacc    3540
atgggagatc cggtgagcaa gggcgaggag ctgttcaccg gggtggtgcc catcctggtc    3600
gagctggacg gcgacgtaaa cggccacaag ttcagcgtgt ccggcgaggg cgagggcgat    3660
gccacctacg gcaagctgac cctgaagttc atctgcacca ccggcaagct gcccgtgccc    3720
tggcccaccc tcgtgaccac cctgacctac ggcgtgcagt gcttcagccg ctaccccgac    3780
cacatgaagc agcacgactt cttcaagtcc gccatgcccg aaggctacgt ccaggagcgc    3840
accatcttct tcaaggacga cggcaactac aagacccgcg ccgaggtgaa gttcgagggc    3900
gacaccctgg tgaaccgcat cgagctgaag ggcatcgact tcaaggagga cggcaacatc    3960
ctggggcaca agctggagta caactacaac agccacaacg tctatatcat ggccgacaag    4020
cagaagaacg gcatcaaggt gaacttcaag atccgccaca acatcgagga cggcagcgtg    4080
cagctcgccg accactacca gcagaacacc cccatcggcg acggccccgt gctgctgccc    4140
gacaaccact acctgagcac ccagtccaag ctgagcaaag accccaacga gaagcgcgat    4200
cacatggtcc tgctggagtt cgtgaccgcc gccgggatca ctctcggcat ggacgagctg    4260
tacaagtaaa ccggtgtcga caagcttatc gataatcaac ctctggatta caaaatttgt    4320
gaaagattga ctggtattct taactatgtt gctccttta cgctatgtgg atacgctgct    4380
ttaatgcctt tgtatcatgc tattgcttcc cgtatggctt tcattttctc ctccttgtat    4440
aaatcctggt tgctgtctct ttatgaggag ttgtggcccg ttgtcaggca acgtggcgtg    4500
gtgtgcactg tgtttgctga cgcaaccccc actggttggg gcattgccac cacctgtcag    4560
ctcctttccg gaactttcgc tttccccctc cctattgcca cggcggaact catcgccgcc    4620
tgccttgccc gctgctggac aggggctcgg ctgttgggca ctgacaattc cgtggtgttg    4680
tcggggaaat catcgtcctt ccttggctg ctcgcctgtg ttgccacctg gattctgcgc    4740
gggacgtcct tctgctacgt cccttcggcc ctcaatccag cggaccttcc ttcccgcggc    4800
ctgctgccgg ctctgcggcc tcttccgcgt cttcgccttc gccctcagac gagtcggatc    4860
tccctttggg ccgcctcccc gcatcgatac cgagcgctgc tcgagagatc tacgggtggc    4920
atccctgtga cccctcccca gtgcctctcc tggccctgga agttgccact ccagtgccca    4980
ccagccttgt cctaataaaa ttaagttgca tcatttgtc tgactaggtg tccttctata    5040
atattatggg tgtgaggggg gtggtatgga gcaaggggca agttgggaag acaacctgta    5100
gggcctgcgg ggtctattgg gaaccaagct ggagtgcagt ggcacaatct ggctcactg    5160 caatctccgc ctcctgggtt caagcgattc tcctgcctca gctcccgag ttgtgggat     5220 tccaggcatg catgaccagg ctcagctaat ttttgttttt ttggtagaga cggggtttca    5280
ccatattggc caggctggtc tccaactcct aatctcaggt gatctaccca ccttggcctc    5340
ccaaattgct gggattacag gcgtgaacca ctgctccctt cctgtccttc tgattttgt    5400 aggtaaccac gtgcggaccg agcggccgca ggaacccta gtgatggagt tggccactcc    5460
ctctctgcgc gctcgctcgc tcactgaggc cgggcgacca aggtcgccc gacgcccggg    5520 cttttgcccgg gcggcctcag tgagcgagcg agcgcgcagc tgcctgcagg ggcgcctgat    5580
```

```
gcggtatttt ctccttacgc atctgtgcgg tatttcacac cgcatacgtc aaagcaacca    5640
tagtacgcgc cctgtagcgg cgcattaagc gcggcgggtg tggtggttac gcgcagcgtg    5700
accgctacac ttgccagcgc cctagcgccc gctcctttcg ctttcttccc ttcctttctc    5760
gccacgttcg ccggctttcc ccgtcaagct ctaaatcggg gctcccttt  agggttccga    5820 tttagtgctt tacggcacct cgaccccaaa aaacttgatt tgggtgatgg ttcacgtagt    5880
gggccatcgc cctgatagac ggttttttcgc ccttttgacgt tggagtccac gttctttaat    5940
agtggactct tgttccaaac tggaacaaca ctcaacccta tctcgggcta ttcttttgat    6000
ttataaggga ttttgccgat tcggcctat  tggttaaaaa atgagctgat ttaacaaaaa    6060
tttaacgcga atttaacaa  aatattaacg tttacaattt tatggtgcac tctcagtaca    6120
atctgctctg atgccgcata gttaagccag ccccgacacc cgccaacacc cgctgacgcg    6180
ccctgacggg cttgtctgct cccggcatcc gcttacagac aagctgtgac cgtctccggg    6240
agctgcatgt gtcagaggtt ttcaccgtca tcaccgaaac gcgcgagacg aaagggcctc    6300
gtgatacgcc tatttttata ggttaatgtc atgataataa tggtttctta cgtcaggt     6360 ggcacttttc ggggaaatgt gcgcggaacc cctatttgtt tatttttcta aatacattca    6420
aatatgtatc cgctcatgag acaataaccc tgataaatgc ttcaataata ttgaaaaagg    6480
aagagtatga gtattcaaca tttccgtgtc gcccttattc cctttttttgc ggcattttgc    6540 cttcctgttt ttgctcaccc agaaacgctg gtgaaagtaa aagatgctga agatcagttg    6600
ggtgcacgag tgggttacat cgaactggat ctcaacagcg gtaagatcct tgagagtttt    6660
cgccccgaag aacgttttcc aatgatgagc acttttaaag ttctgctatg tggcgcggta    6720
ttatcccgta ttgacgccgg gcaagagcaa ctcggtcgcc gcatacacta ttctcagaat    6780
gacttggttg agtactcacc agtcacagaa aagcatctta cggatggcat gacagtaaga    6840
gaattatgca gtgctgccat aaccatgagt gataacactg cggccaactt acttctgaca    6900
acgatcggag gaccgaagga gctaaccgct tttttgcaca acatggggga tcatgtaact    6960
cgccttgatc gttgggaacc ggagctgaat gaagccatac caaacgacga gcgtgacacc    7020
acgatgcctg tagcaatggc aacaacgttg cgcaaactat taactggcga actacttact    7080
ctagcttccc ggcaacaatt aatagactgg atggaggcgg ataaagttgc aggaccactt    7140
ctgcgctcgg cccttccggc tggctggttt attgctgata atctggagc  cggtgagcgt    7200 gggtctcgcg gtatcattgc agcactgggg ccagatggta agccctcccg tatcgtagtt    7260
atctacacga cggggagtca ggcaactatg gatgaacgaa atagacagat cgctgagata    7320
ggtgcctcac tgattaagca ttggtaactg tcagaccaag tttactcata tatactttag    7380
attgatttaa aacttcattt ttaatttaaa aggatctagg tgaagatcct tttttgataat    7440 ctcatgacca aaatccctta acgtgagttt tcgttccact gagcgtcaga ccccgtagaa    7500
aagatcaaag gatcttcttg agatcctttt tttctgcgcg taatctgctg cttgcaaaca    7560
aaaaaaccac cgctaccagc ggtggtttgt ttgccggatc aagagctacc aactcttttt    7620
ccgaaggtaa ctggcttcag cagagcgcag ataccaaata ctgtccttct agtgtagccg    7680
tagttaggcc accacttcaa gaactctgta gcaccgccta catacctcgc tctgctaatc    7740
ctgttaccag tggctgctgc cagtggcgat aagtcgtgtc ttaccgggtt ggactcaaga    7800
cgatagttac cggataaggc gcagcggtcg ggctgaacgg ggggttcgtg cacacagccc    7860
agcttggagc gaacgaccta caccgaactg agatacctac agcgtgagct atgagaaagc    7920
gccacgcttc ccgaagggag aaaggcggac aggtatccgg taagcggcag ggtcggaaca    7980
```

-continued

```
ggagagcgca cgagggagct tccagggggga aacgcctggt atctttatag tcctgtcggg    8040
tttcgccacc tctgacttga gcgtcgattt ttgtgatgct cgtcagggggg gcggagccta    8100 tggaaaaacg ccagcaacgc ggccttttta cggttcctgg ccttttgctg gccttttgct    8160
cacatgt                                                               8167
```

UNITED STATES PATENT AND TRADEMARK OFFICE
CERTIFICATE OF CORRECTION

| | | |
|---|---|---|
| PATENT NO. | : 12,247,064 B2 | Page 1 of 1 |
| APPLICATION NO. | : 17/146906 | |
| DATED | : March 11, 2025 | |
| INVENTOR(S) | : Scott Sternson, Peter Lee and Christopher Magnus | |

It is certified that error appears in the above-identified patent and that said Letters Patent is hereby corrected as shown below:

On the Title Page

Column 2 item (56) (Other Publications), Line 1, delete "Quaterly" and insert -- Quarterly --.

In the Specification

Column 1, Line 8-9 (approx.), after "which" delete "is a".

Signed and Sealed this
Twenty-ninth Day of April, 2025

Coke Morgan Stewart
*Acting Director of the United States Patent and Trademark Office*